United States Patent
Steger et al.

(10) Patent No.: US 12,195,452 B2
(45) Date of Patent: *Jan. 14, 2025

(54) N-(4-(OXAZOL-5-YL)PHENYL) CHROMANE-3-CARBOXAMIDE DERIVATIVES AND RELATED COMPOUNDS AS STIMULATORS OF THE PRODUCTION OF RETINAL PRECURSOR CELLS FOR THE TREATMENT OF NEURORETINAL DISEASES

(71) Applicant: ENDOGENA THERAPEUTICS, INC., San Francisco, CA (US)

(72) Inventors: Matthias Steger, Zurich (CH); Alex Mueller, Zurich (CH); Mauro Marigo, Zurich (CH); Bernhard Fasching, Saint-Louis (FR); Daphna Mokady, Toronto (CA)

(73) Assignee: ENDOGENA THERAPEUTICS, INC., San Francisco, CA (US)

( * ) Notice: Subject to any disclaimer, the term of this patent is extended or adjusted under 35 U.S.C. 154(b) by 785 days.

This patent is subject to a terminal disclaimer.

(21) Appl. No.: 17/418,019

(22) PCT Filed: Dec. 27, 2019

(86) PCT No.: PCT/US2019/068768
§ 371 (c)(1),
(2) Date: Jun. 24, 2021

(87) PCT Pub. No.: WO2020/140050
PCT Pub. Date: Jul. 2, 2020

(65) Prior Publication Data
US 2022/0089583 A1 Mar. 24, 2022

Related U.S. Application Data

(63) Continuation-in-part of application No. 16/235,429, filed on Dec. 28, 2018, now Pat. No. 10,807,973.

(51) Int. Cl.
*C07D 413/12* (2006.01)
*A61K 9/00* (2006.01)
(Continued)

(52) U.S. Cl.
CPC .......... *C07D 413/12* (2013.01); *A61K 9/0019* (2013.01); *A61K 9/0048* (2013.01); *A61P 27/02* (2018.01); *C07D 405/12* (2013.01)

(58) Field of Classification Search
CPC ..... C07D 413/12; C07D 405/12; A61P 27/02; A61K 9/0048; A61K 9/0019
(Continued)

(56) References Cited

U.S. PATENT DOCUMENTS

| 6,066,675 A | 5/2000 | Wen et al. |
| 6,117,675 A | 9/2000 | van der Kooy et al. |

(Continued)

FOREIGN PATENT DOCUMENTS

| AU | 2019226198 A1 | 9/2019 |
| CN | 103656742 A | 3/2014 |

(Continued)

OTHER PUBLICATIONS

Feb. 7, 2024 Extended Search Report issued in European Patent Application No. 20941410.1.
(Continued)

*Primary Examiner* — Kristin A Vajda
(74) *Attorney, Agent, or Firm* — Oliff PLC

(57) ABSTRACT

Compounds and a method of treating a retinal disease that leads to photoreceptor loss or outer-retina degeneration, including administering compound of the formula (I)

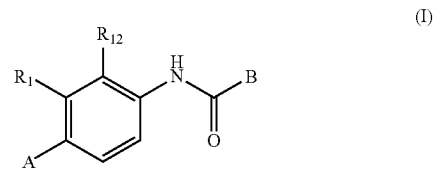

or a pharmaceutically acceptable salt, a racemic mixture, a corresponding enantiomer or, if applicable, a corresponding diastereomer thereof, wherein: A is selected from 5-oxazolyl, pyridine-4-yl, triazolyl, oxadiazolyl, imidazolyl and 2-methyloxazol-5-yl residue, $R_1$, and $R_{12}$ are independently selected from hydrogen, fluoro, chloro, methoxy, trifluoromethyl, methyl and difluoromethoxy, B is selected from a residue of formulae (II)-(IX)

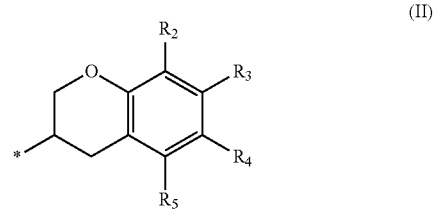

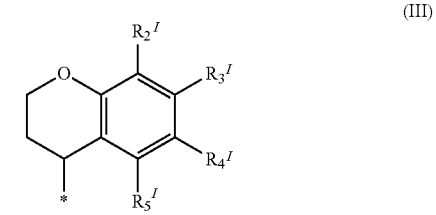

(Continued)

(51) Int. Cl.
*A61P 27/02* (2006.01)
*C07D 405/12* (2006.01)

(58) Field of Classification Search
USPC .......................................................... 514/337
See application file for complete search history.

(56) References Cited

U.S. PATENT DOCUMENTS

| | | | |
|---|---|---|---|
| 9,815,819 B2 | 11/2017 | Altmann et al. | |
| 10,752,593 B2 | 8/2020 | Steger et al. | |
| 10,807,973 B2 | 10/2020 | Steger et al. | |
| 11,541,039 B2 | 1/2023 | Steger et al. | |
| 2006/0148852 A1 | 7/2006 | Takayama et al. | |
| 2009/0325959 A1 | 12/2009 | Vittitow et al. | |
| 2015/0290215 A1 | 10/2015 | Kusari et al. | |
| 2016/0213671 A1 | 7/2016 | Ueffing et al. | |
| 2020/0207749 A1* | 7/2020 | Steger ................. | C07D 401/12 |
| 2022/0089547 A1 | 3/2022 | Steger et al. | |
| 2022/0089583 A1 | 3/2022 | Steger et al. | |
| 2023/0124312 A1 | 4/2023 | Steger et al. | |

FOREIGN PATENT DOCUMENTS

| | | |
|---|---|---|
| EP | 1101759 A1 | 5/2001 |
| RU | 2 628 697 C2 | 8/2017 |
| WO | 99/55663 A1 | 11/1999 |
| WO | 2001/039792 A2 | 6/2001 |
| WO | 02/064545 A1 | 8/2002 |
| WO | 2009/027392 A1 | 3/2009 |
| WO | 2009/075874 A1 | 6/2009 |
| WO | 2009/079008 A1 | 6/2009 |
| WO | 2013/016252 A1 | 1/2013 |
| WO | 2013/029338 A1 | 3/2013 |
| WO | 2014/079850 A1 | 5/2014 |
| WO | 2015/138628 A1 | 9/2015 |
| WO | 2016/029191 A2 | 2/2016 |
| WO | 2016/073931 A1 | 5/2016 |
| WO | 2016/165808 A1 | 10/2016 |
| WO | 2020/140050 A1 | 7/2020 |

OTHER PUBLICATIONS

Bowne et al., "Spectrum and Frequency of Mutations in IMPDH1 Associated with Autosomal Dominant Retinitis Pigmentosa and Leber Congenital Amaurosis", Investigative Opthalmology & Visual Science, Jan. 2006, vol. 47, No. 1.
Loewenstein et al., "Outer Retinal Degeneration, An Electronic Retinal Prosthesis as a Treatment Strategy," Arch Ophthalmol, vol. 122, pp. 587-596, 2004.
Dec. 28, 2018 Office Action issued in U.S. Appl. No. 15/946,469.
May 8, 2019 Office Action issued in U.S. Appl. No. 15/946,469.
Jul. 19, 2019 Office Action issued in U.S. Appl. No. 16/235,543.
Oct. 9, 2019 Office Action Issued in U.S. Appl. No. 16/235,543.
Mar. 23, 2020 Notice of Allowance Issued in U.S. Appl. No. 16/235,543.
Mar. 11, 2020 International Search Report issued in International Patent Application No. PCT/US2019/068759.
Mar. 11, 2020 Written Opinion issued in International Patent Application No. PCT/US2019/068759.
Sep. 24, 2020 International Search Report issued in International Patent Application No. PCT/US2020/038715.
Sep. 24, 2020 Written Opinion issued in International Patent Application No. PCT/US2020/038715.
Dec. 12, 2022 International Preliminary Report on Patentability issued in International Patent Application No. PCT/US2020/038715.
Jan. 4, 2022 International Search Report issued in International Patent Application No. PCT/US2021/053577.
Jan. 4, 2022 Written Opinion issued in International Patent Application No. PCT/US2021/053577.

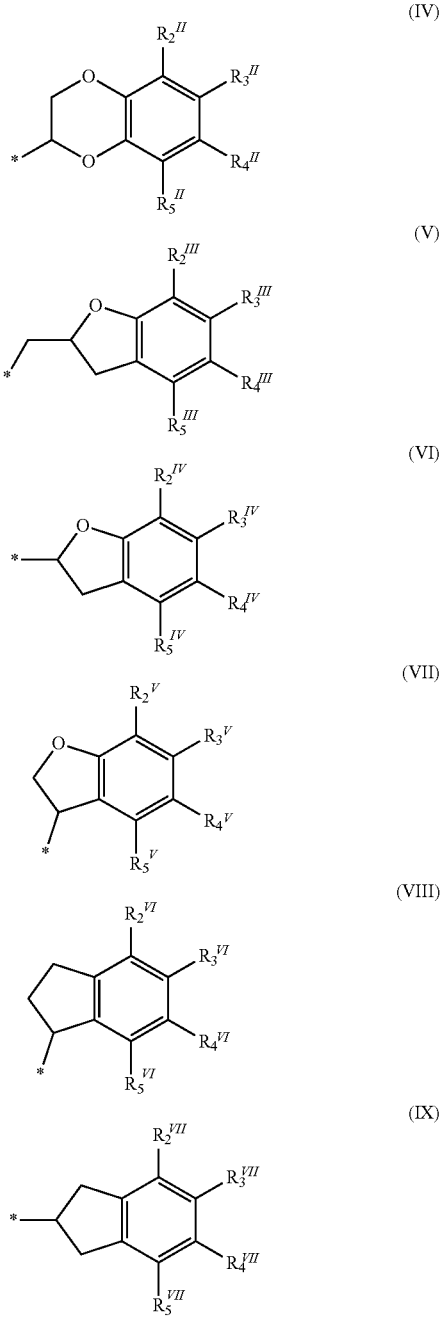

wherein,
"*" denotes the point of attachment to the remainder of the molecule, and
$R_2, R_3, R_4, R_5, R_2^I, R_3^I, R_4^I, R_5^I, R_2^{II}, R_3^{II}, R_4^{II}, R_5^{II}, R_2^{III}, R_3^{III}, R_4^{III}, R_5^{III}, R_2^{IV}, R_3^{IV}, R_4^{IV}, R_5^{IV}, R_2^V, R_3^V, R_4^V, R_5^V, R_2^{VI}, R_3^{VI}, R_4^{VI}, R_5^{VI}, R_2^{VII}, R_3^{VII}, R_4^{VII},$ and $R_5^{VII}$ are independently selected from hydrogen, linear or branched alkyl having 1-3 carbon atoms, fluoro, chloro, bromo, methoxy, ethoxy, propoxy, 2,2,2-trifluoromethyl and difluoromethoxy.

19 Claims, No Drawings

(56) References Cited

OTHER PUBLICATIONS

U.S. Appl. No. 18/011,234, filed Dec. 19, 2022 in the name of Matthias Steger et al.
Feb. 18, 2022 Requirement for Restriction/Election Issued in U.S. Appl. No. 17/065,795.
Jun. 22, 2022 Office Action issued in U.S. Appl. No. 17/065,795.
Aug. 17, 2022 Notice of Allowance Issued in U.S. Appl. No. 17/065,795.
May 9, 2023 Office Action issued in U.S. Appl. No. 17/988,909.
Aug. 21, 2023 Notice of Allowance Issued In U.S. Appl. No. 17/988,909.
U.S. Appl. No. 17/065,795, filed Oct. 8, 2020 in the name of Matthias Steger.
U.S. Appl. No. 17/988,909, filed Nov. 17, 2022 in the name of Matthias Steger.
U.S. Appl. No. 18/030,917, filed Apr. 7, 2023 in the name of Matthias Steger.
U.S. Appl. No. 16/235,429, filed Dec. 28, 2018 in the name of Matthias Steger et al.
U.S. Appl. No. 16/235,543, filed Dec. 28, 2018 in the name of Matthias Steger et al.
U.S. Appl. No. 17/418,057, filed Jun. 24, 2021 in the name of Matthias Steger et al.
Translation of Oct. 11, 2023, Notice of Reasons for Refusal issued in Japanese Patent Application No. 2021-537222.
Database Registry [Online], Retrieved from STN, Mar. 16, 2018, RN:2192535-97-8, and the others, the total of 14 compounds.
U.S. Appl. No. 15/946,469, filed Apr. 5, 2018 in the name of Matthias Steger et al.
Yangbo Feng et al., "Discovery of Substituted 4-(Pyrazol-4-yl)-phenylbenzodioxane-2-carboxamides as Potent and Highly Selective Rho Kinase (ROCK-II) Inhibitors," J. Med. Chem., 2008, vol. 51, pp. 6642-6645.
Mar. 9, 2020 International Search Report issued in International Patent Application No. PCT/US2019/068768.
Mar. 9, 2020 Written Opinion issued in International Patent Application No. PCT/US2019/068768.
Feb. 4, 2020 Office Action issued in U.S. Appl. No. 16/235,429.
Jul. 22, 2020 Notice of Allowance issued in U.S. Appl. No. 16/235,429.
Feb. 29, 2024 Office Action issued in Canadian Application No. 3,125,327.
Jan. 2, 2024 Office Action issued in Chinese Patent Application No. 201980085766.5.
RN: 2192535-97-8, Chemical Abstract, Entry date: Mar. 16, 2018.
RN: 2192535-09-2, Chemical Abstract, Entry date: Mar. 16, 2018.
RN: 2191263-76-8, Chemical Abstract, Entry date: Mar. 14, 2018.
RN: 2176692-30-9, Chemical Abstract, Entry date: Feb. 20, 2018.
RN: 2093772-78-0, Chemical Abstract, Entry date: Apr. 30, 2017.
RN: 2093621-47-5, Chemical Abstract, Entry date: Apr. 28, 2017.
RN: 2093584-39-3, Chemical Abstract, Entry date: Apr. 28, 2017.
RN: 1647398-48-8, Chemical Abstract, Entry date: Feb. 15, 2015.
RN: 1444312-86-0, Chemical Abstract, Entry date: Jul. 16, 2013.
RN: 1436130-27-6, Chemical Abstract, Entry date: Jun. 9, 2013.
RN: 1390017-27-2, Chemical Abstract, Entry date: Aug. 12, 2012.
RN: 1299804-72-0, Chemical Abstract, Entry date: May 24, 2011.
RN: 1294163-48-6, Chemical Abstract, Entry date: May 13, 2011.
RN: 1281131-45-0, Chemical Abstract, Entry date: Apr. 17, 2011.
RN: 1088188-77-5, Chemical Abstract, Entry date: Dec. 22, 2008.

* cited by examiner

N-(4-(OXAZOL-5-YL)PHENYL) CHROMANE-3-CARBOXAMIDE DERIVATIVES AND RELATED COMPOUNDS AS STIMULATORS OF THE PRODUCTION OF RETINAL PRECURSOR CELLS FOR THE TREATMENT OF NEURORETINAL DISEASES

The present invention relates to compounds for use as therapeutically active substances in the treatment and/or prevention of neuroretinal diseases, and in particular in the treatment and/or prevention of neuroretinal diseases leading to photoreceptor loss or degeneration of the outer retina.

The main feature of neurodegenerative diseases is an increasing loss of nerve cells, resulting in various neurological symptoms. The diseases can arise in different periods of life, which proceed diffusely or generalized and produce specific patterns of damage.

Of particular importance are neurodegenerative diseases of the eye. The retinal degeneration is a decay of the retina, which can finally result in the death of the cells of the retina. One of the most important forms of the retina degeneration is the so-called retinitis pigmentosa (RP) or also referred to as retinopathia pigmentosa. The chief function of the retina is transduction of light into nervous impulses by the rods and the cones. Retinitis pigmentosa is a chronic retinal degeneration where the deterioration is accompanied by abnormal deposits of pigment in the rods of the retina. The disease causes a progressive decrease in peripheral vision leading to malfunction of the side vision. Eventually, the person with retinitis pigmentosa can see only straight ahead so that the patient experiences a condition known as "tunnel vision".

The therapeutic strategies for treating loss of vision caused by retinal cell damage vary, but they are all directed to controlling the illness causing the damage rather than reversing the damage caused by an illness by restoring or regenerating retinal cells.

WO 2016/073931 discloses a method for the treatment of retinitis pigmentosa in a human that comprises administering to the human a therapeutically effective amount of N-acetylcysteine amide (NACA) which reduces cone cell death in the eye.

EP 2 734 202 discloses a pharmaceutical composition containing 4-bromo-N-(imidazolidin-2-ylidene)-1H-benzimidazol-5-amine as active ingredient for modulating the alpha 2 adrenergic receptors. It was shown that said compound reduced and protected the retina from the damage caused by blue light.

US 2015/290215 discloses a composition comprising clozapine, n-desmethyl clozapine, olanzapine or derivatives thereof for treating a retinal disorder, which is caused by oxidative stress.

US 2016/0213671 relates to a pharmaceutical composition for the treatment or prophylaxis of a neurodegenerative disease, which is not based on a protein-folding disorder comprising as the active agent an inhibitor of the valosin-containing protein (VCP inhibitor).

WO 2014/079850 discloses both substituted heterocyclic compounds which were believed to stimulate adult neuronal stem cells and that said compounds may be used for a plurality of different diseases. However, although neuronal stem cells have the ability to differentiate into several cell types, it cannot be predicted whether said new cell types can be stimulated by the same compounds. However, a significant number of compounds which stimulate neuronal stem cells have no or only a weak activity with regard to other cell types such as retinal precursor cells.

U.S. Pat. No. 6,117,675 discloses stem cells isolated from the retina of mammals and retinal cells differentiated from these stem cells and a method for obtaining cells from a retinal pigment epithelial layer of a mammal.

There is currently no way to reverse permanent damage to the retina and restore vision. Drug treatments focus on treating the illness and its symptoms to prevent further damage to the retina. There is a need to reverse damage to the retina and restore vision by endogenously generating new retinal cells or transplanting retinal cells.

The term "precursor cells" encompasses in this context any form of proliferative and non-proliferative cells such as stem cells per se and progenitor cells that can give rise to further differentiated functional tissues of the eye. Such precursor cells include in particular retinal precursor cells.

The problem of the present invention is therefore to provide new compound, which stimulate the proliferation of retinal precursor cells.

The problem is solved by a compound of formula (I). Further preferred embodiments are subject of the dependent claims.

It has been shown that a compound of formula (I) stimulates production of mammalian retinal precursor cells. The selective activation of the endogenous precursor cells allows a controlled repair and regeneration of the retina. Thus, it is possible to restore vision by endogenously generating new precursor cells by a compound according to the present invention. Therefore, the compound is useful as a therapeutically active substance in the treatment and/or prevention of neuroretinal diseases, i.e. as a medicament.

Thus, the present invention relates to a compound of formula (I)

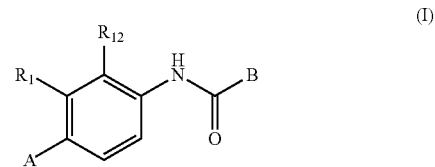

or a pharmaceutically acceptable salt, a racemic mixture, a corresponding enantiomer or, if applicable, a corresponding diastereomer thereof, wherein:

A is selected from the group consisting of a 5-oxazolyl, a pyridine-4-yl, a triazolyl, an oxadiazolyl, an imidazolyl and a 2-methyloxazol-5-yl residue.

$R_1$ and $R_{12}$ are independently selected from the group consisting of hydrogen, fluoro, chloro, methoxy, trifluoromethyl, methyl and difluoromethoxy.

B is selected from the group consisting of a residue of formula (II), (III), (IV), (V), (VI), (VII), (VIII) and (IX)

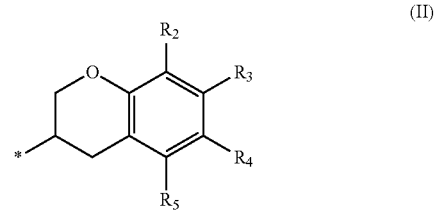

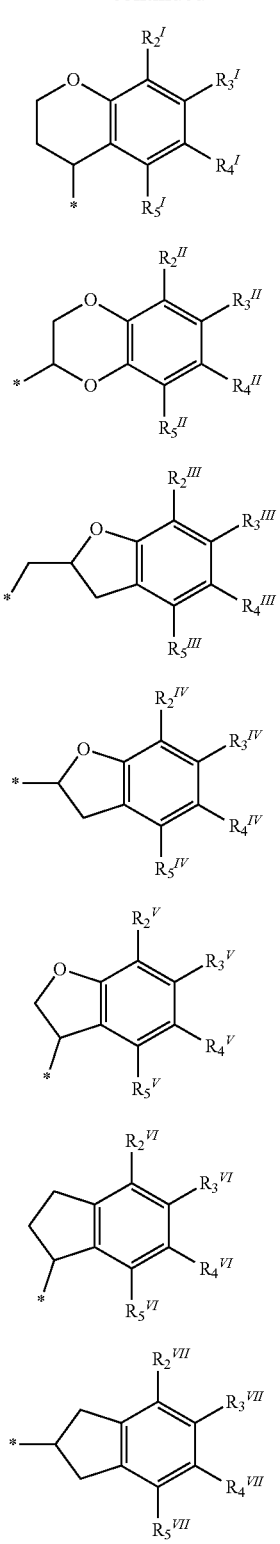

wherein,
"k" denotes the point of attachment to the remainder of the molecule, and
$R_2, R_3, R_4, R_5, R_2^I, R_3^I, R_4^I, R_5^I, R_2^{II}, R_3^{II}, R_4^{II}, R_5^{II}, R_2^{III}, R_3^{III}, R_4^{III}, R_5^{III}, R_2^{IV}, R_3^{IV}, R_4^{IV}, R_5^{IV}, R_2^V, R_3^V, R_4^V, R_5^V, R_2^{VI}, R_3^{VI}, R_4^{VI}, R_5^{VI}, R_2^{VII}, R_3^{VII}, R_4^{VII}$, and $R_5^{VII}$ are independently selected from the group consisting of hydrogen, a linear or branched alkyl having 1 to 3 carbon atoms, fluoro, chloro, bromo, methoxy, ethoxy, propoxy, 2,2,2-trifluoromethyl and difluoromethoxy.

The term "pharmaceutically acceptable salt" stands for therapeutically active, non-toxic acid salt forms, which the compound according to the present invention is able to form.

The residue A may be a 5-oxazolyl residue of the formula (X)

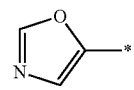

(X)

wherein "*" denotes the point of attachment to the remainder of the molecule.

Alternatively, the residue A may be a pyridine-4-yl residue of the formula (XI)

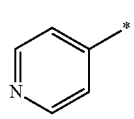

(XI)

wherein "*" denotes the point of attachment to the remainder of the molecule.

Alternatively, the residue A may be a 1,2,4-triazol-1-yl residue of the formula (XII)

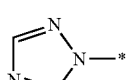

(XII)

wherein "*" denotes the point of attachment to the remainder of the molecule.

Alternatively, the residue A may be an 1,3,4-oxadiazol-2-yl residue of the formula (XIII)

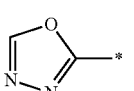

(XIII)

wherein "*" denotes the point of attachment to the remainder of the molecule.

Alternatively, the residue A may be an 1H-imidazol-1-yl residue of the formula (XIV)

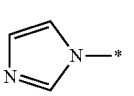

(XIV)

wherein "*" denotes the point of attachment to the remainder of the molecule.

Alternatively, the residue A may be a 2-methyloxazole-5-yl residue of the formula (XV)

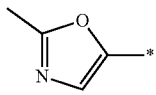
(XV)

wherein "*" denotes the point of attachment to the remainder of the molecule.

In one embodiment of the present invention the asymmetric center at ring position * of the residue of formula (II), (III), (IV), (V), (VI), (VII), (VIII) and (IX) has the configuration as depicted below, that is a compound of formula (Ii)

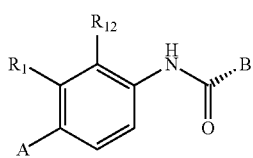
(Ii)

and B is selected from the group consisting of a residue of formula (II), (III), (IV), (V), (VI), (VII), (VIII) and (IX), preferably a residue of formula (II), (III) or (IV),

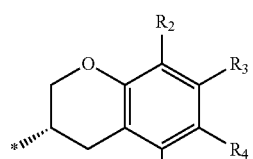
(II)

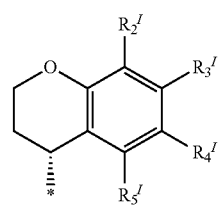
(III)

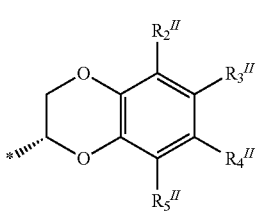
(IV)

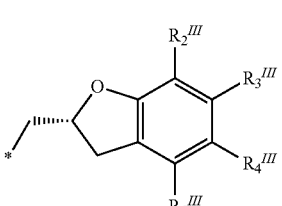
(V)

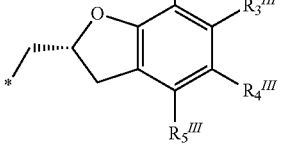

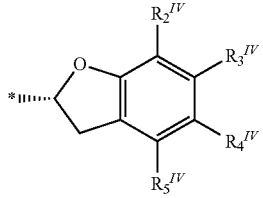
(VI)

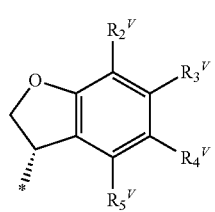
(VII)

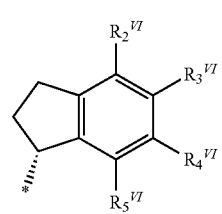
(VIII)

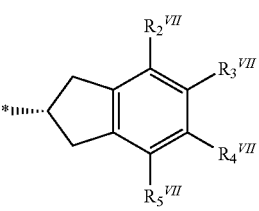
(IX)

and $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$, $R_2^{VI}$, $R_3^{VI}$, $R_4^{VI}$, $R_5^{VI}$, $R_2^{VII}$, $R_3^{VII}$, $R_4^{VII}$, and $R_5^{VII}$ have the same definition as above.

In another embodiment of the present invention the asymmetric center at ring position * of the residue of formula (II), (III), (IV), (V), (VI), (VII), (VIII) and (IX) is in the configuration as depicted below, that is a compound of formula (Iii)

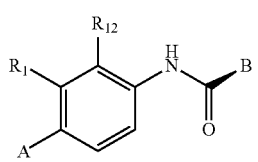
(Iii)

and B is selected from the group consisting of a residue of formula (II), (III), (IV), (V), (VI), (VII), (VIII) and (IX)

(II) 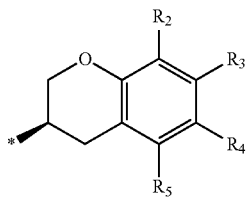

(III) 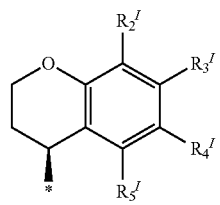

(IV) 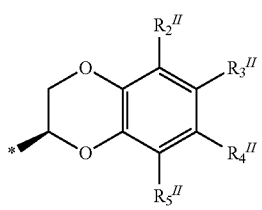

(V) 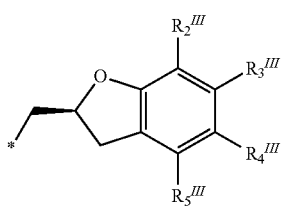

(VI) 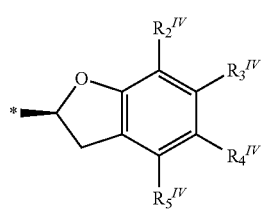

(VII) 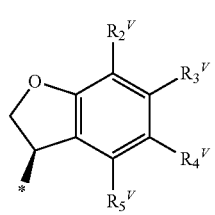

(VIII) 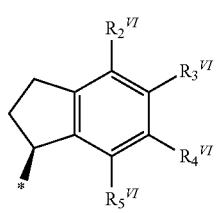

(IX) 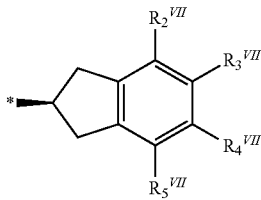

and $R_2, R_3, R_4, R_5, R_2^I, R_3^I, R_4^I, R_5^I, R_2^{II}, R_3^{II}, R_4^{II}, R_5^{II}, R_2^{III}, R_3^{III}, R_4^{III}, R_5^{III}, R_2^{IV}, R_3^{IV}, R_4^{IV}, R_5^{IV}, R_2^V, R_3^V, R_4^V, R_5^V, R_2^{VI}, R_3^{VI}, R_4^{VI}, R_5^{VI}, R_2^{VII}, R_3^{VII}, R_4^{VII}$, and $R_5^{VII}$ have the same definition as above.

In one embodiment, the residue B is preferably unsubstituted, i.e., the residues $R_2, R_3, R_4, R_5, R_2^I, R_3^I, R_4^I, R_5^I, R_2^{II}, R_3^{II}, R_4^{II}, R_5^{II}, R_2^{III}, R_3^{III}, R_4^{III}, R_5^{III}, R_2^{IV}, R_3^{IV}, R_4^{IV}, R_5^{IV}, R_2^V, R_3^V, R_4^V, R_5^V, R_2^{VI}, R_3^{VI}, R_4^{VI}, R_5^{VI}, R_2^{VII}, R_3^{VII}, R_4^{VII}$, and $R_5^{VII}$ are all hydrogen.

In one embodiment, the residue B is preferably monosubstituted, most preferably the residues $R_2, R_3, R_5, R_2^I, R_3^I, R_5^I, R_2^{II}, R_3^{II}, R_5^{II}, R_2^{III}, R_3^{III}, R_5^{III}, R_2^{IV}, R_3^{IV}, R_5^{IV}, R_2^V, R_3^V, R_5^V, R_2^{VI}, R_3^{VI}, R_5^{VI}, R_2^{VII}, R_3^{VII}$, and $R_5^{VII}$ are hydrogen and $R_4^I, R_4^{II}, R_4^{III}, R_4^{IV}, R_4^{VI}$, and $R_4^{VII}$ are selected from the group consisting of hydrogen, methoxy, and ethoxy.

In another embodiment, the residue B is preferably monosubstituted, most preferably the residues $R_2, R_4, R_5, R_2^I, R_4^I, R_5^I, R_2^{II}, R_4^{II}, R_5^{II}, R_2^{III}, R_4^{III}, R_5^{III}, R_2^{IV}, R_4^{IV}, R_5^{IV}, R_2^V, R_4^V, R_5^V, R_2^{VI}, R_4^{VI}, R_5^{VI}, R_2^{VII}, R_4^{VII}$, and $R_5^{VII}$ are hydrogen and $R_3^I, R_3^{II}, R_3^{III}, R_3^{IV}, R_3^{VI}$, and $R_3^{VII}$ are selected from the group consisting of hydrogen, fluoro and chloro.

Preferably, in the compound of the present invention, $R_1$ or $R_{12}$ is selected from the group consisting of methoxy, chloro and fluoro, most preferably methoxy, and $R_2, R_3, R_4, R_5, R_2^I, R_3^I, R_4^I, R_5^I, R_2^{II}, R_3^{II}, R_4^{II}, R_5^{II}, R_2^{III}, R_3^{III}, R_4^{III}, R_5^{III}, R_2^{IV}, R_3^{IV}, R_4^{IV}, R_5^{IV}, R_2^V, R_3^V, R_4^V, R_5^V, R_2^{VI}, R_3^{VI}, R_4^{VI}, R_5^{VI}, R_2^{VII}, R_3^{VII}, R_4^{VII}$, and $R_5^{VII}$ have the same definition as above.

In a preferred embodiment $R_1$ is chloro or methoxy, and $R_3, R_3^I, R_3^{II}, R_3^{III}, R_3^{IV}, R_3^V, R_3^{VI}$ or $R_3^{VII}$, is hydrogen or fluoro. Most preferably, $R_1$ is chloro or methoxy, and $R_4, R_4^I, R_4^{II}, R_4^{III}, R_4^{IV}, R_4^V, R_4^{VI}$ or $R_4^{VII}$, is hydrogen or methoxy. Said compounds show an outstanding biological activity.

One embodiment of the present invention relates to the compound of formula (Ia)

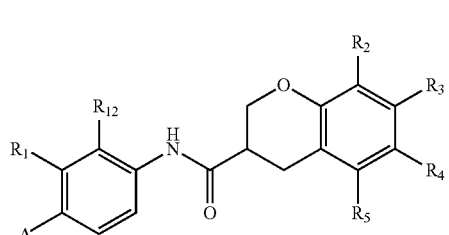

(Ia)

or a pharmaceutically acceptable salt, a racemic mixture, a corresponding enantiomer or, if applicable, a corresponding diastereomer thereof,
wherein:
$A, R_1, R_{12}, R_2, R_3, R_4$ and $R_5$ have the same definition as above. Preferably, $R_3$ and $R_4$ are independently selected from the group consisting of hydrogen, chloro, floro, methoxy and ethoxy, most preferably methoxy. Preferably, $R_3$ is selected from the group consisting of hydrogen, fluoro and chloro, and $R_2$, $R_4$, and $R_5$ are hydrogen. Most preferably, $R_4$ is selected from the group consisting of hydrogen, methoxy and ethoxy, and $R_2$, $R_3$, and $R_5$ are hydrogen.

Another embodiment of the present invention relates to the compound of formula (Ib)

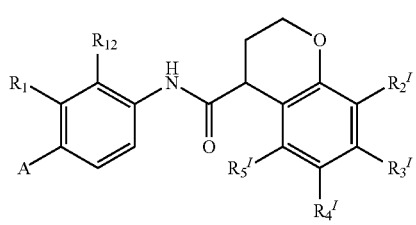

(Ib)

or a pharmaceutically acceptable salt, a racemic mixture, a corresponding enantiomer or, if applicable, a corresponding diastereomer thereof, wherein:

A, $R_1$, $R_{12}$, $R_2^I$, $R_3^I$, $R_4^I$ and $R_5^I$ have the same definition as above. Preferably, $R_3^1$ is selected from the group consisting of hydrogen, fluoro and chloro, and $R_2^I$, $R_4^I$, and $R_5^I$ are hydrogen. Most preferably, $R_4^I$ is selected from the group consisting of hydrogen, methoxy and ethoxy, and $R_2^I$, $R_3^I$, and $R_5^I$ are hydrogen.

Another embodiment of the present invention relates to the compound of formula (Ic)

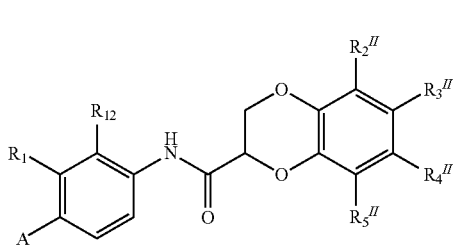

(Ic)

or a pharmaceutically acceptable salt, a racemic mixture, a corresponding enantiomer or, if applicable, a corresponding diastereomer thereof, wherein:

A, $R_1$, $R_{12}$, $R_2^{II}$, $R_3^{II}$, $R_4^{II}$ and $R_5^{II}$ have the same definition as above. Preferably, $R_3^{II}$ is selected from the group consisting of hydrogen, fluoro and chloro, and $R_2^{II}$, $R_4^{II}$, and $R_5^{II}$ are hydrogen. Most preferably, $R_4^{II}$ is selected from the group consisting of hydrogen, methoxy and ethoxy, and $R_2^{II}$, $R_3^{II}$, and $R_5^{II}$ are hydrogen.

Another embodiment of the present invention relates to the compound of formula (Id)

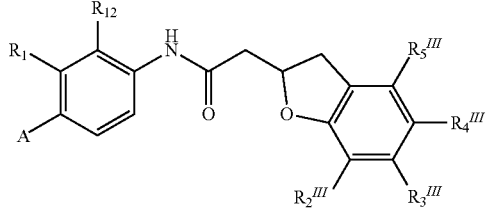

(Id)

or a pharmaceutically acceptable salt, a racemic mixture, a corresponding enantiomer or, if applicable, a corresponding diastereomer thereof, wherein:

A, $R_1$, $R_{12}$, $R_2^{III}$, $R_3^{III}$, $R_4^{III}$ and $R_5^{III}$ have the same definition as above. Preferably, $R_3^{III}$ is selected from the group consisting of hydrogen, fluoro and chloro, and $R_2^{III}$, $R_4^{III}$, and $R_5^{III}$ are hydrogen. Most preferably, $R_4^{III}$ is selected from the group consisting of hydrogen, methoxy and ethoxy, and $R_2^{III}$, $R_3^{III}$, and $R_5^{III}$ are hydrogen.

Another embodiment of the present invention relates to the compound of formula (Ie)

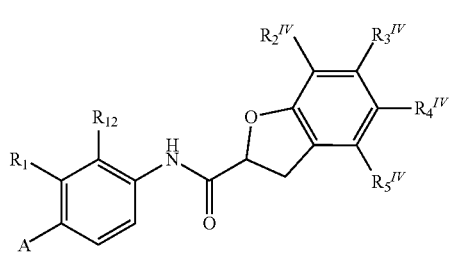

(Ie)

or a pharmaceutically acceptable salt, a racemic mixture, a corresponding enantiomer or, if applicable, a corresponding diastereomer thereof, wherein:

A, $R_1$, $R_2$, $R_2^{IV}$, $R_3^{IV}$, $R_4^{IV}$ and $R_5^{IV}$ have the same definition as above. Preferably, $R_3^{VI}$ is selected from the group consisting of hydrogen, fluoro and chloro, and $R_2^{VI}$, $R_4^{VI}$, and $R_5^{VI}$ are hydrogen. Most preferably, $R_4^{VI}$ is selected from the group consisting of hydrogen, methoxy and ethoxy, and $R_2^{VI}$, $R_3^{VI}$, and $R_5^{IV}$ are hydrogen.

Another embodiment of the present invention relates to the compound of formula (If)

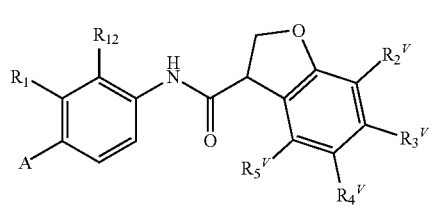

(If)

or a pharmaceutically acceptable salt, a racemic mixture, a corresponding enantiomer or, if applicable, a corresponding diastereomer thereof, wherein:

A, $R_1$, $R_2$, $R_2^V$, $R_3^V$, $R_4^V$ and $R_5^V$ have the same definition as above. Preferably, $R_3^V$ is selected from the group consisting of hydrogen, fluoro and chloro, and $R_2^V$, $R_4^V$, and $R_5^V$ are hydrogen. Most preferably, $R_4^V$ is selected from the group consisting of hydrogen, methoxy and ethoxy, and $R_2^V$, $R_3^V$, and $R_5^V$ are hydrogen.

Another embodiment of the present invention relates to the compound of formula (Ig)

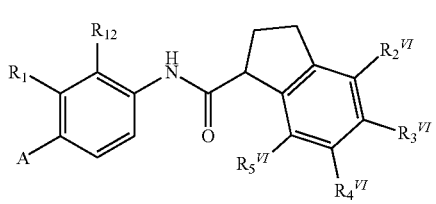

(Ig)

or a pharmaceutically acceptable salt, a racemic mixture, a corresponding enantiomer or, if applicable, a corresponding diastereomer thereof, wherein:

A, $R_1$, $R_2$, $R_2^{VI}$, $R_3^{VI}$, $R_4^{VI}$ and $R_5^{VI}$ have the same definition as above. Preferably, $R_3^{VI}$ is selected from the group consisting of hydrogen, fluoro and chloro, and $R_2^{VI}$, $R_4^{VI}$, and $R_5^{VI}$ are hydrogen. Most preferably, $R_4^{VI}$ is selected from the group consisting of hydrogen, methoxy and ethoxy, and $R_2^{VI}$, $R_3^{VI}$ and $R_5^{VI}$ are hydrogen.

Another embodiment of the present invention relates to the compound of formula (Ih)

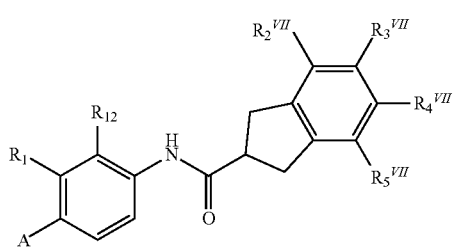

(Ih)

or a pharmaceutically acceptable salt, a racemic mixture, a corresponding enantiomer or, if applicable, a corresponding diastereomer thereof, wherein:

A, $R_1$, $R_2$, $R_2^{VII}$, $R_3^{VII}$, $R_4^{VII}$ and $R_5^{VII}$ have the same definition as above. Preferably, $R_3^{VII}$ is selected from the group consisting of hydrogen, fluoro and chloro, and $R_2^{VII}$, $R_4^{VII}$, and $R_5^{VII}$ are hydrogen. Most preferably, $R_4^{VII}$ is selected from the group consisting of hydrogen, methoxy and ethoxy, and $R_2^{VII}$, $R_3^{VII}$, and $R_5^{VII}$ are hydrogen.

Preferably, the compound of formula (Ia)

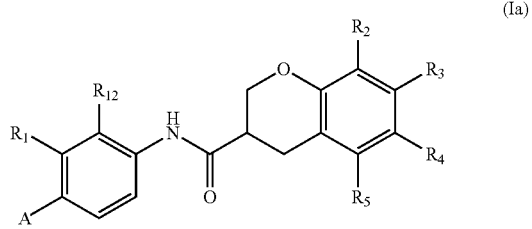

(Ia)

is selected from the group consisting of compounds of the formula (I), wherein A, $R_1$, $R_{12}$, $R_2$, $R_3$, $R_4$ and $R_5$ are as indicated in Table 1:

TABLE 1

| A | $R_1$ | $R_{12}$ | $R_2$ | $R_3$ | $R_4$ | $R_5$ |
|---|---|---|---|---|---|---|
| 1,2,4-triazol-1-yl | $CF_3$ | H | H | $CH_3$ | H | H |
| 1,2,4-triazol-1-yl | $CF_3$ | H | H | F | H | H |
| 1,2,4-triazol-1-yl | $CF_3$ | H | H | H | H | $OCH_3$ |
| 1,2,4-triazol-1-yl | $CF_3$ | H | H | H | $OCF_2H$ | H |
| 1,2,4-triazol-1-yl | $CF_3$ | H | H | H | $OCH_3$ | H |
| 1,2,4-triazol-1-yl | $CH_3$ | H | F | H | H | H |
| 1,2,4-triazol-1-yl | $CH_3$ | H | H | $CH_3$ | H | H |
| 1,2,4-triazol-1-yl | $CH_3$ | H | H | F | H | H |
| 1,2,4-triazol-1-yl | $CH_3$ | H | H | H | H | $OCH_3$ |
| 1,2,4-triazol-1-yl | $CH_3$ | H | H | H | $OCF_2H$ | H |
| 1,2,4-triazol-1-yl | $CH_3$ | H | H | H | $OCH_3$ | H |
| 1,2,4-triazol-1-yl | Cl | H | F | H | H | H |
| 1,2,4-triazol-1-yl | Cl | H | H | $CH_3$ | H | H |
| 1,2,4-triazol-1-yl | Cl | H | H | F | H | H |
| 1,2,4-triazol-1-yl | Cl | H | H | H | H | H |
| 1,2,4-triazol-1-yl | Cl | H | H | H | H | $OCF_2H$ |
| 1,2,4-triazol-1-yl | Cl | H | H | H | H | $OCH_3$ |
| 1,2,4-triazol-1-yl | Cl | H | H | H | $OCF_2H$ | H |
| 1,2,4-triazol-1-yl | Cl | H | H | H | $OCH_3$ | H |
| 1,2,4-triazol-1-yl | F | H | H | $CH_3$ | H | H |
| 1,2,4-triazol-1-yl | F | H | H | F | H | H |
| 1,2,4-triazol-1-yl | F | H | H | H | H | $OCH_3$ |
| 1,2,4-triazol-1-yl | F | H | H | H | $OCF_2H$ | H |
| 1,2,4-triazol-1-yl | F | H | H | H | $OCH_3$ | H |
| 1,2,4-triazol-1-yl | H | $CF_3$ | H | $CH_3$ | H | H |
| 1,2,4-triazol-1-yl | H | $CF_3$ | H | F | H | H |
| 1,2,4-triazol-1-yl | H | $CF_3$ | H | H | H | $OCH_3$ |
| 1,2,4-triazol-1-yl | H | $CF_3$ | H | H | $OCF_2H$ | H |
| 1,2,4-triazol-1-yl | H | $CH_3$ | H | $CH_3$ | H | H |
| 1,2,4-triazol-1-yl | H | $CH_3$ | H | F | H | H |
| 1,2,4-triazol-1-yl | H | $CH_3$ | H | H | H | $OCH_3$ |
| 1,2,4-triazol-1-yl | H | $CH_3$ | H | H | $OCF_2H$ | H |
| 1,2,4-triazol-1-yl | H | $OCF_2H$ | H | $CH_3$ | H | H |
| 1,2,4-triazol-1-yl | H | $OCF_2H$ | H | F | H | H |
| 1,2,4-triazol-1-yl | H | $OCF_2H$ | H | H | H | $OCH_3$ |
| 1,2,4-triazol-1-yl | H | $OCF_2H$ | H | H | $OCF_2H$ | H |
| 1,2,4-triazol-1-yl | $OCF_2H$ | H | F | H | H | H |
| 1,2,4-triazol-1-yl | $OCF_2H$ | H | H | $CH_3$ | H | H |
| 1,2,4-triazol-1-yl | $OCF_2H$ | H | H | F | H | H |
| 1,2,4-triazol-1-yl | $OCF_2H$ | H | H | H | H | $OCH_3$ |
| 1,2,4-triazol-1-yl | $OCF_2H$ | H | H | H | $OCF_2H$ | H |
| 1,2,4-triazol-1-yl | $OCF_2H$ | H | H | H | $OCH_3$ | H |
| 1,2,4-triazol-1-yl | $OCH_3$ | H | F | H | H | H |
| 1,2,4-triazol-1-yl | $OCH_3$ | H | H | $CH_3$ | H | H |
| 1,2,4-triazol-1-yl | $OCH_3$ | H | H | F | H | H |
| 1,2,4-triazol-1-yl | $OCH_3$ | H | H | H | H | H |
| 1,2,4-triazol-1-yl | $OCH_3$ | H | H | H | H | $OCH_3$ |
| 1,2,4-triazol-1-yl | $OCH_3$ | H | H | H | $OCF_2H$ | H |
| 1,2,4-triazol-1-yl | $OCH_3$ | H | H | H | $OCH_3$ | H |
| 1,3,4-oxadiazol-2-yl | $CF_3$ | H | H | $CH_3$ | H | H |
| 1,3,4-oxadiazol-2-yl | $CF_3$ | H | H | F | H | H |
| 1,3,4-oxadiazol-2-yl | $CF_3$ | H | H | H | H | $OCH_3$ |
| 1,3,4-oxadiazol-2-yl | $CF_3$ | H | H | H | $OCF_2H$ | H |
| 1,3,4-oxadiazol-2-yl | $CF_3$ | H | H | H | $OCH_3$ | H |
| 1,3,4-oxadiazol-2-yl | $CH_3$ | H | F | H | H | H |
| 1,3,4-oxadiazol-2-yl | $CH_3$ | H | H | $CH_3$ | H | H |

TABLE 1-continued

| A | R₁ | R₁₂ | R₂ | R₃ | R₄ | R₅ |
|---|---|---|---|---|---|---|
| 1,3,4-oxadiazol-2-yl | CH₃ | H | H | F | H | H |
| 1,3,4-oxadiazol-2-yl | CH₃ | H | H | H | H | OCH₃ |
| 1,3,4-oxadiazol-2-yl | CH₃ | H | H | H | OCF₂H | H |
| 1,3,4-oxadiazol-2-yl | CH₃ | H | H | H | OCH₃ | H |
| 1,3,4-oxadiazol-2-yl | Cl | H | F | H | CH₃ | H |
| 1,3,4-oxadiazol-2-yl | Cl | H | H | CH₃ | H | H |
| 1,3,4-oxadiazol-2-yl | Cl | H | H | F | H | H |
| 1,3,4-oxadiazol-2-yl | Cl | H | H | H | H | H |
| 1,3,4-oxadiazol-2-yl | Cl | H | H | H | H | OCF₂H |
| 1,3,4-oxadiazol-2-yl | Cl | H | H | H | H | OCH₃ |
| 1,3,4-oxadiazol-2-yl | Cl | H | H | H | OCF₂H | H |
| 1,3,4-oxadiazol-2-yl | Cl | H | H | H | OCH₃ | H |
| 1,3,4-oxadiazol-2-yl | F | H | H | CH₃ | H | H |
| 1,3,4-oxadiazol-2-yl | F | H | H | F | H | H |
| 1,3,4-oxadiazol-2-yl | F | H | H | H | H | OCH₃ |
| 1,3,4-oxadiazol-2-yl | F | H | H | H | OCF₂H | H |
| 1,3,4-oxadiazol-2-yl | F | H | H | H | OCH₃ | H |
| 1,3,4-oxadiazol-2-yl | H | CF₃ | H | CH₃ | H | H |
| 1,3,4-oxadiazol-2-yl | H | CF₃ | H | F | H | H |
| 1,3,4-oxadiazol-2-yl | H | CF₃ | H | H | H | OCH₃ |
| 1,3,4-oxadiazol-2-yl | H | CF₃ | H | H | OCF₂H | H |
| 1,3,4-oxadiazol-2-yl | H | CH₃ | H | CH₃ | H | H |
| 1,3,4-oxadiazol-2-yl | H | CH₃ | H | F | H | H |
| 1,3,4-oxadiazol-2-yl | H | CH₃ | H | H | H | OCH₃ |
| 1,3,4-oxadiazol-2-yl | H | CH₃ | H | H | OCF₂H | H |
| 1,3,4-oxadiazol-2-yl | H | OCF₂H | H | CH₃ | H | H |
| 1,3,4-oxadiazol-2-yl | H | OCF₂H | H | F | H | H |
| 1,3,4-oxadiazol-2-yl | H | OCF₂H | H | H | H | OCH₃ |
| 1,3,4-oxadiazol-2-yl | H | OCF₂H | H | H | OCF₂H | H |
| 1,3,4-oxadiazol-2-yl | OCF₂H | H | F | H | H | H |
| 1,3,4-oxadiazol-2-yl | OCF₂H | H | H | CH₃ | H | H |
| 1,3,4-oxadiazol-2-yl | OCF₂H | H | H | F | H | H |
| 1,3,4-oxadiazol-2-yl | OCF₂H | H | H | H | H | H |
| 1,3,4-oxadiazol-2-yl | OCF₂H | H | H | H | OCF₂H | H |
| 1,3,4-oxadiazol-2-yl | OCF₂H | H | H | H | OCH₃ | H |
| 1,3,4-oxadiazol-2-yl | OCH₃ | H | F | H | H | H |
| 1,3,4-oxadiazol-2-yl | OCH₃ | H | H | CH₃ | H | H |
| 1,3,4-oxadiazol-2-yl | OCH₃ | H | H | F | H | H |
| 1,3,4-oxadiazol-2-yl | OCH₃ | H | H | H | H | H |
| 1,3,4-oxadiazol-2-yl | OCH₃ | H | H | H | H | OCH₃ |
| 1,3,4-oxadiazol-2-yl | OCH₃ | H | H | H | OCF₂H | H |
| 1,3,4-oxadiazol-2-yl | OCH₃ | H | H | H | OCH₃ | H |
| 2-methyloxazol-5-yl | CF₃ | H | H | F | H | H |
| 2-methyloxazol-5-yl | CF₃ | H | H | H | H | OCH₃ |
| 2-methyloxazol-5-yl | CF₃ | H | H | H | OCH₃ | H |
| 2-methyloxazol-5-yl | CH₃ | H | H | F | H | H |
| 2-methyloxazol-5-yl | CH₃ | H | H | H | H | OCH₃ |
| 2-methyloxazol-5-yl | CH₃ | H | H | H | OCH₃ | H |
| 2-methyloxazol-5-yl | Cl | H | H | F | H | H |
| 2-methyloxazol-5-yl | Cl | H | H | H | H | H |
| 2-methyloxazol-5-yl | Cl | H | H | H | H | OCH₃ |
| 2-methyloxazol-5-yl | Cl | H | H | H | OCH₃ | H |
| 2-methyloxazol-5-yl | H | CF₃ | H | F | H | H |
| 2-methyloxazol-5-yl | H | CF₃ | H | H | H | OCH₃ |
| 2-methyloxazol-5-yl | H | CF₃ | H | H | OCF₂H | H |
| 2-methyloxazol-5-yl | H | CH₃ | H | F | H | H |
| 2-methyloxazol-5-yl | H | CH₃ | H | H | H | OCH₃ |
| 2-methyloxazol-5-yl | H | CH₃ | H | H | OCF₂H | H |
| 2-methyloxazol-5-yl | H | OCF₂H | H | F | H | H |
| 2-methyloxazol-5-yl | H | OCF₂H | H | H | H | OCH₃ |
| 2-methyloxazol-5-yl | H | OCF₂H | H | H | OCF₂H | H |
| 2-methyloxazol-5-yl | OCF₂H | H | H | F | H | H |
| 2-methyloxazol-5-yl | OCF₂H | H | H | H | H | OCH₃ |
| 2-methyloxazol-5-yl | OCF₂H | H | H | H | OCH₃ | H |
| 2-methyloxazol-5-yl | OCH₃ | H | H | F | H | H |
| 2-methyloxazol-5-yl | OCH₃ | H | H | H | H | H |
| 2-methyloxazol-5-yl | OCH₃ | H | H | H | H | OCH₃ |
| 2-methyloxazol-5-yl | OCH₃ | H | H | H | OCH₃ | H |
| imidazolyl | CF₃ | H | H | CH₃ | H | H |
| imidazolyl | CF₃ | H | H | F | H | H |
| imidazolyl | CF₃ | H | H | H | H | OCH₃ |
| imidazolyl | CF₃ | H | H | H | OCF₂H | H |
| imidazolyl | CF₃ | H | H | H | OCH₃ | H |
| imidazolyl | CH₃ | H | H | F | H | H |
| imidazolyl | CH₃ | H | H | H | H | OCH₃ |
| imidazolyl | CH₃ | H | H | H | OCF₂H | H |
| imidazolyl | CH₃ | H | H | H | OCH₃ | H |
| imidazolyl | Cl | H | F | H | H | H |
| imidazolyl | Cl | H | H | CH₃ | H | H |
| imidazolyl | Cl | H | H | F | H | H |
| imidazolyl | Cl | H | H | H | H | H |
| imidazolyl | Cl | H | H | H | H | OCH₃ |
| imidazolyl | Cl | H | H | H | OCF₂H | H |
| imidazolyl | Cl | H | H | H | OCH₃ | H |
| imidazolyl | F | H | H | CH₃ | H | H |
| imidazolyl | F | H | H | F | H | H |
| imidazolyl | F | H | H | H | H | OCH₃ |
| imidazolyl | F | H | H | H | OCF₂H | H |
| imidazolyl | F | H | H | H | OCH₃ | H |
| imidazolyl | H | CF₃ | H | CH₃ | H | H |
| imidazolyl | H | CF₃ | H | F | H | H |
| imidazolyl | H | CF₃ | H | H | H | OCH₃ |
| imidazolyl | H | CF₃ | H | H | OCF₂H | H |
| imidazolyl | H | CH₃ | H | CH₃ | H | H |
| imidazolyl | H | CH₃ | H | F | H | H |
| imidazolyl | H | CH₃ | H | H | H | OCH₃ |
| imidazolyl | H | CH3 | H | H | OCF₂H | H |
| imidazolyl | H | OCF₂H | H | CH₃ | H | H |
| imidazolyl | H | OCF₂H | H | F | H | H |
| imidazolyl | H | OCF₂H | H | H | H | H |
| imidazolyl | H | OCF₂H | H | H | OCF₂H | H |
| imidazolyl | OCF₂H | H | F | H | H | H |
| imidazolyl | OCF₂H | H | H | CH₃ | H | H |
| imidazolyl | OCF₂H | H | H | F | H | H |
| imidazolyl | OCF₂H | H | H | H | H | OCH₃ |
| imidazolyl | OCF₂H | H | H | H | OCF₂H | H |
| imidazolyl | OCF₂H | H | H | H | OCH₃ | H |
| imidazolyl | OCH₃ | H | H | F | H | H |
| imidazolyl | OCH₃ | H | H | CH₃ | H | H |
| imidazolyl | OCH₃ | H | H | F | H | H |
| imidazolyl | OCH₃ | H | H | H | H | H |
| imidazolyl | OCH₃ | H | H | H | H | OCH₃ |
| imidazolyl | OCH₃ | H | H | H | OCH₃ | H |
| oxazol-5-yl | CF₃ | H | H | CH₃ | H | H |
| oxazol-5-yl | CF₃ | H | H | F | H | H |
| oxazol-5-yl | CF₃ | H | H | H | H | OCH₃ |
| oxazol-5-yl | CF₃ | H | H | H | OCH₃ | H |
| oxazol-5-yl | CH₃ | H | F | H | H | H |
| oxazol-5-yl | CH₃ | H | H | CH₃ | H | H |
| oxazol-5-yl | CH₃ | H | H | F | H | H |
| oxazol-5-yl | CH₃ | H | H | H | H | OCH₃ |
| oxazol-5-yl | CH₃ | H | H | H | OCF₂H | H |
| oxazol-5-yl | CH₃ | H | H | H | OCH₃ | H |
| oxazol-5-yl | Cl | H | F | H | F | H |
| oxazol-5-yl | Cl | H | F | H | H | H |
| oxazol-5-yl | Cl | H | H | CH₃ | H | H |
| oxazol-5-yl | Cl | H | H | F | H | H |
| oxazol-5-yl | Cl | H | H | H | H | Cl |
| oxazol-5-yl | Cl | H | H | H | F | H |
| oxazol-5-yl | Cl | H | H | H | H | H |
| oxazol-5-yl | Cl | H | H | H | H | OCF₂H |
| oxazol-5-yl | Cl | H | H | H | H | OCH₃ |
| oxazol-5-yl | Cl | H | H | H | OCF₂H | H |
| oxazol-5-yl | Cl | H | H | H | OCH₃ | H |
| oxazol-5-yl | F | H | H | CH₃ | H | H |
| oxazol-5-yl | F | H | H | F | H | H |
| oxazol-5-yl | F | H | H | H | H | OCH₃ |
| oxazol-5-yl | F | H | H | H | OCF₂H | H |
| oxazol-5-yl | F | H | H | H | OCH₃ | H |
| oxazol-5-yl | H | CF₃ | H | CH₃ | H | H |
| oxazol-5-yl | H | CF₃ | H | F | H | H |
| oxazol-5-yl | H | CF₃ | H | H | H | OCH₃ |
| oxazol-5-yl | H | CF₃ | H | H | OCF₂H | H |
| oxazol-5-yl | H | CH₃ | H | CH₃ | H | H |
| oxazol-5-yl | H | CH₃ | H | F | H | H |
| oxazol-5-yl | H | CH₃ | H | H | H | OCH3 |
| oxazol-5-yl | H | CH₃ | H | H | OCF₂H | H |
| oxazol-5-yl | H | H | CH₃ | H | H | OCF₂H |
| oxazol-5-yl | H | OCF₂H | F | H | H | H |
| oxazol-5-yl | H | OCF₂H | H | H | H | OCH₃ |
| oxazol-5-yl | H | OCF₂H | H | H | OCF₂H | H |
| oxazol-5-yl | OCF₂H | H | F | H | H | H |
| oxazol-5-yl | OCF₂H | H | H | CH₃ | H | H |

TABLE 1-continued

| A | $R_1$ | $R_{12}$ | $R_2$ | $R_3$ | $R_4$ | $R_5$ |
|---|---|---|---|---|---|---|
| oxazol-5-yl | $OCF_2H$ | H | H | F | H | H |
| oxazol-5-yl | $OCF_2H$ | H | H | H | H | $OCH_3$ |
| oxazol-5-yl | $OCF_2H$ | H | H | H | $OCF_2H$ | H |
| oxazol-5-yl | $OCF_2H$ | H | H | H | $OCH_3$ | H |
| oxazol-5-yl | $OCH_3$ | H | F | H | H | H |
| oxazol-5-yl | $OCH_3$ | H | H | $CH_3$ | H | H |
| oxazol-5-yl | $OCH_3$ | H | H | F | H | H |
| oxazol-5-yl | $OCH_3$ | H | H | H | H | H |
| oxazol-5-yl | $OCH_3$ | H | H | H | H | $OCH_3$ |
| oxazol-5-yl | $OCH_3$ | H | H | H | $OCF_2H$ | H |
| oxazol-5-yl | $OCH_3$ | H | H | H | $OCH_3$ | H |
| pyridine-4-yl | $CF_3$ | H | H | $CH_3$ | H | H |
| pyridine-4-yl | $CF_3$ | H | H | F | H | H |
| pyridine-4-yl | $CF_3$ | H | H | H | H | $OCH_3$ |
| pyridine-4-yl | $CF_3$ | H | H | H | $OCF_2H$ | H |
| pyridine-4-yl | $CF_3$ | H | H | H | $OCH_3$ | H |
| pyridine-4-yl | $CH_3$ | H | F | H | H | H |
| pyridine-4-yl | $CH_3$ | H | H | $CH_3$ | H | H |
| pyridine-4-yl | $CH_3$ | H | H | F | H | H |
| pyridine-4-yl | $CH_3$ | H | H | H | H | $OCH_3$ |
| pyridine-4-yl | $CH_3$ | H | H | H | $OCF_2H$ | H |
| pyridine-4-yl | $CH_3$ | H | H | H | $OCH_3$ | H |
| pyridine-4-yl | Cl | H | F | H | H | H |
| pyridine-4-yl | Cl | H | H | $CH_3$ | H | H |
| pyridine-4-yl | Cl | H | H | F | H | H |
| pyridine-4-yl | Cl | H | H | H | H | H |
| pyridine-4-yl | Cl | H | H | H | H | $OCF_2H$ |
| pyridine-4-yl | Cl | H | H | H | H | $OCH_3$ |
| pyridine-4-yl | Cl | H | H | H | $OCF_2H$ | H |
| pyridine-4-yl | Cl | H | H | H | $OCH_3$ | H |
| pyridine-4-yl | F | H | H | $CH_3$ | H | H |
| pyridine-4-yl | F | H | H | F | H | H |
| pyridine-4-yl | F | H | H | H | H | $OCH_3$ |
| pyridine-4-yl | F | H | H | H | $OCF_2H$ | H |
| pyridine-4-yl | F | H | H | H | $OCH_3$ | H |
| pyridine-4-yl | H | $CF_3$ | H | $CH_3$ | H | H |
| pyridine-4-yl | H | $CF_3$ | H | F | H | H |
| pyridine-4-yl | H | $CF_3$ | H | H | H | $OCH_3$ |
| pyridine-4-yl | H | $CF_3$ | H | H | $OCF_2H$ | H |
| pyridine-4-yl | H | $CH_3$ | H | $CH_3$ | H | H |
| pyridine-4-yl | H | $CH_3$ | H | F | H | H |
| pyridine-4-yl | H | $CH_3$ | H | H | H | $OCH_3$ |
| pyridine-4-yl | H | $CH_3$ | H | H | $OCF_2H$ | H |
| pyridine-4-yl | H | $OCF_2H$ | H | $CH_3$ | H | H |
| pyridine-4-yl | H | $OCF_2H$ | H | F | H | H |
| pyridine-4-yl | H | $OCF_2H$ | H | H | H | $OCH_3$ |
| pyridine-4-yl | H | $OCF_2H$ | H | H | $OCF_2H$ | H |
| pyridine-4-yl | $OCF_2H$ | H | F | H | H | H |
| pyridine-4-yl | $OCF_2H$ | H | H | $CH_3$ | H | H |
| pyridine-4-yl | $OCF_2H$ | H | H | F | H | H |
| pyridine-4-yl | $OCF_2H$ | H | H | H | H | $OCH_3$ |
| pyridine-4-yl | $OCF_2H$ | H | H | H | $OCF_2H$ | H |
| pyridine-4-yl | $OCF_2H$ | H | H | H | $OCH_3$ | H |
| pyridine-4-yl | $OCH_3$ | H | F | H | H | H |
| pyridine-4-yl | $OCH_3$ | H | H | $CH_3$ | H | H |
| pyridine-4-yl | $OCH_3$ | H | H | F | H | H |
| pyridine-4-yl | $OCH_3$ | H | H | H | H | H |
| pyridine-4-yl | $OCH_3$ | H | H | H | H | $OCH_3$ |
| pyridine-4-yl | $OCH_3$ | H | H | H | $OCF_2H$ | H |
| pyridine-4-yl | $OCH_3$ | H | H | H | $OCH_3$ | H |

Preferably, the compound of formula (Ib)

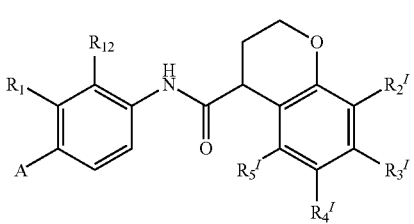

(Ib)

is selected from the group consisting of compounds of the formula (I), wherein A, $R_1$, $R_{12}$, $R_2^I$, $R_3^I$, $R_4^I$ and $R_5^I$ are as indicated in Table 2:

TABLE 2

| A | $R_1$ | $R_{12}$ | $R_2^I$ | $R_3^I$ | $R_4^I$ | $R_5^I$ |
|---|---|---|---|---|---|---|
| 1,2,4-triazol-1-yl | $CF_3$ | H | H | $CH_3$ | H | H |
| 1,2,4-triazol-1-yl | $CF_3$ | H | H | F | H | H |
| 1,2,4-triazol-1-yl | $CF_3$ | H | H | H | H | $OCH_3$ |
| 1,2,4-triazol-1-yl | $CF_3$ | H | H | H | $OCF_2H$ | H |
| 1,2,4-triazol-1-yl | $CF_3$ | H | H | H | $OCH_3$ | H |
| 1,2,4-triazol-1-yl | $CH_3$ | H | F | H | H | H |
| 1,2,4-triazol-1-yl | $CH_3$ | H | H | $CH_3$ | H | H |
| 1,2,4-triazol-1-yl | $CH_3$ | H | H | F | H | H |
| 1,2,4-triazol-1-yl | $CH_3$ | H | H | H | H | $OCH_3$ |
| 1,2,4-triazol-1-yl | $CH_3$ | H | H | H | $OCF_2H$ | H |
| 1,2,4-triazol-1-yl | $CH_3$ | H | H | H | $OCH_3$ | H |
| 1,2,4-triazol-1-yl | Cl | H | F | H | H | H |
| 1,2,4-triazol-1-yl | Cl | H | H | $CH_3$ | H | H |
| 1,2,4-triazol-1-yl | Cl | H | H | F | H | H |
| 1,2,4-triazol-1-yl | Cl | H | H | H | H | H |
| 1,2,4-triazol-1-yl | Cl | H | H | H | H | $OCF_2H$ |
| 1,2,4-triazol-1-yl | Cl | H | H | H | H | $OCH_3$ |
| 1,2,4-triazol-1-yl | Cl | H | H | H | $OCF_2H$ | H |
| 1,2,4-triazol-1-yl | Cl | H | H | H | $OCH_3$ | H |
| 1,2,4-triazol-1-yl | F | H | H | $CH_3$ | H | H |
| 1,2,4-triazol-1-yl | F | H | H | F | H | H |
| 1,2,4-triazol-1-yl | F | H | H | H | H | $OCH_3$ |
| 1,2,4-triazol-1-yl | F | H | H | H | $OCF_2H$ | H |
| 1,2,4-triazol-1-yl | F | H | H | H | $OCH_3$ | H |
| 1,2,4-triazol-1-yl | H | $CF_3$ | H | $CH_3$ | H | H |
| 1,2,4-triazol-1-yl | H | $CF_3$ | H | F | H | H |
| 1,2,4-triazol-1-yl | H | $CF_3$ | H | H | H | $OCH_3$ |
| 1,2,4-triazol-1-yl | H | $CF_3$ | H | H | $OCF_2H$ | H |
| 1,2,4-triazol-1-yl | H | $CH_3$ | H | $CH_3$ | H | H |
| 1,2,4-triazol-1-yl | H | $CH_3$ | H | F | H | H |
| 1,2,4-triazol-1-yl | H | $CH_3$ | H | H | H | $OCH_3$ |
| 1,2,4-triazol-1-yl | H | $CH_3$ | H | H | $OCF_2H$ | H |
| 1,2,4-triazol-1-yl | H | $OCF_2H$ | H | $CH_3$ | H | H |
| 1,2,4-triazol-1-yl | H | $OCF_2H$ | H | F | H | H |
| 1,2,4-triazol-1-yl | H | $OCF_2H$ | H | H | H | $OCH_3$ |
| 1,2,4-triazol-1-yl | H | $OCF_2H$ | H | H | $OCF_2H$ | H |
| 1,2,4-triazol-1-yl | $OCF_2H$ | H | F | H | H | H |
| 1,2,4-triazol-1-yl | $OCF_2H$ | H | H | $CH_3$ | H | H |
| 1,2,4-triazol-1-yl | $OCF_2H$ | H | H | F | H | H |
| 1,2,4-triazol-1-yl | $OCF_2H$ | H | H | H | H | $OCH_3$ |
| 1,2,4-triazol-1-yl | $OCF_2H$ | H | H | H | $OCF_2H$ | H |
| 1,2,4-triazol-1-yl | $OCF_2H$ | H | H | H | $OCH_3$ | H |
| 1,2,4-triazol-1-yl | $OCH_3$ | H | F | H | H | H |
| 1,2,4-triazol-1-yl | $OCH_3$ | H | H | $CH_3$ | H | H |
| 1,2,4-triazol-1-yl | $OCH_3$ | H | H | F | H | H |
| 1,2,4-triazol-1-yl | $OCH_3$ | H | H | H | H | H |
| 1,2,4-triazol-1-yl | $OCH_3$ | H | H | H | H | $OCH_3$ |
| 1,2,4-triazol-1-yl | $OCH_3$ | H | H | H | $OCF_2H$ | H |
| 1,2,4-triazol-1-yl | $OCH_3$ | H | H | H | $OCH_3$ | H |
| 1,3,4-oxadiazol-2-yl | $CF_3$ | H | H | $CH_3$ | H | H |
| 1,3,4-oxadiazol-2-yl | $CF_3$ | H | H | F | H | H |
| 1,3,4-oxadiazol-2-yl | $CF_3$ | H | H | H | H | $OCH_3$ |
| 1,3,4-oxadiazol-2-yl | $CF_3$ | H | H | H | $OCF_2H$ | H |
| 1,3,4-oxadiazol-2-yl | $CF_3$ | H | H | H | $OCH_3$ | H |
| 1,3,4-oxadiazol-2-yl | $CH_3$ | H | F | H | H | H |
| 1,3,4-oxadiazol-2-yl | $CH_3$ | H | H | $CH_3$ | H | H |
| 1,3,4-oxadiazol-2-yl | $CH_3$ | H | H | F | H | H |
| 1,3,4-oxadiazol-2-yl | $CH_3$ | H | H | H | H | $OCH_3$ |
| 1,3,4-oxadiazol-2-yl | $CH_3$ | H | H | H | $OCF_2H$ | H |
| 1,3,4-oxadiazol-2-yl | $CH_3$ | H | H | H | $OCH_3$ | H |
| 1,3,4-oxadiazol-2-yl | Cl | H | F | H | H | H |
| 1,3,4-oxadiazol-2-yl | Cl | H | H | $CH_3$ | H | H |
| 1,3,4-oxadiazol-2-yl | Cl | H | H | F | H | H |
| 1,3,4-oxadiazol-2-yl | Cl | H | H | H | H | H |
| 1,3,4-oxadiazol-2-yl | Cl | H | H | H | H | $OCF_2H$ |
| 1,3,4-oxadiazol-2-yl | Cl | H | H | H | H | $OCH_3$ |
| 1,3,4-oxadiazol-2-yl | Cl | H | H | H | $OCF_2H$ | H |
| 1,3,4-oxadiazol-2-yl | Cl | H | H | H | $OCH_3$ | H |
| 1,3,4-oxadiazol-2-yl | F | H | H | $CH_3$ | H | H |
| 1,3,4-oxadiazol-2-yl | F | H | H | F | H | H |
| 1,3,4-oxadiazol-2-yl | F | H | H | H | H | $OCH_3$ |
| 1,3,4-oxadiazol-2-yl | F | H | H | H | $OCF_2H$ | H |
| 1,3,4-oxadiazol-2-yl | F | H | H | H | $OCH_3$ | H |

TABLE 2-continued

| A | $R_1$ | $R_{12}$ | $R_2^I$ | $R_3^I$ | $R_4^I$ | $R_5^I$ |
|---|---|---|---|---|---|---|
| 1,3,4-oxadiazol-2-yl | H | $CF_3$ | H | $CH_3$ | H | H |
| 1,3,4-oxadiazol-2-yl | H | $CF_3$ | H | F | H | H |
| 1,3,4-oxadiazol-2-yl | H | $CF_3$ | H | H | H | $OCH_3$ |
| 1,3,4-oxadiazol-2-yl | H | $CF_3$ | H | H | $OCF_2H$ | H |
| 1,3,4-oxadiazol-2-yl | H | $CH_3$ | H | $CH_3$ | H | H |
| 1,3,4-oxadiazol-2-yl | H | $CH_3$ | H | F | H | H |
| 1,3,4-oxadiazol-2-yl | H | $CH_3$ | H | H | H | $OCH_3$ |
| 1,3,4-oxadiazol-2-yl | H | $CH_3$ | H | H | $OCF_2H$ | H |
| 1,3,4-oxadiazol-2-yl | H | $OCF_2H$ | H | $CH_3$ | H | H |
| 1,3,4-oxadiazol-2-yl | H | $OCF_2H$ | H | F | H | H |
| 1,3,4-oxadiazol-2-yl | H | $OCF_2H$ | H | H | H | $OCH_3$ |
| 1,3,4-oxadiazol-2-yl | H | $OCF_2H$ | H | H | $OCF_2H$ | H |
| 1,3,4-oxadiazol-2-yl | $OCF_2H$ | H | F | H | H | H |
| 1,3,4-oxadiazol-2-yl | $OCF_2H$ | H | H | $CH_3$ | H | H |
| 1,3,4-oxadiazol-2-yl | $OCF_2H$ | H | H | F | H | H |
| 1,3,4-oxadiazol-2-yl | $OCF_2H$ | H | H | H | H | $OCH_3$ |
| 1,3,4-oxadiazol-2-yl | $OCF_2H$ | H | H | H | $OCF_2H$ | H |
| 1,3,4-oxadiazol-2-yl | $OCF_2H$ | H | H | H | $OCH_3$ | H |
| 1,3,4-oxadiazol-2-yl | $OCH_3$ | H | F | H | H | H |
| 1,3,4-oxadiazol-2-yl | $OCH_3$ | H | H | $CH_3$ | H | H |
| 1,3,4-oxadiazol-2-yl | $OCH_3$ | H | H | F | H | H |
| 1,3,4-oxadiazol-2-yl | $OCH_3$ | H | H | H | H | $OCH_3$ |
| 1,3,4-oxadiazol-2-yl | $OCH_3$ | H | H | H | $OCF_2H$ | H |
| 1,3,4-oxadiazol-2-yl | $OCH_3$ | H | H | H | $OCH_3$ | H |
| 2-methyloxazol-5-yl | $CF_3$ | H | H | F | H | H |
| 2-methyloxazol-5-yl | $CF_3$ | H | H | H | H | $OCH_3$ |
| 2-methyloxazol-5-yl | $CF_3$ | H | H | H | $OCH_3$ | H |
| 2-methyloxazol-5-yl | $CH_3$ | H | H | F | H | H |
| 2-methyloxazol-5-yl | $CH_3$ | H | H | H | H | $OCH_3$ |
| 2-methyloxazol-5-yl | $CH_3$ | H | H | H | $OCH_3$ | H |
| 2-methyloxazol-5-yl | Cl | H | H | F | H | H |
| 2-methyloxazol-5-yl | Cl | H | H | H | H | H |
| 2-methyloxazol-5-yl | Cl | H | H | H | H | $OCH_3$ |
| 2-methyloxazol-5-yl | Cl | H | H | H | $OCH_3$ | H |
| 2-methyloxazol-5-yl | H | $CF_3$ | H | F | H | H |
| 2-methyloxazol-5-yl | H | $CF_3$ | H | H | H | $OCH_3$ |
| 2-methyloxazol-5-yl | H | $CF_3$ | H | H | $OCF_2H$ | H |
| 2-methyloxazol-5-yl | H | $CH_3$ | H | F | H | H |
| 2-methyloxazol-5-yl | H | $CH_3$ | H | H | H | $OCH_3$ |
| 2-methyloxazol-5-yl | H | $CH_3$ | H | H | $OCF_2H$ | H |
| 2-methyloxazol-5-yl | H | $OCF_2H$ | H | F | H | H |
| 2-methyloxazol-5-yl | H | $OCF_2H$ | H | H | H | $OCH_3$ |
| 2-methyloxazol-5-yl | H | $OCF_2H$ | H | H | $OCF_2H$ | H |
| 2-methyloxazol-5-yl | $OCF_2H$ | H | H | F | H | H |
| 2-methyloxazol-5-yl | $OCF_2H$ | H | H | H | H | $OCH_3$ |
| 2-methyloxazol-5-yl | $OCF_2H$ | H | H | H | $OCH_3$ | H |
| 2-methyloxazol-5-yl | $OCH_3$ | H | H | F | H | H |
| 2-methyloxazol-5-yl | $OCH_3$ | H | H | H | H | H |
| 2-methyloxazol-5-yl | $OCH_3$ | H | H | H | H | $OCH_3$ |
| 2-methyloxazol-5-yl | $OCH_3$ | H | H | H | $OCH_3$ | H |
| imidazolyl | $CF_3$ | H | H | $CH_3$ | H | H |
| imidazolyl | $CF_3$ | H | H | F | H | H |
| imidazolyl | $CF_3$ | H | H | H | H | $OCH_3$ |
| imidazolyl | $CF_3$ | H | H | H | $OCF_2H$ | H |
| imidazolyl | $CF_3$ | H | H | H | $OCH_3$ | H |
| imidazolyl | $CH_3$ | H | H | F | H | H |
| imidazolyl | $CH_3$ | H | H | H | H | $OCH3$ |
| imidazolyl | $CH_3$ | H | H | H | $OCF_2H$ | H |
| imidazolyl | $CH_3$ | H | H | H | $OCH_3$ | H |
| imidazolyl | Cl | H | F | H | H | H |
| imidazolyl | Cl | H | H | $CH_3$ | H | H |
| imidazolyl | Cl | H | H | F | H | H |
| imidazolyl | Cl | H | H | H | H | H |
| imidazolyl | Cl | H | H | H | H | $OCF_2H$ |
| imidazolyl | Cl | H | H | H | H | $OCH_3$ |
| imidazolyl | Cl | H | H | H | $OCF_2H$ | H |
| imidazolyl | Cl | H | H | H | $OCH_3$ | H |
| imidazolyl | F | H | H | $CH_3$ | H | H |
| imidazolyl | F | H | H | F | H | H |
| imidazolyl | F | H | H | H | H | $OCH_3$ |
| imidazolyl | F | H | H | H | $OCF_2H$ | H |
| imidazolyl | F | H | H | H | $OCH_3$ | H |
| imidazolyl | H | $CF_3$ | H | $CH_3$ | H | H |
| imidazolyl | H | $CF_3$ | H | F | H | H |
| imidazolyl | H | $CF_3$ | H | H | H | $OCH_3$ |
| imidazolyl | H | $CF_3$ | H | H | $OCF_2H$ | H |
| imidazolyl | H | $CH_3$ | H | $CH_3$ | H | H |
| imidazolyl | H | $CH_3$ | H | F | H | H |
| imidazolyl | H | $CH_3$ | H | H | H | $OCH_3$ |
| imidazolyl | H | $CH_3$ | H | H | $OCF_2H$ | H |
| imidazolyl | H | $OCF_2H$ | H | $CH_3$ | H | H |
| imidazolyl | H | $OCF_2H$ | H | F | H | H |
| imidazolyl | H | $OCF_2H$ | H | H | H | $OCH_3$ |
| imidazolyl | H | $OCF_2H$ | H | H | $OCF_2H$ | H |
| imidazolyl | $OCF_2H$ | H | F | H | H | H |
| imidazolyl | $OCF_2H$ | H | H | $CH_3$ | H | H |
| imidazolyl | $OCF_2H$ | H | H | F | H | H |
| imidazolyl | $OCF_2H$ | H | H | H | H | $OCH_3$ |
| imidazolyl | $OCF_2H$ | H | H | H | $OCF_2H$ | H |
| imidazolyl | $OCF_2H$ | H | H | H | $OCH_3$ | H |
| imidazolyl | $OCH_3$ | H | F | H | H | H |
| imidazolyl | $OCH_3$ | H | H | $CH_3$ | H | H |
| imidazolyl | $OCH_3$ | H | H | F | H | H |
| imidazolyl | $OCH_3$ | H | H | H | H | H |
| imidazolyl | $OCH_3$ | H | H | H | H | $OCH_3$ |
| imidazolyl | $OCH_3$ | H | H | H | $OCF_2H$ | H |
| imidazolyl | $OCH_3$ | H | H | H | $OCH_3$ | H |
| oxazol-5-yl | $CF_3$ | H | H | $CH_3$ | H | H |
| oxazol-5-yl | $CF_3$ | H | H | F | H | H |
| oxazol-5-yl | $CF_3$ | H | H | H | H | $OCH_3$ |
| oxazol-5-yl | $CF_3$ | H | H | H | $OCF_2H$ | H |
| oxazol-5-yl | $CF_3$ | H | H | H | $OCH_3$ | H |
| oxazol-5-yl | $CH_3$ | H | F | H | H | H |
| oxazol-5-yl | $CH_3$ | H | H | $CH_3$ | H | H |
| oxazol-5-yl | $CH_3$ | H | H | F | H | H |
| oxazol-5-yl | $CH_3$ | H | H | H | H | $OCH_3$ |
| oxazol-5-yl | $CH_3$ | H | H | H | $OCF_2H$ | H |
| oxazol-5-yl | $CH_3$ | H | H | H | $OCH_3$ | H |
| oxazol-5-yl | Cl | H | F | H | F | H |
| oxazol-5-yl | Cl | H | F | H | H | H |
| oxazol-5-yl | Cl | H | H | $CH_3$ | H | H |
| oxazol-5-yl | Cl | H | H | F | H | H |
| oxazol-5-yl | Cl | H | H | H | Cl | H |
| oxazol-5-yl | Cl | H | H | H | F | H |
| oxazol-5-yl | Cl | H | H | H | H | H |
| oxazol-5-yl | Cl | H | H | H | H | $OCF_2H$ |
| oxazol-5-yl | Cl | H | H | H | H | $OCH_3$ |
| oxazol-5-yl | Cl | H | H | H | $OCF_2H$ | H |
| oxazol-5-yl | Cl | H | H | H | $OCH_3$ | H |
| oxazol-5-yl | F | H | H | $CH_3$ | H | H |
| oxazol-5-yl | F | H | H | F | H | H |
| oxazol-5-yl | F | H | H | H | H | $OCH_3$ |
| oxazol-5-yl | F | H | H | H | $OCF_2H$ | H |
| oxazol-5-yl | F | H | H | H | $OCH_3$ | H |
| oxazol-5-yl | H | $CF_3$ | H | $CH_3$ | H | H |
| oxazol-5-yl | H | $CF_3$ | H | F | H | H |
| oxazol-5-yl | H | $CF_3$ | H | H | H | $OCH_3$ |
| oxazol-5-yl | H | $CF_3$ | H | H | $OCF_2H$ | H |
| oxazol-5-yl | H | $CH_3$ | H | $CH_3$ | H | H |
| oxazol-5-yl | H | $CH_3$ | H | F | H | H |
| oxazol-5-yl | H | $CH_3$ | H | H | H | $OCH_3$ |
| oxazol-5-yl | H | $CH_3$ | H | H | $OCF_2H$ | H |
| oxazol-5-yl | H | $OCF_2H$ | H | $CH_3$ | H | H |
| oxazol-5-yl | H | $OCF_2H$ | H | F | H | H |
| oxazol-5-yl | H | $OCF_2H$ | H | H | H | $OCH_3$ |
| oxazol-5-yl | H | $OCF_2H$ | H | H | $OCF_2H$ | H |
| oxazol-5-yl | $OCF_2H$ | H | F | H | H | H |
| oxazol-5-yl | $OCF_2H$ | H | H | $CH_3$ | H | H |
| oxazol-5-yl | $OCF_2H$ | H | H | F | H | H |
| oxazol-5-yl | $OCF_2H$ | H | H | H | H | $OCH_3$ |
| oxazol-5-yl | $OCF_2H$ | H | H | H | $OCF_2H$ | H |
| oxazol-5-yl | $OCF_2H$ | H | H | H | $OCH_3$ | H |
| oxazol-5-yl | $OCH_3$ | H | F | H | H | H |
| oxazol-5-yl | $OCH_3$ | H | H | $CH_3$ | H | H |
| oxazol-5-yl | $OCH_3$ | H | H | F | H | H |
| oxazol-5-yl | $OCH_3$ | H | H | H | H | H |
| oxazol-5-yl | $OCH_3$ | H | H | H | H | $OCH_3$ |
| oxazol-5-yl | $OCH_3$ | H | H | H | $OCF_2H$ | H |
| oxazol-5-yl | $OCH_3$ | H | H | H | $OCH_3$ | H |
| pyridine-4-yl | $CF_3$ | H | H | $CH_3$ | H | H |
| pyridine-4-yl | $CF_3$ | H | H | F | H | H |
| pyridine-4-yl | $CF_3$ | H | H | H | H | $OCH_3$ |
| pyridine-4-yl | $CF_3$ | H | H | H | $OCF_2H$ | H |
| pyridine-4-yl | $CF_3$ | H | H | H | $OCH_3$ | H |
| pyridine-4-yl | $CH_3$ | H | F | H | H | H |

TABLE 2-continued

| A | $R_1$ | $R_{12}$ | $R_2^I$ | $R_3^I$ | $R_4^I$ | $R_5^I$ |
|---|---|---|---|---|---|---|
| pyridine-4-yl | $CH_3$ | H | H | $CH_3$ | H | H |
| pyridine-4-yl | $CH_3$ | H | H | F | H | H |
| pyridine-4-yl | $CH_3$ | H | H | H | H | $OCH_3$ |
| pyridine-4-yl | $CH_3$ | H | H | H | $OCF_2H$ | H |
| pyridine-4-yl | $CH_3$ | H | H | H | $OCH_3$ | H |
| pyridine-4-yl | Cl | H | F | H | H | H |
| pyridine-4-yl | Cl | H | H | $CH_3$ | H | H |
| pyridine-4-yl | Cl | H | H | F | H | H |
| pyridine-4-yl | Cl | H | H | H | H | H |
| pyridine-4-yl | Cl | H | H | H | H | $OCF_2H$ |
| pyridine-4-yl | Cl | H | H | H | H | $OCH_3$ |
| pyridine-4-yl | Cl | H | H | H | $OCF_2H$ | H |
| pyridine-4-yl | Cl | H | H | H | $OCH_3$ | H |
| pyridine-4-yl | F | H | H | $CH_3$ | H | H |
| pyridine-4-yl | F | H | H | F | H | H |
| pyridine-4-yl | F | H | H | H | H | $OCH_3$ |
| pyridine-4-yl | F | H | H | H | $OCF_2H$ | H |
| pyridine-4-yl | F | H | H | H | $OCH_3$ | H |
| pyridine-4-yl | H | $CF_3$ | H | $CH_3$ | H | H |
| pyridine-4-yl | H | $CF_3$ | H | F | H | H |
| pyridine-4-yl | H | $CF_3$ | H | H | H | $OCH_3$ |
| pyridine-4-yl | H | $CF_3$ | H | H | $OCF_2H$ | H |
| pyridine-4-yl | H | $CH_3$ | H | $CH_3$ | H | H |
| pyridine-4-yl | H | $CH_3$ | H | F | H | H |
| pyridine-4-yl | H | $CH_3$ | H | H | H | $OCH_3$ |
| pyridine-4-yl | H | $CH_3$ | H | H | $OCF_2H$ | H |
| pyridine-4-yl | H | $OCF_2H$ | H | $CH_3$ | H | H |
| pyridine-4-yl | H | $OCF_2H$ | H | F | H | H |
| pyridine-4-yl | H | $OCF_2H$ | H | H | H | $OCH_3$ |
| pyridine-4-yl | H | $OCF_2H$ | H | H | $OCF_2H$ | H |
| pyridine-4-yl | $OCF_2H$ | H | F | H | H | H |
| pyridine-4-yl | $OCF_2H$ | H | H | $CH_3$ | H | H |
| pyridine-4-yl | $OCF_2H$ | H | H | F | H | H |
| pyridine-4-yl | $OCF_2H$ | H | H | H | H | $OCH_3$ |
| pyridine-4-yl | $OCF_2H$ | H | H | H | $OCF_2H$ | H |
| pyridine-4-yl | $OCF_2H$ | H | H | H | $OCH_3$ | H |
| pyridine-4-yl | $OCH_3$ | H | F | H | H | H |
| pyridine-4-yl | $OCH_3$ | H | H | $CH_3$ | H | H |
| pyridine-4-yl | $OCH_3$ | H | H | F | H | H |
| pyridine-4-yl | $OCH_3$ | H | H | H | H | H |
| pyridine-4-yl | $OCH_3$ | H | H | H | H | $OCH_3$ |
| pyridine-4-yl | $OCH_3$ | H | H | H | $OCF_2H$ | H |
| pyridine-4-yl | $OCH_3$ | H | H | H | $OCH_3$ | H |

Preferably, the compound of formula (Ic)

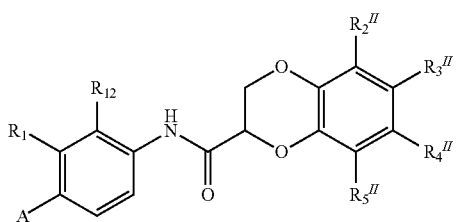

is selected from the group consisting of compounds of the formula (I), wherein A, $R_1$, $R_{12}$, $R_2^{II}$, $R_3^{II}$, $R_4^{II}$ and $R_5^{II}$ are as indicated in Table 3:

TABLE 3

| A | $R_1$ | $R_{12}$ | $R_2^{II}$ | $R_3^{II}$ | $R_4^{II}$ | $R_5^{II}$ |
|---|---|---|---|---|---|---|
| 1,2,4-triazol-1-yl | $CF_3$ | H | H | $CH_3$ | H | H |
| 1,2,4-triazol-1-yl | $CF_3$ | H | H | F | H | H |
| 1,2,4-triazol-1-yl | $CF_3$ | H | H | H | H | $OCH_3$ |
| 1,2,4-triazol-1-yl | $CF_3$ | H | H | H | $OCF_2H$ | H |
| 1,2,4-triazol-1-yl | $CF_3$ | H | H | H | $OCH_3$ | H |
| 1,2,4-triazol-1-yl | $CH_3$ | H | F | H | H | H |
| 1,2,4-triazol-1-yl | $CH_3$ | H | H | $CH_3$ | H | H |
| 1,2,4-triazol-1-yl | $CH_3$ | H | H | F | H | H |
| 1,2,4-triazol-1-yl | $CH_3$ | H | H | H | H | $OCH_3$ |
| 1,2,4-triazol-1-yl | $CH_3$ | H | H | H | $OCF_2H$ | H |
| 1,2,4-triazol-1-yl | $CH_3$ | H | H | H | $OCH_3$ | H |
| 1,2,4-triazol-1-yl | Cl | H | F | H | H | H |
| 1,2,4-triazol-1-yl | Cl | H | H | $CH_3$ | H | H |
| 1,2,4-triazol-1-yl | Cl | H | H | F | H | H |
| 1,2,4-triazol-1-yl | Cl | H | H | H | H | H |
| 1,2,4-triazol-1-yl | Cl | H | H | H | H | $OCF_2H$ |
| 1,2,4-triazol-1-yl | Cl | H | H | H | H | $OCH_3$ |
| 1,2,4-triazol-1-yl | Cl | H | H | H | $OCF_2H$ | H |
| 1,2,4-triazol-1-yl | Cl | H | H | H | $OCH_3$ | H |
| 1,2,4-triazol-1-yl | F | H | H | $CH_3$ | H | H |
| 1,2,4-triazol-1-yl | F | H | H | F | H | H |
| 1,2,4-triazol-1-yl | F | H | H | H | H | $OCH_3$ |
| 1,2,4-triazol-1-yl | F | H | H | H | $OCF_2H$ | H |
| 1,2,4-triazol-1-yl | F | H | H | H | $OCH_3$ | H |
| 1,2,4-triazol-1-yl | H | $CF_3$ | H | $CH_3$ | H | H |
| 1,2,4-triazol-1-yl | H | $CF_3$ | H | F | H | H |
| 1,2,4-triazol-1-yl | H | $CF_3$ | H | H | H | $OCH_3$ |
| 1,2,4-triazol-1-yl | H | $CF_3$ | H | H | $OCF_2H$ | H |
| 1,2,4-triazol-1-yl | H | $CH_3$ | H | $CH_3$ | H | H |
| 1,2,4-triazol-1-yl | H | $CH_3$ | H | F | H | H |
| 1,2,4-triazol-1-yl | H | $CH_3$ | H | H | H | $OCH_3$ |
| 1,2,4-triazol-1-yl | H | $CH_3$ | H | H | $OCF_2H$ | H |
| 1,2,4-triazol-1-yl | H | $OCF_2H$ | H | $CH_3$ | H | H |
| 1,2,4-triazol-1-yl | H | $OCF_2H$ | H | F | H | H |
| 1,2,4-triazol-1-yl | H | $OCF_2H$ | H | H | H | $OCH_3$ |
| 1,2,4-triazol-1-yl | H | $OCF_2H$ | H | H | $OCF_2H$ | H |
| 1,2,4-triazol-1-yl | $OCF_2H$ | H | F | H | H | H |
| 1,2,4-triazol-1-yl | $OCF_2H$ | H | H | $CH_3$ | H | H |
| 1,2,4-triazol-1-yl | $OCF_2H$ | H | H | F | H | H |
| 1,2,4-triazol-1-yl | $OCF_2H$ | H | H | H | H | $OCH_3$ |
| 1,2,4-triazol-1-yl | $OCF_2H$ | H | H | H | $OCF_2H$ | H |
| 1,2,4-triazol-1-yl | $OCF_2H$ | H | H | H | $OCH_3$ | H |
| 1,2,4-triazol-1-yl | $OCH_3$ | H | F | H | H | H |
| 1,2,4-triazol-1-yl | $OCH_3$ | H | H | $CH_3$ | H | H |
| 1,2,4-triazol-1-yl | $OCH_3$ | H | H | F | H | H |
| 1,2,4-triazol-1-yl | $OCH_3$ | H | H | H | H | H |
| 1,2,4-triazol-1-yl | $OCH_3$ | H | H | H | H | $OCH_3$ |
| 1,2,4-triazol-1-yl | $OCH_3$ | H | H | H | $OCF_2H$ | H |
| 1,2,4-triazol-1-yl | $OCH_3$ | H | H | H | $OCH_3$ | H |
| 1,3,4-oxadiazol-2-yl | $CF_3$ | H | H | $CH_3$ | H | H |
| 1,3,4-oxadiazol-2-yl | $CF_3$ | H | H | F | H | H |
| 1,3,4-oxadiazol-2-yl | $CF_3$ | H | H | H | H | $OCH_3$ |
| 1,3,4-oxadiazol-2-yl | $CF_3$ | H | H | H | $OCF_2H$ | H |
| 1,3,4-oxadiazol-2-yl | $CF_3$ | H | H | H | $OCH_3$ | H |
| 1,3,4-oxadiazol-2-yl | $CH_3$ | H | F | H | H | H |
| 1,3,4-oxadiazol-2-yl | $CH_3$ | H | H | $CH_3$ | H | H |
| 1,3,4-oxadiazol-2-yl | $CH_3$ | H | H | F | H | H |
| 1,3,4-oxadiazol-2-yl | $CH_3$ | H | H | H | H | $OCH_3$ |
| 1,3,4-oxadiazol-2-yl | $CH_3$ | H | H | H | $OCF_2H$ | H |
| 1,3,4-oxadiazol-2-yl | $CH_3$ | H | H | H | $OCH_3$ | H |
| 1,3,4-oxadiazol-2-yl | Cl | H | F | H | H | H |
| 1,3,4-oxadiazol-2-yl | Cl | H | H | $CH_3$ | H | H |
| 1,3,4-oxadiazol-2-yl | Cl | H | H | F | H | H |
| 1,3,4-oxadiazol-2-yl | Cl | H | H | H | H | H |
| 1,3,4-oxadiazol-2-yl | Cl | H | H | H | H | $OCF_2H$ |
| 1,3,4-oxadiazol-2-yl | Cl | H | H | H | H | $OCH_3$ |
| 1,3,4-oxadiazol-2-yl | Cl | H | H | H | $OCF_2H$ | H |
| 1,3,4-oxadiazol-2-yl | Cl | H | H | H | $OCH_3$ | H |
| 1,3,4-oxadiazol-2-yl | F | H | H | $CH_3$ | H | H |
| 1,3,4-oxadiazol-2-yl | F | H | H | F | H | H |
| 1,3,4-oxadiazol-2-yl | F | H | H | H | H | $OCH_3$ |
| 1,3,4-oxadiazol-2-yl | F | H | H | H | $OCF_2H$ | H |
| 1,3,4-oxadiazol-2-yl | F | H | H | H | $OCH_3$ | H |
| 1,3,4-oxadiazol-2-yl | H | $CF_3$ | H | $CH_3$ | H | H |
| 1,3,4-oxadiazol-2-yl | H | $CF_3$ | H | F | H | H |
| 1,3,4-oxadiazol-2-yl | H | $CF_3$ | H | H | H | $OCH_3$ |
| 1,3,4-oxadiazol-2-yl | H | $CF_3$ | H | H | $OCF_2H$ | H |
| 1,3,4-oxadiazol-2-yl | H | $CH_3$ | H | $CH_3$ | H | H |
| 1,3,4-oxadiazol-2-yl | H | $CH_3$ | H | F | H | H |
| 1,3,4-oxadiazol-2-yl | H | $CH_3$ | H | H | H | $OCH_3$ |
| 1,3,4-oxadiazol-2-yl | H | $CH_3$ | H | H | $OCF_2H$ | H |
| 1,3,4-oxadiazol-2-yl | H | $OCF_2H$ | H | $CH_3$ | H | H |
| 1,3,4-oxadiazol-2-yl | H | $OCF_2H$ | H | F | H | H |
| 1,3,4-oxadiazol-2-yl | H | $OCF_2H$ | H | H | H | $OCH_3$ |
| 1,3,4-oxadiazol-2-yl | H | $OCF_2H$ | H | H | $OCF_2H$ | H |

TABLE 3-continued

| A | $R_1$ | $R_{12}$ | $R_2^{II}$ | $R_3^{II}$ | $R_4^{II}$ | $R_5^{II}$ |
|---|---|---|---|---|---|---|
| 1,3,4-oxadiazol-2-yl | $OCF_2H$ | H | F | H | H | H |
| 1,3,4-oxadiazol-2-yl | $OCF_2H$ | H | H | $CH_3$ | H | H |
| 1,3,4-oxadiazol-2-yl | $OCF_2H$ | H | H | F | H | H |
| 1,3,4-oxadiazol-2-yl | $OCF_2H$ | H | H | H | H | $OCH_3$ |
| 1,3,4-oxadiazol-2-yl | $OCF_2H$ | H | H | H | $OCF_2H$ | H |
| 1,3,4-oxadiazol-2-yl | $OCF_2H$ | H | H | H | $OCH_3$ | H |
| 1,3,4-oxadiazol-2-yl | $OCH_3$ | H | F | H | H | H |
| 1,3,4-oxadiazol-2-yl | $OCH_3$ | H | H | $CH_3$ | H | H |
| 1,3,4-oxadiazol-2-yl | $OCH_3$ | H | H | F | H | H |
| 1,3,4-oxadiazol-2-yl | $OCH_3$ | H | H | H | H | H |
| 1,3,4-oxadiazol-2-yl | $OCH_3$ | H | H | H | H | $OCH_3$ |
| 1,3,4-oxadiazol-2-yl | $OCH_3$ | H | H | H | $OCF_2H$ | H |
| 1,3,4-oxadiazol-2-yl | $OCH_3$ | H | H | H | $OCH_3$ | H |
| 2-methyloxazol-5-yl | $CF_3$ | H | H | F | H | H |
| 2-methyloxazol-5-yl | $CF_3$ | H | H | H | H | $OCH_3$ |
| 2-methyloxazol-5-yl | $CF_3$ | H | H | H | $OCH_3$ | H |
| 2-methyloxazol-5-yl | $CH_3$ | H | H | F | H | H |
| 2-methyloxazol-5-yl | $CH_3$ | H | H | H | H | $OCH_3$ |
| 2-methyloxazol-5-yl | $CH_3$ | H | H | H | $OCH_3$ | H |
| 2-methyloxazol-5-yl | Cl | H | H | F | H | H |
| 2-methyloxazol-5-yl | Cl | H | H | H | H | H |
| 2-methyloxazol-5-yl | Cl | H | H | H | H | $OCH_3$ |
| 2-methyloxazol-5-yl | Cl | H | H | H | $OCH_3$ | H |
| 2-methyloxazol-5-yl | H | $CF_3$ | H | F | H | H |
| 2-methyloxazol-5-yl | H | $CF_3$ | H | H | H | $OCH_3$ |
| 2-methyloxazol-5-yl | H | $CF_3$ | H | H | $OCF_2H$ | H |
| 2-methyloxazol-5-yl | H | $CH_3$ | H | F | H | H |
| 2-methyloxazol-5-yl | H | $CH_3$ | H | H | H | $OCH_3$ |
| 2-methyloxazol-5-yl | H | $CH_3$ | H | H | $OCF_2H$ | H |
| 2-methyloxazol-5-yl | H | $OCF_2H$ | H | F | H | H |
| 2-methyloxazol-5-yl | H | $OCF_2H$ | H | H | H | $OCH_3$ |
| 2-methyloxazol-5-yl | H | $OCF_2H$ | H | H | $OCF_2H$ | H |
| 2-methyloxazol-5-yl | $OCF_2H$ | H | H | F | H | H |
| 2-methyloxazol-5-yl | $OCF_2H$ | H | H | H | H | $OCH_3$ |
| 2-methyloxazol-5-yl | $OCF_2H$ | H | H | H | $OCH_3$ | H |
| 2-methyloxazol-5-yl | $OCH_3$ | H | H | F | H | H |
| 2-methyloxazol-5-yl | $OCH_3$ | H | H | H | H | H |
| 2-methyloxazol-5-yl | $OCH_3$ | H | H | H | H | $OCH_3$ |
| 2-methyloxazol-5-yl | $OCH_3$ | H | H | H | $OCH_3$ | H |
| imidazolyl | $CF_3$ | H | H | $CH_3$ | H | H |
| imidazolyl | $CF_3$ | H | H | H | H | H |
| imidazolyl | $CF_3$ | H | H | H | H | $OCH_3$ |
| imidazolyl | $CF_3$ | H | H | H | $OCF_2H$ | H |
| imidazolyl | $CF_3$ | H | H | H | $OCH_3$ | H |
| imidazolyl | $CH_3$ | H | H | F | H | H |
| imidazolyl | $CH_3$ | H | H | H | H | $OCH_3$ |
| imidazolyl | $CH_3$ | H | H | H | $OCF_2H$ | H |
| imidazolyl | $CH_3$ | H | H | H | $OCH_3$ | H |
| imidazolyl | Cl | H | F | H | H | H |
| imidazolyl | Cl | H | H | $CH_3$ | H | H |
| imidazolyl | Cl | H | F | H | H | H |
| imidazolyl | Cl | H | H | H | H | H |
| imidazolyl | Cl | H | H | H | H | $OCF_2H$ |
| imidazolyl | Cl | H | H | H | H | $OCH_3$ |
| imidazolyl | Cl | H | H | H | $OCF_2H$ | H |
| imidazolyl | Cl | H | H | H | $OCH_3$ | H |
| imidazolyl | F | H | H | $CH_3$ | H | H |
| imidazolyl | F | H | H | F | H | H |
| imidazolyl | F | H | H | H | H | $OCH_3$ |
| imidazolyl | F | H | H | H | $OCF_2H$ | H |
| imidazolyl | F | H | H | H | $OCH_3$ | H |
| imidazolyl | H | $CF_3$ | H | $CH_3$ | H | H |
| imidazolyl | H | $CF_3$ | H | F | H | H |
| imidazolyl | H | $CF_3$ | H | H | H | $OCH_3$ |
| imidazolyl | H | $CF_3$ | H | H | $OCF_2H$ | H |
| imidazolyl | H | $CH_3$ | H | $CH_3$ | H | H |
| imidazolyl | H | $CH_3$ | H | F | H | H |
| imidazolyl | H | $CH_3$ | H | H | H | $OCH_3$ |
| imidazolyl | H | $CH_3$ | H | H | $OCF_2H$ | H |
| imidazolyl | H | $OCF_2H$ | H | $CH_3$ | H | H |
| imidazolyl | H | $OCF_2H$ | H | F | H | H |
| imidazolyl | H | $OCF_2H$ | H | H | H | $OCH_3$ |
| imidazolyl | H | $OCF_2H$ | H | H | $OCF_2H$ | H |
| imidazolyl | $OCF_2H$ | H | F | H | H | H |
| imidazolyl | $OCF_2H$ | H | H | $CH_3$ | H | H |
| imidazolyl | $OCF_2H$ | H | H | F | H | H |
| imidazolyl | $OCF_2H$ | H | H | H | H | $OCH_3$ |
| imidazolyl | $OCF_2H$ | H | H | H | $OCF_2H$ | H |
| imidazolyl | $OCF_2H$ | H | H | H | $OCH_3$ | H |
| imidazolyl | $OCH_3$ | H | F | H | H | H |
| imidazolyl | $OCH_3$ | H | H | $CH_3$ | H | H |
| imidazolyl | $OCH_3$ | H | H | F | H | H |
| imidazolyl | $OCH_3$ | H | H | H | H | H |
| imidazolyl | $OCH_3$ | H | H | H | H | $OCH_3$ |
| imidazolyl | $OCH_3$ | H | H | H | $OCF_2H$ | H |
| imidazolyl | $OCH_3$ | H | H | H | $OCH_3$ | H |
| oxazol-5-yl | $CF_3$ | H | H | $CH_3$ | H | H |
| oxazol-5-yl | $CF_3$ | H | H | F | H | H |
| oxazol-5-yl | $CF_3$ | H | H | H | H | $OCH_3$ |
| oxazol-5-yl | $CF_3$ | H | H | H | $OCF_2H$ | H |
| oxazol-5-yl | $CF_3$ | H | H | H | $OCH_3$ | H |
| oxazol-5-yl | $CH_3$ | H | H | F | H | H |
| oxazol-5-yl | $CH_3$ | H | H | $CH_3$ | H | H |
| oxazol-5-yl | $CH_3$ | H | H | F | H | H |
| oxazol-5-yl | $CH_3$ | H | H | H | H | $OCH_3$ |
| oxazol-5-yl | $CH_3$ | H | H | H | $OCF_2H$ | H |
| oxazol-5-yl | $CH_3$ | H | H | H | $OCH_3$ | H |
| oxazol-5-yl | Cl | H | F | H | F | H |
| oxazol-5-yl | Cl | H | F | H | H | H |
| oxazol-5-yl | Cl | H | H | $CH_3$ | H | H |
| oxazol-5-yl | Cl | H | H | F | H | H |
| oxazol-5-yl | Cl | H | H | H | Cl | H |
| oxazol-5-yl | Cl | H | H | H | F | H |
| oxazol-5-yl | Cl | H | H | H | H | H |
| oxazol-5-yl | Cl | H | H | H | H | $OCF_2H$ |
| oxazol-5-yl | Cl | H | H | H | H | $OCH_3$ |
| oxazol-5-yl | Cl | H | H | H | $OCF_2H$ | H |
| oxazol-5-yl | Cl | H | H | H | $OCH_3$ | H |
| oxazol-5-yl | F | H | H | $CH_3$ | H | H |
| oxazol-5-yl | F | H | H | F | H | H |
| oxazol-5-yl | F | H | H | H | H | $OCH_3$ |
| oxazol-5-yl | F | H | H | H | $OCF_2H$ | H |
| oxazol-5-yl | F | H | H | H | $OCH_3$ | H |
| oxazol-5-yl | H | $CF_3$ | H | $CH_3$ | H | H |
| oxazol-5-yl | H | $CF_3$ | H | F | H | H |
| oxazol-5-yl | H | $CF_3$ | H | H | H | $OCH_3$ |
| oxazol-5-yl | H | $CF_3$ | H | H | $OCF_2H$ | H |
| oxazol-5-yl | H | $CH_3$ | H | $CH_3$ | H | H |
| oxazol-5-yl | H | $CH_3$ | H | F | H | H |
| oxazol-5-yl | H | $CH_3$ | H | H | H | $OCH_3$ |
| oxazol-5-yl | H | $CH_3$ | H | H | $OCF_2H$ | H |
| oxazol-5-yl | H | $OCF_2H$ | H | CH3 | H | H |
| oxazol-5-yl | H | $OCF_2H$ | H | F | H | H |
| oxazol-5-yl | H | $OCF_2H$ | H | H | H | $OCH_3$ |
| oxazol-5-yl | H | $OCF_2H$ | H | H | $OCF_2H$ | H |
| oxazol-5-yl | $OCF_2H$ | H | F | H | H | H |
| oxazol-5-yl | $OCF_2H$ | H | H | $CH_3$ | H | H |
| oxazol-5-yl | $OCF_2H$ | H | H | F | H | H |
| oxazol-5-yl | $OCF_2H$ | H | H | H | H | $OCH_3$ |
| oxazol-5-yl | $OCF_2H$ | H | H | H | $OCF_2H$ | H |
| oxazol-5-yl | $OCF_2H$ | H | H | H | $OCH_3$ | H |
| oxazol-5-yl | $OCH_3$ | H | F | H | H | H |
| oxazol-5-yl | $OCH_3$ | H | H | $CH_3$ | H | H |
| oxazol-5-yl | $OCH_3$ | H | H | F | H | H |
| oxazol-5-yl | $OCH_3$ | H | H | H | H | H |
| oxazol-5-yl | $OCH_3$ | H | H | H | H | $OCH_3$ |
| oxazol-5-yl | $OCH_3$ | H | H | H | $OCF_2H$ | H |
| oxazol-5-yl | $OCH_3$ | H | H | H | $OCH_3$ | H |
| pyridine-4-yl | $CF_3$ | H | H | $CH_3$ | H | H |
| pyridine-4-yl | $CF_3$ | H | H | F | H | H |
| pyridine-4-yl | $CF_3$ | H | H | H | H | $OCH_3$ |
| pyridine-4-yl | $CF_3$ | H | H | H | $OCF_2H$ | H |
| pyridine-4-yl | $CF_3$ | H | H | H | $OCH_3$ | H |
| pyridine-4-yl | $CH_3$ | H | H | F | H | H |
| pyridine-4-yl | $CH_3$ | H | H | $CH_3$ | H | H |
| pyridine-4-yl | $CH_3$ | H | H | F | H | H |
| pyridine-4-yl | $CH_3$ | H | H | H | H | $OCH_3$ |
| pyridine-4-yl | $CH_3$ | H | H | H | $OCF_2H$ | H |
| pyridine-4-yl | $CH_3$ | H | H | H | $OCH_3$ | H |
| pyridine-4-yl | Cl | H | F | H | H | H |
| pyridine-4-yl | Cl | H | H | $CH_3$ | H | H |
| pyridine-4-yl | Cl | H | H | F | H | H |
| pyridine-4-yl | Cl | H | H | H | H | H |
| pyridine-4-yl | Cl | H | H | H | H | $OCF_2H$ |
| pyridine-4-yl | Cl | H | H | H | H | $OCH_3$ |
| pyridine-4-yl | Cl | H | H | H | $OCF_2H$ | H |

TABLE 3-continued

| A | $R_1$ | $R_{12}$ | $R_2^{II}$ | $R_3^{II}$ | $R_4^{II}$ | $R_5^{II}$ |
|---|---|---|---|---|---|---|
| pyridine-4-yl | Cl | H | H | H | $OCH_3$ | H |
| pyridine-4-yl | F | H | H | $CH_3$ | H | H |
| pyridine-4-yl | F | H | H | F | H | H |
| pyridine-4-yl | F | H | H | H | H | $OCH_3$ |
| pyridine-4-yl | F | H | H | H | $OCF_2H$ | H |
| pyridine-4-yl | F | H | H | H | $OCH_3$ | H |
| pyridine-4-yl | H | $CF_3$ | H | $CH_3$ | H | H |
| pyridine-4-yl | H | $CF_3$ | H | F | H | H |
| pyridine-4-yl | H | $CF_3$ | H | H | H | $OCH_3$ |
| pyridine-4-yl | H | $CF_3$ | H | H | $OCF_2H$ | H |
| pyridine-4-yl | H | $CH_3$ | H | $CH_3$ | H | H |
| pyridine-4-yl | H | $CH_3$ | H | F | H | H |
| pyridine-4-yl | H | $CH_3$ | H | H | H | $OCH_3$ |
| pyridine-4-yl | H | $CH_3$ | H | H | $OCF_2H$ | H |
| pyridine-4-yl | H | $OCF_2H$ | H | $CH_3$ | H | H |
| pyridine-4-yl | H | $OCF_2H$ | H | F | H | H |
| pyridine-4-yl | H | $OCF_2H$ | H | H | H | $OCH_3$ |
| pyridine-4-yl | H | $OCF_2H$ | H | H | $OCF_2H$ | H |
| pyridine-4-yl | $OCF_2H$ | H | F | H | H | H |
| pyridine-4-yl | $OCF_2H$ | H | H | $CH_3$ | H | H |
| pyridine-4-yl | $OCF_2H$ | H | H | F | H | H |
| pyridine-4-yl | $OCF_2H$ | H | H | H | H | $OCH_3$ |
| pyridine-4-yl | $OCF_2H$ | H | H | H | $OCF_2H$ | H |
| pyridine-4-yl | $OCF_2H$ | H | H | H | $OCH_3$ | H |
| pyridine-4-yl | $OCH_3$ | H | F | H | H | H |
| pyridine-4-yl | $OCH_3$ | H | H | $CH_3$ | H | H |
| pyridine-4-yl | $OCH_3$ | H | H | F | H | H |
| pyridine-4-yl | $OCH_3$ | H | H | H | H | H |
| pyridine-4-yl | $OCH_3$ | H | H | H | H | $OCH_3$ |
| pyridine-4-yl | $OCH_3$ | H | H | H | $OCF_2H$ | H |
| pyridine-4-yl | $OCH_3$ | H | H | H | $OCH_3$ | H |

Preferably, the compound of formula (Id)

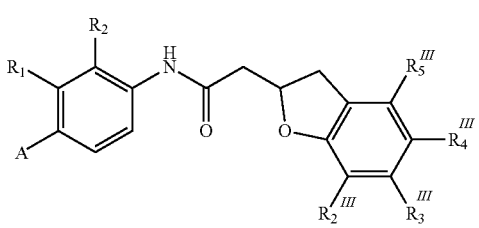

(Id)

is selected from the group consisting of compounds of the formula (I), wherein A, $R_1$, $R_{12}$, $R_2^{III}$, $R_3^{III}$, $R_4^{III}$ and $R_5^{III}$ are as indicated in Table 4:

TABLE 4

| A | $R_1$ | $R_{12}$ | $R_2^{III}$ | $R_3^{III}$ | $R_4^{III}$ | $R_5^{III}$ |
|---|---|---|---|---|---|---|
| 1,2,4-triazol-1-yl | $CF_3$ | H | H | $CH_3$ | H | H |
| 1,2,4-triazol-1-yl | $CF_3$ | H | H | F | H | H |
| 1,2,4-triazol-1-yl | $CF_3$ | H | H | H | H | $OCH_3$ |
| 1,2,4-triazol-1-yl | $CF_3$ | H | H | H | $OCF_2H$ | H |
| 1,2,4-triazol-1-yl | $CF_3$ | H | H | H | $OCH_3$ | H |
| 1,2,4-triazol-1-yl | $CH_3$ | H | F | H | H | H |
| 1,2,4-triazol-1-yl | $CH_3$ | H | H | $CH_3$ | H | H |
| 1,2,4-triazol-1-yl | $CH_3$ | H | H | F | H | H |
| 1,2,4-triazol-1-yl | $CH_3$ | H | H | H | H | $OCH_3$ |
| 1,2,4-triazol-1-yl | $CH_3$ | H | H | H | $OCF_2H$ | H |
| 1,2,4-triazol-1-yl | $CH_3$ | H | H | H | $OCH_3$ | H |
| 1,2,4-triazol-1-yl | Cl | H | F | H | H | H |
| 1,2,4-triazol-1-yl | Cl | H | H | $CH_3$ | H | H |
| 1,2,4-triazol-1-yl | Cl | H | H | F | H | H |
| 1,2,4-triazol-1-yl | Cl | H | H | H | H | H |
| 1,2,4-triazol-1-yl | Cl | H | H | H | H | $OCF_2H$ |
| 1,2,4-triazol-1-yl | Cl | H | H | H | H | $OCH_3$ |
| 1,2,4-triazol-1-yl | Cl | H | H | H | $OCF_2H$ | H |
| 1,2,4-triazol-1-yl | Cl | H | H | H | $OCH_3$ | H |

TABLE 4-continued

| A | $R_1$ | $R_{12}$ | $R_2^{III}$ | $R_3^{III}$ | $R_4^{III}$ | $R_5^{III}$ |
|---|---|---|---|---|---|---|
| 1,2,4-triazol-1-yl | F | H | H | $CH_3$ | H | H |
| 1,2,4-triazol-1-yl | F | H | H | F | H | H |
| 1,2,4-triazol-1-yl | F | H | H | H | H | $OCH_3$ |
| 1,2,4-triazol-1-yl | F | H | H | H | $OCF_2H$ | H |
| 1,2,4-triazol-1-yl | F | H | H | H | $OCH_3$ | H |
| 1,2,4-triazol-1-yl | H | $CF_3$ | H | $CH_3$ | H | H |
| 1,2,4-triazol-1-yl | H | $CF_3$ | H | F | H | H |
| 1,2,4-triazol-1-yl | H | $CF_3$ | H | H | H | $OCH_3$ |
| 1,2,4-triazol-1-yl | H | $CF_3$ | H | H | $OCF_2H$ | H |
| 1,2,4-triazol-1-yl | H | $CH_3$ | H | $CH_3$ | H | H |
| 1,2,4-triazol-1-yl | H | $CH_3$ | H | F | H | H |
| 1,2,4-triazol-1-yl | H | $CH_3$ | H | H | H | $OCH_3$ |
| 1,2,4-triazol-1-yl | H | $CH_3$ | H | H | $OCF_2H$ | H |
| 1,2,4-triazol-1-yl | H | $OCF_2H$ | H | CH3 | H | H |
| 1,2,4-triazol-1-yl | H | $OCF_2H$ | H | F | H | H |
| 1,2,4-triazol-1-yl | H | $OCF_2H$ | H | H | H | $OCH_3$ |
| 1,2,4-triazol-1-yl | H | $OCF_2H$ | H | H | $OCF_2H$ | H |
| 1,2,4-triazol-1-yl | $OCF_2H$ | H | F | H | H | H |
| 1,2,4-triazol-1-yl | $OCF_2H$ | H | H | $CH_3$ | H | H |
| 1,2,4-triazol-1-yl | $OCF_2H$ | H | H | F | H | H |
| 1,2,4-triazol-1-yl | $OCF_2H$ | H | H | H | H | $OCH_3$ |
| 1,2,4-triazol-1-yl | $OCF_2H$ | H | H | H | $OCF_2H$ | H |
| 1,2,4-triazol-1-yl | $OCF_2H$ | H | H | H | $OCH_3$ | H |
| 1,2,4-triazol-1-yl | $OCH_3$ | H | F | H | H | H |
| 1,2,4-triazol-1-yl | $OCH_3$ | H | H | $CH_3$ | H | H |
| 1,2,4-triazol-1-yl | $OCH_3$ | H | H | F | H | H |
| 1,2,4-triazol-1-yl | $OCH_3$ | H | H | H | H | H |
| 1,2,4-triazol-1-yl | $OCH_3$ | H | H | H | H | $OCH_3$ |
| 1,2,4-triazol-1-yl | $OCH_3$ | H | H | H | $OCF_2H$ | H |
| 1,2,4-triazol-1-yl | $OCH_3$ | H | H | H | $OCH_3$ | H |
| 1,3,4-oxadiazol-2-yl | $CF_3$ | H | H | $CH_3$ | H | H |
| 1,3,4-oxadiazol-2-yl | $CF_3$ | H | H | F | H | H |
| 1,3,4-oxadiazol-2-yl | $CF_3$ | H | H | H | H | $OCH_3$ |
| 1,3,4-oxadiazol-2-yl | $CF_3$ | H | H | H | $OCF_2H$ | H |
| 1,3,4-oxadiazol-2-yl | $CF_3$ | H | H | H | $OCH_3$ | H |
| 1,3,4-oxadiazol-2-yl | $CH_3$ | H | F | H | H | H |
| 1,3,4-oxadiazol-2-yl | $CH_3$ | H | H | $CH_3$ | H | H |
| 1,3,4-oxadiazol-2-yl | $CH_3$ | H | H | F | H | H |
| 1,3,4-oxadiazol-2-yl | $CH_3$ | H | H | H | H | $OCH_3$ |
| 1,3,4-oxadiazol-2-yl | $CH_3$ | H | H | H | $OCF_2H$ | H |
| 1,3,4-oxadiazol-2-yl | $CH_3$ | H | H | H | $OCH_3$ | H |
| 1,3,4-oxadiazol-2-yl | Cl | H | F | H | H | H |
| 1,3,4-oxadiazol-2-yl | Cl | H | H | $CH_3$ | H | H |
| 1,3,4-oxadiazol-2-yl | Cl | H | H | F | H | H |
| 1,3,4-oxadiazol-2-yl | Cl | H | H | H | H | H |
| 1,3,4-oxadiazol-2-yl | Cl | H | H | H | H | $OCF_2H$ |
| 1,3,4-oxadiazol-2-yl | Cl | H | H | H | H | $OCH_3$ |
| 1,3,4-oxadiazol-2-yl | Cl | H | H | H | $OCF_2H$ | H |
| 1,3,4-oxadiazol-2-yl | Cl | H | H | H | $OCH_3$ | H |
| 1,3,4-oxadiazol-2-yl | F | H | H | $CH_3$ | H | H |
| 1,3,4-oxadiazol-2-yl | F | H | H | F | H | H |
| 1,3,4-oxadiazol-2-yl | F | H | H | H | H | $OCH_3$ |
| 1,3,4-oxadiazol-2-yl | F | H | H | H | $OCF_2H$ | H |
| 1,3,4-oxadiazol-2-yl | F | H | H | H | $OCH_3$ | H |
| 1,3,4-oxadiazol-2-yl | H | $CF_3$ | H | $CH_3$ | H | H |
| 1,3,4-oxadiazol-2-yl | H | $CF_3$ | H | F | H | H |
| 1,3,4-oxadiazol-2-yl | H | $CF_3$ | H | H | H | $OCH_3$ |
| 1,3,4-oxadiazol-2-yl | H | $CF_3$ | H | H | $OCF_2H$ | H |
| 1,3,4-oxadiazol-2-yl | H | $CH_3$ | H | $CH_3$ | H | H |
| 1,3,4-oxadiazol-2-yl | H | $CH_3$ | H | F | H | H |
| 1,3,4-oxadiazol-2-yl | H | $CH_3$ | H | H | H | $OCH_3$ |
| 1,3,4-oxadiazol-2-yl | H | $CH_3$ | H | H | $OCF_2H$ | H |
| 1,3,4-oxadiazol-2-yl | H | $OCF_2H$ | H | $CH_3$ | H | H |
| 1,3,4-oxadiazol-2-yl | H | $OCF_2H$ | H | F | H | H |
| 1,3,4-oxadiazol-2-yl | H | $OCF_2H$ | H | H | H | $OCH_3$ |
| 1,3,4-oxadiazol-2-yl | H | $OCF_2H$ | H | H | $OCF_2H$ | H |
| 1,3,4-oxadiazol-2-yl | $OCF_2H$ | H | F | H | H | H |
| 1,3,4-oxadiazol-2-yl | $OCF_2H$ | H | H | $CH_3$ | H | H |
| 1,3,4-oxadiazol-2-yl | $OCF_2H$ | H | H | F | H | H |
| 1,3,4-oxadiazol-2-yl | $OCF_2H$ | H | H | H | H | $OCH_3$ |
| 1,3,4-oxadiazol-2-yl | $OCF_2H$ | H | H | H | $OCF_2H$ | H |
| 1,3,4-oxadiazol-2-yl | $OCF_2H$ | H | H | H | $OCH_3$ | H |
| 1,3,4-oxadiazol-2-yl | $OCH_3$ | H | F | H | H | H |
| 1,3,4-oxadiazol-2-yl | $OCH_3$ | H | H | $CH_3$ | H | H |
| 1,3,4-oxadiazol-2-yl | $OCH_3$ | H | H | F | H | H |
| 1,3,4-oxadiazol-2-yl | $OCH_3$ | H | H | H | H | H |
| 1,3,4-oxadiazol-2-yl | $OCH_3$ | H | H | H | H | $OCH_3$ |
| 1,3,4-oxadiazol-2-yl | $OCH_3$ | H | H | H | $OCF_2H$ | H |

TABLE 4-continued

| A | R$_1$ | R$_{12}$ | R$_2{}^{III}$ | R$_3{}^{III}$ | R$_4{}^{III}$ | R$_5{}^{III}$ |
|---|---|---|---|---|---|---|
| 1,3,4-oxadiazol-2-yl | OCH$_3$ | H | H | H | OCH$_3$ | H |
| 2-methyloxazol-5-yl | CF$_3$ | H | H | F | H | H |
| 2-methyloxazol-5-yl | CF$_3$ | H | H | H | H | OCH$_3$ |
| 2-methyloxazol-5-yl | CF$_3$ | H | H | H | OCH$_3$ | H |
| 2-methyloxazol-5-yl | CH$_3$ | H | H | F | H | H |
| 2-methyloxazol-5-yl | CH$_3$ | H | H | H | H | OCH$_3$ |
| 2-methyloxazol-5-yl | CH$_3$ | H | H | H | OCH$_3$ | H |
| 2-methyloxazol-5-yl | Cl | H | H | F | H | H |
| 2-methyloxazol-5-yl | Cl | H | H | H | H | H |
| 2-methyloxazol-5-yl | Cl | H | H | H | H | OCH$_3$ |
| 2-methyloxazol-5-yl | Cl | H | H | H | OCH$_3$ | H |
| 2-methyloxazol-5-yl | H | CF$_3$ | H | F | H | H |
| 2-methyloxazol-5-yl | H | CF$_3$ | H | H | H | OCH$_3$ |
| 2-methyloxazol-5-yl | H | CF$_3$ | H | H | OCF$_2$H | H |
| 2-methyloxazol-5-yl | H | CH$_3$ | H | F | H | H |
| 2-methyloxazol-5-yl | H | CH$_3$ | H | H | H | OCH$_3$ |
| 2-methyloxazol-5-yl | H | CH$_3$ | H | H | OCF$_2$H | H |
| 2-methyloxazol-5-yl | H | OCF$_2$H | H | F | H | H |
| 2-methyloxazol-5-yl | H | OCF$_2$H | H | H | H | OCH$_3$ |
| 2-methyloxazol-5-yl | H | OCF$_2$H | H | H | OCF$_2$H | H |
| 2-methyloxazol-5-yl | OCF$_2$H | H | H | F | H | H |
| 2-methyloxazol-5-yl | OCF$_2$H | H | H | H | H | OCH$_3$ |
| 2-methyloxazol-5-yl | OCF$_2$H | H | H | H | OCH$_3$ | H |
| 2-methyloxazol-5-yl | OCH$_3$ | H | H | F | H | H |
| 2-methyloxazol-5-yl | OCH$_3$ | H | H | H | H | H |
| 2-methyloxazol-5-yl | OCH$_3$ | H | H | H | H | OCH$_3$ |
| 2-methyloxazol-5-yl | OCH$_3$ | H | H | H | OCH$_3$ | H |
| imidazolyl | CF$_3$ | H | H | CH$_3$ | H | H |
| imidazolyl | CF$_3$ | H | H | F | H | H |
| imidazolyl | CF$_3$ | H | H | H | H | OCH$_3$ |
| imidazolyl | CF$_3$ | H | H | H | OCF$_2$H | H |
| imidazolyl | CF$_3$ | H | H | H | OCH$_3$ | H |
| imidazolyl | CH$_3$ | H | H | F | H | H |
| imidazolyl | CH$_3$ | H | H | H | H | OCH$_3$ |
| imidazolyl | CH$_3$ | H | H | H | OCF$_2$H | H |
| imidazolyl | CH$_3$ | H | H | H | OCH$_3$ | H |
| imidazolyl | Cl | H | F | H | H | H |
| imidazolyl | Cl | H | H | CH3 | H | H |
| imidazolyl | Cl | H | H | F | H | H |
| imidazolyl | Cl | H | H | H | H | H |
| imidazolyl | Cl | H | H | H | H | OCF$_2$H |
| imidazolyl | Cl | H | H | H | H | OCH$_3$ |
| imidazolyl | Cl | H | H | H | OCF$_2$H | H |
| imidazolyl | Cl | H | H | H | OCH$_3$ | H |
| imidazolyl | F | H | H | CH$_3$ | H | H |
| imidazolyl | F | H | H | F | H | H |
| imidazolyl | F | H | H | H | H | OCH$_3$ |
| imidazolyl | F | H | H | H | OCH$_3$ | H |
| imidazolyl | H | CF$_3$ | H | CH$_3$ | H | H |
| imidazolyl | H | CF$_3$ | H | F | H | H |
| imidazolyl | H | CF$_3$ | H | H | H | OCH$_3$ |
| imidazolyl | H | CF$_3$ | H | H | OCF2H | H |
| imidazolyl | H | CH$_3$ | H | CH$_3$ | H | H |
| imidazolyl | H | CH$_3$ | H | F | H | H |
| imidazolyl | H | CH$_3$ | H | H | H | OCH$_3$ |
| imidazolyl | H | CH$_3$ | H | H | OCF$_2$H | H |
| imidazolyl | H | OCF$_2$H | H | CH$_3$ | H | H |
| imidazolyl | H | OCF$_2$H | H | F | H | H |
| imidazolyl | H | OCF$_2$H | H | H | H | OCH$_3$ |
| imidazolyl | H | OCF$_2$H | H | H | OCF$_2$H | H |
| imidazolyl | OCF$_2$H | H | F | H | H | H |
| imidazolyl | OCF$_2$H | H | H | CH$_3$ | H | H |
| imidazolyl | OCF$_2$H | H | H | F | H | H |
| imidazolyl | OCF$_2$H | H | H | H | H | OCH$_3$ |
| imidazolyl | OCF$_2$H | H | H | H | OCF$_2$H | H |
| imidazolyl | OCF$_2$H | H | H | H | OCH$_3$ | H |
| imidazolyl | OCH$_3$ | H | F | H | H | H |
| imidazolyl | OCH$_3$ | H | H | CH$_3$ | H | H |
| imidazolyl | OCH$_3$ | H | H | F | H | H |
| imidazolyl | OCH$_3$ | H | H | H | H | H |
| imidazolyl | OCH$_3$ | H | H | H | H | OCH$_3$ |
| imidazolyl | OCH$_3$ | H | H | H | OCF$_2$H | H |
| imidazolyl | OCH$_3$ | H | H | H | OCH$_3$ | H |
| oxazol-5-yl | CF$_3$ | H | H | CH$_3$ | H | H |
| oxazol-5-yl | CF$_3$ | H | H | F | H | H |
| oxazol-5-yl | CF$_3$ | H | H | H | H | OCH$_3$ |
| oxazol-5-yl | CF$_3$ | H | H | H | OCF$_2$H | H |
| oxazol-5-yl | CF$_3$ | H | H | H | OCH$_3$ | H |
| oxazol-5-yl | CH$_3$ | H | F | H | H | H |
| oxazol-5-yl | CH$_3$ | H | H | CH$_3$ | H | H |
| oxazol-5-yl | CH$_3$ | H | H | F | H | H |
| oxazol-5-yl | CH$_3$ | H | H | H | H | OCH$_3$ |
| oxazol-5-yl | CH$_3$ | H | H | H | OCF$_2$H | H |
| oxazol-5-yl | CH$_3$ | H | H | H | OCH$_3$ | H |
| oxazol-5-yl | Cl | H | F | H | F | H |
| oxazol-5-yl | Cl | H | F | H | H | H |
| oxazol-5-yl | Cl | H | H | CH$_3$ | H | H |
| oxazol-5-yl | Cl | H | H | F | H | H |
| oxazol-5-yl | Cl | H | H | H | H | Cl |
| oxazol-5-yl | Cl | H | H | H | H | F |
| oxazol-5-yl | Cl | H | H | H | H | H |
| oxazol-5-yl | Cl | H | H | H | H | OCF$_2$H |
| oxazol-5-yl | Cl | H | H | H | H | OCH$_3$ |
| oxazol-5-yl | Cl | H | H | H | OCF$_2$H | H |
| oxazol-5-yl | Cl | H | H | H | OCH$_3$ | H |
| oxazol-5-yl | F | H | H | H | CH$_3$ | H |
| oxazol-5-yl | F | H | H | H | F | H |
| oxazol-5-yl | F | H | H | H | H | OCH$_3$ |
| oxazol-5-yl | F | H | H | H | OCF$_2$H | H |
| oxazol-5-yl | F | H | H | H | OCH$_3$ | H |
| oxazol-5-yl | H | CF$_3$ | H | CH$_3$ | H | H |
| oxazol-5-yl | H | CF$_3$ | H | F | H | H |
| oxazol-5-yl | H | CF$_3$ | H | H | H | OCH$_3$ |
| oxazol-5-yl | H | CF$_3$ | H | H | OCF$_2$H | H |
| oxazol-5-yl | H | CH$_3$ | H | CH$_3$ | H | H |
| oxazol-5-yl | H | CH$_3$ | H | F | H | H |
| oxazol-5-yl | H | CH$_3$ | H | H | H | OCH$_3$ |
| oxazol-5-yl | H | CH$_3$ | H | H | OCF$_2$H | H |
| oxazol-5-yl | H | OCF$_2$H | H | F | H | H |
| oxazol-5-yl | H | OCF$_2$H | H | H | H | OCH$_3$ |
| oxazol-5-yl | H | OCF$_2$H | H | H | OCF$_2$H | H |
| oxazol-5-yl | OCF$_2$H | H | F | H | H | H |
| oxazol-5-yl | OCF$_2$H | H | H | CH$_3$ | H | H |
| oxazol-5-yl | OCF$_2$H | H | H | F | H | H |
| oxazol-5-yl | OCF$_2$H | H | H | H | H | OCH$_3$ |
| oxazol-5-yl | OCF$_2$H | H | H | H | OCF$_2$H | H |
| oxazol-5-yl | OCF$_2$H | H | H | H | OCH$_3$ | H |
| oxazol-5-yl | OCH$_3$ | H | F | H | H | H |
| oxazol-5-yl | OCH$_3$ | H | H | CH$_3$ | H | H |
| oxazol-5-yl | OCH$_3$ | H | H | F | H | H |
| oxazol-5-yl | OCH$_3$ | H | H | H | H | H |
| oxazol-5-yl | OCH$_3$ | H | H | H | H | OCH$_3$ |
| oxazol-5-yl | OCH$_3$ | H | H | H | OCF$_2$H | H |
| oxazol-5-yl | OCH$_3$ | H | H | H | OCH$_3$ | H |
| pyridine-4-yl | CF$_3$ | H | H | CH3 | H | H |
| pyridine-4-yl | CF$_3$ | H | H | F | H | H |
| pyridine-4-yl | CF$_3$ | H | H | H | H | OCH$_3$ |
| pyridine-4-yl | CF$_3$ | H | H | H | OCF$_2$H | H |
| pyridine-4-yl | CF$_3$ | H | H | H | OCH$_3$ | H |
| pyridine-4-yl | CH$_3$ | H | H | F | H | H |
| pyridine-4-yl | CH$_3$ | H | H | H | CH$_3$ | H |
| pyridine-4-yl | CH$_3$ | H | H | H | F | H |
| pyridine-4-yl | CH$_3$ | H | H | H | H | OCH$_3$ |
| pyridine-4-yl | CH$_3$ | H | H | H | H | OCF$_2$H |
| pyridine-4-yl | CH$_3$ | H | H | H | OCH$_3$ | H |
| pyridine-4-yl | Cl | H | H | F | H | H |
| pyridine-4-yl | Cl | H | H | CH$_3$ | H | H |
| pyridine-4-yl | Cl | H | H | F | H | H |
| pyridine-4-yl | Cl | H | H | H | H | H |
| pyridine-4-yl | Cl | H | H | H | H | OCF$_2$H |
| pyridine-4-yl | Cl | H | H | H | H | OCH$_3$ |
| pyridine-4-yl | Cl | H | H | H | OCF$_2$H | H |
| pyridine-4-yl | Cl | H | H | H | OCH$_3$ | H |
| pyridine-4-yl | F | H | H | CH$_3$ | H | H |
| pyridine-4-yl | F | H | H | F | H | H |
| pyridine-4-yl | F | H | H | H | H | OCH$_3$ |
| pyridine-4-yl | F | H | H | H | OCF$_2$H | H |
| pyridine-4-yl | F | H | H | H | OCH$_3$ | H |
| pyridine-4-yl | H | CF$_3$ | H | CH$_3$ | H | H |
| pyridine-4-yl | H | CF$_3$ | H | F | H | H |
| pyridine-4-yl | H | CF$_3$ | H | H | H | OCH$_3$ |
| pyridine-4-yl | H | CF$_3$ | H | H | OCF$_2$H | H |
| pyridine-4-yl | H | CH$_3$ | H | CH$_3$ | H | H |
| pyridine-4-yl | H | CH$_3$ | H | F | H | H |

TABLE 4-continued

| A | $R_1$ | $R_{12}$ | $R_2^{III}$ | $R_3^{III}$ | $R_4^{III}$ | $R_5^{III}$ |
|---|---|---|---|---|---|---|
| pyridine-4-yl | H | $CH_3$ | H | H | H | $OCH_3$ |
| pyridine-4-yl | H | $CH_3$ | H | H | $OCF_2H$ | H |
| pyridine-4-yl | H | $OCF_2H$ | H | $CH_3$ | H | H |
| pyridine-4-yl | H | $OCF_2H$ | H | F | H | H |
| pyridine-4-yl | H | $OCF_2H$ | H | H | H | $OCH_3$ |
| pyridine-4-yl | H | $OCF_2H$ | H | H | $OCF_2H$ | H |
| pyridine-4-yl | $OCF_2H$ | H | F | H | H | H |
| pyridine-4-yl | $OCF_2H$ | H | H | $CH_3$ | H | H |
| pyridine-4-yl | $OCF_2H$ | H | H | F | H | H |
| pyridine-4-yl | $OCF_2H$ | H | H | H | H | $OCH_3$ |
| pyridine-4-yl | $OCF_2H$ | H | H | H | $OCF_2H$ | H |
| pyridine-4-yl | $OCF_2H$ | H | H | H | $OCH_3$ | H |
| pyridine-4-yl | $OCH_3$ | H | F | H | H | H |
| pyridine-4-yl | $OCH_3$ | H | H | $CH_3$ | H | H |
| pyridine-4-yl | $OCH_3$ | H | H | F | H | H |
| pyridine-4-yl | $OCH_3$ | H | H | H | H | H |
| pyridine-4-yl | $OCH_3$ | H | H | H | H | $OCH_3$ |
| pyridine-4-yl | $OCH_3$ | H | H | H | $OCF_2H$ | H |
| pyridine-4-yl | $OCH_3$ | H | H | H | $OCH_3$ | H |

Preferably, the compound of formula (Ie)

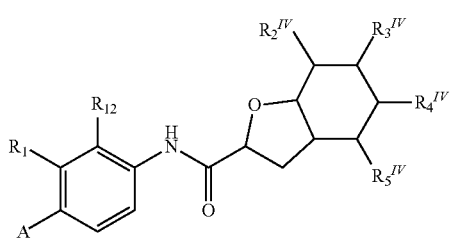

is selected from the group consisting of compounds of the formula (I), wherein A, $R_1$, $R_{12}$, $R_2^{IV}$, $R_3^{IV}$, $R_4^{IV}$ and $R_5^{IV}$ are as indicated in Table 5:

TABLE 5

| A | $R_1$ | $R_{12}$ | $R_2^{IV}$ | $R_3^{IV}$ | $R_4^{IV}$ | $R_5^{IV}$ |
|---|---|---|---|---|---|---|
| 1,2,4-triazol-1-yl | $CF_3$ | H | H | $CH_3$ | H | H |
| 1,2,4-triazol-1-yl | $CF_3$ | H | H | F | H | H |
| 1,2,4-triazol-1-yl | $CF_3$ | H | H | H | H | $OCH_3$ |
| 1,2,4-triazol-1-yl | $CF_3$ | H | H | H | $OCF_2H$ | H |
| 1,2,4-triazol-1-yl | $CF_3$ | H | H | H | $OCH_3$ | H |
| 1,2,4-triazol-1-yl | $CH_3$ | H | F | H | H | H |
| 1,2,4-triazol-1-yl | $CH_3$ | H | H | $CH_3$ | H | H |
| 1,2,4-triazol-1-yl | $CH_3$ | H | H | F | H | H |
| 1,2,4-triazol-1-yl | $CH_3$ | H | H | H | H | $OCH_3$ |
| 1,2,4-triazol-1-yl | $CH_3$ | H | H | H | $OCF_2H$ | H |
| 1,2,4-triazol-1-yl | $CH_3$ | H | H | H | $OCH_3$ | H |
| 1,2,4-triazol-1-yl | Cl | H | F | H | H | H |
| 1,2,4-triazol-1-yl | Cl | H | H | $CH_3$ | H | H |
| 1,2,4-triazol-1-yl | Cl | H | H | F | H | H |
| 1,2,4-triazol-1-yl | Cl | H | H | H | H | H |
| 1,2,4-triazol-1-yl | Cl | H | H | H | H | $OCF_2H$ |
| 1,2,4-triazol-1-yl | Cl | H | H | H | H | $OCH_3$ |
| 1,2,4-triazol-1-yl | Cl | H | H | H | $OCF_2H$ | H |
| 1,2,4-triazol-1-yl | Cl | H | H | H | $OCH_3$ | H |
| 1,2,4-triazol-1-yl | F | H | H | $CH_3$ | H | H |
| 1,2,4-triazol-1-yl | F | H | H | F | H | H |
| 1,2,4-triazol-1-yl | F | H | H | H | H | $OCH_3$ |
| 1,2,4-triazol-1-yl | F | H | H | H | $OCF_2H$ | H |
| 1,2,4-triazol-1-yl | F | H | H | H | $OCH_3$ | H |
| 1,2,4-triazol-1-yl | H | $CF_3$ | H | $CH_3$ | H | H |
| 1,2,4-triazol-1-yl | H | $CF_3$ | H | F | H | H |
| 1,2,4-triazol-1-yl | H | $CF_3$ | H | H | H | $OCH_3$ |
| 1,2,4-triazol-1-yl | H | $CF_3$ | H | H | $OCF_2H$ | H |
| 1,2,4-triazol-1-yl | H | $CH_3$ | H | $CH_3$ | H | H |
| 1,2,4-triazol-1-yl | H | $CH_3$ | H | F | H | H |
| 1,2,4-triazol-1-yl | H | $CH_3$ | H | H | H | $OCH_3$ |
| 1,2,4-triazol-1-yl | H | $CH_3$ | H | H | $OCF_2H$ | H |
| 1,2,4-triazol-1-yl | H | $OCF_2H$ | H | $CH_3$ | H | H |
| 1,2,4-triazol-1-yl | H | $OCF_2H$ | H | F | H | H |
| 1,2,4-triazol-1-yl | H | $OCF_2H$ | H | H | H | $OCH_3$ |
| 1,2,4-triazol-1-yl | H | $OCF_2H$ | H | H | $OCF_2H$ | H |
| 1,2,4-triazol-1-yl | $OCF_2H$ | H | F | H | H | H |
| 1,2,4-triazol-1-yl | $OCF_2H$ | H | H | $CH_3$ | H | H |
| 1,2,4-triazol-1-yl | $OCF_2H$ | H | H | F | H | H |
| 1,2,4-triazol-1-yl | $OCF_2H$ | H | H | H | H | $OCH_3$ |
| 1,2,4-triazol-1-yl | $OCF_2H$ | H | H | H | $OCF_2H$ | H |
| 1,2,4-triazol-1-yl | $OCF_2H$ | H | H | H | $OCH_3$ | H |
| 1,2,4-triazol-1-yl | $OCH_3$ | H | F | H | H | H |
| 1,2,4-triazol-1-yl | $OCH_3$ | H | H | $CH_3$ | H | H |
| 1,2,4-triazol-1-yl | $OCH_3$ | H | H | F | H | H |
| 1,2,4-triazol-1-yl | $OCH_3$ | H | H | H | H | H |
| 1,2,4-triazol-1-yl | $OCH_3$ | H | H | H | H | $OCH_3$ |
| 1,2,4-triazol-1-yl | $OCH_3$ | H | H | H | $OCF_2H$ | H |
| 1,2,4-triazol-1-yl | $OCH_3$ | H | H | H | $OCH_3$ | H |
| 1,3,4-oxadiazol-2-yl | $CF_3$ | H | H | $CH_3$ | H | H |
| 1,3,4-oxadiazol-2-yl | $CF_3$ | H | H | F | H | H |
| 1,3,4-oxadiazol-2-yl | $CF_3$ | H | H | H | H | $OCH_3$ |
| 1,3,4-oxadiazol-2-yl | $CF_3$ | H | H | H | $OCF_2H$ | H |
| 1,3,4-oxadiazol-2-yl | $CF_3$ | H | H | H | $OCH_3$ | H |
| 1,3,4-oxadiazol-2-yl | $CH_3$ | H | F | H | H | H |
| 1,3,4-oxadiazol-2-yl | $CH_3$ | H | H | $CH_3$ | H | H |
| 1,3,4-oxadiazol-2-yl | $CH_3$ | H | H | F | H | H |
| 1,3,4-oxadiazol-2-yl | $CH_3$ | H | H | H | H | $OCH_3$ |
| 1,3,4-oxadiazol-2-yl | $CH_3$ | H | H | H | $OCF_2H$ | H |
| 1,3,4-oxadiazol-2-yl | $CH_3$ | H | H | H | $OCH_3$ | H |
| 1,3,4-oxadiazol-2-yl | Cl | H | F | H | H | H |
| 1,3,4-oxadiazol-2-yl | Cl | H | H | $CH_3$ | H | H |
| 1,3,4-oxadiazol-2-yl | Cl | H | H | F | H | H |
| 1,3,4-oxadiazol-2-yl | Cl | H | H | H | H | H |
| 1,3,4-oxadiazol-2-yl | Cl | H | H | H | H | $OCF_2H$ |
| 1,3,4-oxadiazol-2-yl | Cl | H | H | H | H | $OCH_3$ |
| 1,3,4-oxadiazol-2-yl | Cl | H | H | H | $OCF_2H$ | H |
| 1,3,4-oxadiazol-2-yl | Cl | H | H | H | $OCH_3$ | H |
| 1,3,4-oxadiazol-2-yl | F | H | H | $CH_3$ | H | H |
| 1,3,4-oxadiazol-2-yl | F | H | H | F | H | H |
| 1,3,4-oxadiazol-2-yl | F | H | H | H | H | $OCH_3$ |
| 1,3,4-oxadiazol-2-yl | F | H | H | H | $OCF_2H$ | H |
| 1,3,4-oxadiazol-2-yl | F | H | H | H | $OCH_3$ | H |
| 1,3,4-oxadiazol-2-yl | H | $CF_3$ | H | $CH_3$ | H | H |
| 1,3,4-oxadiazol-2-yl | H | $CF_3$ | H | F | H | H |
| 1,3,4-oxadiazol-2-yl | H | $CF_3$ | H | H | H | $OCH_3$ |
| 1,3,4-oxadiazol-2-yl | H | $CF_3$ | H | H | $OCF_2H$ | H |
| 1,3,4-oxadiazol-2-yl | H | $CH_3$ | H | $CH_3$ | H | H |
| 1,3,4-oxadiazol-2-yl | H | $CH_3$ | H | F | H | H |
| 1,3,4-oxadiazol-2-yl | H | $CH_3$ | H | H | H | $OCH_3$ |
| 1,3,4-oxadiazol-2-yl | H | $CH_3$ | H | H | $OCF_2H$ | H |
| 1,3,4-oxadiazol-2-yl | H | $OCF_2H$ | H | $CH_3$ | H | H |
| 1,3,4-oxadiazol-2-yl | H | $OCF_2H$ | H | F | H | H |
| 1,3,4-oxadiazol-2-yl | H | $OCF_2H$ | H | H | H | $OCH_3$ |
| 1,3,4-oxadiazol-2-yl | H | $OCF_2H$ | H | H | $OCF_2H$ | H |
| 1,3,4-oxadiazol-2-yl | $OCF_2H$ | H | F | H | H | H |
| 1,3,4-oxadiazol-2-yl | $OCF_2H$ | H | H | $CH_3$ | H | H |
| 1,3,4-oxadiazol-2-yl | $OCF_2H$ | H | H | F | H | H |
| 1,3,4-oxadiazol-2-yl | $OCF_2H$ | H | H | H | H | $OCH_3$ |
| 1,3,4-oxadiazol-2-yl | $OCF_2H$ | H | H | H | $OCF_2H$ | H |
| 1,3,4-oxadiazol-2-yl | $OCF_2H$ | H | H | H | $OCH_3$ | H |
| 1,3,4-oxadiazol-2-yl | $OCH_3$ | H | F | H | H | H |
| 1,3,4-oxadiazol-2-yl | $OCH_3$ | H | H | $CH_3$ | H | H |
| 1,3,4-oxadiazol-2-yl | $OCH_3$ | H | H | F | H | H |
| 1,3,4-oxadiazol-2-yl | $OCH_3$ | H | H | H | H | H |
| 1,3,4-oxadiazol-2-yl | $OCH_3$ | H | H | H | H | $OCH_3$ |
| 1,3,4-oxadiazol-2-yl | $OCH_3$ | H | H | H | $OCF_2H$ | H |
| 1,3,4-oxadiazol-2-yl | $OCH_3$ | H | H | H | $OCH_3$ | H |
| 2-methyloxazol-5-yl | $CF_3$ | H | H | F | H | H |
| 2-methyloxazol-5-yl | $CF_3$ | H | H | H | H | $OCH_3$ |
| 2-methyloxazol-5-yl | $CH_3$ | H | H | F | H | H |
| 2-methyloxazol-5-yl | $CH_3$ | H | H | H | H | $OCH_3$ |
| 2-methyloxazol-5-yl | $CH_3$ | H | H | H | $OCH_3$ | H |
| 2-methyloxazol-5-yl | Cl | H | H | F | H | H |
| 2-methyloxazol-5-yl | Cl | H | H | H | H | H |
| 2-methyloxazol-5-yl | Cl | H | H | H | H | $OCH_3$ |
| 2-methyloxazol-5-yl | Cl | H | H | H | $OCH_3$ | H |
| 2-methyloxazol-5-yl | H | $CF_3$ | H | F | H | H |

TABLE 5-continued

| A | $R_1$ | $R_{12}$ | $R_2^{IV}$ | $R_3^{IV}$ | $R_4^{IV}$ | $R_5^{IV}$ |
|---|---|---|---|---|---|---|
| 2-methyloxazol-5-yl | H | $CF_3$ | H | H | H | $OCH_3$ |
| 2-methyloxazol-5-yl | H | $CF_3$ | H | H | $OCF_2H$ | H |
| 2-methyloxazol-5-yl | H | $CH_3$ | H | F | H | H |
| 2-methyloxazol-5-yl | H | $CH_3$ | H | H | H | $OCH_3$ |
| 2-methyloxazol-5-yl | H | $CH_3$ | H | H | $OCF_2H$ | H |
| 2-methyloxazol-5-yl | H | $OCF_2H$ | H | F | H | H |
| 2-methyloxazol-5-yl | H | $OCF_2H$ | H | H | H | $OCH_3$ |
| 2-methyloxazol-5-yl | H | $OCF_2H$ | H | H | $OCF_2H$ | H |
| 2-methyloxazol-5-yl | $OCF_2H$ | H | H | F | H | H |
| 2-methyloxazol-5-yl | $OCF_2H$ | H | H | H | H | $OCH_3$ |
| 2-methyloxazol-5-yl | $OCF_2H$ | H | H | H | $OCH_3$ | H |
| 2-methyloxazol-5-yl | $OCH_3$ | H | H | F | H | H |
| 2-methyloxazol-5-yl | $OCH_3$ | H | H | H | H | H |
| 2-methyloxazol-5-yl | $OCH_3$ | H | H | H | H | $OCH_3$ |
| 2-methyloxazol-5-yl | $OCH_3$ | H | H | H | $OCH_3$ | H |
| imidazolyl | $CF_3$ | H | H | $CH_3$ | H | H |
| imidazolyl | $CF_3$ | H | H | F | H | H |
| imidazolyl | $CF_3$ | H | H | H | H | $OCH_3$ |
| imidazolyl | $CF_3$ | H | H | H | $OCF_2H$ | H |
| imidazolyl | $CF_3$ | H | H | H | $OCH_3$ | H |
| imidazolyl | $CH_3$ | H | H | F | H | H |
| imidazolyl | $CH_3$ | H | H | H | H | $OCH_3$ |
| imidazolyl | $CH_3$ | H | H | H | $OCF_2H$ | H |
| imidazolyl | $CH_3$ | H | H | H | $OCH_3$ | H |
| imidazolyl | Cl | H | F | H | H | H |
| imidazolyl | Cl | H | H | $CH_3$ | H | H |
| imidazolyl | Cl | H | F | H | H | H |
| imidazolyl | Cl | H | H | H | H | H |
| imidazolyl | Cl | H | H | H | H | $OCF_2H$ |
| imidazolyl | Cl | H | H | H | H | $OCH_3$ |
| imidazolyl | Cl | H | H | H | $OCF_2H$ | H |
| imidazolyl | Cl | H | H | H | $OCH_3$ | H |
| imidazolyl | F | H | H | $CH_3$ | H | H |
| imidazolyl | F | H | H | F | H | H |
| imidazolyl | F | H | H | H | H | $OCH_3$ |
| imidazolyl | F | H | H | H | $OCH_3$ | H |
| imidazolyl | H | $CF_3$ | H | $CH_3$ | H | H |
| imidazolyl | H | $CF_3$ | H | F | H | H |
| imidazolyl | H | $CF_3$ | H | H | H | $OCH_3$ |
| imidazolyl | H | $CF_3$ | H | H | $OCF_2H$ | H |
| imidazolyl | H | $CH_3$ | H | $CH_3$ | H | H |
| imidazolyl | H | $CH_3$ | H | F | H | H |
| imidazolyl | H | $CH_3$ | H | H | H | $OCH_3$ |
| imidazolyl | H | $CH_3$ | H | H | $OCF_2H$ | H |
| imidazolyl | H | $OCF_2H$ | H | $CH_3$ | H | H |
| imidazolyl | H | $OCF_2H$ | H | F | H | H |
| imidazolyl | H | $OCF_2H$ | H | H | H | $OCH_3$ |
| imidazolyl | H | $OCF_2H$ | H | H | $OCF_2H$ | H |
| imidazolyl | $OCF_2H$ | H | F | H | H | H |
| imidazolyl | $OCF_2H$ | H | H | $CH_3$ | H | H |
| imidazolyl | $OCF_2H$ | H | F | H | H | H |
| imidazolyl | $OCF_2H$ | H | H | H | H | $OCH_3$ |
| imidazolyl | $OCF_2H$ | H | H | H | $OCF_2H$ | H |
| imidazolyl | $OCF_2H$ | H | H | H | $OCH_3$ | H |
| imidazolyl | $OCH_3$ | H | F | H | H | H |
| imidazolyl | $OCH_3$ | H | H | $CH_3$ | H | H |
| imidazolyl | $OCH_3$ | H | H | F | H | H |
| imidazolyl | $OCH_3$ | H | H | H | H | H |
| imidazolyl | $OCH_3$ | H | H | H | H | $OCH_3$ |
| imidazolyl | $OCH_3$ | H | H | H | $OCF_2H$ | H |
| imidazolyl | $OCH_3$ | H | H | H | $OCH_3$ | H |
| oxazol-5-yl | $CF_3$ | H | H | $CH_3$ | H | H |
| oxazol-5-yl | $CF_3$ | H | H | F | H | H |
| oxazol-5-yl | $CF_3$ | H | H | H | H | $OCH_3$ |
| oxazol-5-yl | $CF_3$ | H | H | H | $OCF_2H$ | H |
| oxazol-5-yl | $CF_3$ | H | H | H | $OCH_3$ | H |
| oxazol-5-yl | $CH_3$ | H | F | H | H | H |
| oxazol-5-yl | $CH_3$ | H | H | $CH_3$ | H | H |
| oxazol-5-yl | $CH_3$ | H | H | F | H | H |
| oxazol-5-yl | $CH_3$ | H | H | H | H | $OCH_3$ |
| oxazol-5-yl | $CH_3$ | H | H | H | $OCF_2H$ | H |
| oxazol-5-yl | $CH_3$ | H | H | H | $OCH_3$ | H |
| oxazol-5-yl | Cl | H | F | H | F | H |
| oxazol-5-yl | Cl | H | F | H | H | H |
| oxazol-5-yl | Cl | H | H | $CH_3$ | H | H |
| oxazol-5-yl | Cl | H | H | F | H | H |
| oxazol-5-yl | Cl | H | H | H | Cl | H |
| oxazol-5-yl | Cl | H | H | H | F | H |
| oxazol-5-yl | Cl | H | H | H | H | H |
| oxazol-5-yl | Cl | H | H | H | H | $OCF_2H$ |
| oxazol-5-yl | Cl | H | H | H | H | $OCH_3$ |
| oxazol-5-yl | Cl | H | H | H | $OCF_2H$ | H |
| oxazol-5-yl | Cl | H | H | H | $OCH_3$ | H |
| oxazol-5-yl | F | H | H | $CH_3$ | H | H |
| oxazol-5-yl | F | H | H | F | H | H |
| oxazol-5-yl | F | H | H | H | H | $OCH_3$ |
| oxazol-5-yl | F | H | H | H | $OCF_2H$ | H |
| oxazol-5-yl | F | H | H | H | $OCH_3$ | H |
| oxazol-5-yl | H | $CF_3$ | H | $CH_3$ | H | H |
| oxazol-5-yl | H | $CF_3$ | H | F | H | H |
| oxazol-5-yl | H | $CF_3$ | H | H | H | $OCH_3$ |
| oxazol-5-yl | H | $CF_3$ | H | H | $OCF_2H$ | H |
| oxazol-5-yl | H | $CH_3$ | H | $CH_3$ | H | H |
| oxazol-5-yl | H | $CH_3$ | H | F | H | H |
| oxazol-5-yl | H | $CH_3$ | H | H | H | $OCH_3$ |
| oxazol-5-yl | H | $CH_3$ | H | H | $OCF_2H$ | H |
| oxazol-5-yl | H | $OCF_2H$ | H | $CH_3$ | H | H |
| oxazol-5-yl | H | $OCF_2H$ | H | F | H | H |
| oxazol-5-yl | H | $OCF_2H$ | H | H | H | $OCH_3$ |
| oxazol-5-yl | H | $OCF_2H$ | H | H | $OCF_2H$ | H |
| oxazol-5-yl | $OCF_2H$ | H | H | F | H | H |
| oxazol-5-yl | $OCF_2H$ | H | H | $CH_3$ | H | H |
| oxazol-5-yl | $OCF_2H$ | H | H | F | H | H |
| oxazol-5-yl | $OCF_2H$ | H | H | H | H | $OCH_3$ |
| oxazol-5-yl | $OCF_2H$ | H | H | H | $OCF_2H$ | H |
| oxazol-5-yl | $OCF_2H$ | H | H | H | $OCH_3$ | H |
| oxazol-5-yl | $OCH_3$ | H | F | H | H | H |
| oxazol-5-yl | $OCH_3$ | H | H | $CH_3$ | H | H |
| oxazol-5-yl | $OCH_3$ | H | H | F | H | H |
| oxazol-5-yl | $OCH_3$ | H | H | H | H | H |
| oxazol-5-yl | $OCH_3$ | H | H | H | H | $OCH_3$ |
| oxazol-5-yl | $OCH_3$ | H | H | H | $OCF_2H$ | H |
| oxazol-5-yl | $OCH_3$ | H | H | H | $OCH_3$ | H |
| pyridine-4-yl | $CF_3$ | H | H | $CH_3$ | H | H |
| pyridine-4-yl | $CF_3$ | H | H | F | H | H |
| pyridine-4-yl | $CF_3$ | H | H | H | H | $OCH_3$ |
| pyridine-4-yl | $CF_3$ | H | H | H | $OCF_2H$ | H |
| pyridine-4-yl | $CF_3$ | H | H | H | $OCH_3$ | H |
| pyridine-4-yl | $CH_3$ | H | H | F | H | H |
| pyridine-4-yl | $CH_3$ | H | H | $CH_3$ | H | H |
| pyridine-4-yl | $CH_3$ | H | H | F | H | H |
| pyridine-4-yl | $CH_3$ | H | H | H | H | $OCH_3$ |
| pyridine-4-yl | $CH_3$ | H | H | H | $OCF_2H$ | H |
| pyridine-4-yl | $CH_3$ | H | H | H | $OCH_3$ | H |
| pyridine-4-yl | Cl | H | F | H | H | H |
| pyridine-4-yl | Cl | H | H | $CH_3$ | H | H |
| pyridine-4-yl | Cl | H | H | F | H | H |
| pyridine-4-yl | Cl | H | H | H | H | H |
| pyridine-4-yl | Cl | H | H | H | H | $OCF_2H$ |
| pyridine-4-yl | Cl | H | H | H | H | $OCH_3$ |
| pyridine-4-yl | Cl | H | H | H | $OCF_2H$ | H |
| pyridine-4-yl | Cl | H | H | H | $OCH_3$ | H |
| pyridine-4-yl | F | H | H | $CH_3$ | H | H |
| pyridine-4-yl | F | H | H | F | H | H |
| pyridine-4-yl | F | H | H | H | H | $OCH_3$ |
| pyridine-4-yl | F | H | H | H | $OCF_2H$ | H |
| pyridine-4-yl | F | H | H | H | $OCH_3$ | H |
| pyridine-4-yl | H | $CF_3$ | H | $CH_3$ | H | H |
| pyridine-4-yl | H | $CF_3$ | H | F | H | H |
| pyridine-4-yl | H | $CF_3$ | H | H | H | $OCH_3$ |
| pyridine-4-yl | H | $CF_3$ | H | H | $OCF_2H$ | H |
| pyridine-4-yl | H | $CH_3$ | H | $CH_3$ | H | H |
| pyridine-4-yl | H | $CH_3$ | H | F | H | H |
| pyridine-4-yl | H | $CH_3$ | H | H | H | $OCH_3$ |
| pyridine-4-yl | H | $CH_3$ | H | H | $OCF_2H$ | H |
| pyridine-4-yl | H | $OCF_2H$ | H | $CH_3$ | H | H |
| pyridine-4-yl | H | $OCF_2H$ | H | F | H | H |
| pyridine-4-yl | H | $OCF_2H$ | H | H | H | $OCH_3$ |
| pyridine-4-yl | H | $OCF_2H$ | H | H | $OCF_2H$ | H |
| pyridine-4-yl | $OCF_2H$ | H | F | H | $CH_3$ | H |
| pyridine-4-yl | $OCF_2H$ | H | H | F | H | H |
| pyridine-4-yl | $OCF_2H$ | H | H | H | H | $OCH_3$ |
| pyridine-4-yl | $OCF_2H$ | H | H | H | $OCF_2H$ | H |
| pyridine-4-yl | $OCF_2H$ | H | H | H | $OCH_3$ | H |

TABLE 5-continued

| A | $R_1$ | $R_{12}$ | $R_2^{IV}$ | $R_3^{IV}$ | $R_4^{IV}$ | $R_5^{IV}$ |
|---|---|---|---|---|---|---|
| pyridine-4-yl | OCH$_3$ | H | F | H | H | H |
| pyridine-4-yl | OCH$_3$ | H | H | CH$_3$ | H | H |
| pyridine-4-yl | OCH$_3$ | H | H | F | H | H |
| pyridine-4-yl | OCH$_3$ | H | H | H | H | H |
| pyridine-4-yl | OCH$_3$ | H | H | H | H | OCH$_3$ |
| pyridine-4-yl | OCH$_3$ | H | H | H | OCF$_2$H | H |
| pyridine-4-yl | OCH$_3$ | H | H | H | OCH$_3$ | H |

Preferably, the compound of formula (If)

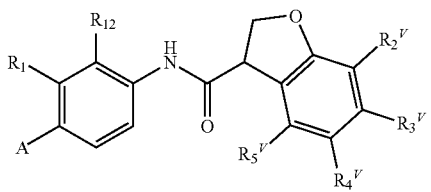

is selected from the group consisting of compounds of the formula (I), wherein A, $R_1$, $R_{12}$, $R_2^V$, $R_3^V$, $R_4^V$ and $R_5^V$ are as indicated in Table 6:

TABLE 6

| A | $R_1$ | $R_{12}$ | $R_2^V$ | $R_3^V$ | $R_4^V$ | $R_5^V$ |
|---|---|---|---|---|---|---|
| 1,2,4-triazol-1-yl | CF$_3$ | H | H | CH$_3$ | H | H |
| 1,2,4-triazol-1-yl | CF$_3$ | H | H | F | H | H |
| 1,2,4-triazol-1-yl | CF$_3$ | H | H | H | H | OCH$_3$ |
| 1,2,4-triazol-1-yl | CF$_3$ | H | H | H | OCF$_2$H | H |
| 1,2,4-triazol-1-yl | CF$_3$ | H | H | H | OCH$_3$ | H |
| 1,2,4-triazol-1-yl | CH$_3$ | H | F | H | H | H |
| 1,2,4-triazol-1-yl | CH$_3$ | H | H | CH$_3$ | H | H |
| 1,2,4-triazol-1-yl | CH$_3$ | H | H | F | H | H |
| 1,2,4-triazol-1-yl | CH$_3$ | H | H | H | H | OCH$_3$ |
| 1,2,4-triazol-1-yl | CH$_3$ | H | H | H | OCF$_2$H | H |
| 1,2,4-triazol-1-yl | CH$_3$ | H | H | H | OCH$_3$ | H |
| 1,2,4-triazol-1-yl | Cl | H | F | H | H | H |
| 1,2,4-triazol-1-yl | Cl | H | H | CH$_3$ | H | H |
| 1,2,4-triazol-1-yl | Cl | H | H | F | H | H |
| 1,2,4-triazol-1-yl | Cl | H | H | H | H | H |
| 1,2,4-triazol-1-yl | Cl | H | H | H | H | OCF$_2$H |
| 1,2,4-triazol-1-yl | Cl | H | H | H | H | OCH$_3$ |
| 1,2,4-triazol-1-yl | Cl | H | H | H | OCF$_2$H | H |
| 1,2,4-triazol-1-yl | Cl | H | H | H | OCH$_3$ | H |
| 1,2,4-triazol-1-yl | F | H | H | CH$_3$ | H | H |
| 1,2,4-triazol-1-yl | F | H | H | F | H | H |
| 1,2,4-triazol-1-yl | F | H | H | H | H | OCH$_3$ |
| 1,2,4-triazol-1-yl | F | H | H | H | OCF$_2$H | H |
| 1,2,4-triazol-1-yl | F | H | H | H | OCH$_3$ | H |
| 1,2,4-triazol-1-yl | H | CF$_3$ | H | CH$_3$ | H | H |
| 1,2,4-triazol-1-yl | H | CF$_3$ | H | F | H | H |
| 1,2,4-triazol-1-yl | H | CF$_3$ | H | H | H | OCH$_3$ |
| 1,2,4-triazol-1-yl | H | CF$_3$ | H | H | OCF$_2$H | H |
| 1,2,4-triazol-1-yl | H | CH$_3$ | H | CH$_3$ | H | H |
| 1,2,4-triazol-1-yl | H | CH$_3$ | H | F | H | H |
| 1,2,4-triazol-1-yl | H | CH$_3$ | H | H | H | OCH$_3$ |
| 1,2,4-triazol-1-yl | H | CH$_3$ | H | H | OCF$_2$H | H |
| 1,2,4-triazol-1-yl | H | OCF$_2$H | H | CH$_3$ | H | H |
| 1,2,4-triazol-1-yl | H | OCF$_2$H | H | F | H | H |
| 1,2,4-triazol-1-yl | H | OCF$_2$H | H | H | H | OCH$_3$ |
| 1,2,4-triazol-1-yl | H | OCF$_2$H | H | H | OCF$_2$H | H |
| 1,2,4-triazol-1-yl | OCF$_2$H | H | F | H | H | H |
| 1,2,4-triazol-1-yl | OCF$_2$H | H | H | CH$_3$ | H | H |
| 1,2,4-triazol-1-yl | OCF$_2$H | H | H | F | H | H |
| 1,2,4-triazol-1-yl | OCF$_2$H | H | H | H | H | OCH$_3$ |
| 1,2,4-triazol-1-yl | OCF$_2$H | H | H | H | OCF$_2$H | H |
| 1,2,4-triazol-1-yl | OCF$_2$H | H | H | H | OCH$_3$ | H |
| 1,2,4-triazol-1-yl | OCH$_3$ | H | F | H | H | H |
| 1,2,4-triazol-1-yl | OCH$_3$ | H | H | CH$_3$ | H | H |
| 1,2,4-triazol-1-yl | OCH$_3$ | H | H | F | H | H |
| 1,2,4-triazol-1-yl | OCH$_3$ | H | H | H | H | H |

TABLE 6-continued

| A | $R_1$ | $R_{12}$ | $R_2^V$ | $R_3^V$ | $R_4^V$ | $R_5^V$ |
|---|---|---|---|---|---|---|
| 1,2,4-triazol-1-yl | OCH$_3$ | H | H | H | H | OCH$_3$ |
| 1,2,4-triazol-1-yl | OCH$_3$ | H | H | H | OCF$_2$H | H |
| 1,2,4-triazol-1-yl | OCH$_3$ | H | H | H | OCH$_3$ | H |
| 1,3,4-oxadiazol-2-yl | CF$_3$ | H | H | CH$_3$ | H | H |
| 1,3,4-oxadiazol-2-yl | CF$_3$ | H | H | F | H | H |
| 1,3,4-oxadiazol-2-yl | CF$_3$ | H | H | H | H | OCH$_3$ |
| 1,3,4-oxadiazol-2-yl | CF$_3$ | H | H | H | OCF$_2$H | H |
| 1,3,4-oxadiazol-2-yl | CF$_3$ | H | H | H | OCH$_3$ | H |
| 1,3,4-oxadiazol-2-yl | CH$_3$ | H | F | H | H | H |
| 1,3,4-oxadiazol-2-yl | CH$_3$ | H | H | CH$_3$ | H | H |
| 1,3,4-oxadiazol-2-yl | CH$_3$ | H | H | F | H | H |
| 1,3,4-oxadiazol-2-yl | CH$_3$ | H | H | H | H | OCH$_3$ |
| 1,3,4-oxadiazol-2-yl | CH$_3$ | H | H | H | OCF$_2$H | H |
| 1,3,4-oxadiazol-2-yl | CH$_3$ | H | H | H | OCH$_3$ | H |
| 1,3,4-oxadiazol-2-yl | Cl | H | F | H | H | H |
| 1,3,4-oxadiazol-2-yl | Cl | H | H | CH$_3$ | H | H |
| 1,3,4-oxadiazol-2-yl | Cl | H | H | F | H | H |
| 1,3,4-oxadiazol-2-yl | Cl | H | H | H | H | H |
| 1,3,4-oxadiazol-2-yl | Cl | H | H | H | H | OCF$_2$H |
| 1,3,4-oxadiazol-2-yl | Cl | H | H | H | H | OCH$_3$ |
| 1,3,4-oxadiazol-2-yl | Cl | H | H | H | OCF$_2$H | H |
| 1,3,4-oxadiazol-2-yl | Cl | H | H | H | OCH$_3$ | H |
| 1,3,4-oxadiazol-2-yl | F | H | H | CH$_3$ | H | H |
| 1,3,4-oxadiazol-2-yl | F | H | H | F | H | H |
| 1,3,4-oxadiazol-2-yl | F | H | H | H | H | OCH$_3$ |
| 1,3,4-oxadiazol-2-yl | F | H | H | H | OCF$_2$H | H |
| 1,3,4-oxadiazol-2-yl | F | H | H | H | OCH$_3$ | H |
| 1,3,4-oxadiazol-2-yl | H | CF$_3$ | H | CH$_3$ | H | H |
| 1,3,4-oxadiazol-2-yl | H | CF$_3$ | H | F | H | H |
| 1,3,4-oxadiazol-2-yl | H | CF$_3$ | H | H | H | OCH$_3$ |
| 1,3,4-oxadiazol-2-yl | H | CF$_3$ | H | H | OCF$_2$H | H |
| 1,3,4-oxadiazol-2-yl | H | CH$_3$ | H | CH$_3$ | H | H |
| 1,3,4-oxadiazol-2-yl | H | CH$_3$ | H | F | H | H |
| 1,3,4-oxadiazol-2-yl | H | CH$_3$ | H | H | H | OCH$_3$ |
| 1,3,4-oxadiazol-2-yl | H | CH$_3$ | H | H | OCF$_2$H | H |
| 1,3,4-oxadiazol-2-yl | H | OCF$_2$H | H | CH$_3$ | H | H |
| 1,3,4-oxadiazol-2-yl | H | OCF$_2$H | H | F | H | H |
| 1,3,4-oxadiazol-2-yl | H | OCF$_2$H | H | H | H | OCH$_3$ |
| 1,3,4-oxadiazol-2-yl | H | OCF$_2$H | H | H | OCF$_2$H | H |
| 1,3,4-oxadiazol-2-yl | OCF$_2$H | H | F | H | H | H |
| 1,3,4-oxadiazol-2-yl | OCF$_2$H | H | H | CH$_3$ | H | H |
| 1,3,4-oxadiazol-2-yl | OCF$_2$H | H | H | F | H | H |
| 1,3,4-oxadiazol-2-yl | OCF$_2$H | H | H | H | H | OCH$_3$ |
| 1,3,4-oxadiazol-2-yl | OCF$_2$H | H | H | H | OCF$_2$H | H |
| 1,3,4-oxadiazol-2-yl | OCF$_2$H | H | H | H | OCH$_3$ | H |
| 1,3,4-oxadiazol-2-yl | OCH$_3$ | H | F | H | H | H |
| 1,3,4-oxadiazol-2-yl | OCH$_3$ | H | H | CH$_3$ | H | H |
| 1,3,4-oxadiazol-2-yl | OCH$_3$ | H | H | F | H | H |
| 1,3,4-oxadiazol-2-yl | OCH$_3$ | H | H | H | H | H |
| 1,3,4-oxadiazol-2-yl | OCH$_3$ | H | H | H | H | OCH$_3$ |
| 1,3,4-oxadiazol-2-yl | OCH$_3$ | H | H | H | OCF$_2$H | H |
| 1,3,4-oxadiazol-2-yl | OCH$_3$ | H | H | H | OCH$_3$ | H |
| 2-methyloxazol-5-yl | CF$_3$ | H | H | F | H | H |
| 2-methyloxazol-5-yl | CF$_3$ | H | H | H | H | OCH$_3$ |
| 2-methyloxazol-5-yl | CF$_3$ | H | H | H | OCH$_3$ | H |
| 2-methyloxazol-5-yl | CH$_3$ | H | H | F | H | H |
| 2-methyloxazol-5-yl | CH$_3$ | H | H | H | H | OCH$_3$ |
| 2-methyloxazol-5-yl | CH$_3$ | H | H | H | OCH$_3$ | H |
| 2-methyloxazol-5-yl | Cl | H | H | F | H | H |
| 2-methyloxazol-5-yl | Cl | H | H | H | H | H |
| 2-methyloxazol-5-yl | Cl | H | H | H | H | OCH$_3$ |
| 2-methyloxazol-5-yl | Cl | H | H | H | OCH$_3$ | H |
| 2-methyloxazol-5-yl | H | CF$_3$ | H | F | H | H |
| 2-methyloxazol-5-yl | H | CF$_3$ | H | H | H | OCH$_3$ |
| 2-methyloxazol-5-yl | H | CF$_3$ | H | H | OCF$_2$H | H |
| 2-methyloxazol-5-yl | H | CH$_3$ | H | F | H | H |
| 2-methyloxazol-5-yl | H | CH$_3$ | H | H | H | OCH$_3$ |
| 2-methyloxazol-5-yl | H | CH$_3$ | H | H | OCF$_2$H | H |
| 2-methyloxazol-5-yl | H | OCF$_2$H | H | F | H | H |
| 2-methyloxazol-5-yl | H | OCF$_2$H | H | H | H | OCH$_3$ |
| 2-methyloxazol-5-yl | H | OCF$_2$H | H | H | OCF$_2$H | H |
| 2-methyloxazol-5-yl | OCF$_2$H | H | H | F | H | H |
| 2-methyloxazol-5-yl | OCF$_2$H | H | H | H | H | OCH$_3$ |
| 2-methyloxazol-5-yl | OCF$_2$H | H | H | H | OCH$_3$ | H |
| 2-methyloxazol-5-yl | OCH$_3$ | H | H | F | H | H |
| 2-methyloxazol-5-yl | OCH$_3$ | H | H | H | H | H |
| 2-methyloxazol-5-yl | OCH$_3$ | H | H | H | H | OCH$_3$ |
| 2-methyloxazol-5-yl | OCH$_3$ | H | H | H | OCH$_3$ | H |

TABLE 6-continued

| A | $R_1$ | $R_{12}$ | $R_2^V$ | $R_3^V$ | $R_4^V$ | $R_5^V$ |
|---|---|---|---|---|---|---|
| imidazolyl | $CF_3$ | H | H | $CH_3$ | H | H |
| imidazolyl | $CF_3$ | H | H | F | H | H |
| imidazolyl | $CF_3$ | H | H | H | H | $OCH_3$ |
| imidazolyl | $CF_3$ | H | H | H | $OCF_2H$ | H |
| imidazolyl | $CF_3$ | H | H | H | $OCH_3$ | H |
| imidazolyl | $CH_3$ | H | H | F | H | H |
| imidazolyl | $CH_3$ | H | H | H | H | $OCH_3$ |
| imidazolyl | $CH_3$ | H | H | H | $OCF_2H$ | H |
| imidazolyl | $CH_3$ | H | H | H | $OCH_3$ | H |
| imidazolyl | Cl | H | F | H | H | H |
| imidazolyl | Cl | H | H | $CH_3$ | H | H |
| imidazolyl | Cl | H | H | F | H | H |
| imidazolyl | Cl | H | H | H | H | H |
| imidazolyl | Cl | H | H | H | H | $OCF_2H$ |
| imidazolyl | Cl | H | H | H | H | $OCH_3$ |
| imidazolyl | Cl | H | H | H | $OCF_2H$ | H |
| imidazolyl | Cl | H | H | H | $OCH_3$ | H |
| imidazolyl | F | H | H | $CH_3$ | H | H |
| imidazolyl | F | H | H | F | H | H |
| imidazolyl | F | H | H | H | H | $OCH_3$ |
| imidazolyl | F | H | H | H | $OCF_2H$ | H |
| imidazolyl | F | H | H | H | $OCH_3$ | H |
| imidazolyl | H | $CF_3$ | H | $CH_3$ | H | H |
| imidazolyl | H | $CF_3$ | H | F | H | H |
| imidazolyl | H | $CF_3$ | H | H | H | $OCH_3$ |
| imidazolyl | H | $CF_3$ | H | H | $OCF_2H$ | H |
| imidazolyl | H | $CH_3$ | H | $CH_3$ | H | H |
| imidazolyl | H | $CH_3$ | H | F | H | H |
| imidazolyl | H | $CH_3$ | H | H | H | $OCH_3$ |
| imidazolyl | H | $CH_3$ | H | H | $OCF_2H$ | H |
| imidazolyl | H | $OCF_2H$ | H | $CH_3$ | H | H |
| imidazolyl | H | $OCF_2H$ | H | F | H | H |
| imidazolyl | H | $OCF_2H$ | H | H | H | $OCH_3$ |
| imidazolyl | H | $OCF_2H$ | H | H | $OCF_2H$ | H |
| imidazolyl | $OCF_2H$ | H | F | H | H | H |
| imidazolyl | $OCF_2H$ | H | H | $CH_3$ | H | H |
| imidazolyl | $OCF_2H$ | H | H | F | H | H |
| imidazolyl | $OCF_2H$ | H | H | H | H | $OCH_3$ |
| imidazolyl | $OCF_2H$ | H | H | H | $OCF_2H$ | H |
| imidazolyl | $OCF_2H$ | H | H | H | $OCH_3$ | H |
| imidazolyl | $OCH_3$ | H | F | H | H | H |
| imidazolyl | $OCH_3$ | H | H | $CH_3$ | H | H |
| imidazolyl | $OCH_3$ | H | H | F | H | H |
| imidazolyl | $OCH_3$ | H | H | H | H | H |
| imidazolyl | $OCH_3$ | H | H | H | H | $OCH_3$ |
| imidazolyl | $OCH_3$ | H | H | H | $OCF_2H$ | H |
| imidazolyl | $OCH_3$ | H | H | H | $OCH_3$ | H |
| oxazol-5-yl | $CF_3$ | H | H | $CH_3$ | H | H |
| oxazol-5-yl | $CF_3$ | H | H | F | H | H |
| oxazol-5-yl | $CF_3$ | H | H | H | H | $OCH_3$ |
| oxazol-5-yl | $CF_3$ | H | H | H | $OCF_2H$ | H |
| oxazol-5-yl | $CF_3$ | H | H | H | $OCH_3$ | H |
| oxazol-5-yl | $CH_3$ | H | F | H | H | H |
| oxazol-5-yl | $CH_3$ | H | H | $CH_3$ | H | H |
| oxazol-5-yl | $CH_3$ | H | H | F | H | H |
| oxazol-5-yl | $CH_3$ | H | H | H | H | $OCH_3$ |
| oxazol-5-yl | $CH_3$ | H | H | H | $OCF_2H$ | H |
| oxazol-5-yl | $CH_3$ | H | H | H | $OCH_3$ | H |
| oxazol-5-yl | Cl | H | F | H | F | H |
| oxazol-5-yl | Cl | H | F | H | H | H |
| oxazol-5-yl | Cl | H | H | $CH_3$ | H | H |
| oxazol-5-yl | Cl | H | H | F | H | H |
| oxazol-5-yl | Cl | H | H | H | Cl | H |
| oxazol-5-yl | Cl | H | H | H | F | H |
| oxazol-5-yl | Cl | H | H | H | H | H |
| oxazol-5-yl | Cl | H | H | H | H | $OCF_2H$ |
| oxazol-5-yl | Cl | H | H | H | H | $OCH_3$ |
| oxazol-5-yl | Cl | H | H | H | $OCF_2H$ | H |
| oxazol-5-yl | Cl | H | H | H | $OCH_3$ | H |
| oxazol-5-yl | F | H | H | $CH_3$ | H | H |
| oxazol-5-yl | F | H | H | F | H | H |
| oxazol-5-yl | F | H | H | H | H | $OCH_3$ |
| oxazol-5-yl | F | H | H | H | $OCF_2H$ | H |
| oxazol-5-yl | F | H | H | H | $OCH_3$ | H |
| oxazol-5-yl | H | $CF_3$ | H | $CH_3$ | H | H |
| oxazol-5-yl | H | $CF_3$ | H | F | H | H |
| oxazol-5-yl | H | $CF_3$ | H | H | H | $OCH_3$ |
| oxazol-5-yl | H | $CF_3$ | H | H | $OCF_2H$ | H |
| oxazol-5-yl | H | $CH_3$ | H | $CH_3$ | H | H |
| oxazol-5-yl | H | $CH_3$ | H | F | H | H |
| oxazol-5-yl | H | $CH_3$ | H | H | H | $OCH_3$ |
| oxazol-5-yl | H | $CH_3$ | H | H | $OCF_2H$ | H |
| oxazol-5-yl | H | $OCF_2H$ | H | $CH_3$ | H | H |
| oxazol-5-yl | H | $OCF_2H$ | H | F | H | H |
| oxazol-5-yl | H | $OCF_2H$ | H | H | H | $OCH_3$ |
| oxazol-5-yl | H | $OCF_2H$ | H | H | $OCF_2H$ | H |
| oxazol-5-yl | $OCF_2H$ | H | F | H | H | H |
| oxazol-5-yl | $OCF_2H$ | H | H | $CH_3$ | H | H |
| oxazol-5-yl | $OCF_2H$ | H | H | F | H | H |
| oxazol-5-yl | $OCF_2H$ | H | H | H | H | $OCH_3$ |
| oxazol-5-yl | $OCF_2H$ | H | H | H | $OCF_2H$ | H |
| oxazol-5-yl | $OCF_2H$ | H | H | H | $OCH_3$ | H |
| oxazol-5-yl | $OCH_3$ | H | F | H | H | H |
| oxazol-5-yl | $OCH_3$ | H | H | $CH_3$ | H | H |
| oxazol-5-yl | $OCH_3$ | H | H | F | H | H |
| oxazol-5-yl | $OCH_3$ | H | H | H | H | H |
| oxazol-5-yl | $OCH_3$ | H | H | H | H | $OCH_3$ |
| oxazol-5-yl | $OCH_3$ | H | H | H | $OCF_2H$ | H |
| oxazol-5-yl | $OCH_3$ | H | H | H | $OCH_3$ | H |
| pyridine-4-yl | $CF_3$ | H | H | $CH_3$ | H | H |
| pyridine-4-yl | $CF_3$ | H | H | F | H | H |
| pyridine-4-yl | $CF_3$ | H | H | H | H | $OCH_3$ |
| pyridine-4-yl | $CF_3$ | H | H | H | $OCF_2H$ | H |
| pyridine-4-yl | $CF_3$ | H | H | H | $OCH_3$ | H |
| pyridine-4-yl | $CH_3$ | H | F | H | H | H |
| pyridine-4-yl | $CH_3$ | H | H | $CH_3$ | H | H |
| pyridine-4-yl | $CH_3$ | H | H | F | H | H |
| pyridine-4-yl | $CH_3$ | H | H | H | H | $OCH_3$ |
| pyridine-4-yl | $CH_3$ | H | H | H | $OCF_2H$ | H |
| pyridine-4-yl | $CH_3$ | H | H | H | $OCH_3$ | H |
| pyridine-4-yl | Cl | H | F | H | H | H |
| pyridine-4-yl | Cl | H | H | $CH_3$ | H | H |
| pyridine-4-yl | Cl | H | H | F | H | H |
| pyridine-4-yl | Cl | H | H | H | H | H |
| pyridine-4-yl | Cl | H | H | H | H | $OCF_2H$ |
| pyridine-4-yl | Cl | H | H | H | H | $OCH_3$ |
| pyridine-4-yl | Cl | H | H | H | $OCF_2H$ | H |
| pyridine-4-yl | Cl | H | H | H | $OCH_3$ | H |
| pyridine-4-yl | F | H | H | $CH_3$ | H | H |
| pyridine-4-yl | F | H | H | F | H | H |
| pyridine-4-yl | F | H | H | H | H | $OCH_3$ |
| pyridine-4-yl | F | H | H | H | $OCF_2H$ | H |
| pyridine-4-yl | F | H | H | H | $OCH_3$ | H |
| pyridine-4-yl | H | $CF_3$ | H | $CH_3$ | H | H |
| pyridine-4-yl | H | $CF_3$ | H | F | H | H |
| pyridine-4-yl | H | $CF_3$ | H | H | H | $OCH_3$ |
| pyridine-4-yl | H | $CF_3$ | H | H | $OCF_2H$ | H |
| pyridine-4-yl | H | $CH_3$ | H | $CH_3$ | H | H |
| pyridine-4-yl | H | $CH_3$ | H | F | H | H |
| pyridine-4-yl | H | $CH_3$ | H | H | H | $OCH_3$ |
| pyridine-4-yl | H | $CH_3$ | H | H | $OCF_2H$ | H |
| pyridine-4-yl | H | $OCF_2H$ | H | $CH_3$ | H | H |
| pyridine-4-yl | H | $OCF_2H$ | H | F | H | H |
| pyridine-4-yl | H | $OCF_2H$ | H | H | H | $OCH_3$ |
| pyridine-4-yl | H | $OCF_2H$ | H | H | $OCF_2H$ | H |
| pyridine-4-yl | $OCF_2H$ | H | F | H | H | H |
| pyridine-4-yl | $OCF_2H$ | H | H | $CH_3$ | H | H |
| pyridine-4-yl | $OCF_2H$ | H | H | F | H | H |
| pyridine-4-yl | $OCF_2H$ | H | H | H | H | $OCH_3$ |
| pyridine-4-yl | $OCF_2H$ | H | H | H | $OCF_2H$ | H |
| pyridine-4-yl | $OCF_2H$ | H | H | H | $OCH_3$ | H |
| pyridine-4-yl | $OCH_3$ | H | F | H | H | H |
| pyridine-4-yl | $OCH_3$ | H | H | $CH_3$ | H | H |
| pyridine-4-yl | $OCH_3$ | H | H | F | H | H |
| pyridine-4-yl | $OCH_3$ | H | H | H | H | H |
| pyridine-4-yl | $OCH_3$ | H | H | H | H | $OCH_3$ |
| pyridine-4-yl | $OCH_3$ | H | H | H | $OCF_2H$ | H |
| pyridine-4-yl | $OCH_3$ | H | H | H | $OCH_3$ | H |

Preferably, the compound of formula (Ig)

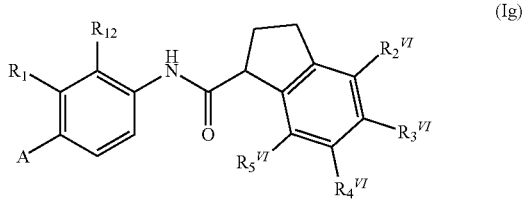

is selected from the group consisting of compounds of the formula (I), wherein A, $R_1$, $R_{12}$, $R_2^{VI}$, $R_3^{VI}$, $R_4^{VI}$ and $R_5^{VI}$ are as indicated in Table 7:

TABLE 7

| A | $R_1$ | $R_{12}$ | $R_2^{VI}$ | $R_3^{VI}$ | $R_4^{VI}$ | $R_5^{VI}$ |
|---|---|---|---|---|---|---|
| 1,2,4-triazol-1-yl | $CF_3$ | H | H | $CH_3$ | H | H |
| 1,2,4-triazol-1-yl | $CF_3$ | H | H | F | H | H |
| 1,2,4-triazol-1-yl | $CF_3$ | H | H | H | H | $OCH_3$ |
| 1,2,4-triazol-1-yl | $CF_3$ | H | H | H | $OCF_2H$ | H |
| 1,2,4-triazol-1-yl | $CF_3$ | H | H | H | $OCH_3$ | H |
| 1,2,4-triazol-1-yl | $CH_3$ | H | F | H | H | H |
| 1,2,4-triazol-1-yl | $CH_3$ | H | H | $CH_3$ | H | H |
| 1,2,4-triazol-1-yl | $CH_3$ | H | H | F | H | H |
| 1,2,4-triazol-1-yl | $CH_3$ | H | H | H | H | $OCH_3$ |
| 1,2,4-triazol-1-yl | $CH_3$ | H | H | H | $OCF_2H$ | H |
| 1,2,4-triazol-1-yl | $CH_3$ | H | H | H | $OCH_3$ | H |
| 1,2,4-triazol-1-yl | Cl | H | F | H | H | H |
| 1,2,4-triazol-1-yl | Cl | H | H | $CH_3$ | H | H |
| 1,2,4-triazol-1-yl | Cl | H | H | F | H | H |
| 1,2,4-triazol-1-yl | Cl | H | H | H | H | H |
| 1,2,4-triazol-1-yl | Cl | H | H | H | H | $OCF_2H$ |
| 1,2,4-triazol-1-yl | Cl | H | H | H | H | $OCH_3$ |
| 1,2,4-triazol-1-yl | Cl | H | H | H | $OCF_2H$ | H |
| 1,2,4-triazol-1-yl | Cl | H | H | H | $OCH_3$ | H |
| 1,2,4-triazol-1-yl | F | H | H | $CH_3$ | H | H |
| 1,2,4-triazol-1-yl | F | H | H | F | H | H |
| 1,2,4-triazol-1-yl | F | H | H | H | H | $OCH_3$ |
| 1,2,4-triazol-1-yl | F | H | H | H | $OCF_2H$ | H |
| 1,2,4-triazol-1-yl | F | H | H | H | $OCH_3$ | H |
| 1,2,4-triazol-1-yl | H | $CF_3$ | H | $CH_3$ | H | H |
| 1,2,4-triazol-1-yl | H | $CF_3$ | H | F | H | H |
| 1,2,4-triazol-1-yl | H | $CF_3$ | H | H | H | $OCH_3$ |
| 1,2,4-triazol-1-yl | H | $CF_3$ | H | H | $OCF_2H$ | H |
| 1,2,4-triazol-1-yl | H | $CH_3$ | H | $CH_3$ | H | H |
| 1,2,4-triazol-1-yl | H | $CH_3$ | H | F | H | H |
| 1,2,4-triazol-1-yl | H | $CH_3$ | H | H | H | $OCH_3$ |
| 1,2,4-triazol-1-yl | H | $CH_3$ | H | H | $OCF_2H$ | H |
| 1,2,4-triazol-1-yl | H | $OCF_2H$ | H | $CH_3$ | H | H |
| 1,2,4-triazol-1-yl | H | $OCF_2H$ | H | F | H | H |
| 1,2,4-triazol-1-yl | H | $OCF_2H$ | H | H | H | $OCH_3$ |
| 1,2,4-triazol-1-yl | H | $OCF_2H$ | H | H | $OCF_2H$ | H |
| 1,2,4-triazol-1-yl | $OCF_2H$ | H | F | H | H | H |
| 1,2,4-triazol-1-yl | $OCF_2H$ | H | H | $CH_3$ | H | H |
| 1,2,4-triazol-1-yl | $OCF_2H$ | H | H | F | H | H |
| 1,2,4-triazol-1-yl | $OCF_2H$ | H | H | H | H | $OCH_3$ |
| 1,2,4-triazol-1-yl | $OCF_2H$ | H | H | H | $OCF_2H$ | H |
| 1,2,4-triazol-1-yl | $OCF_2H$ | H | H | H | $OCH_3$ | H |
| 1,2,4-triazol-1-yl | $OCH_3$ | H | F | H | H | H |
| 1,2,4-triazol-1-yl | $OCH_3$ | H | H | $CH_3$ | H | H |
| 1,2,4-triazol-1-yl | $OCH_3$ | H | H | F | H | H |
| 1,2,4-triazol-1-yl | $OCH_3$ | H | H | H | H | H |
| 1,2,4-triazol-1-yl | $OCH_3$ | H | H | H | H | $OCH_3$ |
| 1,2,4-triazol-1-yl | $OCH_3$ | H | H | H | $OCF_2H$ | H |
| 1,2,4-triazol-1-yl | $OCH_3$ | H | H | H | $OCH_3$ | H |
| 1,3,4-oxadiazol-2-yl | $CF_3$ | H | H | $CH_3$ | H | H |
| 1,3,4-oxadiazol-2-yl | $CF_3$ | H | H | F | H | H |
| 1,3,4-oxadiazol-2-yl | $CF_3$ | H | H | H | H | $OCH_3$ |
| 1,3,4-oxadiazol-2-yl | $CF_3$ | H | H | H | $OCF_2H$ | H |
| 1,3,4-oxadiazol-2-yl | $CF_3$ | H | H | H | $OCH_3$ | H |
| 1,3,4-oxadiazol-2-yl | $CH_3$ | H | F | H | H | H |
| 1,3,4-oxadiazol-2-yl | $CH_3$ | H | H | $CH_3$ | H | H |
| 1,3,4-oxadiazol-2-yl | $CH_3$ | H | H | F | H | H |
| 1,3,4-oxadiazol-2-yl | $CH_3$ | H | H | H | H | $OCH_3$ |
| 1,3,4-oxadiazol-2-yl | $CH_3$ | H | H | H | $OCF_2H$ | H |
| 1,3,4-oxadiazol-2-yl | $CH_3$ | H | H | H | $OCH_3$ | H |
| 1,3,4-oxadiazol-2-yl | Cl | H | F | H | H | H |
| 1,3,4-oxadiazol-2-yl | Cl | H | H | $CH_3$ | H | H |
| 1,3,4-oxadiazol-2-yl | Cl | H | H | F | H | H |
| 1,3,4-oxadiazol-2-yl | Cl | H | H | H | H | H |
| 1,3,4-oxadiazol-2-yl | Cl | H | H | H | H | $OCF_2H$ |
| 1,3,4-oxadiazol-2-yl | Cl | H | H | H | H | $OCH_3$ |
| 1,3,4-oxadiazol-2-yl | Cl | H | H | H | $OCF_2H$ | H |
| 1,3,4-oxadiazol-2-yl | Cl | H | H | H | $OCH_3$ | H |
| 1,3,4-oxadiazol-2-yl | F | H | H | $CH_3$ | H | H |
| 1,3,4-oxadiazol-2-yl | F | H | H | F | H | H |
| 1,3,4-oxadiazol-2-yl | F | H | H | H | H | $OCH_3$ |
| 1,3,4-oxadiazol-2-yl | F | H | H | H | $OCF_2H$ | H |
| 1,3,4-oxadiazol-2-yl | F | H | H | H | $OCH_3$ | H |
| 1,3,4-oxadiazol-2-yl | H | $CF_3$ | H | $CH_3$ | H | H |
| 1,3,4-oxadiazol-2-yl | H | $CF_3$ | H | F | H | H |
| 1,3,4-oxadiazol-2-yl | H | $CF_3$ | H | H | H | $OCH_3$ |
| 1,3,4-oxadiazol-2-yl | H | $CF_3$ | H | H | $OCF_2H$ | H |
| 1,3,4-oxadiazol-2-yl | H | $CH_3$ | H | $CH_3$ | H | H |
| 1,3,4-oxadiazol-2-yl | H | $CH_3$ | H | F | H | H |
| 1,3,4-oxadiazol-2-yl | H | $CH_3$ | H | H | H | $OCH_3$ |
| 1,3,4-oxadiazol-2-yl | H | $CH_3$ | H | H | $OCF_2H$ | H |
| 1,3,4-oxadiazol-2-yl | H | $OCF_2H$ | H | $CH_3$ | H | H |
| 1,3,4-oxadiazol-2-yl | H | $OCF_2H$ | H | F | H | H |
| 1,3,4-oxadiazol-2-yl | H | $OCF_2H$ | H | H | H | $OCH_3$ |
| 1,3,4-oxadiazol-2-yl | H | $OCF_2H$ | H | H | $OCF_2H$ | H |
| 1,3,4-oxadiazol-2-yl | $OCF_2H$ | H | F | H | H | H |
| 1,3,4-oxadiazol-2-yl | $OCF_2H$ | H | H | $CH_3$ | H | H |
| 1,3,4-oxadiazol-2-yl | $OCF_2H$ | H | H | F | H | H |
| 1,3,4-oxadiazol-2-yl | $OCF_2H$ | H | H | H | H | $OCH_3$ |
| 1,3,4-oxadiazol-2-yl | $OCF_2H$ | H | H | H | $OCF_2H$ | H |
| 1,3,4-oxadiazol-2-yl | $OCF_2H$ | H | H | H | $OCH_3$ | H |
| 1,3,4-oxadiazol-2-yl | $OCH_3$ | H | F | H | H | H |
| 1,3,4-oxadiazol-2-yl | $OCH_3$ | H | H | $CH_3$ | H | H |
| 1,3,4-oxadiazol-2-yl | $OCH_3$ | H | H | F | H | H |
| 1,3,4-oxadiazol-2-yl | $OCH_3$ | H | H | H | H | H |
| 1,3,4-oxadiazol-2-yl | $OCH_3$ | H | H | H | H | $OCH_3$ |
| 1,3,4-oxadiazol-2-yl | $OCH_3$ | H | H | H | $OCF_2H$ | H |
| 1,3,4-oxadiazol-2-yl | $OCH_3$ | H | H | H | $OCH_3$ | H |
| 2-methyloxazol-5-yl | $CF_3$ | H | H | F | H | H |
| 2-methyloxazol-5-yl | $CF_3$ | H | H | H | H | $OCH_3$ |
| 2-methyloxazol-5-yl | $CF_3$ | H | H | H | $OCH_3$ | H |
| 2-methyloxazol-5-yl | $CH_3$ | H | H | F | H | H |
| 2-methyloxazol-5-yl | $CH_3$ | H | H | H | H | $OCH_3$ |
| 2-methyloxazol-5-yl | $CH_3$ | H | H | H | $OCH_3$ | H |
| 2-methyloxazol-5-yl | Cl | H | H | F | H | H |
| 2-methyloxazol-5-yl | Cl | H | H | H | H | H |
| 2-methyloxazol-5-yl | Cl | H | H | H | H | $OCH_3$ |
| 2-methyloxazol-5-yl | Cl | H | H | H | $OCH_3$ | H |
| 2-methyloxazol-5-yl | H | $CF_3$ | H | F | H | H |
| 2-methyloxazol-5-yl | H | $CF_3$ | H | H | H | $OCH_3$ |
| 2-methyloxazol-5-yl | H | $CF_3$ | H | H | $OCF_2H$ | H |
| 2-methyloxazol-5-yl | H | $CH_3$ | H | F | H | H |
| 2-methyloxazol-5-yl | H | $CH_3$ | H | H | H | $OCH_3$ |
| 2-methyloxazol-5-yl | H | $CH_3$ | H | H | $OCF_2H$ | H |
| 2-methyloxazol-5-yl | H | $OCF_2H$ | H | F | H | H |
| 2-methyloxazol-5-yl | H | $OCF_2H$ | H | H | H | $OCH_3$ |
| 2-methyloxazol-5-yl | H | $OCF_2H$ | H | H | $OCF_2H$ | H |
| 2-methyloxazol-5-yl | $OCF_2H$ | H | H | F | H | H |
| 2-methyloxazol-5-yl | $OCF_2H$ | H | H | H | H | $OCH_3$ |
| 2-methyloxazol-5-yl | $OCF_2H$ | H | H | H | $OCH_3$ | H |
| 2-methyloxazol-5-yl | $OCH_3$ | H | H | F | H | H |
| 2-methyloxazol-5-yl | $OCH_3$ | H | H | H | H | H |
| 2-methyloxazol-5-yl | $OCH_3$ | H | H | H | H | $OCH_3$ |
| 2-methyloxazol-5-yl | $OCH_3$ | H | H | H | $OCH_3$ | H |
| imidazolyl | $CF_3$ | H | H | $CH_3$ | H | H |
| imidazolyl | $CF_3$ | H | H | F | H | H |
| imidazolyl | $CF_3$ | H | H | H | H | $OCH_3$ |
| imidazolyl | $CF_3$ | H | H | H | $OCF_2H$ | H |
| imidazolyl | $CF_3$ | H | H | H | $OCH_3$ | H |
| imidazolyl | $CH_3$ | H | H | F | H | H |
| imidazolyl | $CH_3$ | H | H | H | H | $OCH_3$ |
| imidazolyl | $CH_3$ | H | H | H | $OCF_2H$ | H |
| imidazolyl | $CH_3$ | H | H | H | $OCH_3$ | H |
| imidazolyl | Cl | H | F | H | H | H |
| imidazolyl | Cl | H | H | $CH_3$ | H | H |
| imidazolyl | Cl | H | H | F | H | H |

TABLE 7-continued

| A | $R_1$ | $R_{12}$ | $R_2^{VII}$ | $R_3^{VII}$ | $R_4^{VII}$ | $R_5^{VII}$ |
|---|---|---|---|---|---|---|
| imidazolyl | Cl | H | H | H | H | H |
| imidazolyl | Cl | H | H | H | H | $OCF_2H$ |
| imidazolyl | Cl | H | H | H | H | $OCH_3$ |
| imidazolyl | Cl | H | H | H | $OCF_2H$ | H |
| imidazolyl | Cl | H | H | H | $OCH_3$ | H |
| imidazolyl | F | H | H | $CH_3$ | H | H |
| imidazolyl | F | H | H | F | H | H |
| imidazolyl | F | H | H | H | H | $OCH_3$ |
| imidazolyl | F | H | H | H | $OCF_2H$ | H |
| imidazolyl | F | H | H | H | $OCH_3$ | H |
| imidazolyl | H | $CF_3$ | H | $CH_3$ | H | H |
| imidazolyl | H | $CF_3$ | H | F | H | H |
| imidazolyl | H | $CF_3$ | H | H | H | $OCH_3$ |
| imidazolyl | H | $CF_3$ | H | H | $OCF_2H$ | H |
| imidazolyl | H | $CH_3$ | H | $CH_3$ | H | H |
| imidazolyl | H | $CH_3$ | H | F | H | H |
| imidazolyl | H | $CH_3$ | H | H | H | $OCH_3$ |
| imidazolyl | H | $CH_3$ | H | H | $OCF_2H$ | H |
| imidazolyl | H | $OCF_2H$ | H | $CH_3$ | H | H |
| imidazolyl | H | $OCF_2H$ | H | F | H | H |
| imidazolyl | H | $OCF_2H$ | H | H | H | $OCH_3$ |
| imidazolyl | H | $OCF_2H$ | H | H | $OCF_2H$ | H |
| imidazolyl | $OCF_2H$ | H | F | H | H | H |
| imidazolyl | $OCF_2H$ | H | H | $CH_3$ | H | H |
| imidazolyl | $OCF_2H$ | H | H | F | H | H |
| imidazolyl | $OCF_2H$ | H | H | H | H | $OCH_3$ |
| imidazolyl | $OCF_2H$ | H | H | H | $OCF_2H$ | H |
| imidazolyl | $OCF_2H$ | H | H | H | $OCH_3$ | H |
| imidazolyl | $OCH_3$ | H | F | H | H | H |
| imidazolyl | $OCH_3$ | H | H | $CH_3$ | H | H |
| imidazolyl | $OCH_3$ | H | H | F | H | H |
| imidazolyl | $OCH_3$ | H | H | H | H | H |
| imidazolyl | $OCH_3$ | H | H | H | H | $OCH_3$ |
| imidazolyl | $OCH_3$ | H | H | H | $OCF_2H$ | H |
| imidazolyl | $OCH_3$ | H | H | H | $OCH_3$ | H |
| oxazol-5-yl | $CF_3$ | H | H | $CH_3$ | H | H |
| oxazol-5-yl | $CF_3$ | H | H | F | H | H |
| oxazol-5-yl | $CF_3$ | H | H | H | H | $OCH_3$ |
| oxazol-5-yl | $CF_3$ | H | H | H | $OCF_2H$ | H |
| oxazol-5-yl | $CF_3$ | H | H | H | $OCH_3$ | H |
| oxazol-5-yl | $CH_3$ | H | F | H | H | H |
| oxazol-5-yl | $CH_3$ | H | H | $CH_3$ | H | H |
| oxazol-5-yl | $CH_3$ | H | H | F | H | H |
| oxazol-5-yl | $CH_3$ | H | H | H | H | $OCH_3$ |
| oxazol-5-yl | $CH_3$ | H | H | H | $OCF_2H$ | H |
| oxazol-5-yl | $CH_3$ | H | H | H | $OCH_3$ | H |
| oxazol-5-yl | Cl | H | F | H | F | H |
| oxazol-5-yl | Cl | H | F | H | H | H |
| oxazol-5-yl | Cl | H | H | $CH_3$ | H | H |
| oxazol-5-yl | Cl | H | H | F | H | H |
| oxazol-5-yl | Cl | H | H | H | Cl | H |
| oxazol-5-yl | Cl | H | H | H | F | H |
| oxazol-5-yl | Cl | H | H | H | H | H |
| oxazol-5-yl | Cl | H | H | H | H | $OCF_2H$ |
| oxazol-5-yl | Cl | H | H | H | H | $OCH_3$ |
| oxazol-5-yl | Cl | H | H | H | $OCF_2H$ | H |
| oxazol-5-yl | Cl | H | H | H | $OCH_3$ | H |
| oxazol-5-yl | F | H | H | $CH_3$ | H | H |
| oxazol-5-yl | F | H | H | F | H | H |
| oxazol-5-yl | F | H | H | H | H | $OCH_3$ |
| oxazol-5-yl | F | H | H | H | $OCF_2H$ | H |
| oxazol-5-yl | F | H | H | H | $OCH_3$ | H |
| oxazol-5-yl | H | $CF_3$ | H | $CH_3$ | H | H |
| oxazol-5-yl | H | $CF_3$ | H | F | H | H |
| oxazol-5-yl | H | $CF_3$ | H | H | H | $OCH_3$ |
| oxazol-5-yl | H | $CF_3$ | H | H | $OCF_2H$ | H |
| oxazol-5-yl | H | $CH_3$ | H | $CH_3$ | H | H |
| oxazol-5-yl | H | $CH_3$ | H | F | H | H |
| oxazol-5-yl | H | $CH_3$ | H | H | H | $OCH_3$ |
| oxazol-5-yl | H | $CH_3$ | H | H | $OCF_2H$ | H |
| oxazol-5-yl | H | $OCF_2H$ | H | $CH_3$ | H | H |
| oxazol-5-yl | H | $OCF_2H$ | H | F | H | H |
| oxazol-5-yl | H | $OCF_2H$ | H | H | H | $OCH_3$ |
| oxazol-5-yl | H | $OCF_2H$ | H | H | $OCF_2H$ | H |
| oxazol-5-yl | $OCF_2H$ | H | F | H | H | H |
| oxazol-5-yl | $OCF_2H$ | H | H | $CH_3$ | H | H |
| oxazol-5-yl | $OCF_2H$ | H | H | F | H | H |
| oxazol-5-yl | $OCF_2H$ | H | H | H | H | $OCH_3$ |
| oxazol-5-yl | $OCF_2H$ | H | H | H | $OCF_2H$ | H |
| oxazol-5-yl | $OCF_2H$ | H | H | H | $OCH_3$ | H |
| oxazol-5-yl | $OCH_3$ | H | F | H | H | H |
| oxazol-5-yl | $OCH_3$ | H | H | $CH_3$ | H | H |
| oxazol-5-yl | $OCH_3$ | H | H | F | H | H |
| oxazol-5-yl | $OCH_3$ | H | H | H | H | H |
| oxazol-5-yl | $OCH_3$ | H | H | H | H | $OCH_3$ |
| oxazol-5-yl | $OCH_3$ | H | H | H | $OCF_2H$ | H |
| oxazol-5-yl | $OCH_3$ | H | H | H | $OCH_3$ | H |
| pyridine-4-yl | $CF_3$ | H | H | $CH_3$ | H | H |
| pyridine-4-yl | $CF_3$ | H | H | F | H | H |
| pyridine-4-yl | $CF_3$ | H | H | H | H | $OCH_3$ |
| pyridine-4-yl | $CF_3$ | H | H | H | $OCF_2H$ | H |
| pyridine-4-yl | $CF_3$ | H | H | H | $OCH_3$ | H |
| pyridine-4-yl | $CH_3$ | H | F | H | H | H |
| pyridine-4-yl | $CH_3$ | H | H | $CH_3$ | H | H |
| pyridine-4-yl | $CH_3$ | H | H | F | H | H |
| pyridine-4-yl | $CH_3$ | H | H | H | H | $OCH_3$ |
| pyridine-4-yl | $CH_3$ | H | H | H | $OCF_2H$ | H |
| pyridine-4-yl | $CH_3$ | H | H | H | $OCH_3$ | H |
| pyridine-4-yl | Cl | H | F | H | H | H |
| pyridine-4-yl | Cl | H | H | $CH_3$ | H | H |
| pyridine-4-yl | Cl | H | H | F | H | H |
| pyridine-4-yl | Cl | H | H | H | H | H |
| pyridine-4-yl | Cl | H | H | H | H | $OCF_2H$ |
| pyridine-4-yl | Cl | H | H | H | H | $OCH_3$ |
| pyridine-4-yl | Cl | H | H | H | $OCF_2H$ | H |
| pyridine-4-yl | Cl | H | H | H | $OCH_3$ | H |
| pyridine-4-yl | F | H | H | $CH_3$ | H | H |
| pyridine-4-yl | F | H | H | F | H | H |
| pyridine-4-yl | F | H | H | H | H | $OCH_3$ |
| pyridine-4-yl | F | H | H | H | $OCF_2H$ | H |
| pyridine-4-yl | F | H | H | H | $OCH_3$ | H |
| pyridine-4-yl | H | $CF_3$ | H | $CH_3$ | H | H |
| pyridine-4-yl | H | $CF_3$ | H | F | H | H |
| pyridine-4-yl | H | $CF_3$ | H | H | H | $OCH_3$ |
| pyridine-4-yl | H | $CF_3$ | H | H | $OCF_2H$ | H |
| pyridine-4-yl | H | $CH_3$ | H | $CH_3$ | H | H |
| pyridine-4-yl | H | $CH_3$ | H | F | H | H |
| pyridine-4-yl | H | $CH_3$ | H | H | H | $OCH_3$ |
| pyridine-4-yl | H | $CH_3$ | H | H | $OCF_2H$ | H |
| pyridine-4-yl | H | $OCF_2H$ | H | $CH_3$ | H | H |
| pyridine-4-yl | H | $OCF_2H$ | H | F | H | H |
| pyridine-4-yl | H | $OCF_2H$ | H | H | H | $OCH_3$ |
| pyridine-4-yl | H | $OCF_2H$ | H | H | $OCF_2H$ | H |
| pyridine-4-yl | $OCF_2H$ | H | F | H | H | H |
| pyridine-4-yl | $OCF_2H$ | H | H | $CH_3$ | H | H |
| pyridine-4-yl | $OCF_2H$ | H | H | F | H | H |
| pyridine-4-yl | $OCF_2H$ | H | H | H | H | $OCH_3$ |
| pyridine-4-yl | $OCF_2H$ | H | H | H | $OCF_2H$ | H |
| pyridine-4-yl | $OCF_2H$ | H | H | H | $OCH_3$ | H |
| pyridine-4-yl | $OCH_3$ | H | F | H | H | H |
| pyridine-4-yl | $OCH_3$ | H | H | $CH_3$ | H | H |
| pyridine-4-yl | $OCH_3$ | H | H | F | H | H |
| pyridine-4-yl | $OCH_3$ | H | H | H | H | H |
| pyridine-4-yl | $OCH_3$ | H | H | H | H | $OCH_3$ |
| pyridine-4-yl | $OCH_3$ | H | H | H | $OCF_2H$ | H |
| pyridine-4-yl | $OCH_3$ | H | H | H | $OCH_3$ | H |

Preferably, the compound of formula (Ih)

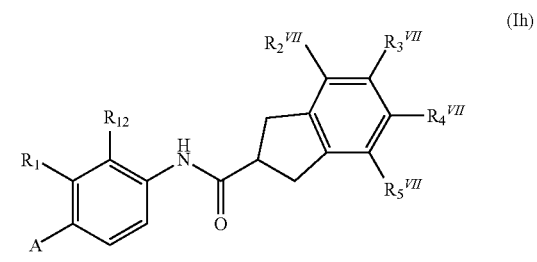

(Ih)

is selected from the group consisting of compounds of the formula (I), wherein A, $R_1$, $R_{12}$, $R_2^{VII}$, $R_3^{VII}$, $R_4^{VII}$ and $R_5^{VII}$ are as indicated in Table 8:

TABLE 8

| A | $R_1$ | $R_{12}$ | $R_2^{VII}$ | $R_3^{VII}$ | $R_4^{VII}$ | $R_5^{VII}$ |
|---|---|---|---|---|---|---|
| 1,2,4-triazol-1-yl | $CF_3$ | H | H | $CH_3$ | H | H |
| 1,2,4-triazol-1-yl | $CF_3$ | H | H | F | H | H |
| 1,2,4-triazol-1-yl | $CF_3$ | H | H | H | H | $OCH_3$ |
| 1,2,4-triazol-1-yl | $CF_3$ | H | H | H | $OCF_2H$ | H |
| 1,2,4-triazol-1-yl | $CF_3$ | H | H | H | $OCH_3$ | H |
| 1,2,4-triazol-1-yl | $CH_3$ | H | F | H | H | H |
| 1,2,4-triazol-1-yl | $CH_3$ | H | H | $CH_3$ | H | H |
| 1,2,4-triazol-1-yl | $CH_3$ | H | H | F | H | H |
| 1,2,4-triazol-1-yl | $CH_3$ | H | H | H | H | $OCH_3$ |
| 1,2,4-triazol-1-yl | $CH_3$ | H | H | H | $OCF_2H$ | H |
| 1,2,4-triazol-1-yl | $CH_3$ | H | H | H | $OCH_3$ | H |
| 1,2,4-triazol-1-yl | Cl | H | F | H | H | H |
| 1,2,4-triazol-1-yl | Cl | H | H | $CH_3$ | H | H |
| 1,2,4-triazol-1-yl | Cl | H | H | F | H | H |
| 1,2,4-triazol-1-yl | Cl | H | H | H | H | H |
| 1,2,4-triazol-1-yl | Cl | H | H | H | H | $OCF_2H$ |
| 1,2,4-triazol-1-yl | Cl | H | H | H | H | $OCH_3$ |
| 1,2,4-triazol-1-yl | Cl | H | H | H | $OCF_2H$ | H |
| 1,2,4-triazol-1-yl | Cl | H | H | H | $OCH_3$ | H |
| 1,2,4-triazol-1-yl | F | H | H | $CH_3$ | H | H |
| 1,2,4-triazol-1-yl | F | H | H | F | H | H |
| 1,2,4-triazol-1-yl | F | H | H | H | H | $OCH_3$ |
| 1,2,4-triazol-1-yl | F | H | H | H | $OCF_2H$ | H |
| 1,2,4-triazol-1-yl | F | H | H | H | $OCH_3$ | H |
| 1,2,4-triazol-1-yl | H | $CF_3$ | H | $CH_3$ | H | H |
| 1,2,4-triazol-1-yl | H | $CF_3$ | H | F | H | H |
| 1,2,4-triazol-1-yl | H | $CF_3$ | H | H | H | $OCH_3$ |
| 1,2,4-triazol-1-yl | H | $CF_3$ | H | H | $OCF_2H$ | H |
| 1,2,4-triazol-1-yl | H | $CH_3$ | H | $CH_3$ | H | H |
| 1,2,4-triazol-1-yl | H | $CH_3$ | H | F | H | H |
| 1,2,4-triazol-1-yl | H | $CH_3$ | H | H | H | $OCH_3$ |
| 1,2,4-triazol-1-yl | H | $CH_3$ | H | H | $OCF_2H$ | H |
| 1,2,4-triazol-1-yl | H | $OCF_2H$ | H | $CH_3$ | H | H |
| 1,2,4-triazol-1-yl | H | $OCF_2H$ | H | F | H | H |
| 1,2,4-triazol-1-yl | H | $OCF_2H$ | H | H | H | $OCH_3$ |
| 1,2,4-triazol-1-yl | H | $OCF_2H$ | H | H | $OCF_2H$ | H |
| 1,2,4-triazol-1-yl | $OCF_2H$ | H | F | H | H | H |
| 1,2,4-triazol-1-yl | $OCF_2H$ | H | H | $CH_3$ | H | H |
| 1,2,4-triazol-1-yl | $OCF_2H$ | H | H | F | H | H |
| 1,2,4-triazol-1-yl | $OCF_2H$ | H | H | H | H | $OCH_3$ |
| 1,2,4-triazol-1-yl | $OCF_2H$ | H | H | H | $OCF_2H$ | H |
| 1,2,4-triazol-1-yl | $OCF_2H$ | H | H | H | $OCH_3$ | H |
| 1,2,4-triazol-1-yl | $OCH_3$ | H | F | H | H | H |
| 1,2,4-triazol-1-yl | $OCH_3$ | H | H | $CH_3$ | H | H |
| 1,2,4-triazol-1-yl | $OCH_3$ | H | H | F | H | H |
| 1,2,4-triazol-1-yl | $OCH_3$ | H | H | H | H | H |
| 1,2,4-triazol-1-yl | $OCH_3$ | H | H | H | H | $OCH_3$ |
| 1,2,4-triazol-1-yl | $OCH_3$ | H | H | H | $OCF_2H$ | H |
| 1,2,4-triazol-1-yl | $OCH_3$ | H | H | H | $OCH_3$ | H |
| 1,3,4-oxadiazol-2-yl | $CF_3$ | H | H | $CH_3$ | H | H |
| 1,3,4-oxadiazol-2-yl | $CF_3$ | H | H | F | H | H |
| 1,3,4-oxadiazol-2-yl | $CF_3$ | H | H | H | H | $OCH_3$ |
| 1,3,4-oxadiazol-2-yl | $CF_3$ | H | H | H | $OCF_2H$ | H |
| 1,3,4-oxadiazol-2-yl | $CF_3$ | H | H | H | $OCH_3$ | H |
| 1,3,4-oxadiazol-2-yl | $CH_3$ | H | F | H | H | H |
| 1,3,4-oxadiazol-2-yl | $CH_3$ | H | H | $CH_3$ | H | H |
| 1,3,4-oxadiazol-2-yl | $CH_3$ | H | H | F | H | H |
| 1,3,4-oxadiazol-2-yl | $CH_3$ | H | H | H | H | $OCH_3$ |
| 1,3,4-oxadiazol-2-yl | $CH_3$ | H | H | H | $OCF_2H$ | H |
| 1,3,4-oxadiazol-2-yl | $CH_3$ | H | H | H | $OCH_3$ | H |
| 1,3,4-oxadiazol-2-yl | Cl | H | F | H | H | H |
| 1,3,4-oxadiazol-2-yl | Cl | H | H | $CH_3$ | H | H |
| 1,3,4-oxadiazol-2-yl | Cl | H | H | F | H | H |
| 1,3,4-oxadiazol-2-yl | Cl | H | H | H | H | H |
| 1,3,4-oxadiazol-2-yl | Cl | H | H | H | H | $OCF_2H$ |
| 1,3,4-oxadiazol-2-yl | Cl | H | H | H | H | $OCH_3$ |
| 1,3,4-oxadiazol-2-yl | Cl | H | H | H | $OCF_2H$ | H |
| 1,3,4-oxadiazol-2-yl | Cl | H | H | H | $OCH_3$ | H |
| 1,3,4-oxadiazol-2-yl | F | H | H | $CH_3$ | H | H |
| 1,3,4-oxadiazol-2-yl | F | H | H | F | H | H |
| 1,3,4-oxadiazol-2-yl | F | H | H | H | H | $OCH_3$ |
| 1,3,4-oxadiazol-2-yl | F | H | H | H | $OCF_2H$ | H |
| 1,3,4-oxadiazol-2-yl | F | H | H | H | $OCH_3$ | H |
| 1,3,4-oxadiazol-2-yl | H | $CF_3$ | H | $CH_3$ | H | H |
| 1,3,4-oxadiazol-2-yl | H | $CF_3$ | H | F | H | H |
| 1,3,4-oxadiazol-2-yl | H | $CF_3$ | H | H | H | $OCH_3$ |
| 1,3,4-oxadiazol-2-yl | H | $CF_3$ | H | H | $OCF_2H$ | H |
| 1,3,4-oxadiazol-2-yl | H | $CH_3$ | H | $CH_3$ | H | H |
| 1,3,4-oxadiazol-2-yl | H | $CH_3$ | H | F | H | H |
| 1,3,4-oxadiazol-2-yl | H | $CH_3$ | H | H | H | $OCH_3$ |
| 1,3,4-oxadiazol-2-yl | H | $CH_3$ | H | H | $OCF_2H$ | H |
| 1,3,4-oxadiazol-2-yl | H | $OCF_2H$ | H | $CH_3$ | H | H |
| 1,3,4-oxadiazol-2-yl | H | $OCF_2H$ | H | F | H | H |
| 1,3,4-oxadiazol-2-yl | H | $OCF_2H$ | H | H | H | $OCH_3$ |
| 1,3,4-oxadiazol-2-yl | H | $OCF_2H$ | H | H | $OCF_2H$ | H |
| 1,3,4-oxadiazol-2-yl | $OCF_2H$ | H | F | H | H | H |
| 1,3,4-oxadiazol-2-yl | $OCF_2H$ | H | H | $CH_3$ | H | H |
| 1,3,4-oxadiazol-2-yl | $OCF_2H$ | H | H | F | H | H |
| 1,3,4-oxadiazol-2-yl | $OCF_2H$ | H | H | H | H | $OCH_3$ |
| 1,3,4-oxadiazol-2-yl | $OCF_2H$ | H | H | H | $OCF_2H$ | H |
| 1,3,4-oxadiazol-2-yl | $OCF_2H$ | H | H | H | $OCH_3$ | H |
| 1,3,4-oxadiazol-2-yl | $OCH_3$ | H | F | H | H | H |
| 1,3,4-oxadiazol-2-yl | $OCH_3$ | H | H | $CH_3$ | H | H |
| 1,3,4-oxadiazol-2-yl | $OCH_3$ | H | H | F | H | H |
| 1,3,4-oxadiazol-2-yl | $OCH_3$ | H | H | H | H | H |
| 1,3,4-oxadiazol-2-yl | $OCH_3$ | H | H | H | H | $OCH_3$ |
| 1,3,4-oxadiazol-2-yl | $OCH_3$ | H | H | H | $OCF_2H$ | H |
| 1,3,4-oxadiazol-2-yl | $OCH_3$ | H | H | H | $OCH_3$ | H |
| 2-methyloxazol-5-yl | $CF_3$ | H | H | F | H | H |
| 2-methyloxazol-5-yl | $CF_3$ | H | H | H | H | $OCH_3$ |
| 2-methyloxazol-5-yl | $CF_3$ | H | H | H | $OCH_3$ | H |
| 2-methyloxazol-5-yl | $CH_3$ | H | H | F | H | H |
| 2-methyloxazol-5-yl | $CH_3$ | H | H | H | H | $OCH_3$ |
| 2-methyloxazol-5-yl | $CH_3$ | H | H | H | $OCH_3$ | H |
| 2-methyloxazol-5-yl | Cl | H | H | F | H | H |
| 2-methyloxazol-5-yl | Cl | H | H | H | H | H |
| 2-methyloxazol-5-yl | Cl | H | H | H | H | $OCH_3$ |
| 2-methyloxazol-5-yl | H | $CF_3$ | H | F | H | H |
| 2-methyloxazol-5-yl | H | $CF_3$ | H | H | H | $OCH_3$ |
| 2-methyloxazol-5-yl | H | $CF_3$ | H | H | $OCF_2H$ | H |
| 2-methyloxazol-5-yl | H | $CH_3$ | H | F | H | H |
| 2-methyloxazol-5-yl | H | $CH_3$ | H | H | H | $OCH_3$ |
| 2-methyloxazol-5-yl | H | $CH_3$ | H | H | $OCF_2H$ | H |
| 2-methyloxazol-5-yl | H | $OCF_2H$ | H | F | H | H |
| 2-methyloxazol-5-yl | H | $OCF_2H$ | H | H | H | $OCH_3$ |
| 2-methyloxazol-5-yl | H | $OCF_2H$ | H | H | $OCF_2H$ | H |
| 2-methyloxazol-5-yl | $OCF_2H$ | H | H | F | H | H |
| 2-methyloxazol-5-yl | $OCF_2H$ | H | H | H | H | $OCH_3$ |
| 2-methyloxazol-5-yl | $OCF_2H$ | H | H | H | $OCH_3$ | H |
| 2-methyloxazol-5-yl | $OCH_3$ | H | H | F | H | H |
| 2-methyloxazol-5-yl | $OCH_3$ | H | H | H | H | H |
| 2-methyloxazol-5-yl | $OCH_3$ | H | H | H | H | $OCH_3$ |
| 2-methyloxazol-5-yl | $OCH_3$ | H | H | H | $OCH_3$ | H |
| imidazolyl | $CF_3$ | H | H | $CH_3$ | H | H |
| imidazolyl | $CF_3$ | H | H | F | H | H |
| imidazolyl | $CF_3$ | H | H | H | H | $OCH_3$ |
| imidazolyl | $CF_3$ | H | H | H | $OCF_2H$ | H |
| imidazolyl | $CF_3$ | H | H | H | $OCH_3$ | H |
| imidazolyl | $CH_3$ | H | H | F | H | H |
| imidazolyl | $CH_3$ | H | H | H | H | $OCH_3$ |
| imidazolyl | $CH_3$ | H | H | H | $OCF_2H$ | H |
| imidazolyl | $CH_3$ | H | H | H | $OCH_3$ | H |
| imidazolyl | Cl | H | F | H | H | H |
| imidazolyl | Cl | H | H | $CH_3$ | H | H |
| imidazolyl | Cl | H | H | F | H | H |
| imidazolyl | Cl | H | H | H | H | H |
| imidazolyl | Cl | H | H | H | H | $OCF_2H$ |
| imidazolyl | Cl | H | H | H | H | $OCH_3$ |
| imidazolyl | Cl | H | H | H | $OCF_2H$ | H |
| imidazolyl | Cl | H | H | H | $OCH_3$ | H |
| imidazolyl | F | H | H | $CH_3$ | H | H |
| imidazolyl | F | H | H | F | H | H |
| imidazolyl | F | H | H | H | H | $OCH_3$ |
| imidazolyl | F | H | H | H | $OCF_2H$ | H |
| imidazolyl | F | H | H | H | $OCH_3$ | H |
| imidazolyl | H | $CF_3$ | H | $CH_3$ | H | H |
| imidazolyl | H | $CF_3$ | H | F | H | H |
| imidazolyl | H | $CF_3$ | H | H | H | $OCH_3$ |
| imidazolyl | H | $CF_3$ | H | H | $OCF_2H$ | H |
| imidazolyl | H | $CH_3$ | H | $CH_3$ | H | H |

TABLE 8-continued

| A | $R_1$ | $R_{12}$ | $R_2^{VII}$ | $R_3^{VII}$ | $R_4^{VII}$ | $R_5^{VII}$ |
|---|---|---|---|---|---|---|
| imidazolyl | H | $CH_3$ | H | F | H | H |
| imidazolyl | H | $CH_3$ | H | H | H | $OCH_3$ |
| imidazolyl | H | $CH_3$ | H | H | $OCF_2H$ | H |
| imidazolyl | H | $OCF_2H$ | H | $CH_3$ | H | H |
| imidazolyl | H | $OCF_2H$ | H | F | H | H |
| imidazolyl | H | $OCF_2H$ | H | H | H | $OCH_3$ |
| imidazolyl | H | $OCF_2H$ | H | H | $OCF_2H$ | H |
| imidazolyl | $OCF_2H$ | H | F | H | H | H |
| imidazolyl | $OCF_2H$ | H | H | $CH_3$ | H | H |
| imidazolyl | $OCF_2H$ | H | H | F | H | H |
| imidazolyl | $OCF_2H$ | H | H | H | H | $OCH_3$ |
| imidazolyl | $OCF_2H$ | H | H | H | $OCF_2H$ | H |
| imidazolyl | $OCF2H$ | H | H | H | $OCH_3$ | H |
| imidazolyl | $OCH_3$ | H | F | H | H | H |
| imidazolyl | $OCH_3$ | H | H | $CH_3$ | H | H |
| imidazolyl | $OCH_3$ | H | H | F | H | H |
| imidazolyl | $OCH_3$ | H | H | H | H | H |
| imidazolyl | $OCH_3$ | H | H | H | H | $OCH_3$ |
| imidazolyl | $OCH_3$ | H | H | H | $OCF_2H$ | H |
| imidazolyl | $OCH_3$ | H | H | H | $OCH_3$ | H |
| oxazol-5-yl | $CF_3$ | H | H | $CH_3$ | H | H |
| oxazol-5-yl | $CF_3$ | H | H | F | H | H |
| oxazol-5-yl | $CF_3$ | H | H | H | H | $OCH_3$ |
| oxazol-5-yl | $CF_3$ | H | H | H | $OCF_2H$ | H |
| oxazol-5-yl | $CF_3$ | H | H | H | $OCH_3$ | H |
| oxazol-5-yl | $CH_3$ | H | F | H | H | H |
| oxazol-5-yl | $CH_3$ | H | H | $CH_3$ | H | H |
| oxazol-5-yl | $CH_3$ | H | H | F | H | H |
| oxazol-5-yl | $CH_3$ | H | H | H | H | $OCH_3$ |
| oxazol-5-yl | $CH_3$ | H | H | H | $OCF_2H$ | H |
| oxazol-5-yl | $CH_3$ | H | H | H | $OCH_3$ | H |
| oxazol-5-yl | Cl | H | F | H | F | H |
| oxazol-5-yl | Cl | H | F | H | H | H |
| oxazol-5-yl | Cl | H | H | $CH_3$ | H | H |
| oxazol-5-yl | Cl | H | H | F | H | H |
| oxazol-5-yl | Cl | H | H | H | Cl | H |
| oxazol-5-yl | Cl | H | H | H | F | H |
| oxazol-5-yl | Cl | H | H | H | H | H |
| oxazol-5-yl | Cl | H | H | H | H | $OCF_2H$ |
| oxazol-5-yl | Cl | H | H | H | H | $OCH_3$ |
| oxazol-5-yl | Cl | H | H | H | $OCF_2H$ | H |
| oxazol-5-yl | Cl | H | H | H | $OCH_3$ | H |
| oxazol-5-yl | F | H | H | $CH_3$ | H | H |
| oxazol-5-yl | F | H | H | F | H | H |
| oxazol-5-yl | F | H | H | H | H | $OCH_3$ |
| oxazol-5-yl | F | H | H | H | $OCF_2H$ | H |
| oxazol-5-yl | F | H | H | H | $OCH_3$ | H |
| oxazol-5-yl | H | $CF_3$ | H | $CH_3$ | H | H |
| oxazol-5-yl | H | $CF_3$ | H | F | H | H |
| oxazol-5-yl | H | $CF_3$ | H | H | H | $OCH_3$ |
| oxazol-5-yl | H | $CF_3$ | H | H | $OCF_2H$ | H |
| oxazol-5-yl | H | $CH_3$ | H | $CH_3$ | H | H |
| oxazol-5-yl | H | $CH_3$ | H | F | H | H |
| oxazol-5-yl | H | $CH_3$ | H | H | H | $OCH_3$ |
| oxazol-5-yl | H | $CH_3$ | H | H | $OCF_2H$ | H |
| oxazol-5-yl | H | $OCF_2H$ | H | $CH_3$ | H | H |
| oxazol-5-yl | H | $OCF_2H$ | H | F | H | H |
| oxazol-5-yl | H | $OCF_2H$ | H | H | H | $OCH_3$ |
| oxazol-5-yl | H | $OCF_2H$ | H | H | $OCF_2H$ | H |
| oxazol-5-yl | $OCF_2H$ | H | F | H | H | H |
| oxazol-5-yl | $OCF_2H$ | H | H | $CH_3$ | H | H |
| oxazol-5-yl | $OCF_2H$ | H | H | F | H | H |
| oxazol-5-yl | $OCF_2H$ | H | H | H | H | $OCH_3$ |
| oxazol-5-yl | $OCF_2H$ | H | H | H | $OCF_2H$ | H |
| oxazol-5-yl | $OCF_2H$ | H | H | H | $OCH_3$ | H |
| oxazol-5-yl | $OCH_3$ | H | F | H | H | H |
| oxazol-5-yl | $OCH_3$ | H | H | $CH_3$ | H | H |
| oxazol-5-yl | $OCH_3$ | H | H | F | H | H |
| oxazol-5-yl | $OCH_3$ | H | H | H | H | H |
| oxazol-5-yl | $OCH_3$ | H | H | H | H | $OCH_3$ |
| oxazol-5-yl | $OCH_3$ | H | H | H | $OCF_2H$ | H |
| oxazol-5-yl | $OCH_3$ | H | H | H | $OCH_3$ | H |
| pyridine-4-yl | $CF_3$ | H | H | $CH_3$ | H | H |
| pyridine-4-yl | $CF_3$ | H | H | F | H | H |
| pyridine-4-yl | $CF_3$ | H | H | H | H | $OCH_3$ |
| pyridine-4-yl | $CF_3$ | H | H | H | $OCF_2H$ | H |
| pyridine-4-yl | $CF_3$ | H | H | H | $OCH_3$ | H |
| pyridine-4-yl | $CH_3$ | H | F | H | H | H |
| pyridine-4-yl | $CH_3$ | H | H | $CH_3$ | H | H |
| pyridine-4-yl | $CH_3$ | H | H | F | H | H |
| pyridine-4-yl | $CH_3$ | H | H | H | H | $OCH_3$ |
| pyridine-4-yl | $CH_3$ | H | H | H | $OCF_2H$ | H |
| pyridine-4-yl | $CH_3$ | H | H | H | $OCH_3$ | H |
| pyridine-4-yl | Cl | H | F | H | H | H |
| pyridine-4-yl | Cl | H | H | $CH_3$ | H | H |
| pyridine-4-yl | Cl | H | H | F | H | H |
| pyridine-4-yl | Cl | H | H | H | H | H |
| pyridine-4-yl | Cl | H | H | H | H | $OCF_2H$ |
| pyridine-4-yl | Cl | H | H | H | H | $OCH_3$ |
| pyridine-4-yl | Cl | H | H | H | $OCF_2H$ | H |
| pyridine-4-yl | Cl | H | H | H | $OCH_3$ | H |
| pyridine-4-yl | F | H | H | $CH_3$ | H | H |
| pyridine-4-yl | F | H | H | F | H | H |
| pyridine-4-yl | F | H | H | H | H | $OCH_3$ |
| pyridine-4-yl | F | H | H | H | $OCF_2H$ | H |
| pyridine-4-yl | F | H | H | H | $OCH_3$ | H |
| pyridine-4-yl | H | $CF_3$ | H | $CH_3$ | H | H |
| pyridine-4-yl | H | $CF_3$ | H | F | H | H |
| pyridine-4-yl | H | $CF_3$ | H | H | H | $OCH_3$ |
| pyridine-4-yl | H | $CF_3$ | H | H | $OCF_2H$ | H |
| pyridine-4-yl | H | $CH_3$ | H | $CH_3$ | H | H |
| pyridine-4-yl | H | $CH_3$ | H | F | H | H |
| pyridine-4-yl | H | $CH_3$ | H | H | H | $OCH_3$ |
| pyridine-4-yl | H | $CH_3$ | H | H | $OCF_2H$ | H |
| pyridine-4-yl | H | $OCF_2H$ | H | $CH_3$ | H | H |
| pyridine-4-yl | H | $OCF_2H$ | H | F | H | H |
| pyridine-4-yl | H | $OCF_2H$ | H | H | H | $OCH_3$ |
| pyridine-4-yl | H | $OCF_2H$ | H | H | $OCF_2H$ | H |
| pyridine-4-yl | $OCF_2H$ | H | F | H | H | H |
| pyridine-4-yl | $OCF_2H$ | H | H | $CH_3$ | H | H |
| pyridine-4-yl | $OCF_2H$ | H | H | F | H | H |
| pyridine-4-yl | $OCF_2H$ | H | H | H | H | $OCH_3$ |
| pyridine-4-yl | $OCF_2H$ | H | H | H | $OCF_2H$ | H |
| pyridine-4-yl | $OCF_2H$ | H | H | H | $OCH_3$ | H |
| pyridine-4-yl | $OCH_3$ | H | F | H | H | H |
| pyridine-4-yl | $OCH_3$ | H | H | $CH_3$ | H | H |
| pyridine-4-yl | $OCH_3$ | H | H | F | H | H |
| pyridine-4-yl | $OCH_3$ | H | H | H | H | H |
| pyridine-4-yl | $OCH_3$ | H | H | H | H | $OCH_3$ |
| pyridine-4-yl | $OCH_3$ | H | H | H | $OCF_2H$ | H |
| pyridine-4-yl | $OCH_3$ | H | H | H | $OCH_3$ | H |

Especially good results could be obtained by the following compounds according to the present invention:

TABLE 9
| Comp. No. | Chemical structure | Cell proliferation within one week [%] |
|---|---|---|
| 1 | 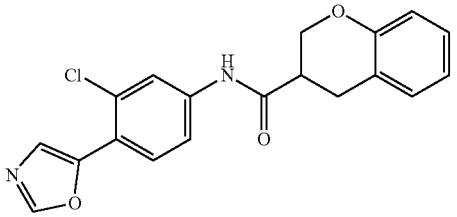 [SMILES: O=C(Nc1ccc(-c2cnco2)c(Cl)c1)C1COc2ccccc2C1]<br>(racemate) | 179 |
| 2 | 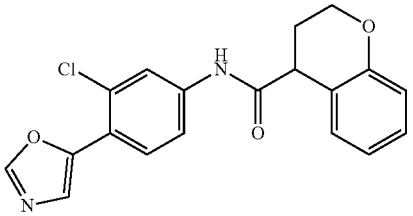<br>(racemate) | 128 |
| 3 | 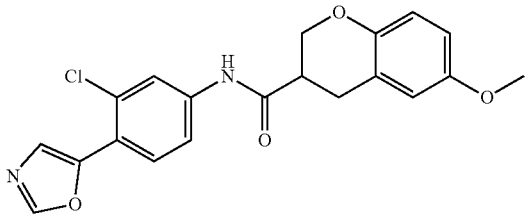<br>(racemate) | 138 |
| 4 | 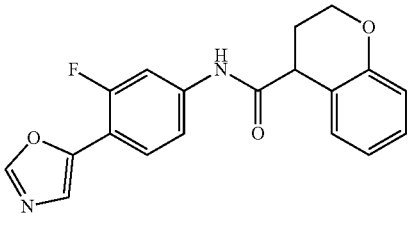 [SMILES: O=C(Nc1ccc(-c2cnco2)c(F)c1)C1CCOc2ccccc21]<br>(racemate) | 106 |
| 5 | 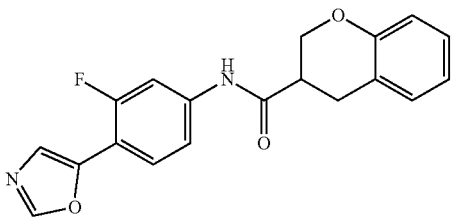 [SMILES: O=C(Nc1ccc(-c2cnco2)c(F)c1)C1COc2ccccc2C1]<br>(racemate) | 133 |

TABLE 9-continued

| Comp. No. | Chemical structure | Cell proliferation within one week [%] |
|---|---|---|
| 6 | (racemate) | 120 |
| 7 | (racemate) | 123 |
| 8 | (racemate) | 117 |
| 9 | (racemate) | 118 |
| 10 | (racemate) | 121 |

TABLE 9-continued

| Comp. No. | Chemical structure | Cell proliferation within one week [%] |
|---|---|---|
| 11 | (racemate) | 140 |
| 12 | (racemate) | 230 |
| 13 | (racemate) | 137 |
| 14 | (racemate) | 196 |
| 15 | (racemate) | 122 |

TABLE 9-continued

| Comp. No. | Chemical structure | Cell proliferation within one week [%] |
|---|---|---|
| 16 | (racemate) | 143 |
| 17 | (racemate) | 114 |
| 18 | (racemate) | 104 |
| 19 | (racemate) | 110 |
| 20 | (racemate) | 113 |

TABLE 9-continued

| Comp. No. | Chemical structure | Cell proliferation within one week [%] |
|---|---|---|
| 21 | [structure: 3-chloro-4-(oxazol-5-yl)phenyl chroman-3-carboxamide] enantiomer with the shorter retention time from the chiral HPLC resolution | 126 |
| 22 | [structure: 3-methyl-4-(oxazol-5-yl)phenyl chroman-3-carboxamide] (racemate) | 120 |
| 23 | [structure: 2-methyl-4-(oxazol-5-yl)phenyl chroman-3-carboxamide] (racemate) | 116 |
| 24 | [structure: 2-(difluoromethoxy)-4-(oxazol-5-yl)phenyl chroman-3-carboxamide] (racemate) | 126 |
| 25 | [structure: 3-methyl-4-(oxazol-5-yl)phenyl chroman-3-carboxamide] enantiomer with the shorter retention time from the chiral HPLC resolution | 120 |

TABLE 9-continued

| Comp. No. | Chemical structure | Cell proliferation within one week [%] |
|---|---|---|
| 26 | (structure: 2-(difluoromethoxy)-4-(oxazol-5-yl)phenyl chroman-3-carboxamide) enantiomer with the shorter retention time from the chiral HPLC resolution | 138 |
| 27 | (structure: 2-(difluoromethoxy)-4-(furan-2-yl)phenyl chroman-3-carboxamide) enantiomer with the longer retention time from the chiral HPLC resolution | 106 |
| 28 | (structure: 3-(trifluoromethyl)-4-(1H-1,2,4-triazol-1-yl)phenyl chroman-3-carboxamide) (racemate) | 118 |
| 29 | (structure: 3-fluoro-4-(1,3,4-oxadiazol-2-yl)phenyl chroman-3-carboxamide) (racemate) | 108 |
| 30 | (structure: 3-chloro-4-(2-methyloxazol-5-yl)phenyl chroman-3-carboxamide) (racemate) | 119 |

TABLE 9-continued
| Comp. No. | Chemical structure | Cell proliferation within one week [%] |
|---|---|---|
| 31 | 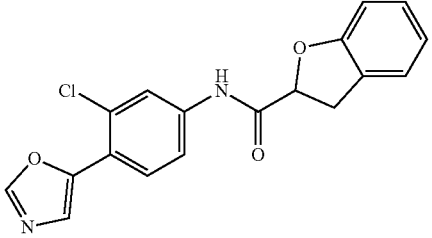 [SMILES: O=C(Nc1ccc(-c2cnco2)c(Cl)c1)C1Cc2ccccc2O1] (racemate) | 137 |
| 32 | 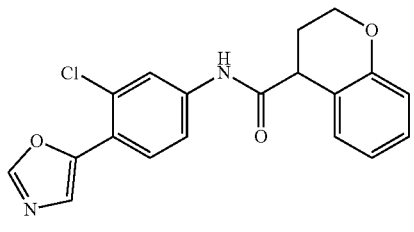 (racemate) | 113 |
| 33 | 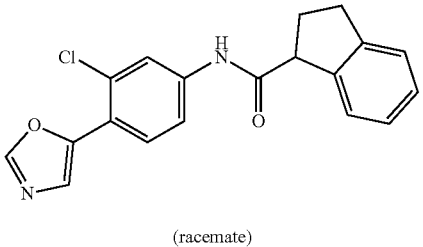 (racemate) | 116 |
| 34 | 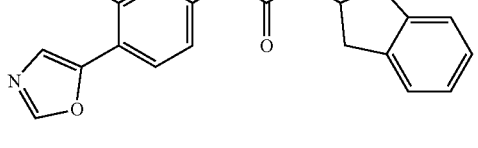 (racemate) | 129 |
| 35 | 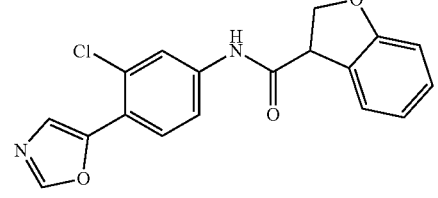 (racemate) | 125 |
| 36 | 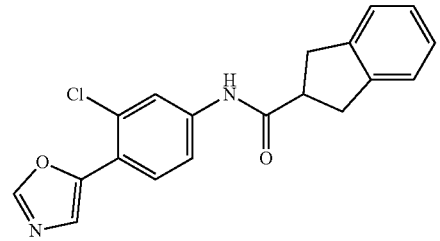 (racemate) | 124 |

TABLE 9-continued
| Comp. No. | Chemical structure | Cell proliferation within one week [%] |
|---|---|---|
| 37 | 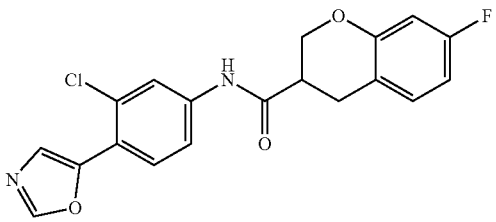 [SMILES: O=C(Nc1ccc(-c2cnco2)c(Cl)c1)C1COc2cc(F)ccc2C1] (racemate) | 158 |
| 38 | 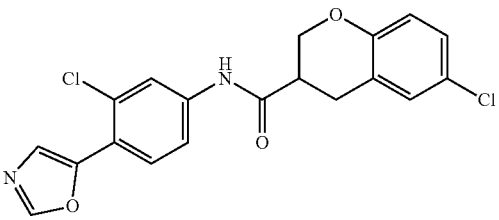 [SMILES: O=C(Nc1ccc(-c2cnco2)c(Cl)c1)C1COc2ccc(Cl)cc2C1] (racemate) | 122 |
| 39 | 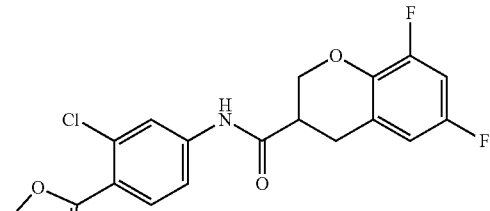 (racemate) | 132 |
| 40 | 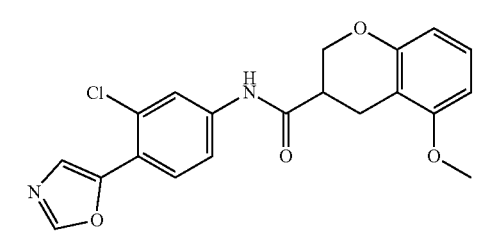 (racemate) | 107 |
| 41 |  (racemate) | 114 |

TABLE 9-continued

| Comp. No. | Chemical structure | Cell proliferation within one week [%] |
|---|---|---|
| 42 | 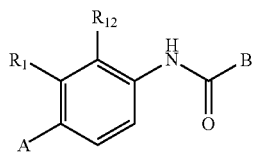<br>enantiomer with the shorter retention time from the chiral HPLC resolution | 124 |
| C* | — | 100 |

C* = Control experiment (absence of a compound according to the present invention)

The expression "enantiomer with the shorter retention time from the chiral HPLC resolution" means that the enantiomer comes first in the chiral HPLC when applying the conditions described in the corresponding Chiral Separation Method A, B, C or D. Within the context of the present invention the enantiomer with the shorter retention time is also called "first enantiomer" and the one with the longer retention time "second enantiomer".

In particular, the compounds of formula (1), (11), (12), (14), (16) and (38) show excellent results with regard to the stimulation of precursor cells, and in particular of retinal precursor cells. Within one week, the compound of formula (1) showed an increase of cell proliferation of 79%, the compound of formula (11) of 40%, the compound of formula (12) of 130%, the compound of formula (14) of 96%, compound of formula (16) of 43%, and compound of formula (38) of 58%.

In a further embodiment, the present invention relates to the compounds according to the present invention for use as a medicament.

In a further embodiment, the present invention relates to a pharmaceutical composition comprising a pharmaceutically acceptable carrier and/or adjuvant; and a compound of the formula (I)

(I)

or a pharmaceutically acceptable salt, a racemic mixture, a corresponding enantiomer or, if applicable, a corresponding diastereomer thereof, wherein:

A is selected from the group consisting of a 5-oxazolyl, a pyridine-4-yl, a triazolyl, a oxadiazolyl, an imidazolyl and a 2-methyloxazol-5-yl residue.

$R_1$ and $R_{12}$ are independently selected from the group consisting of hydrogen, fluoro, chloro, methoxy, trifluoromethyl, methyl and difluoromethoxy.

B is selected from the group consisting of a residue of formula (II), (III), (IV), (V), (VI), (VII), (VIII) and (IX)

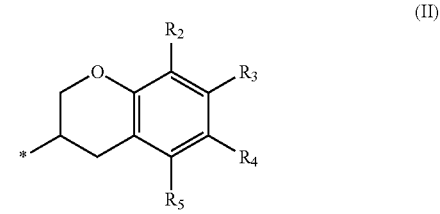

(II)

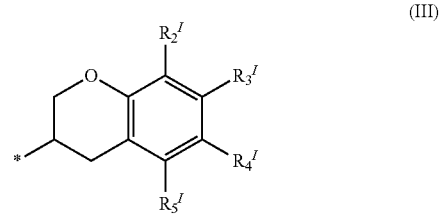

(III)

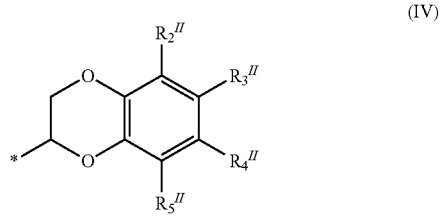

(IV)

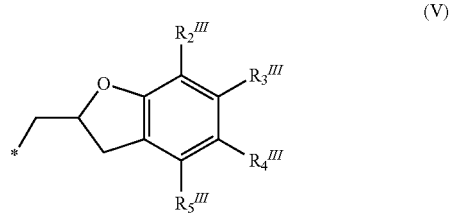

(V)

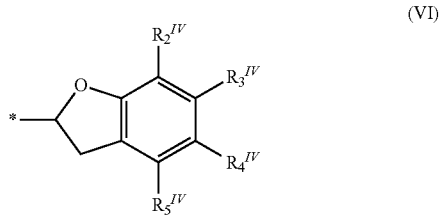

(VI)

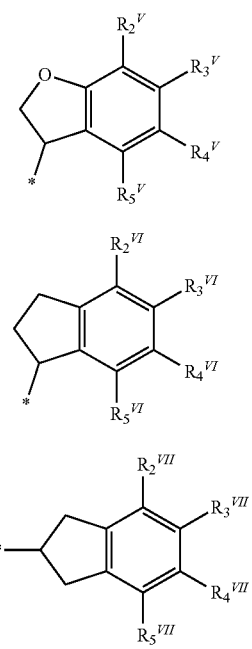

wherein,

"*" denotes the point of attachment to the remainder of the molecule, and $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$, $R_2^{VI}$, $R_3^{VI}$, $R_4^{VI}$, $R_5^{VI}$, $R_2^{VII}$, $R_3^{VII}$, $R_4^{VII}$, and $R_5^{VII}$ are independently selected from the group consisting of hydrogen, fluoro, chloro, methoxy and ethoxy as a therapeutically active substance.

The term "pharmaceutical composition" as used here means a composition that is suitable for administering to human patients for the treatment and/or prevention of diseases. Said pharmaceutical composition efficiently stimulates proliferation, migration or both proliferation and migration of endogenous retinal precursor cells in a patient.

The term "prevention" refers to the prevention or reduction of signs and symptoms associated with neuroretinal diseases, in particular of primary neuroretinal diseases leading to photoreceptor loss or degeneration of the photoreceptor layer of the retina in subjects who are at risk for developing the disease. In these subjects a predisposing factor may be retained, but the signs and/or symptoms of the disease do not occur or take significantly longer to develop. Further, it also includes the prevention of a further deterioration of the symptoms once the disease has occurred.

In a preferred embodiment of the present invention, the pharmaceutical composition comprises a pharmaceutically acceptable carrier and/or adjuvant; and a compound of the formula (I) as defined above, preferably a compound of formula (Ia), (Ib), (Ic), (Id), (Ie), (If), (Ig) or (Ih). Most preferably, it comprises a compound of formula (Ia), (Ib), (Ic), (Id), (Ie), (If), (Ig) or (Ih) as disclosed in Table 1, Table 2, Table 3, Table 4, Table 5, Table 6, Table 7 and Table 8 above.

As already mentioned, it could be shown that the compounds according to the present invention and the compositions according to the present invention stimulate the proliferation of retinal precursor cells. Thus, they are suitable in the treatment and/or prevention of retinal diseases, in particular of retinal diseases leading to photoreceptor loss or degeneration of the outer retina.

Compounds and compositions according to the present invention are particularly useful in the treatment and/or prevention of a disease selected from the group consisting of inherited retinal dystrophies, acquired or drug-induced photoreceptor degeneration, infectious eye diseases and inflammatory eye diseases by inducing the proliferation of retinal precursor cells. Thus, due to the compounds and compositions of the present invention, it is possible to reverse photoreceptor damage caused by an illness by restoring or regenerating retinal precursor cells, and not only to treat the loss of vision caused by retinal cell damage.

Retinal diseases which may be treated with the compounds according to the present invention are preferably selected from the group consisting of retinitis pigmentosa (RP), including syndromic and non-syndromic forms, X-chromosome linked, recessive, dominant and sporadic forms, rod-cone dystrophies, Usher's syndrome, Stargardt's disease, cone-rod dystrophies, cone dystrophies, achromatopsia, blue cone monochromacy, enhanced S-cone syndrome, rod dystrophies, choroideremia, Leber's congenital amaurosis, juvenile X-chromosome linked retinoschisis (JXLR), fundus albipunctatus, retinitis *punctata albescens*, fleck retina of Kandori, bietti crystalline retinal dystrophy, fenestrated sheen macular dystrophy, adult-onset foveomacular vitelliform dystrophy, Batten's disease, congenital stationary night blindness, familial exudative vitreoretinopathy (FEVR), ocular albinism, oculocutaneous albinism, fovea hypoplasia, abetalipoproteinemia, Stickler syndrome, retinal dystrophy (Bothnia type), crystalline maculopathy (drug-related, hyperoxaluria, cystinosis, Sjogren-Larsson syndrome), west African crystalline maculopathy, solar retinopathy, talc retinopathy, diabetic retinopathy, sickle cell retinopathy, macular telangectasia, eales disease, central/branch retinal artery occlusion (CRAO/BRAO), central/branch retinal vein occlusion (CRVO/BRVO), haemorrhagic occlusive retinal vasculitis (HORV), drug-induced maculopathies including chloroquine, hydroxychloroquine, phenothiazine, quinine sulfate, thioridazine, clofazimine, cholopromazine, deferoxamine, chloroquine-derivatives, cisplatin, carmustine, chlofazimine and vigabatrin; crystal-induced maculopathies including tamoxifen, talc, canthaxanthine, methoxyflurane and nitrofurantoin; cystoid macular edema (CME) including epinephrine, latanoprost, nicotinic acid; progressive outer retinal necrosis (PORN), acute retinal necrosis (ARN), CMV-retinitis, Sarcoidosis, acute syphilitic posterior placoid chorioretinitis, tuberculosis chorioretinitis, toxoplasmic retinochoroiditis, posterior Uveitis and retinal vasculitis, intermediate uveitis, pars planitis+/− CME, enophthalmitis (anterior and/or posterior), posterior scleritis, masquerade syndromes, multifocal choroiditis and panuveitis (MCP), punctate inner choroidopathy (PIC), birdshot retinochoroidopathy, acute macular neuroretinopathy (AMN) and acute zonal occult outer retinopathy (AZOOR).

Compounds and compositions according to the present invention are suitable for the use in the treatment a disease selected from the group consisting of inherited retinal dystrophies including retinitis pigmentosa (RP), including syndromic and non-syndromic forms, X-chromosome linked, recessive, dominant and sporadic forms, rod-cone dystrophies, Usher's syndrome, Stargardt's disease, cone-rod dystrophies, cone dystrophies, achromatopsia, blue cone monochromacy, enhanced S-cone syndrome, rod dystrophies, choroideremia, Leber's congenital amaurosis, juvenile X-chromosome linked retinoschisis (JXLR), fundus albipunctatus, retinitis *punctata albescens*, fleck retina of Kandori, bietti crystalline retinal dystrophy, fenestrated sheen macular dystrophy, adult-onset foveomacular vitelliform dystrophy, Batten's disease, congenital stationary night blindness, familial exudative vitreoretinopathy (FEVR), ocular albinism, oculocutaneous albinism, fovea hypoplasia, abetalipoproteinemia, Stickler syndrome and retinal dystrophy (Bothnia type). Most preferably, the compound of the present invention is used in the treatment and/or prevention of retinitis pigmentosa (RP), including syndromic and non-syndromic forms, X-chromosome linked, recessive, dominant and sporadic forms.

Compounds and compositions according to the present invention are suitable for the use in the treatment and/or prevention of acquired degeneration selected from the group consisting of crystalline maculopathy (drug-related, hyperoxaluria, cystinosis, Sjogren-Larsson syndrome), west African crystalline maculopathy, solar retinopathy, talc retinopathy, diabetic retinopathy, sickle cell retinopathy, macular telangectasia, eales disease, peripheral retinoschisis.

Compounds and compositions according to the present invention are suitable for the use in the treatment and/or prevention of vascular related retinal degeneration selected from the group consisting of central/branch retinal artery occlusion (CRAO/BRAO), central/branch retinal vein occlusion (CRVO/BRVO), haemorrhagic occlusive retinal vasculitis (HORV).

Compounds and compositions according to the present invention are suitable for the use in the treatment and/or prevention of drug-induced maculopathies selected from the group consisting of chloroquine, hydroxychloroquine, phenothiazine, quinine sulfate, thioridazine, clofazimine, cholopromazine, deferoxamine, chloroquine-derivatives, cisplatin, carmustine, chlofazimine and vigabatrin as well as crystal-induced maculopathies including tamoxifen, talc, canthaxanthine, methoxyflurane, nitrofurantoin, cystoid macular edema (CME) including Epinephrine, latanoprost and nicotinic acid.

Compounds and compositions according to the present invention are suitable for the use in the treatment and/or prevention of infectious and/or inflammatory eye diseases selected from the group consisting of progressive outer retinal necrosis (PORN), acute retinal necrosis (ARN), CMV-retinitis, Sarcoidosis, acute syphilitic posterior placoid chorioretinitis, tuberculosis chorioretinitis, toxoplasmic retinochoroiditis, posterior Uveitis and retinal vasculitis, intermediate uveitis, pars planitis+/−CME, enophthalmitis (anterior and/or posterior), posterior scleritis and masquerade syndromes.

Compounds and compositions according to the present invention are suitable for the use in the treatment and/or prevention of white dot syndromes selected from the group consisting of multifocal choroiditis and panuveitis (MCP), punctate inner choroidopathy (PIC), birdshot retinochoroidopathy, presumed ocular histoplasmosis syndrome (POHS), acute macular neuroretinopathy (AMN) and acute zonal occult outer retinopathy (AZOOR).

The compound or the composition according to the present invention can be administered to a patient, either alone or in combination with one or more additional therapeutic agents. "Patient" as used herein, includes mammals such as humans, non-human primates, rats, mice, rabbits, hares, dogs, cats, horses, cows and pigs, preferably human.

The pharmaceutical composition according to the present invention may comprise one or more additional therapeutic agents.

Preferably, such a pharmaceutical composition provides controlled release properties. The term "controlled release pharmaceutical compositions" herein refers to any composition or dosage form, which comprises the compound of the present invention and which is formulated to provide a longer duration of pharmacological response after administration of the dosage form than is ordinarily experienced after administration of a corresponding immediate release composition comprising the same drug in the same amount. Controlled release may be extended up to several months depending on the matrix used. Preferably, the release of the compound according to the present invention takes place over a period of up to 12 months, most preferably over a period of up to 6 months. Such a controlled release formulation results in an increased patient comfort and in significant lower costs.

The matrix material used for a pharmaceutical composition according to the present may comprise hydrophobic release controlling agents. It is preferably selected from but not limited to polyvinyl acetate dispersion, ethyl cellulose, cellulose acetate, cellulose propionate (lower, medium or higher molecular weight), cellulose acetate propionate, cellulose acetate butyrate, cellulose acetate phthalate, cellulose triacetate, poly (methyl methacrylate), poly (ethyl methacrylate), poly (butyl methacrylate), poly (isobutyl methacrylate), and poly (hexyl methacrylate), poly (isodecyl methacrylate), poly (lauryl methacrylate), poly (phenyl methacrylate), poly (methyl acrylate), poly (isopropyl acrylate), poly (isobutyl acrylate), poly (octadecyl acrylate), waxes such as beeswax, carnauba wax, paraffin wax, microcrystalline wax, and ozokerite; fatty alcohols such as cetostearyl alcohol, stearyl alcohol, cetyl alcohol and myristyl alcohol, and fatty acid esters such as glyceryl monostearate; glycerol monooleate, acetylated monoglycerides, tristearin, tripalmitin, cetyl esters wax, glyceryl palmitostearate, glyceryl behenate, or hydrogenated vegetable oils.

The compound of the invention can be delivered to the eye through a variety of routes, including but not limited to topical application to the eye or by intraocular injection into, for example, the vitreous or subretinal (interphotoreceptor) space; locally by insertion or injection into the tissue surrounding the eye; systemically through an oral route or by subcutaneous, intravenous or intramuscular injection; or via catheter or implant. Most preferably, the compound of the present invention is delivered by intraocular injection. The compound of the invention can be administered prior to the onset of the condition to prevent its occurrence, such as during eye surgery, immediately after the onset of the pathological condition, or during the occurrence of an acute or protracted condition.

Depending on the intended mode of administration, the compound according to the present invention may be incorporated in any pharmaceutically acceptable dosage form, such as for example, liquids, including solutions, suspensions and emulsions, tablets, suppositories, pills, capsules, powders or the like, preferably dosage forms suitable for single administration of precise dosages, or sustained release dosage forms for continuous controlled administration. Most preferred are liquids.

Liquid pharmaceutically administrable dosage forms can be for example a solution, a suspension or an emulsion, preferably a solution comprising a compound of the present invention and optional pharmaceutical adjutants in a carrier, such as for example, water, saline, aqueous dextrose, glycerol, ethanol, DMSO and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate and triethanolamine oleate.

The present invention also relates to a method of treating a retinal disease that leads to photoreceptor loss or outer-retina degeneration, comprising administering a compound of formula (I), preferably (Ia), (Ib), (Ic), (Id), (Ie), (If), (Ig) and (Ih) or a pharmaceutically acceptable salt, a racemic mixture, a corresponding enantiomer or, if applicable, a corresponding diastereomer thereof to a patient having the retinal disease so as to be delivered to an eye of the patient in an amount effective to treat the retinal disease. The compounds of formula Ia), (Ib), (Ic), (Id), (Ie), (If), (Ig) and (Ih) are defined above in detail.

Experimental Section

Preparation of the Compounds of the Invention

The compounds of formula (I) may be prepared by methods described below, together with synthetic methods known in the art of organic chemistry, or modifications that are familiar to those of ordinary skill in the art. The starting materials used herein are available commercially or may be prepared by routine methods known in the art, such as those methods described in standard reference books such as "Compendium of Organic Synthetic Methods, Vol. I-XlN" (published with Wiley-Interscience, ISSN: 1934-4783). Preferred methods include, but are not limited to, those described below.

The schemes are representative of methods useful in synthesizing the compounds of the present invention and the supporting examples. They are not to constrain the scope of the invention in anyway.

General Methods—Synthesis

Method 1:

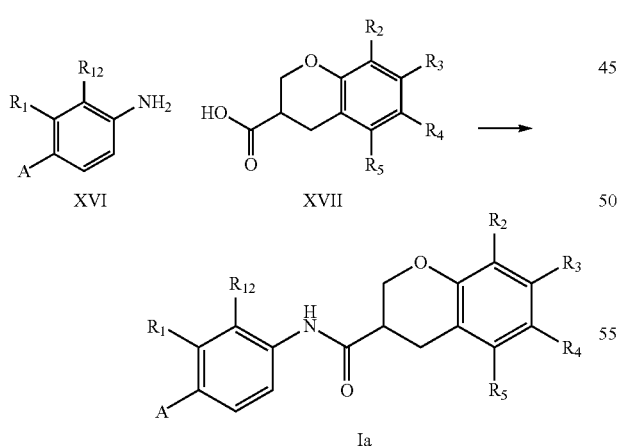

Ia where $R_1$, $R_{12}$, $R_2$, $R_3$, $R_4$ and $R_5$ are as described in formula I.

Compounds of general formula Ia (Scheme 1) may be prepared by reacting compounds of general formula XVI with a carboxylic acid of general formula XVII using procedures known to chemists skilled in the art.

Method 2

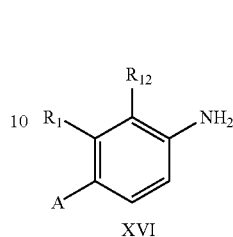

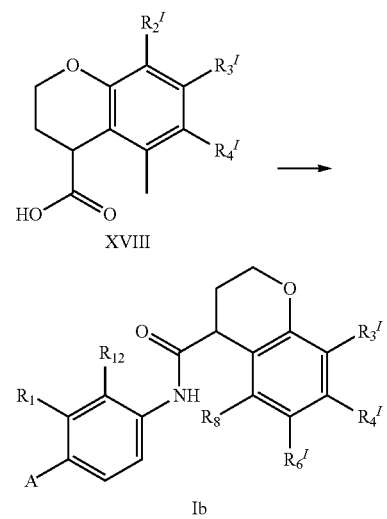

Ib

Where A, $R_1$, $R_{12}$, $R_2^I$, $R_3^I$, $R_4^I$ and $R_5^I$ are as described in formula I.

Compounds of general formula Ib (Scheme 2) may be prepared by reacting compounds of general formula XVI with a carboxylic acid of general formula XVIII using procedures known to chemists skilled in the art.

Method 3:

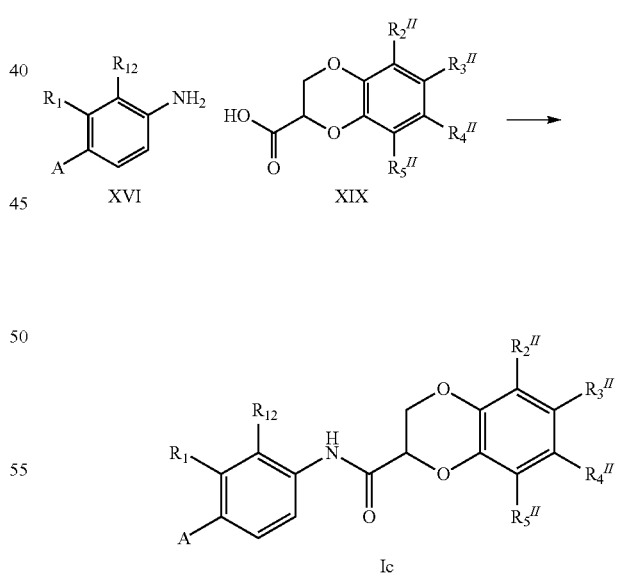

Ic where A, $R_1$, $R_{12}$, $R_2^{II}$, $R_3^{II}$, $R_4^{II}$ and $R_5^{II}$ are as described in formula I.

Compounds of general formula Ic (Scheme 3) may be prepared by reacting compounds of general formula XVI with a carboxylic acid of general formula XIX using procedures known to chemists skilled in the art.

Method 4:

Scheme 4

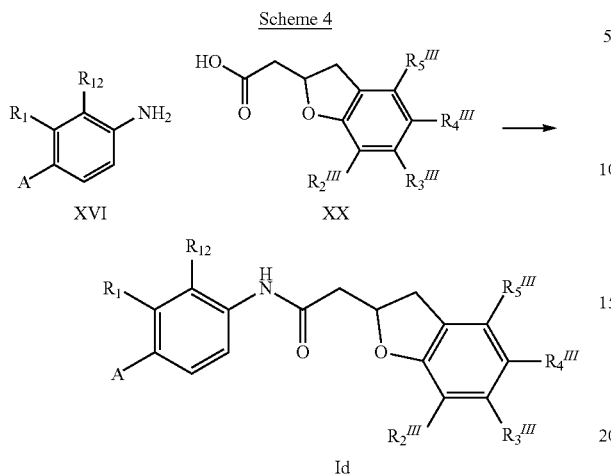

Id where A, $R_1$, $R_{12}$, $R_2^{III}$, $R_3^{III}$, $R_4^{III}$ and $R_5^{III}$ are as described in formula I.

Compounds of general formula Id (Scheme 4) may be prepared by reacting compounds of general formula XVI with a carboxylic acid of general formula XX using procedures known to chemists skilled in the art.

Method 5:

Scheme 5

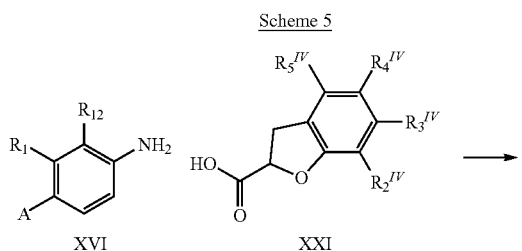

Ie where A, $R_1$, $R_{12}$, $R_2^{IV}$, $R_3^{IV}$, $R_4^{IV}$ and $R_5^{IV}$ are as described in formula I.

Compounds of general formula Ie (Scheme 5) may be prepared by reacting compounds of general formula XVI with a carboxylic acid of general formula XXI using procedures known to chemists skilled in the art.

Method 6:

Scheme 6

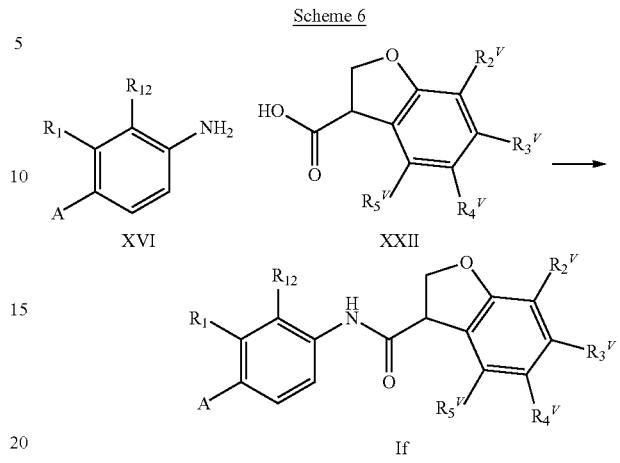

If where A, $R_1$, $R_{12}$, $R_2^V$, $R_3^V$, $R_4^V$ and $R_5^V$ are as described in formula I.

Compounds of general formula If (Scheme 6) may be prepared by reacting compounds of general formula XVI with a carboxylic acid of general formula XXII using procedures known to chemists skilled in the art.

Method 7:

Scheme 7

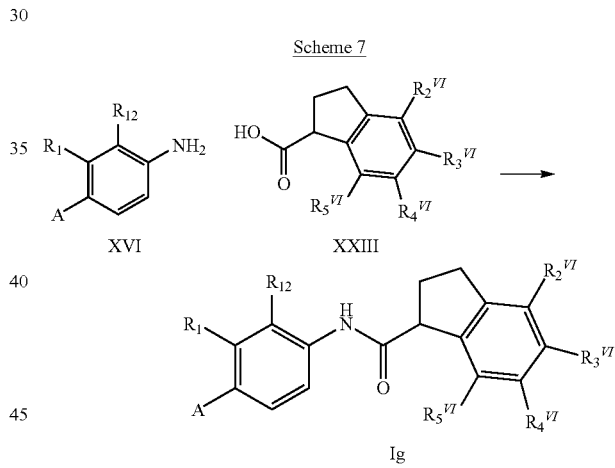

Ig where A, $R_1$, $R_{12}$, $R_2^{VI}$, $R_3^{VI}$, $R_4^{VI}$ and $R_5^{VI}$ are as described in formula I.

Compounds of general formula Ig (Scheme 7) may be prepared by reacting compounds of general formula XVI with a carboxylic acid of general formula XXIII using procedures known to chemists skilled in the art.

Method 8:

Scheme 8

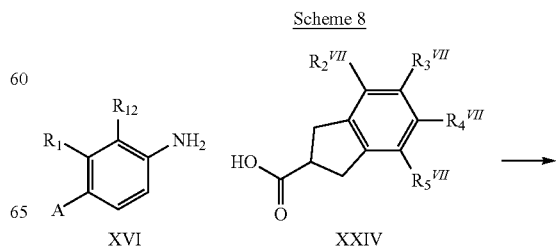

-continued

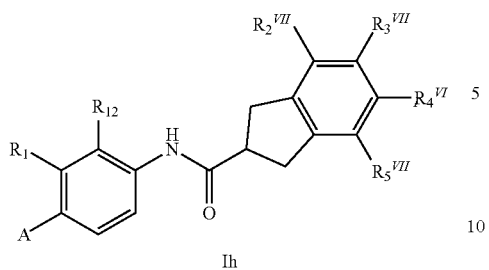

Ih where A, $R_1$, $R_{12}$, $R_2^{VII}$, $R_3^{VII}$, $R_4^{VII}$ and $R_5^{VII}$ are as described in formula I.

Compounds of general formula Ih (Scheme 8) may be prepared by reacting compounds of general formula XVI with a carboxylic acid of general formula XXIV using procedures known to chemists skilled in the art.

Method 9:

Scheme 9

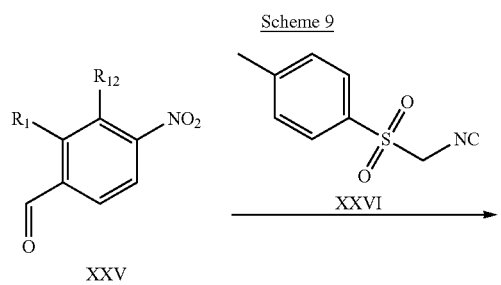

XXV    XXVI

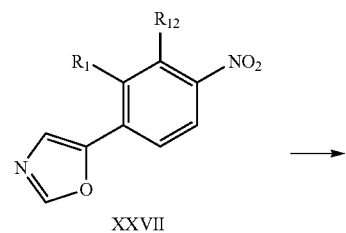

XVIa where $R_1$, $R_{12}$ are as described in formula I.

Compounds of general formula XVIa (Scheme 9) may be prepared by reduction of the nitro group in compounds of general formula XXVII using procedures known to chemists skilled in the art. Compounds of general formula XXVII may be prepared from aldehydes of general formula XXV by reaction in the presence of a reagent such as isocyanometh-ane)sulfonyl-4-methylbenzene (XXVI) in the presence of a base such as potassium carbonate.

Method 10:

Scheme 10

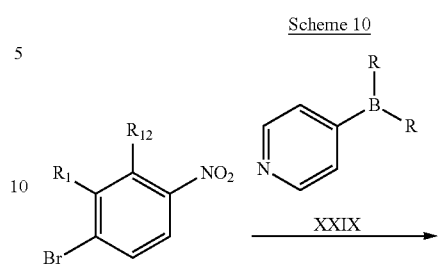

XXVIII    XXIX

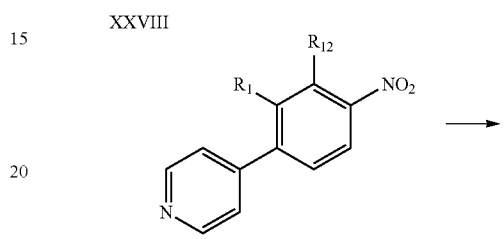

XXX

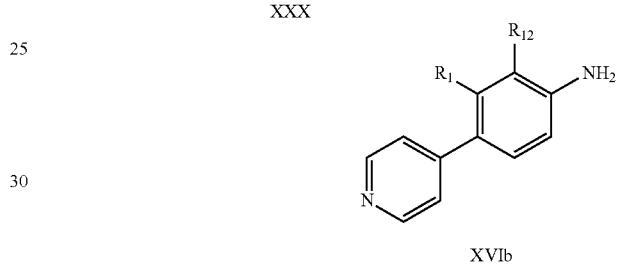

XVIb where $R_1$, $R_{12}$ are as described in formula I and R are hydroxy groups or R together with the boron atom form a 4,4,5,5-tetramethyl-1,3,2-dioxaborolane group.

Compounds of general formula XVIb (Scheme 10) may be prepared by reduction of the nitro group in compounds of general formula XXX using procedures known to chemists skilled in the art. Compounds of general formula XXX can be prepared from compounds of general formulae XXVIII and XXIX in the presence of a palladium catalyst such as tetrakis(triphenylphosphin)palladium(0) and a base such as potassium carbonate or other Suzuki-Miyaura coupling reaction conditions known to chemists skilled in the art of organic synthesis.

Method 11:

Scheme 11

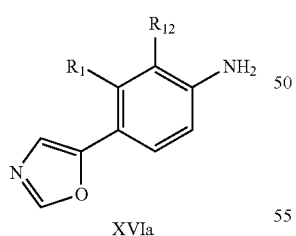

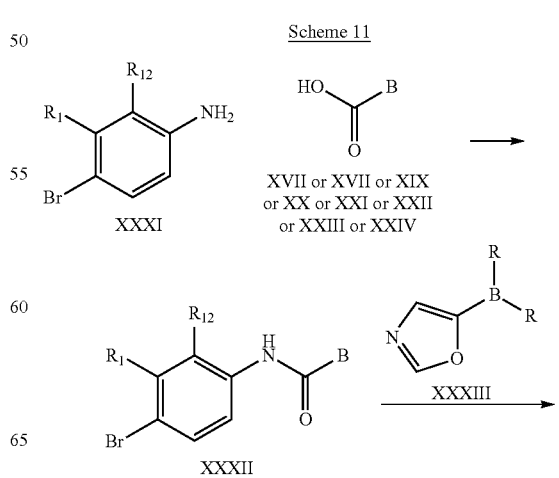

XXXI    XVII or XVII or XIX or XX or XXI or XXII or XXIII or XXIV

XXXII    XXXIII

-continued

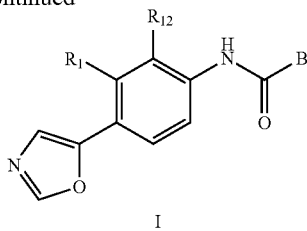

I where $R_1$, $R_{12}$ are as described in formula I, R are hydroxy groups or R together with the boron atom form a 4,4,5,5-tetramethyl-1,3,2-dioxaborolane group.

Compounds of general formula I (Scheme 11) may be prepared from compounds of general formulae XXXIII and XXXII in the presence of a palladium catalyst such as tetrakis(triphenylphosphin)palladium(0) and a base such as potassium carbonate or other Suzuki-Miyaura coupling reaction conditions known to chemists skilled in the art of organic synthesis. Compounds of general formula XXXII may be prepared by reacting compounds of general formula from XXXI with a carboxylic acid of general formula XVII-XXIV using procedures known to chemists skilled in the art.

Method 12:

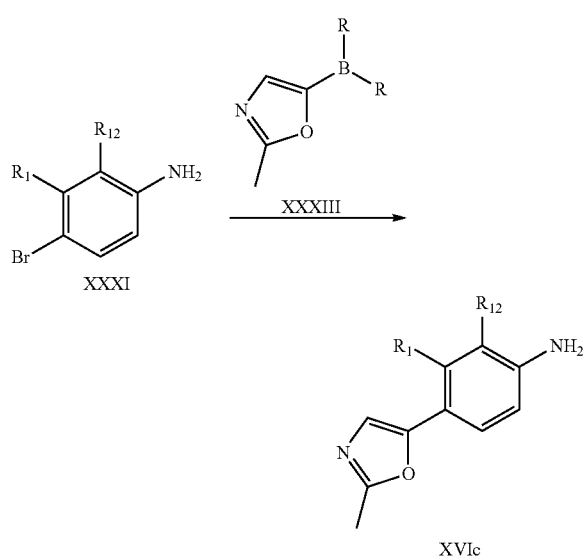

Scheme 12 where $R_1$, $R_{12}$ are as described in formula I, R are hydroxy groups or R together with the boron atom form a 4,4,5,5-tetramethyl-1,3,2-dioxaborolane group.

Compounds of general formula XVIc (Scheme 12) may be prepared from compounds of general formulae XXXI and XXXIII in the presence of a palladium catalyst such as tetrakis(triphenylphosphin)palladium(0) and a base such as potassium carbonate or other Suzuki-Miyaura coupling reaction conditions known to chemists skilled in the art of organic synthesis.

Analytic Methods $^1$H NMR spectra were recorded in DMSO-$d_6$/CD$_3$OD/CDCl$_3$ solution in 5 mm o.d. tubes [Wilmad NMR tubes (Sigma-Aldrich), 5 mm Thin Wall, 7" Length] at 300.0 K and were collected on Bruker Avance NMRS-400 at 400 MHz for 1H. The chemical shifts (5) are relative to CDCl$_3$ (CDCl$_3$=7.26 ppm), DMSO-$d_6$ (DMSO-$d_6$=2.5 ppm), CD$_3$OD (CD$_3$OD=3.3 ppm) and expressed in ppm. The chemical shifts in CDCl$_3$, DMSO-$d_6$ and CD$_3$OD are relative to tetramethylsilane (TMS, =0.00 ppm) and expressed in ppm.

Analytical HPLC

Analytical HPLC Method A: Chromegabond WR C18 (3 cm×3.2 mm, 3µ) column operated with a flow rate of 1.5 mL/min. As mobile phases, 0.02% TFA in water (mobile phase C) and 0.02% TFA in CH$_3$CN (mobile phase D) were used in a gradient starting at 90% C and 10% D, changed to 10% C and 90% D in 3.0 min, then to 90% C and 10% D in 4.0 min, which was held constant up to 5.1 min.

Analytical HPLC Method B: Restek Ultra AQ C18 (30× 2.1 mm, 3 u) column operated with a flow rate of 1.5 mL/min. As mobile phases, 0.05% HCOOH in water (mobile phase A) and CH$_3$CN (mobile phase B) were used in a gradient starting at 98% A and 2% B held for 0.75 min, then to 90% A and 10% B in 1.5 min, further to 2% A and 98% B in 3.0 min, held this mobile phase composition up to 4.0 min and finally back to initial condition at 5.0 min.

Preparative HPLC

Preparative HPLC Method A: Waters Sunfire C18 OBD Prep Column, 100 A, 5 µm, 19 mm×100 mm with SunFire C18 Prep Guard Cartridge, 100 A, 10 µm, 19 mm×10 mm was used. Deionized Water (phase A) and HPLC-grade Methanol (phase B) were used as an eluent.

Preparative HPLC Method B: Waters auto purification instrument with a YMC Triart C18 (250×21.2 mm, 5µ) column operated at rt with a flow rate of 16 mL/min. Samples were eluted with 20 mM ammonium bicarbonate in water (mobile phase A) and acetonitrile (mobile phase B) and a gradient profile of 70% A and 30% B initially, then 45% A and 55% B in 3 min, adapted to 20% A and 80% B in 20 min, then to 5% A and 95% B in 21 min, which was held constant for 2 min. Pure fractions were concentrated to yield the final product.

Methods for Chiral Separation

Chiral SFC

Chiral Separation Method A: Separation was accomplished using Agilent Prep-HPLC, Column: Regis Reflect C-Amylose A containing Amylose tris(3,5-dimethylphenylcarbamate) (250×30 mm, 5µ), Flow: 35 g/min, Mobile Phase: 35% CO$_2$+65% (0.1% NH3 in MeOH), ABPR: 100 bar, Temperature: 35° C.

Chiral Separation Method B: Separation was accomplished using Agilent Prep-HPLC, Column: Daicel Chiralpak IG (250×20 mm) containing tris (3-chloro-5 methylphenylcarbamate) substituted amylose immobilized on 5 µm silica; Flow: 25 g/min, Mobile Phase: 45% CO$_2$+55% (0.1% NH3 in MeOH), ABPR: 120 bar, Temperature: 35° C.

Chiral Separation Method C: Separation was accomplished using: Column: Regis Reflect C-Amylose A containing Amylose tris (3,5-dimethylphenylcarbamate) (250× 30 mm, 5µ), Mobile phase: 40% CO2+60% (0.1% ammonia in MeOH), Flow rate: 25.0 g/min, Run time: 10 min, Wave length: 220 nm, ABPR: 110 bar, Temperature: 35° C., Solubility: Methanol.

Chiral Preparative HPLC

Chiral Separation Method D: performed using a Daicel Chiralpak AD-H (250×20 mm×5 µm) column coated with amylose-tris(3,5-dimethylphenylcarbamate); Mobile phase: Hexane-IPA-MeOH, 70-15-15 Flow Rate: 12 mL/min; Column Temperature: 24° C.; Wavelength: 210 nm, 225 nm, 254 nm).

General Synthetic Procedures

Coupling procedure A: the carboxylic acid (1.1 mmol) and a solution of N-hydroxybenzotriazole in DMSO (100 g/L, 2 mL, 1.5 mmol) were placed in a vial, and the aniline derivative (1 mmol) was added. If amine was used as a hydrochloride, Et$_3$N (1 mmol) was also added. The reaction mixture was stirred for 30 min in a shaker, and EDC (1.2 mmol) was added. After all the reagents were loaded, the vial was sealed and stirred in a shaker for 1 h. If clear solution was formed, the vial was left at rt for 24 h. Otherwise, the reaction mixture was kept in a sonication bath for 24 h (strong heating should be avoided). If strong thickening of the reaction mixture was observed so that stirring was not effective, 0.2 mL of DMSO might be added in one portion. The crude reaction mixture was analyzed by LC-MS and then subjected to chromatographic purification. The purification was performed using Agilent 1260 Infinity systems equipped with DAD and mass-detector.

Synthesis of Intermediates

Preparation of 5-(2-methoxy-4-nitrophenyl)oxazole

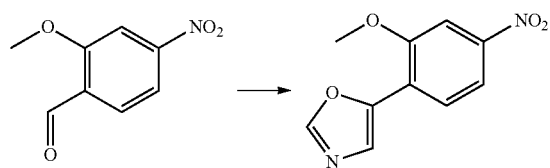 [SMILES: COc1cc([N+](=O)[O-])ccc1C=O ; COc1cc([N+](=O)[O-])ccc1-c1cnco1]

To a stirred solution of 2-methody-4-nitrobenzaldehyde (3.00 g, 16.6 mmol) in methanol (20 mL) was added 1-(isocyanomethane)sulfonyl-4-methylbenzene (3.80 g, 19.9 mmol) followed by K$_2$CO$_3$ (8.00 g, 58.0 mmol) and the reaction mixture was heated to 80° C. for 2 h. After completion of the reaction, reaction mass was poured into sat NaHCO$_3$ solution (20 mL) and extracted into ethyl acetate (3×100 mL). The organic layer was washed with water, brine, dried over anhydrous sodium sulphate and concentrated under vacuum to get a crude which was purified by flash silica gel chromatography (eluted at 30% ethyl acetate in hexane) to get 5-(2-methoxy-4-nitrophenyl)-1,3-oxazole (2.1 g, 57%). LCMS: 221 (M+H).

Preparation of 3-methoxy-4-(1,3-oxazol-5-yl)aniline

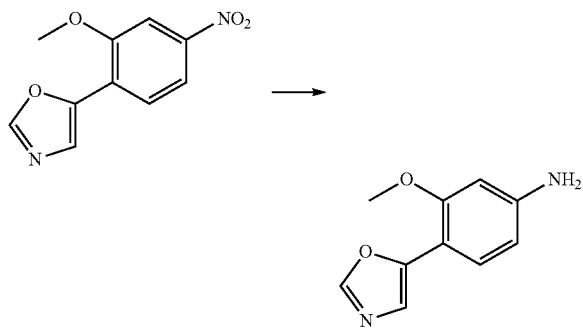

To a stirred solution of 5-(2-methoxy-4-nitrophenyl)-1,3-oxazole (1.00 g, 4.52 mmol) in ethanol (20 mL) were added tin(II)chloride (5.14 g, 27.1 mmol) and conc. HCl (6 mL) solution drop wise at 0° C. and then stirred for 6 h at room temperature. After completion of the reaction, the reaction mixture was diluted with sat. NaHCO$_3$ solution (20 mL), extracted with ethyl acetate (3×200 mL) and the organic layer was washed with water, brine, dried over anhydrous sodium sulphate and concentrated under vacuum to get crude of 3-methoxy-4-(1,3-oxazol-5-yl)aniline (700 mg, 81%). LCMS: 191 (M+H).

Preparation of 5-(2-chloro-4-nitrophenyl)-1,3-oxazole

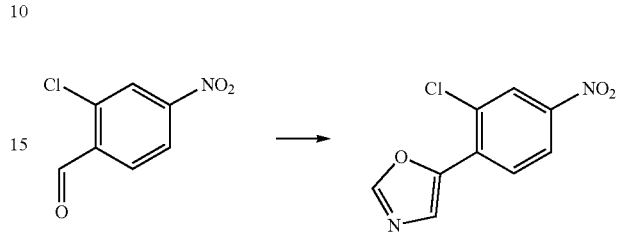

To a stirred solution of 2-chloro-4-nitrobenzaldehyde (3 g, 16.16 mmol) and 1-(isocyanomethane) sulfonyl-4-methylbenzene (4.1 g, 21.0 mmol) in MeOH (30 mL) was added K$_2$CO$_3$ (8.9 g, 64.66 mmol) and the reaction mixture was heated to 80° C. for 2 h. After completion of the reaction, the reaction mass was poured into saturated NaHCO$_3$ solution (20 mL) and extracted with ethyl acetate (2×50 mL). The organic layer was washed with water, brine, dried over anhydrous sodium sulphate and concentrated under vacuum to get a crude which was purified by flash silica gel chromatography (eluted with 30% ethyl acetate in hexane) to afford 5-(2-chloro-4-nitrophenyl)-1,3-oxazole (2.1 g, 57%). LCMS: 225.2 (M+H).

Preparation of 3-chloro-4-(1,3-oxazol-5-yl)aniline

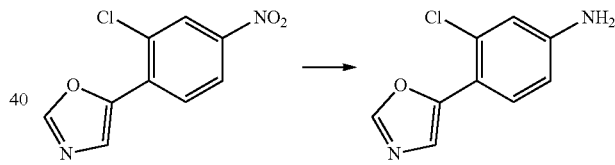

To a stirred solution of 5-(2-chloro-4-nitrophenyl)-1,3-oxazole (3 g, 13.4 mmol) in EtOH (40 mL) were added SnCl$_2$ dihydrate (12.08 g, 53.57 mmol) and conc. HCl (5 mL) dropwise at 0° C. and the reaction mixture was stirred for 30 min at 80° C. After completion of the reaction, the reaction mass was neutralized using a 2N NaOH solution and extracted with ethyl acetate (2×50 mL). The organic layer was thoroughly washed with water, dried over anhydrous sodium sulphate and concentrated under vacuum to afford 3-chloro-4-(1,3-oxazol-5-yl)aniline (1.5 g, 57%). LCMS: 195 (M+H).

Preparation of 5-(2-fluoro-4-nitrophenyl)-1,3-oxazole

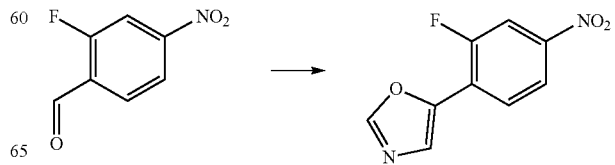

To a stirred solution of 2-fluoro-4-nitro benzaldehyde (5 g, 29.56 mmol) and 1-(isocyanomethane)sulfonyl-4-methylbenzene (7.5 g, 38.43 mmol) in MeOH (35 mL) was added K₂CO₃ (16.3 g, 118.27 mmol) and the reaction mixture was heated to 80° C. for 2 h. After completion of the reaction, reaction mass was poured into saturated NaHCO₃ solution (50 mL) and extracted with ethyl acetate (2×50 mL). The organic layer was washed with water, brine, dried over anhydrous sodium sulphate and concentrated under vacuum to get a crude which was purified by flash silica gel chromatography (eluted with 30% ethyl acetate in hexane) to afford 5-(2-fluoro-4-nitrophenyl)-1,3-oxazole (2.5 g, 40%). LCMS: 209.2 (M+H).

Preparation of 3-fluoro-4-(1,3-oxazol-5-yl)aniline

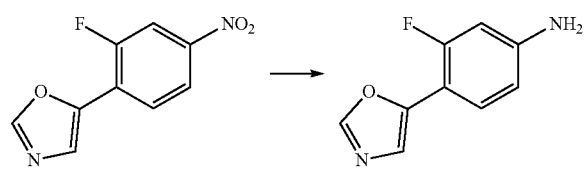

To a stirred solution of 5-(2-fluoro-4-nitrophenyl)-1,3-oxazole (700 mg, 3.36 mmol) in EtOH (35 mL) were added tin(II) chloride SnCl₂ dihydrate (3.03 g, 13.46 mmol) and conc. HCl (2 mL) dropwise at 0° C. and the reaction mixture was stirred for 30 min at 80° C. After completion of the reaction, the reaction mass was neutralized with a 2N NaOH solution and extracted with ethyl acetate (2×50 mL). The organic layer was thoroughly washed with water, dried over anhydrous sodium sulphate and concentrated under vacuum to afford 3-fluoro-4-(1,3-oxazol-5-yl)aniline (350 mg, 53%). LCMS: 179 (M+H).

Preparation of 5-(2-methyl-4-nitrophenyl)oxazole

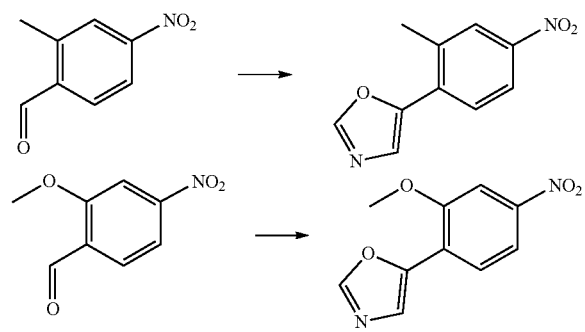

To a stirred solution of 2-methyl-4-nitrobenzaldehyde (1.02 g, 6.05 mmol) and 1-(isocyanomethane)sulfonyl-4-methylbenzene (1.36 g, 7.05 mmol) in MeOH (25 mL) was added potassium carbonate (1.67 g, 12.1 mmol) and the reaction mixture was heated to reflux for 2 h. After consumption of starting material by TLC, the reaction mixture was cooled to room temperature, the solvent was evaporated under reduced pressure, the residue was treated with saturated aqueous solution of NaHCO₃ (20 mL), and extracted with ethyl acetate (3×30 mL). The organic layer was washed with water (30 mL), brine (20 mL), dried over anhydrous Na2SO4, and concentrated under reduced pressure to get crude which was purified by flash column chromatography to get 5-(2-methyl-4-nitrophenyl)oxazole (1.2 g, 91%).

Preparation of 3-methyl-4-(oxazol-5-yl)aniline

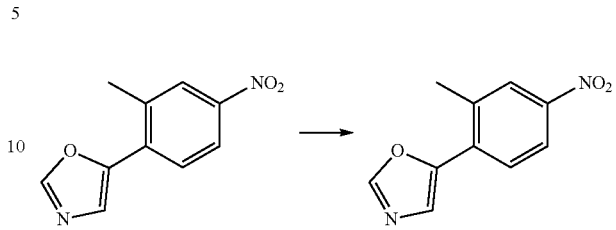

To a stirred solution of 5-(2-methyl-4-nitrophenyl)oxazole (1.1 g, 5.39 mmol) in ethanol (20 mL) was added tin(II) chloride dihyrate (4.08 g, 21.5 mmol) at room temperature. The mixture was cooled to 0° C. and conc. HCl (3.0 mL) was added drop wise. The reaction mixture was then stirred for 0.5 h at 80° C. After completion of the reaction by TLC, the reaction mixture was cooled to room temperature, diluted with saturated aqueous solution of NaHCO₃ solution (30 mL), and extracted with ethyl acetate (3×30 mL). Organic layers were combined, washed with water (20 mL), brine (15 mL), dried over anhydrous Na₂SO₄, and concentrated under reduced pressure. The crude was purified by column chromatography to get 3-methyl-4-(oxazol-5-yl)aniline (2C1) (610 mg, 65%).

Preparation of 5-(3-methyl-4-nitrophenyl)oxazole

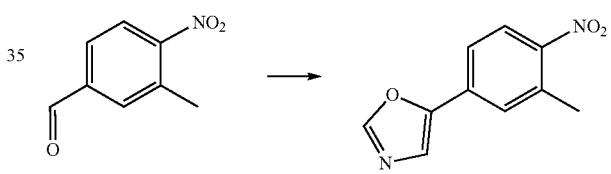

To a stirred solution of 3-methyl-4-nitrobenzaldehyde (2.01 g, 12.1 mmol) and 1-(isocyanomethane)sulfonyl-4-methylbenzene (2.6 g, 13.3 mmol) in MeOH (50 mL) was added K₂CO₃ (3.34 g, 24.2 mmol) and the reaction mixture was heated to reflux for 2 h. After complete consumption of starting material by TLC, the reaction was cooled to room temperature, solvent was evaporated under reduced pressure, the residue was treated with saturated aqueous solution of NaHCO₃ (40 mL), and extracted with ethyl acetate (3×40 mL). The organic layers were combined, washed with water (30 mL) and brine (20 mL), dried over Na₂SO₄, and concentrated under reduced pressure. The crude was purified by column chromatography using silica (to get 5-(3-methyl-4-nitrophenyl)oxazole (1.9 g, 76%).

Preparation of 2-methyl-4-(oxazol-5-yl)aniline

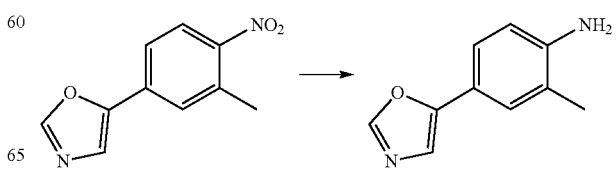

To a stirred solution of 5-(3-methyl-4-nitrophenyl)oxazole) (1.8 g, 5.39 mmol) in methanol (20 mL) was added Raney Ni (2.0 g) at room temperature. The reaction mixture was stirred under $H_2$ atmosphere for 18 h. After complete consumption of starting material, reaction mixture was filtered through a bed of celite and the filtrate was concentrated under reduced pressure. The crude was purified by column chromatography to get 2-methyl-4-(oxazol-5-yl)aniline (1.3 g, 84%).

LCMS: 174.7 (M+H)

Preparation of
5-(4-nitro-2-(trifluoromethyl)phenyl)oxazole

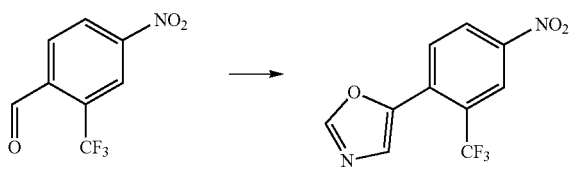 [SMILES: O=Cc1ccc([N+](=O)[O-])cc1C(F)(F)F ; O=[N+]([O-])c1ccc(-c2cnco2)c(C(F)(F)F)c1]

To a stirred solution of 4-nitro-2-(trifluorometyl)benzaldehyde (2.0 g, 9.13 mmol) and 1-(isocyanomethane)sulfonyl-4-methylbenzene (2.05 g, 10.5 mmol) in MeOH (50 mL) was added $K_2CO_3$ (2.52 g, 18.26 mmol) and the reaction mixture was heated to reflux for 2 h. After consumption of starting material by TLC, the reaction mixture was cooled to room temperature, the solvent was evaporated under reduced pressure, the residue was treated with saturated aqueous solution of $NaHCO_3$ (20 mL), and extracted with ethyl acetate (3×30 mL). The organic layer was washed with water (30 mL), brine (20 mL), dried over $Na_2SO_4$, and concentrated under reduced pressure to get crude which was purified by column chromatography to get 5-(4-nitro-2-(trifluoromethyl)phenyl)oxazole (1.66 g, 72%).

Preparation of
4-(oxazol-5-yl)-3-(trifluoromethyl)aniline

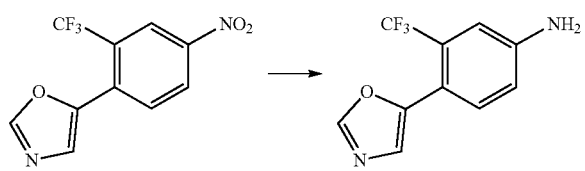 [SMILES: O=[N+]([O-])c1ccc(-c2cnco2)c(C(F)(F)F)c1 ; Nc1ccc(-c2cnco2)c(C(F)(F)F)c1]

To a stirred solution of 5-(4-nitro-2-(trifluoromethyl)phenyl)oxazole (1.545 g, 5.99 mmol) in ethanol (30 mL) was added tin(II) chloride dihydrate (5.40 g, 23.95 mmol) at room temperature. The mixture was cooled to 0° C. and conc. HCl (3.5 mL) was added drop wise. The reaction mixture was then stirred for 2.0 h at 80° C. After completion of the reaction by TLC, the reaction mixture was cooled to room temperature, diluted with saturated aqueous solution of $NaHCO_3$ solution (70 mL), and extracted with ethyl acetate (3×50 mL). Organic layers were combined, washed with water (40 mL), brine (30 mL), dried over anhydrous $Na_2SO_4$, and concentrated under reduced pressure. The crude was purified by column chromatography to get 4-(oxazol-5-yl)-3-(trifluoromethyl)aniline (1.13 mg, 83%).

Preparation of 4-(2-methoxy-4-nitrophenyl)pyridine

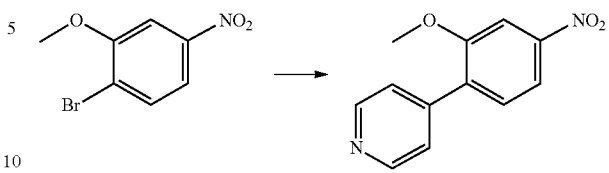

To a stirred solution of 1-bromo-2-methoxy-4-nitrobenzene (5 g, 21.55 mmol) in 1.4 dioxane (50 ml) and water (10 ml) were added (pyridin-4-yl)boronic acid (3.97 g, 32.32 mmol) and $K_2CO_3$ (8.92 g, 64.65 mmol). After degassing with nitrogen for 10 min $Pd(Ph_3P)_4$ (0.498 g, 0.431 mmol) was added and the flask was degassed again with nitrogen to then let the reaction mixture be stirred at 85-90° C. for 12 h. After completion of the reaction the reaction mixture was diluted with ethyl acetate (100 ml) followed by washing the ethyl acetate layer with water (2×50 ml) and brine (2×50 ml) successively. The organic layer was dried with $Na_2SO_4$ and concentrated to dryness and the crude mass was purified by flash column chromatography to afford 4-(2-methoxy-4-nitrophenyl)pyridine.

LCMS: 230 (M+H).

Preparation of 3-methoxy-4-(pyridin-4-yl)aniline

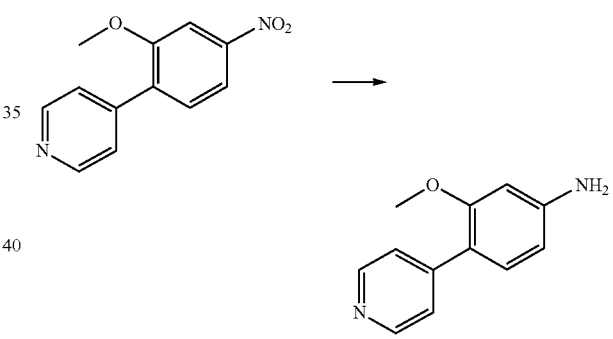

A flask containing 4-(2-methoxy-4-nitrophenyl) pyridine (2.5 g, 10.8 mmol) was flushed with nitrogen gas and 10% Pd/C (2.3 g, 21.7 mmol) was added. Ethyl acetate (50 mL) was added to the mixture, the $N_2$ supply was replaced with $H_2$ and the black suspension was stirred under $H_2$ for 5 h after which the reaction was completed. The suspension was filtered through celite, washed with ethyl acetate and concentrated under vacuum to yield 3-methoxy-4-(pyridin-4-yl)aniline (1.42 g, 65.2%).

LCMS: 200 (M+H).

Preparation of 7-methoxy-2,3-dihydrobenzo[b][1,4]dioxine-2-carboxylic acid

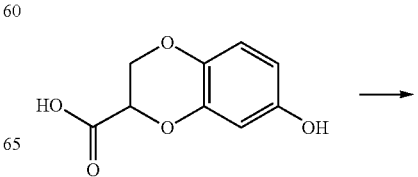

-continued

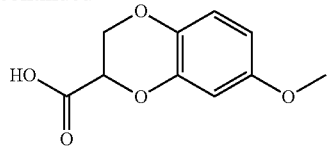

To a stirred solution of 7-hydroxy-2,3-dihydro-1,4-benzodioxine-2-carboxylic acid (200 mg, 1.02 mmol) in 1,4-Dioxane (4 mL) at room temperature was added 10% aqueous NaOH solution (1.5 mL), followed by dropwise addition of $Me_2SO_4$ (dimethyl sulphate) (0.24 mL). The reaction mixture was heated to 50° C. for 10 min followed by further addition of 10% aqueous NaOH (1.5 mL). The mixture was kept for 1 h at 50° C. before it was cooled and poured into ice cold water (10 mL), acidified with 6N HCl and extracted with 10% MeOH/DCM (1×15 mL). The organic part was dried over anhydrous sodium sulphate, concentrated and washed with ether and pentane to afford 7-methoxy-2,3-dihydrobenzo[b][1,4]dioxine-2-carboxylic acid (150 mg, 69%).

LCMS: 211.2 (M+H).

Preparation of Chroman-3-carbonyl chloride

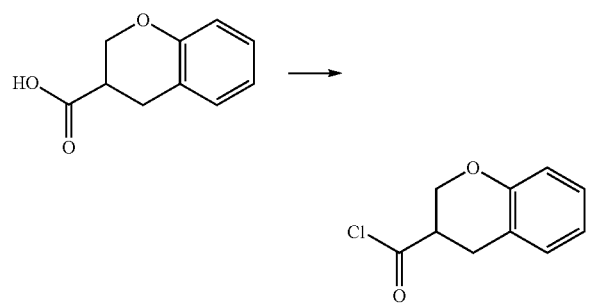

To a solution of chroman-3-carboxylic acid (750 mg, 4.21 mmol) in dry DCM (10 mL) was added thionyl chloride (0.45 mL, 6.32 mmol) at 0° C. followed by DMF (catalytic). After the addition, the reaction mixture was warmed to room temperature and heated to reflux for 2.0 h. The reaction mass was cooled to room temperature, the solvent was evaporated under reduced pressure, and dried under vacuum.

Preparation of
N-(4-bromo-2-(difluoromethoxy)phenyl)
chroman-3-carboxamide

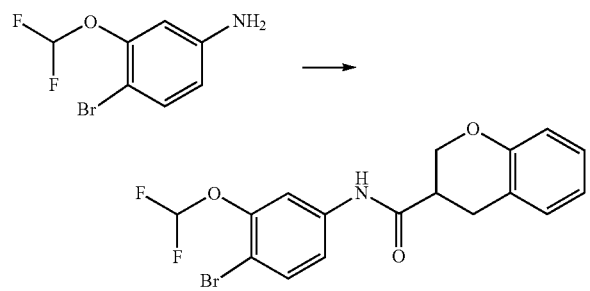

A solution of chroman-3-carbonyl chloride in dry DCM (10 mL) was added to the mixture of 4-bromo-2-(difluoromethoxy)aniline (600 mg, 2.521 mmol) and triethylamine (1.1 mL, 7.563 mmol) in dry DCM (10 mL) at 0° C. After the addition, reaction was slowly warmed to room temperature over 3 h. The reaction was diluted with DCM (5 mL), washed with water (10 mL) and brine (15 mL), dried over $Na_2SO_4$, and concentrated under reduced pressure to get crude. Purification of the crude by column chromatography gave N-(4-bromo-2-(difluoromethoxy)phenyl)chroman-3-carboxamide (520 mg, 62%).

Compound (1): N-(3-chloro-4-(1,3-oxazol-5-yl)
phenyl) chromane-3-carboxamide

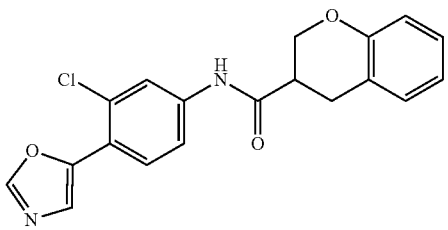 [SMILES: O=C(Nc1ccc(-c2cnco2)c(Cl)c1)C1COc2ccccc2C1]

To a stirred solution of 3-chloro-4-(oxazol-5-yl)aniline (100 mg, 0.51 mmol) and chromane-3-carboxylic acid (109 mg, 0.61 mmol) in DMF (1 mL) were added DIPEA (0.26 mL) and HATU (392 mg, 1.03 mmol) at room temperature and the reaction was stirred for 16 h at rt. After completion of the reaction, the reaction mixture was purified by preparative HPLC to yield N-(3-chloro-4-(1,3-oxazol-5-yl)phenyl)chromane-3-carboxamide (34 mg, 18%).

Analytical HPLC Method A. Rt: 1.73 min; MS: 355 (M+H).

Compound (2): N-(3-chloro-4-(oxazol-5-yl)phenyl)
chromane-4-carboxamide

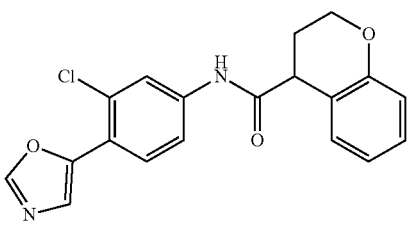 [SMILES: O=C(Nc1ccc(-c2cnco2)c(Cl)c1)C1CCOc2ccccc21]

To a stirred solution of 3-chloro-4-(oxazol-5-yl)aniline (100 mg, 0.51 mmol) and 3,4-dihydro-2H-1-benzopyran-4-carboxylic acid (119.4 mg, 0.67 mmol) in DMF (1 mL) were added DIPEA (0.26 mL) and HATU (392 mg, 1.03 mmol) at room temperature and the reaction was stirred for 16 h at rt. After completion of the reaction, the reaction mixture was purified by preparative HPLC to yield N-(3-chloro-4-(oxazol-5-yl)phenyl)chromane-4-carboxamide (56 mg, 30%).

Analytical HPLC Method A. Rt: 1.55 min; MS: 355.2 (M+H).

Compound (3): N-(3-chloro-4-(oxazol-5-yl)phenyl)-6-methoxychromane-3-carboxamide

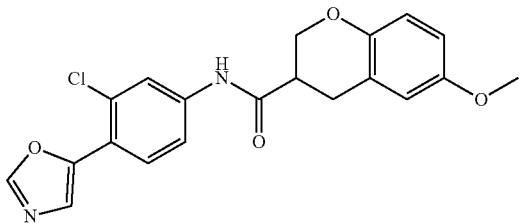 [SMILES: COc1ccc2c(c1)CC(C(=O)Nc1ccc(-c3cnco3)c(Cl)c1)CO2]

To a stirred solution of 3-chloro-4-(oxazol-5-yl)aniline (200 mg, 1.03 mmol) and 6-methoxy-3,4-dihydro-2H-1-benzopyran-3-carboxylic acid (278.76 mg, 1.34 mmol) in DMF (2 mL) were added DIPEA (0.52 mL) and HATU (784 mg, 2.06 mmol) at room temperature and the reaction was stirred for 16 h at rt. After completion of the reaction, the reaction mixture was purified by preparative HPLC to yield N-(3-chloro-4-(oxazol-5-yl)phenyl)-6-methoxychromane-3-carboxamide (143 mg, 36%).

Analytical HPLC Method A. Rt: 1.73 min; MS: 385.2 (M+H).

Compound (4): N-(3-fluoro-4-(oxazol-5-yl)phenyl)chromane-4-carboxamide

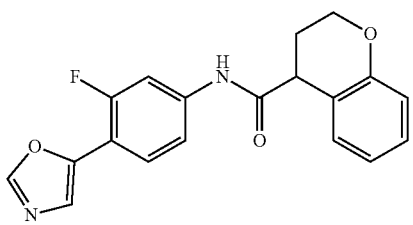 [SMILES: O=C(Nc1ccc(-c2cnco2)c(F)c1)C1CCOc2ccccc21]

To a stirred solution of 3-fluoro-4-(1,3-oxazol-5-yl)aniline (150 mg, 0.84 mmol) and 3,4-dihydro-2H-1-benzopyran-4-carboxylic acid (195.21 mg, 1.09 mmol) in DMF (2 mL) were added DIPEA (0.44 mL) and HATU (640 mg, 1.68 mmol) at room temperature and the reaction was stirred for 16 h at rt. After completion of the reaction, the reaction mixture was purified by preparative HPLC to yield N-(3-fluoro-4-(oxazol-5-yl)phenyl)chromane-4-carboxamide (102 mg, 35%).

Analytical HPLC Method A. Rt: 1.50 min; MS: 339.2 (M+H).

Compound (5): N-(3-fluoro-4-(oxazol-5-yl)phenyl)chromane-3-carboxamide

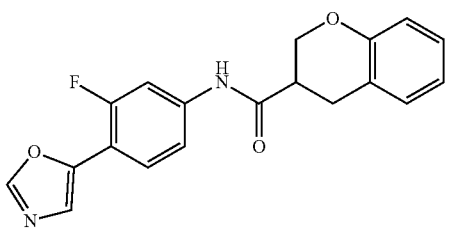 [SMILES: O=C(Nc1ccc(-c2cnco2)c(F)c1)C1COc2ccccc2C1]

To a stirred solution of 3-fluoro-4-(1,3-oxazol-5-yl)aniline (100 mg, 0.56 mmol) and 3,4-dihydro-2H-1-benzopyran-3-carboxylic acid (130.7 mg, 0.73 mmol) in DMF (1 mL) were added DIPEA (0.29 mL) and HATU (427 mg, 1.12 mmol) at room temperature and the reaction was stirred for 16 h at rt. After completion of the reaction, the reaction mixture was purified by preparative HPLC to yield N-(3-fluoro-4-(oxazol-5-yl)phenyl)chromane-3-carboxamide (70 mg, 36%).

Analytical HPLC Method A. Rt: 1.62 min; MS: 339.2 (M+H).

Compound (6): N-(3-chloro-4-(oxazol-5-yl)phenyl)-2,3-dihydrobenzo[b][1,4]dioxine-2-carboxamide

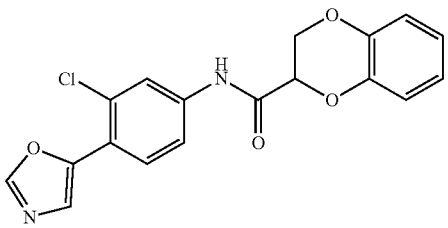 [SMILES: O=C(Nc1ccc(-c2cnco2)c(Cl)c1)C1COc2ccccc2O1]

To a stirred solution of 3-chloro-4-(oxazol-5-yl)aniline (100 mg, 0.51 mmol) and 2,3-dihydro-1,4-benzodioxine-2-carboxylic acid (120.72 mg, 0.67 mmol) in DMF (1 mL) were added DIPEA (0.26 mL) and HATU (392 mg, 1.03 mmol) at room temperature and the reaction was stirred for 16 h at rt. After completion of the reaction, the reaction mixture was purified by preparative HPLC to yield N-(3-chloro-4-(oxazol-5-yl)phenyl)-2,3-dihydrobenzo[b][1,4]dioxine-2-carboxamide (42 mg, 22%).

Analytical HPLC Method A. Rt: 1.71; MS: 357.2 (M+H).

Compound (7): N-(3-fluoro-4-(oxazol-5-yl)phenyl)-7-methoxy-2,3-dihydrobenzo[b][1,4]dioxine-2-carboxamide

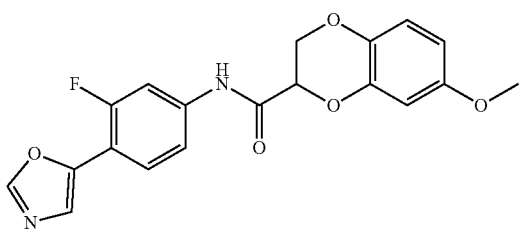 [SMILES: COc1ccc2c(c1)OC(C(=O)Nc1ccc(-c3cnco3)c(F)c1)CO2]

To a stirred solution of 3-fluoro-4-(1,3-oxazol-5-yl)aniline (100 mg, 0.56 mmol) and 7-methoxy-2,3-dihydrobenzo[b][1,4]dioxine-2-carboxylic acid (153.5 mg, 0.73 mmol) in DMF (1 mL) were added DIPEA (0.29 mL) and HATU (427 mg, 1.12 mmol) at room temperature and the reaction was stirred for 16 h at rt. After completion of the reaction, the reaction mixture was purified by preparative HPLC to yield N-(3-fluoro-4-(oxazol-5-yl)phenyl)-7-methoxy-2,3-dihydrobenzo[b][1,4]dioxine-2-carboxamide (79 mg, 37%).

Analytical HPLC Method A. Rt: 1.62 min; MS: 371.2 (M+H).

Compound (8): N-(3-chloro-4-(oxazol-5-yl)phenyl)-7-methoxy-2,3-dihydrobenzo[b][1,4]dioxine-2-carboxamide

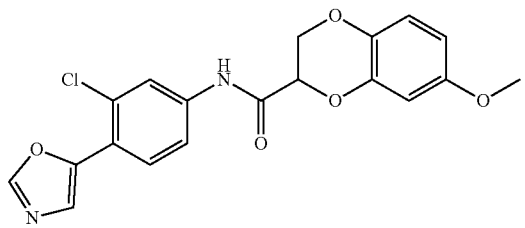 [SMILES: COc1ccc2c(c1)OC(C(=O)Nc1ccc(-c3cnco3)c(Cl)c1)CO2]

To a stirred solution of 3-chloro-4-(oxazol-5-yl)aniline (100 mg, 0.51 mmol) and 7-methoxy-2,3-dihydrobenzo[b][1,4]dioxine-2-carboxylic acid (140.72 mg, 0.67 mmol) in DMF (1 mL) were added DIPEA (0.26 mL) and HATU (392 mg, 1.03 mmol) at room temperature and the reaction was stirred for 16 h at rt. After completion of the reaction, the reaction mixture was purified by preparative HPLC to yield N-(3-chloro-4-(oxazol-5-yl)phenyl)-7-methoxy-2,3-dihydrobenzo[b][1,4]dioxine-2-carboxamide (58 mg, 29%).

Analytical HPLC Method A. Rt: 1.73 min; MS: 387.2 (M+H).

Compound (9): N-(3-fluoro-4-(oxazol-5-yl)phenyl)-2,3-dihydrobenzo[b][1,4]dioxine-2-carboxamide

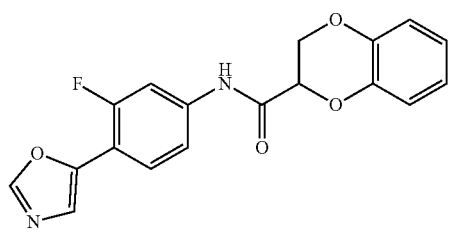 [SMILES: O=C(Nc1ccc(-c2cnco2)c(F)c1)C1COc2ccccc2O1]

To a stirred solution of 3-fluoro-4-(1,3-oxazol-5-yl)aniline (150 mg, 0.84 mmol) and 2,3-dihydro-1,4-benzodioxine-2-carboxylic acid (197.36 mg, 1.09 mmol) in DMF (1.5 mL) were added DIPEA (0.44 mL) and HATU (640.5 mg, 1.68 mmol) at room temperature and the reaction was stirred for 16 h at rt. After completion of the reaction, the reaction mixture was purified by preparative HPLC to yield N-(3-fluoro-4-(oxazol-5-yl)phenyl)-2,3-dihydrobenzo[b][1,4]dioxine-2-carboxamide (104 mg, 36%).

Analytical HPLC Method A. Rt: 1.62 min; MS: 341.2 (M+H).

Compound (10): N-(3-fluoro-4-(oxazol-5-yl)phenyl)-6-methoxychromane-3-carboxamide

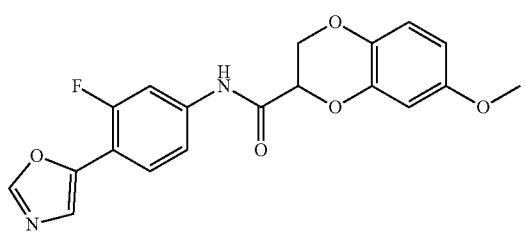 [SMILES: COc1ccc2c(c1)OC(C(=O)Nc1ccc(-c3cnco3)c(F)c1)CO2]

To a stirred solution of 3-fluoro-4-(1,3-oxazol-5-yl)aniline (150 mg, 0.84 mmol) and 6-methoxy-3,4-dihydro-2H-1-benzopyran-3-carboxylic acid (227.86 mg, 1.09 mmol) in DMF (1.5 mL) were added DIPEA (0.44 mL) and HATU (640.5 mg, 1.68 mmol) at room temperature and the reaction was stirred for 16 h at rt. After completion of the reaction, the reaction mixture was purified by preparative HPLC to yield N-(3-fluoro-4-(oxazol-5-yl)phenyl)-6-methoxychromane-3-carboxamide (Compound (10)) (121 mg, 38%).

Analytical HPLC Method A. Rt: 1.64 min; MS: 369.3 (M+H).

Compound (11): N-(3-methoxy-4-(oxazol-5-yl)phenyl) chromane-4-carboxamide

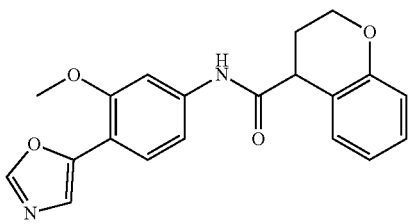 [SMILES: COc1cc(NC(=O)C2CCOc3ccccc32)ccc1-c1cnco1]

To a stirred solution of 3-methoxy-4-(oxazol-5-yl)aniline (75 mg, 0.395 mmol) and 3,4-dihydro-2H-1-benzopyran-4-carboxylic acid (105.3 mg, 0.592 mmol) in DMF (3 mL) were added DIPEA (0.15 mL) and HATU (226 mg, 0.592 mmol) at room temperature and the reaction was stirred for 12 h at rt. After completion of the reaction, the reaction mixture was purified by preparative HPLC to yield N-(3-methoxy-4-(oxazol-5-yl)phenyl)chromane-4-carboxamide (60.07 mg, 44%)

Analytical HPLC Method A. Rt: 1.42 min; MS: 351.2 (M+H).

Compound (12): N-(3-methoxy-4-(oxazol-5-yl)phenyl) chromane-3-carboxamide

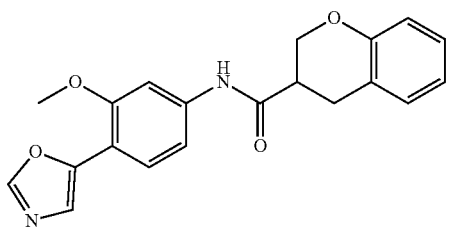 [SMILES: COc1cc(NC(=O)C2COc3ccccc3C2)ccc1-c1cnco1]

To a stirred solution of 3-methoxy-4-(oxazol-5-yl)aniline (75 mg, 0.395 mmol) and 3, 4-dihydro-2H-1-benzopyran-3-carboxylic acid (105.3 mg, 0.592 mmol) in DMF (3 mL) were added DIPEA (0.15 mL) and HATU (226 mg, 0.592 mmol) at room temperature and the reaction was stirred for 12 h at rt. After completion of the reaction, the reaction mixture was purified by preparative HPLC to yield N-(3-methoxy-4-(oxazol-5-yl)phenyl)chromane-3-carboxamide (77.6 mg, 56%).

Analytical HPLC Method A. Rt: 1.59 min; MS: 351.2 (M+H).

Compound (13): N-(3-methoxy-4-(oxazol-5-yl)phenyl)-2,3-dihydrobenzo[b][1,4]dioxine-2-carboxamide

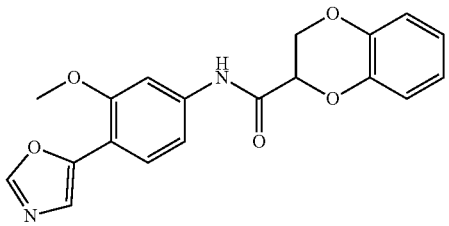 [SMILES: COc1cc(NC(=O)C2COc3ccccc3O2)ccc1-c1cnco1]

To a stirred solution of 3-methoxy-4-(oxazol-5-yl)aniline (75 mg, 0.395 mmol) and 2,3-dihydro-1,4-benzodioxine-2-carboxylic acid (106.5 mg, 0.592 mmol) in DMF (3 mL) were added DIPEA (0.15 mL) and HATU (226 mg, 0.592 mmol) at room temperature and the reaction was stirred for 12 h at rt. After completion of the reaction, the reaction mixture was purified by preparative HPLC to yield N-(3-methoxy-4-(oxazol-5-yl)phenyl)-2,3-dihydrobenzo[b][1,4]dioxine-2-carboxamide (38 mg, 28%).

Analytical HPLC Method A. Rt: 1.56 min; MS: 353.2 (M+H).

Compound (14): 6-methoxy-N-(3-methoxy-4-(oxazol-5-yl)phenyl)chromane-3-carboxamide

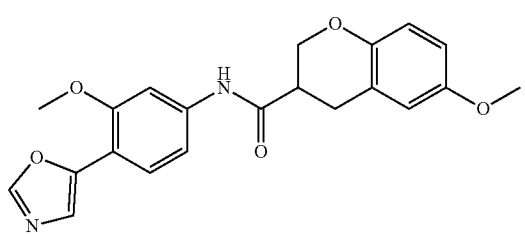 [SMILES: COc1ccc2c(c1)CC(C(=O)Nc1ccc(-c3cnco3)c(OC)c1)CO2]

To a stirred solution of 3-methoxy-4-(oxazol-5-yl)aniline (75 mg, 0.395 mmol) and 6-methoxy-3,4-dihydro-2H-1-benzopyran-3-carboxylic acid (123.1 mg, 0.592 mmol) in DMF (3 mL) were added DIPEA (0.15 mL) and HATU (226 mg, 0.592 mmol) at room temperature and the reaction was stirred for 12 h at rt. After completion of the reaction, the reaction mixture was purified by preparative HPLC to yield 6-methoxy-N-(3-methoxy-4-(oxazol-5-yl)phenyl)chromane-3-carboxamide (72.3 mg, 48%).

Analytical HPLC Method A. Rt: 1.55 min; MS: 381.2 (M+H).

Compound (15): N-(3-methoxy-4-(pyridin-4-yl)phenyl)chromane-4-carboxamide

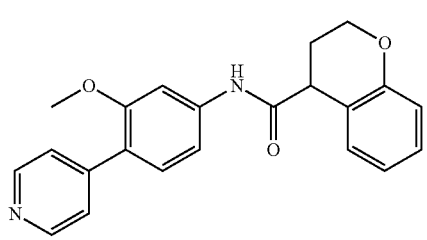 [SMILES: COc1cc(NC(=O)C2CCOc3ccccc32)ccc1-c1ccncc1]

To a stirred solution of 3-methoxy-4-(pyridin-4-yl)aniline (75 mg, 0.375 mmol) and 3,4-dihydro-2H-1-benzopyran-4-carboxylic acid (100 mg, 0.563 mmol) in DMF (2 mL) were added DPIEA (0.144 mL) and HATU (214.8 mg, 0.563 mmol) at room temperature and the reaction was stirred for 12 h at rt. After completion of the reaction, the reaction mixture was purified by preparative HPLC to yield N-(3-methoxy-4-(pyridin-4-yl)phenyl)chromane-4-carboxamide (61.5 mg, 46%).

Analytical HPLC Method A. Rt: 0.94 min; MS: 361.3 (M+H).

Compound (16): 6-methoxy-N-(3-methoxy-4-(pyridin-4-yl)phenyl)chromane-3-carboxamide

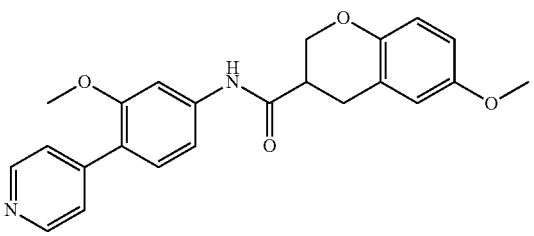 [SMILES: COc1ccc2c(c1)CC(C(=O)Nc1ccc(-c3ccncc3)c(OC)c1)CO2]

To a stirred solution of 3-methoxy-4-(pyridin-4-yl)aniline (75 mg, 0.375 mmol) and 6-methoxy-3,4-dihydro-2H-1-benzopyran-3-carboxylic acid (117 mg, 0.563 mmol) in DMF (2 mL) were added DPIEA (0.144 mL) and HATU (214.8 mg, 0.563 mmol) at room temperature and the reaction was stirred for 12 h at rt. After completion of the reaction, the reaction mixture was purified by preparative HPLC to yield 6-methoxy-N-(3-methoxy-4-(pyridin-4-yl)phenyl)chromane-3-carboxamide (45.5 mg, 31%).

Analytical HPLC Method A. Rt: 1.07 min; MS: 391.3 (M+H).

Compound (17): N-(3-methoxy-4-(pyridin-4-yl)phenyl)chromane-3-carboxamide

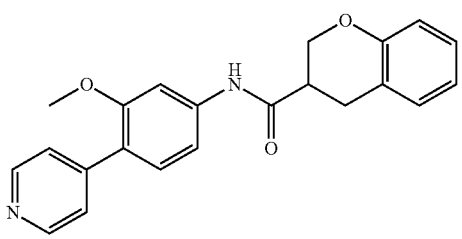 [SMILES: COc1cc(NC(=O)C2COc3ccccc3C2)ccc1-c1ccncc1]

To a stirred solution of 3-methoxy-4-(pyridin-4-yl)aniline (75 mg, 0.375 mmol) and 3,4-dihydro-2H-1-benzopyran-3-carboxylic acid (100 mg, 0.563 mmol) in DMF (2 mL) were added DPIEA (0.144 mL) and HATU (214.8 mg, 0.563 mmol) at room temperature and the reaction was stirred for 12 h at rt. After completion of the reaction, the reaction mixture was purified by preparative HPLC to yield N-(3-methoxy-4-(pyridin-4-yl)phenyl)chromane-3-carboxamide (63.6 mg, 47%).

Analytical HPLC Method A. Rt: 1.10 min; MS: 361.3 (M+H).

Compound (18): 7-methoxy-N-(3-methoxy-4-(pyridin-4-yl)phenyl)-2,3-dihydrobenzo[b][1,4]dioxine-2-carboxamide

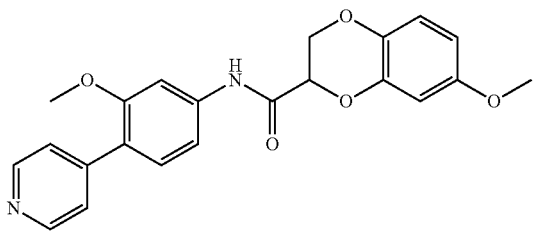 [SMILES: COc1ccc2c(c1)OC(C(=O)Nc1ccc(-c3ccncc3)c(OC)c1)CO2]

To a stirred solution of 3-methoxy-4-(pyridin-4-yl)aniline (75 mg, 0.375 mmol) and 7-methoxy-2,3-dihydrobenzo[b][1,4]dioxine-2-carboxylic acid (118.1 mg, 0.563 mmol) in DMF (2 mL) were added DPIEA (0.144 mL) and HATU (214.8 mg, 0.563 mmol) at room temperature and the reaction was stirred for 12 h at rt. After completion of the reaction, the reaction mixture was purified by preparative HPLC to yield 7-methoxy-N-(3-methoxy-4-(pyridin-4-yl)phenyl)-2,3-dihydrobenzo[b][1,4]dioxine-2-carboxamide (67.2 mg, 46%).

Analytical HPLC Method A. Rt: 1.09 min; MS: 393.3 (M+H).

Compound (19): N-(3-methoxy-4-(pyridin-4-yl)phenyl)-2,3-dihydrobenzo[b][1,4]dioxine-2-carboxamide

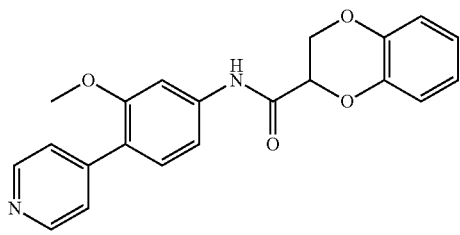 [SMILES: COc1cc(NC(=O)C2COc3ccccc3O2)ccc1-c1ccncc1]

To a stirred solution of 3-methoxy-4-(pyridin-4-yl)aniline (75 mg, 0.375 mmol) and 2,3-dihydro-1,4-benzodioxine-2-carboxylic acid (100 mg, 0.56 mmol) in DMF (2 mL) were added DPIEA (0.144 mL) and HATU (214.8 mg, 0.563 mmol) at room temperature and the reaction was stirred for 12 h at rt. After completion of the reaction, the reaction mixture was purified by preparative HPLC to yield N-(3-methoxy-4-(pyridin-4-yl)phenyl)-2,3-dihydrobenzo[b][1,4]dioxine-2-carboxamide (23 mg, 17%).

Analytical HPLC Method A. Rt: 1.06 min; MS: 363.2 (M+H).

Compound (20): 7-methoxy-N-(3-methoxy-4-(oxazol-5-yl)phenyl)-2,3-dihydrobenzo[b][1,4]dioxine-2-carboxamide

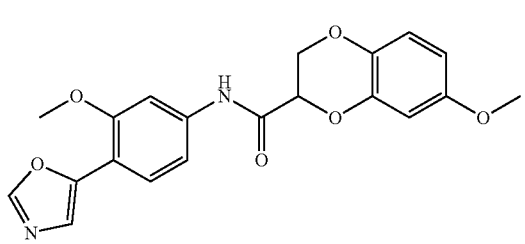 [SMILES: COc1ccc2c(c1)OC(C(=O)Nc1ccc(-c3cnco3)c(OC)c1)CO2]

To a stirred solution of 3-methoxy-4-(oxazol-5-yl)aniline (100 mg, 0.52 mmol) and 7-methoxy-2,3-dihydrobenzo[b][1,4]dioxine-2-carboxylic acid (124.3 mg, 0.592 mmol) in DMF (3 mL) were added DIPEA (0.15 mL) and HATU (226 mg, 0.592 mmol) at room temperature and the reaction was stirred for 12 h at rt. After completion of the reaction, the reaction mixture was purified by preparative HPLC to yield 7-methoxy-N-(3-methoxy-4-(oxazol-5-yl)phenyl)-2,3-dihydrobenzo[b][1,4]dioxine-2-carboxamide (90.8 mg, 60%).

Analytical HPLC Method A. Rt: 1.56 min; MS: 383.2 (M+H).

Compound (21): First (−)-N-(3-chloro-4-(1,3-oxazol-5-yl)phenyl)chromane-3-carboxamide

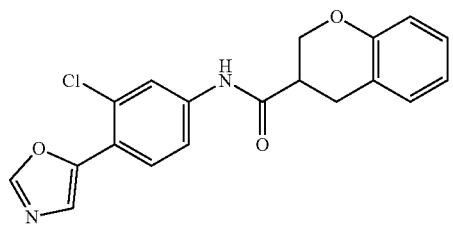 [SMILES: O=C(Nc1ccc(-c2cnco2)c(Cl)c1)C1COc2ccccc2C1]

Racemic N-(3-chloro-4-(1,3-oxazol-5-yl)phenyl)chromane-3-carboxamide (Compound (1)) was separated by chiral chromatography using Chiral Separation Method C to yield Compound (21), which is characterized by retention time=4.76 min (the second enantiomer with optical rotation (+) is characterized by retention time=6.04 min).

MS: 355 (M+H).

Compound (22): N-(3-methyl-4-(oxazol-5-yl)phenyl) chromane-3-carboxamide

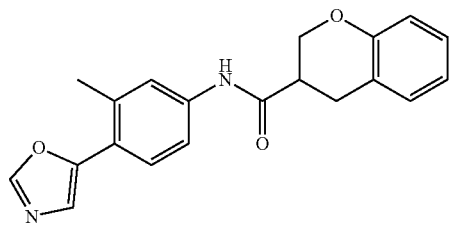 [SMILES: Cc1cc(NC(=O)C2COc3ccccc3C2)ccc1-c1cnco1]

A solution of chroman-3-carbonyl chloride prepared freshly in dry DCM (10 mL) was added to the mixture of 3-methyl-4-(oxazol-5-yl) aniline (500 mg, 2.87 mmol) and triethylamine (1.25 mL, 8.61 mmol) in dry DCM (10 mL) at 0° C. After the addition, reaction was slowly warmed to room temperature over 3 h. The reaction was monitored by TLC, after maximum conversion (part of the starting materials remained unreacted) diluted with DCM (5 mL), washed with water (10 mL) and brine (15 mL), dried over $Na_2SO_4$, and concentrated under reduced pressure. The crude was purified by column chromatography followed by trituration with MTBE to obtain N-(3-methyl-4-(oxazol-5-yl)phenyl) chroman-3-carboxamide (240 mg, 25%).

Analytical HPLC Method B. Rt: 2.47 min, LCMS: 335.08 (M+H).

Compound (23): N-(2-methyl-4-(oxazol-5-yl)phenyl) chroman-3-carboxamide

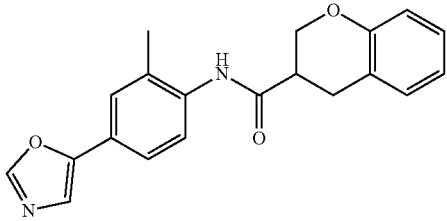 [SMILES: Cc1cc(-c2cnco2)ccc1NC(=O)C1COc2ccccc2C1]

A solution of chroman-3-carbonyl chloride prepared freshly in dry DCM (10 mL) was added to the mixture of 3-methyl-4-(oxazol-5-yl) aniline (500 mg, 2.87 mmol) and triethylamine (1.25 mL, 8.61 mmol) in dry DCM (10 mL) at 0° C. After the addition, reaction was slowly warmed to room temperature over 3 h. The reaction was monitored by TLC, after maximum conversion (part of the starting materials remained unreacted) diluted with DCM (5 mL), washed with water (10 mL) and brine (15 mL), dried over $Na_2SO_4$, and concentrated under reduced pressure. The crude was purified by column chromatography followed by trituration with MTBE to give N-(2-methyl-4-(oxazol-5-yl)phenyl) chroman-3-carboxamide (210 mg, 22%).

Analytical HPLC Method B. Rt: 2.56 min, LCMS: 335.1

Compound (24): N-(2-(difluoromethoxy)-4-(oxazol-5-yl)phenyl)chroman-3-carboxamide

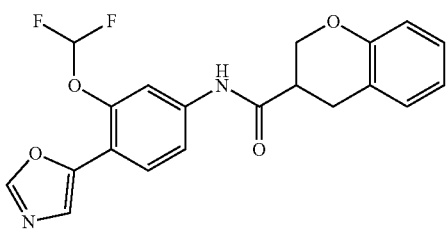

To a stirred solution of N-(4-bromo-2-(difluoromethoxy) phenyl)chroman-3-carboxamide (400 mg, 1.01 mmol) in 1,4-dioxane/water (20 mL, 2:1) 5-(4,4,5,5-tetramethyl-1,3,2-dioxaborolan-2-yl)oxazole (255 mg, 1.31 mmol) and $Na_2CO_3$ (213 mg, 2.02 mmol) were added under argon. The reaction mixture was degassed with argon for 20 min. Then $Pd(PPh_3)_4$ (58 mg, 0.05 mmol) was added and degassed with argon for 5 min. The reaction mixture was sealed and stirred at 80° C. for 10 h. After the maximum consumption of the starting material, the reaction mixture was cooled to room temperature, diluted with water (5.0 mL), and extracted with EtOAc (2×50 mL). Organic layers were combined, washed with water (10 mL) and brine (10 mL), dried over anhydrous $Na_2SO_4$, and evaporated under reduced pressure. The crude was purified column chromatography to give N-(2-(difluoromethoxy)-4-(oxazol-5-yl)phenyl)chroman-3-carboxamide (152 mg, 39%).

Analytical HPLC Method B. Rt: 2.50 min, LCMS: 387.

Compound (25): first N-(3-methyl-4-(oxazol-5-yl) phenyl)chromane-3-carboxamide

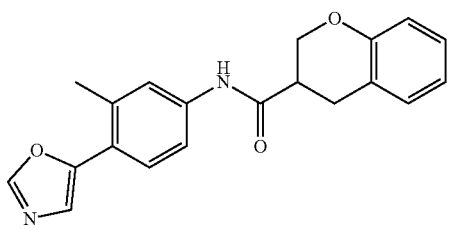 [SMILES: Cc1cc(NC(=O)C2COc3ccccc3C2)ccc1-c1cnco1]

Chiral separation of Compound (22) using Chiral Separation Method A yields Compound (25) (65.6 mg) characterized by retention time=5.41. (the second enantiomer (75.6 mg) is characterized by retention time=11.73 min).

Compound (26): first N-(2-(difluoromethoxy)-4-(oxazol-5-yl)phenyl)chroman-3-carboxamide

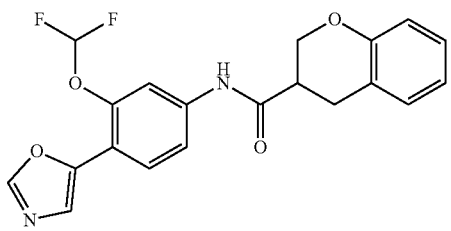 [SMILES: O=C(Nc1ccc(-c2cnco2)c(OC(F)F)c1)C1COc2ccccc2C1]

Chiral separation of compound 22 using Chiral Separation Method B yields Compound (25) (44.9 mg) characterized by retention time=6.64 min.

Compound (27): second N-(2-(difluoromethoxy)-4-(oxazol-5-yl)phenyl)chroman-3-carboxamide

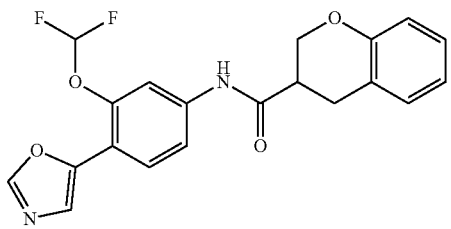 [SMILES: O=C(Nc1ccc(-c2cnco2)c(OC(F)F)c1)C1COc2ccccc2C1]

Chiral separation of compound 22 using Chiral Separation Method B yields Compound (27) (47.0 mg) characterized by retention time=8.87 min.

Compound (28): N-(4-(1H-1,2,4-triazol-1-yl)-3-(trifluoromethyl)phenyl)chromane-3-carboxamide

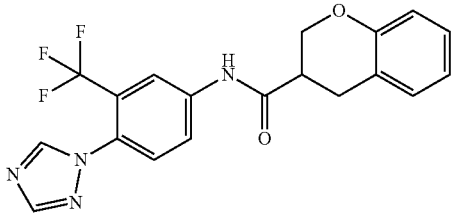 [SMILES: O=C(Nc1ccc(-n2cncn2)c(C(F)(F)F)c1)C1COc2ccccc2C1]

The title compound was prepared from 3,4-dihydro-2H-1-benzopyran-3-carboxylic acid and 4-(1H-1,2,4-triazol-1-yl)-3-(trifluoromethyl)aniline using coupling procedure A and preparative HPLC Method A (yield 8%).
MS: 389.1 (M+H).

Compound (29): N-(3-fluoro-4-(1,3,4-oxadiazol-2-yl)phenyl)chromane-3-carboxamide

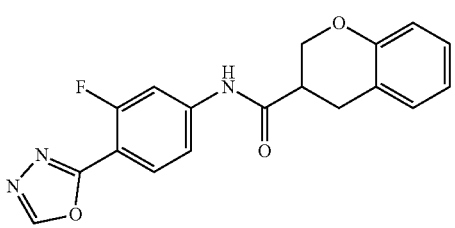

A mixture of 3-fluoro-4-(1,3,4-oxadiazol-2-yl)aniline (158 mg, 0.884 mmol), 3,4-dihydro-2H-1-benzopyran-3-carboxylic acid (173 mg, 0,997 mmol) and 132 mg (0,973 mmol) of N-hydroxybenzotriazole was dissolved in 1 ml of dry DMF and cooled to −10 deg. C. Then 165 mg (1.061 mmol) of EDC were added and the mixture was stirred for 16 h at RT. 30 ml of water were added, the obtained precipitate was filtered, washed three times with 10 ml of water, once with 3 ml of isopropanol and twice with 10 ml of hexane. Then it was dried on air at 50 deg to give 110 mg of Compound (29) (yield 37%).
MS: 340.0 (M+H).
$^1$H NMR (400 MHz, DMSO-$d_6$) δ 10.76 (s, 1H), 9.37 (s, 1H), 8.13-7.96 (m, 1H), 7.87 (d, J=13.0 Hz, 1H), 7.53 (d, J=6.5 Hz, 1H), 7.15 (d, J=7.2 Hz, 1H), 7.11-7.06 (m, 1H), 6.93-6.84 (m, 1H), 6.79 (d, J=7.6 Hz, 1H), 4.47 (d, J=9.5 Hz, 1H), 4.11-3.97 (m, 1H), 3.16-2.91 (m, 3H).

Compound (30): N-(3-chloro-4-(2-methyloxazol-5-yl)phenyl)chromane-3-carboxamide

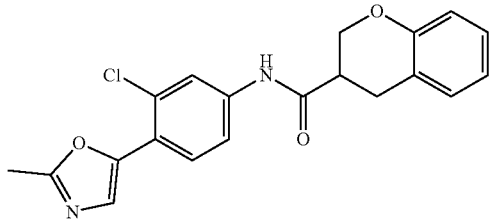 [SMILES: Cc1ncc(-c2ccc(NC(=O)C3COc4ccccc4C3)cc2Cl)o1]

A mixture of 0.8 ml of dry triethylamine, 3-chloro-4-(2-methyloxazol-5-yl)aniline (300 mg, 1.44 mmol) and 3,4-dihydro-2H-1-benzopyran-3-carboxylic acid (282 mg, 1.58 mmol) was dissolved in 5 ml of dry DMF. 578 mg of TBTU (CAS 125700-67-6) were added thereto, and the obtained solution was stirred overnight. Water and ethyl acetate were added, the organic phase was once washed with water and once with brine, dried over anhydrous sodium sulfate and evaporated. Purification by preparative HPLC Method A yielded 33 mg of Compound (30) (yield 6%).
MS: 369.0 (M+H).

Compound (31): N-(3-chloro-4-(oxazol-5-yl)phenyl)-2,3-dihydrobenzofuran-2-carboxamide

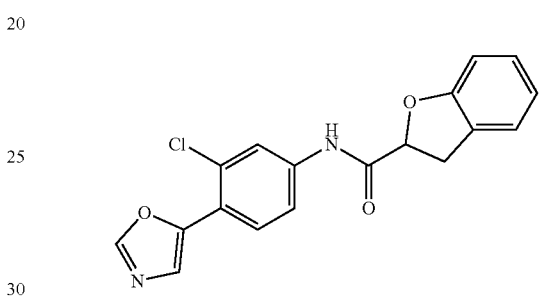

The title compound was prepared from 2,3-dihydrobenzofuran-2-carboxylic acid and 3-chloro-4-(oxazol-5-yl)aniline using coupling procedure A and preparative HPLC Method A (yield: 34%).
MS: 341.0 (M+H).
$^1$H NMR (400 MHz, DMSO-$d_6$) δ 10.52 (s, 1H), 8.53 (s, 1H), 8.12-8.02 (m, 1H), 7.88-7.74 (m, 2H), 7.72 (s, 1H), 7.25 (d, J=7.2 Hz, 1H), 7.15 (t, J=7.6, 7.6 Hz, 1H), 6.94-6.86 (m, 2H), 5.35 (dd, J=10.3, 6.7 Hz, 1H), 3.55 (dd, J=15.9, 10.5 Hz, 1H), 3.40 (dd, J=16.0, 6.8 Hz, 1H).

Compound (32): N-(3-chloro-4-(oxazol-5-yl)phenyl)chromane-4-carboxamide

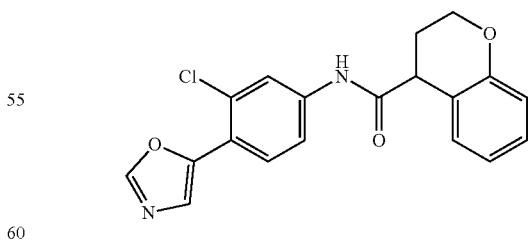

The title compound was prepared from 3,4-dihydro-2H-1-benzopyran-4-carboxylic acid and 3-chloro-4-(oxazol-5-yl)aniline using coupling procedure A and preparative HPLC Method A (yield 12%).
MS: 355.0 (M+H).

Compound (33): N-(3-chloro-4-(oxazol-5-yl)phenyl)-2,3-dihydro-1H-indene-1-carboxamide

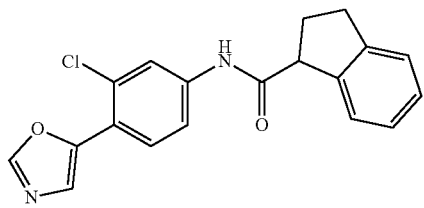 [SMILES: O=C(Nc1ccc(-c2cnco2)c(Cl)c1)C1CCc2ccccc21]

The title compound was prepared from 2,3-dihydro-1H-indene-1-carboxylic acid and 3-chloro-4-(oxazol-5-yl)aniline using coupling procedure A and preparative HPLC Method A (yield 9%).

MS: 339.0 (M+H).

Compound (34): N-(3-chloro-4-(oxazol-5-yl)phenyl)-2-(2,3-dihydrobenzofuran-2-yl)acetamide

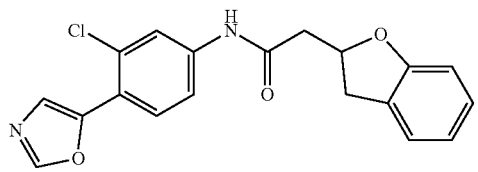 [SMILES: O=C(CC1Cc2ccccc2O1)Nc1ccc(-c2cnco2)c(Cl)c1]

The title compound was prepared from 2-(2,3-dihydrobenzofuran-2-yl) acetic acid and 3-chloro-4-(oxazol-5-yl) aniline using coupling procedure A and preparative HPLC Method A (yield 19%).

MS: 355.0 (M+H).

Compound (35): N-(3-chloro-4-(oxazol-5-yl)phenyl)-2,3-dihydrobenzofuran-3-carboxamide

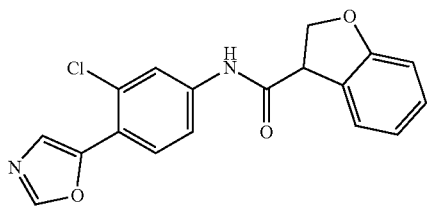 [SMILES: O=C(Nc1ccc(-c2cnco2)c(Cl)c1)C1COc2ccccc21]

The title compound was prepared from 2,3-dihydrobenzofuran-3-carboxylic acid and 3-chloro-4-(oxazol-5-yl)aniline using coupling procedure A and preparative HPLC Method A (yield 15%).

MS: 341.0 (M+H).

Compound (36): N-(3-chloro-4-(oxazol-5-yl)phenyl)-2,3-dihydro-1H-indene-2-carboxamide

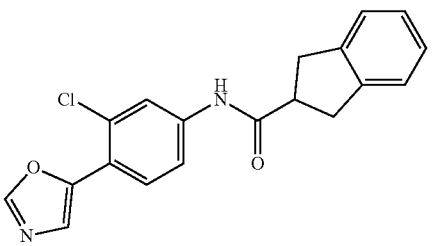 [SMILES: O=C(Nc1ccc(-c2cnco2)c(Cl)c1)C1Cc2ccccc2C1]

The title compound was prepared from 2,3-dihydro-1H-indene-2-carboxylic acid and 3-chloro-4-(oxazol-5-yl)aniline using coupling procedure A and preparative HPLC Method A (yield 14%).

MS: 339.2 (M+H).

Compound (37): N-(3-chloro-4-(oxazol-5-yl)phenyl)-7-fluorochromane-3-carboxamide

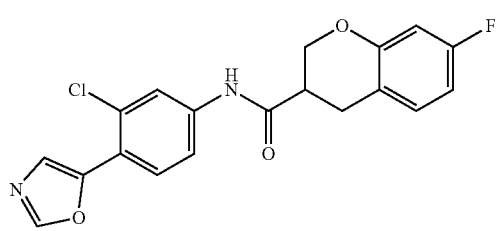 [SMILES: O=C(Nc1ccc(-c2cnco2)c(Cl)c1)C1COc2cc(F)ccc2C1]

The title compound was prepared from 7-fluorochromane-3-carboxylic acid and 3-chloro-4-(oxazol-5-yl)aniline using coupling procedure A and preparative HPLC Method A (yield 17%).

MS: 373.0 (M+H).

Compound (38): 6-chloro-N-(3-chloro-4-(oxazol-5-yl)phenyl)chromane-3-carboxamide

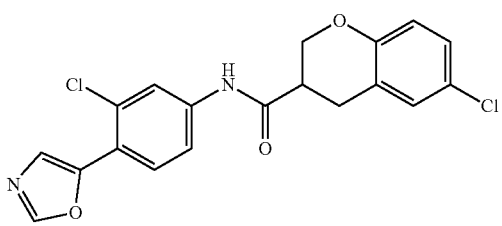 [SMILES: O=C(Nc1ccc(-c2cnco2)c(Cl)c1)C1COc2ccc(Cl)cc2C1]

The title compound was prepared from 6-chlorochromane-3-carboxylic acid and 3-chloro-4-(oxazol-5-yl)aniline using coupling procedure A and preparative HPLC Method A (yield 16%).

MS: 389.0 (M+H).

Compound (39): N-(3-chloro-4-(oxazol-5-yl)phenyl)-6,8-difluorochromane-3-carboxamide

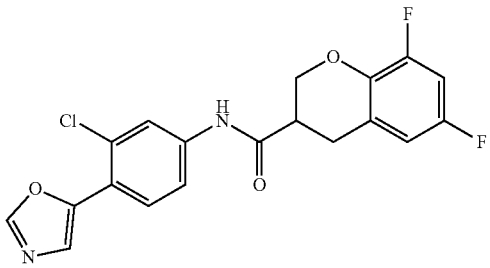 [SMILES: O=C(Nc1ccc(-c2cnco2)c(Cl)c1)C1COc2c(F)cc(F)cc2C1]

The title compound was prepared from 6,8-difluorochromane-3-carboxylic acid and 3-chloro-4-(oxazol-5-yl)aniline using coupling procedure A and preparative HPLC Method A (yield 18%).
MS: 391.0 (M+H).
$^1$H NMR (500 MHz, DMSO-d$_6$) δ 10.58 (s, 1H), 8.52 (s, 1H), 8.01-7.97 (m, 1H), 7.79 (d, J=8.6 Hz, 1H), 7.71 (s, 1H), 7.61 (dd, J=8.5, 1.6 Hz, 1H), 7.14-7.06 (m, 1H), 6.93 (d, J=8.4 Hz, 1H), 4.54-4.48 (m, 1H), 4.16-4.08 (m, 1H), 3.13-3.08 (m, 1H), 3.08-3.00 (m, 2H).

Compound (40): N-(3-chloro-4-(oxazol-5-yl)phenyl)-5-methoxychromane-3-carboxamide

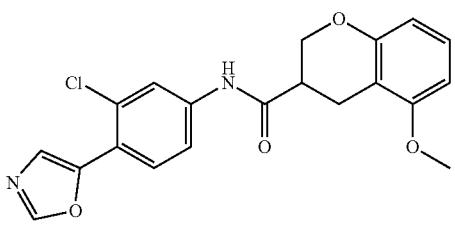 [SMILES: COc1cccc2c1CC(C(=O)Nc1ccc(-c3cnco3)c(Cl)c1)CO2]

The title compound was prepared from 5-methoxychromane-3-carboxylic acid and 3-chloro-4-(oxazol-5-yl)aniline using coupling procedure A and preparative HPLC Method A (yield 17%).
MS: 385.0 (M+H).
$^1$H NMR (500 MHz, DMSO-d$_6$) δ 10.58 (s, 1H), 8.52 (s, 1H), 8.01-7.97 (m, 1H), 7.79 (d, J=8.6 Hz, 1H), 7.71 (s, 1H), 7.61 (dd, J=8.5, 1.6 Hz, 1H), 7.14-7.06 (m, 1H), 6.93 (d, J=8.4 Hz, 1H), 4.54-4.48 (m, 1H), 4.16-4.08 (m, 1H), 3.13-3.08 (m, 1H), 3.08-3.00 (m, 2H).

Compound (41): N-(3-chloro-4-(oxazol-5-yl)phenyl)-2,3-dihydrobenzo[b][1,4]dioxine-2-carboxamide

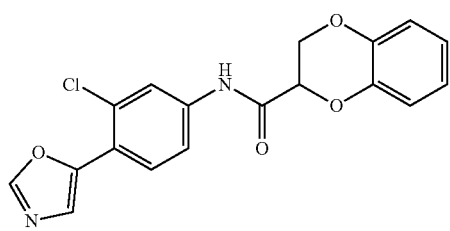

The title compound was prepared from 2,3-dihydrobenzo[b][1,4]dioxine-2-carboxylic acid and 3-chloro-4-(oxazol-5-yl)aniline using coupling procedure A and preparative HPLC Method A (yield 34%).
MS: 357.2 (M+H).
$^1$H NMR (400 MHz, DMSO-d$_6$) δ 10.49 (s, 1H), 8.53 (s, 1H), 8.01 (s, 1H), 7.81 (d, J=8.7 Hz, 1H), 7.75-7.69 (m, 2H), 7.05 (d, J=8.0 Hz, 1H), 6.93-6.84 (m, 3H), 5.07-5.00 (m, 1H), 4.45 (dd, J=11.7, 2.5 Hz, 1H), 4.38 (dd, J=11.7, 5.5 Hz, 1H).

Compound (42): first N-(3-chloro-4-(oxazol-5-yl)phenyl)-6-fluorochromane-3-carboxamide

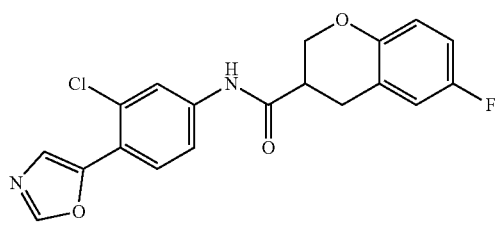 [SMILES: O=C(Nc1ccc(-c2cnco2)c(Cl)c1)C1COc2ccc(F)cc2C1]

The racemic title compound was prepared from 6-fluorochromane-3-carboxylic acid and 3-chloro-4-(oxazol-5-yl)aniline using coupling procedure A and preparative HPLC Method A.
MS: 373. (M+H).
Chiral separation using Chiral Separation Method D yields Compound (42) characterized by retention time=10.9 min (the second enantiomer is characterized by retention time=18.9 min).
Preparation of Dissecting Solutions and Enzyme Solutions
Kynurenic Acid (0.2 mg/mL), trypsin (1.33 mg/mL), and hyaluronidase (0.67 mg/mL) were weighed out and dissolved in high magnesium/low calcium artificial cerebral spinal fluid (aCSF) at 37° C. Fibroblast growth factor 2 (FGF2; 10 ng/mL) and heparin (2 µg/mL) were added to 100 mL of serum-free media (SFM). Ovomucoid trypsin inhibitor (1 mg/mL) was dissolved in warm SFM and sterile filtered (22 µm).
Isolation of Retinal Precursor Cells from the Ciliary Epithelium of the Eye and Primary Sphere Assay
A dissecting microscope, cold light source, and sterile surgical instruments were set up inside of a sterile biological safety cabinet (BSC). Mammalian eyes were enucleated and placed in a petri dish containing cold, sterile aCSF. Under the dissecting microscope, hair, connective tissue, and the dorsal and ventral oblique muscles were cleared from the scleral/corneal border with two sets of forceps. Next, curved or angled micro-dissecting scissors were used to cleave any remaining extraocular muscle tissue, the optic nerve, and cut the eyeball into symmetrical halves; beginning and finishing the cut from the hole left by the optic nerve. Using two sets of forceps to grasp the cornea, the two eye halves were peeled apart. The lens, optic nerve, and vitreous were separated from the eye shells and the eye shells were transferred into a new petri dish (also containing cold, sterile aCSF). To isolate the ciliary epithelium (CE), eye shells were oriented with the cornea on the right and retinal pigmented epithelium (RPE) on the left. A pair of straight forceps were used to pin down the eye shell on the RPE side while a scalpel blade was inserted between the CE and the iris, using pressure to slice the iris/cornea side off from the rest of the shell. Next, the scalpel was run along the border between the CE and the RPE to obtain the CE isolated as a thin strip of tissue. The CE strips were then transferred to a 35 mm dish containing 2 mL of dispase solution (Sigma; T1005) and incubated for 10 minutes at 37° C. Next, the strips were transferred from dispase into a 35 mm dish containing 2 mL of sterile filtered kynurenic acid, trypsin and hyaluronidase solution and incubated at 37° C. for 10 minutes. After incubation, the dish was returned to the dissecting scope, and the CE strips were pinned down with straight, non-serrated forceps, while non-serrated curved forceps were used to scrape the CE off from the underlying sclera. The bare scleral strips were then discarded, such that only the CE cells remained in the enzyme solution. Using a fire-polished, cotton-plugged glass pipette, the cells and enzyme solution were transferred to a 15 mL tube and triturated approximately 45 times to break apart the tissue. The 15 mL tube/cell suspension was centrifuged for 5 minutes at 1500 rpm. The supernatant was gently aspirated from the resulting pellet using a fire-polished, cotton-plugged glass pipette and 2 mL of trypsin inhibitor solution was added to the pellet. Using a small borehole, fire-polished, cotton-plugged glass pipette, the sample was triturated approximately 45 times until it was a single-cell suspension. The 15 mL tube/cell suspension was centrifuged for 5 minutes at 1500 rpm. The supernatant was gently aspirated from the resulting pellet and 1-2 mL of SFM with FGF2 and heparin (plating media) was added. The cells and media were mixed to ensure a uniform cell suspension and a 10 uL sample was taken and cell density was determined. The cells were then seeded and cultured at 10c/μL in culture-treated plates or flasks. After one week, roughly 1 in 500 cells proliferated to form free-floating, clonal spheres greater than 80 μm in diameter.

Sphere Passaging and High-Throughput Drug Screening

Human-derived spheres were passaged using the kynurenic acid, trypsin, hyaluronidase enzyme solution with the addition of collagenase I (0.5 mg/mL), collagenase II (0.5 mg/mL) and elastase (0.1 mg/mL). Mouse-derived spheres were passaged using hyaluronidase (0.67 mg/mL), collagenase I (0.5 mg/mL), and collagenase II (0.5 mg/mL) dissolved in Accustase solution (Sigma; SCR005). Spheres were collected en masse from culture plates or flasks, transferred into one or more 50 mL tubes and centrifuged for 5 minutes at 1500 rpm. The supernatant was gently aspirated from the pellet and 2-5 mL of enzyme solution was added to the pellet and mixed thoroughly. The 2-5 mL enzyme and sphere suspension was transferred to a 15 mL tube and laid horizontally on an automated rocker at 37° C. for 45 minutes. After incubation, the enzyme solution with spheres was triturated approximately 45 times to mechanically dissociate the spheres. The cell suspension was centrifuged for 5 minutes at 1500 rpm. The supernatant was gently aspirated and 1-2 mL of trypsin inhibitor solution was added to the pellet and triturated approximately 45 times. The cell suspension was centrifuged for 5 minutes at 1500 rpm. The supernatant was gently aspirated from the resulting pellet and 1-2 mL of SFM with FGF2 and heparin (plating media) was added. The cells and media were mixed to ensure a uniform cell suspension and a 10 uL sample was taken and cell density was determined from that sample. The remaining cells were then seeded and cultured at 10c/μL in prepared 96-well or 24-well plates with 0.1% DMSO or a selected concentration of drug in 0.1% DMSO. Cells were grown for one week and then live stained for nuclei (Hoechst 33258; 10 μp/mL). For mouse tissue, an actin-green fluorescent protein (GFP) transgenic mouse strain (FVB.Cg-Tg (CAG-EGFP)B5Nagy/J) was used and cell number comparisons were made based on nuclei and GFP-based quantification. For human tissue, the green fluorescent cell viability dye, calcein AM (ThermoFisher C3100MP; 2 μM) was used and cell number comparisons were made based on nuclei and calcein fluorescence-based quantification.

Statistical Evaluation of Drug Screening Results

Statistic significance was evaluated on a plate to plate basis employing control wells with no drug treatment and equivalent concentration of DMSO in the medium. The minimal number of control wells was 8 for 96 well plates and 6 for 24 well plates. Average and standard deviations were determined and compound wells with cell numbers outside the three standard deviations range around the control value were classified as hits. Individual compound treatment conditions on each plate were always at least present in duplicates to internally verify the validity of results. Numerical values of three sigma significant hits were then averaged for each compound.

Results

TABLE 10

| Comp. No. | Chemical structure | Cell proliferation within one week [%] |
|---|---|---|
| 1 | 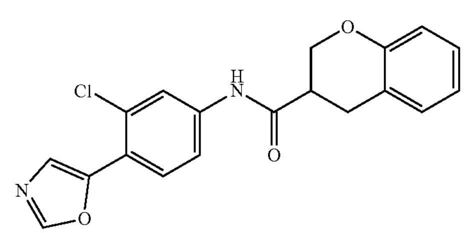 [SMILES: O=C(Nc1ccc(-c2cnco2)c(Cl)c1)C1COc2ccccc2C1] | 179 |

TABLE 10-continued

| Comp. No. | Chemical structure | Cell proliferation within one week [%] |
|---|---|---|
| 2 | 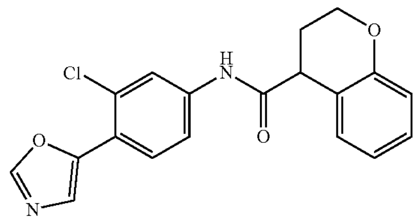 [SMILES: O=C(Nc1ccc(-c2cnco2)c(Cl)c1)C1CCOc2ccccc21] | 128 |
| 3 | 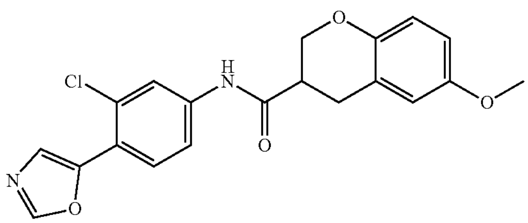 | 138 |
| 4 | 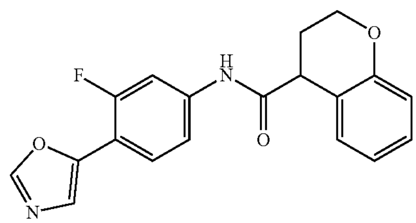 [SMILES: O=C(Nc1ccc(-c2cnco2)c(F)c1)C1CCOc2ccccc21] | 106 |
| 5 | 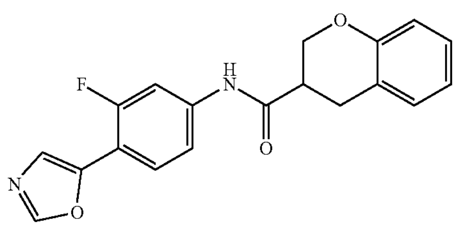 [SMILES: O=C(Nc1ccc(-c2cnco2)c(F)c1)C1COc2ccccc2C1] | 133 |
| 6 | 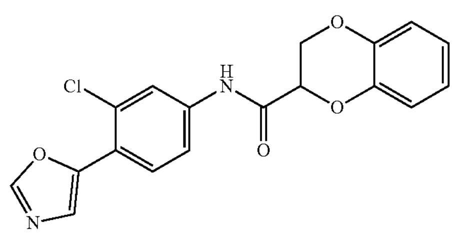 | 120 |
| 7 | 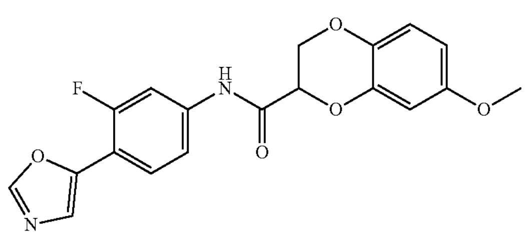 [SMILES: COc1ccc2c(c1)OC(C(=O)Nc1ccc(-c3cnco3)c(F)c1)CO2] | 123 |

TABLE 10-continued
| Comp. No. | Chemical structure | Cell proliferation within one week [%] |
|---|---|---|
| 8 | 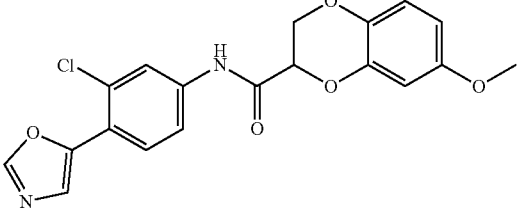 | 117 |
| 9 | 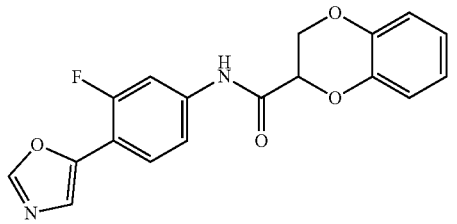 | 118 |
| 10 | 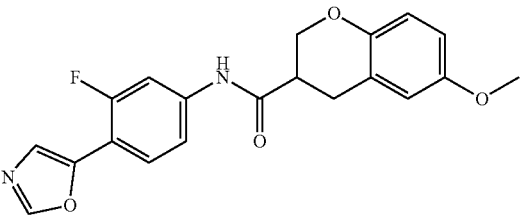 | 121 |
| 11 | 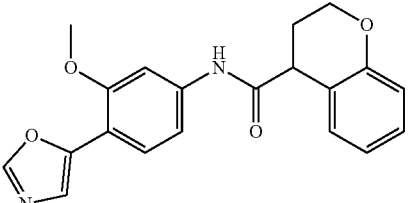 | 140 |
| 12 | 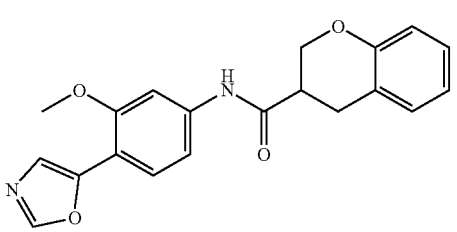 [SMILES: COc1cc(NC(=O)C2COc3ccccc3C2)ccc1-c1cnco1] | 230 |
| 13 | 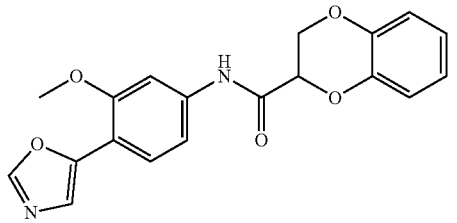 [SMILES: COc1cc(NC(=O)C2COc3ccccc3O2)ccc1-c1cnco1] | 137 |

TABLE 10-continued

| Comp. No. | Chemical structure | Cell proliferation within one week [%] |
|---|---|---|
| 14 | 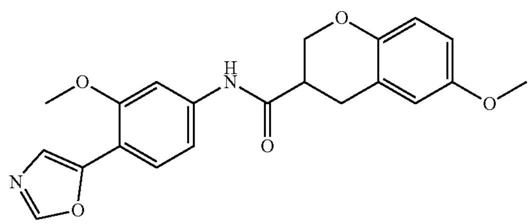 [SMILES: COc1ccc2c(c1)CC(C(=O)Nc1ccc(-c3cnco3)c(OC)c1)CO2] | 196 |
| 15 | 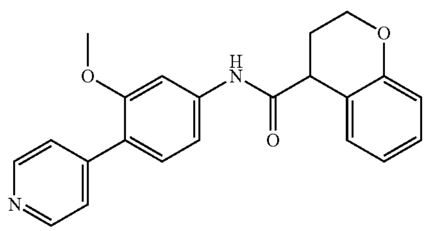 [SMILES: COc1cc(NC(=O)C2CCOc3ccccc32)ccc1-c1ccncc1] | 122 |
| 16 | 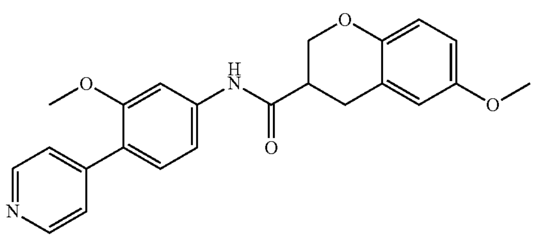 [SMILES: COc1ccc2c(c1)CC(C(=O)Nc1ccc(-c3ccncc3)c(OC)c1)CO2] | 143 |
| 17 | 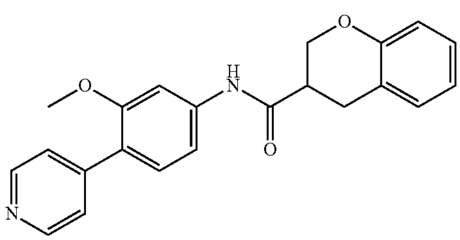 [SMILES: COc1cc(NC(=O)C2COc3ccccc3C2)ccc1-c1ccncc1] | 114 |
| 18 | 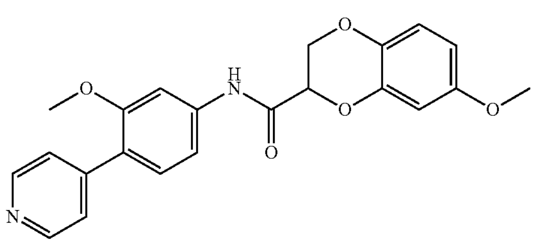 [SMILES: COc1ccc2c(c1)OC(C(=O)Nc1ccc(-c3ccncc3)c(OC)c1)CO2] | 104 |
| 19 | 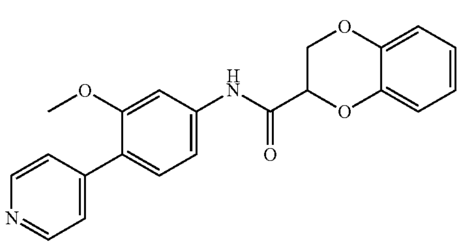 [SMILES: COc1cc(NC(=O)C2COc3ccccc3O2)ccc1-c1ccncc1] | 110 |

TABLE 10-continued

| Comp. No. | Chemical structure | Cell proliferation within one week [%] |
|---|---|---|
| 20 | 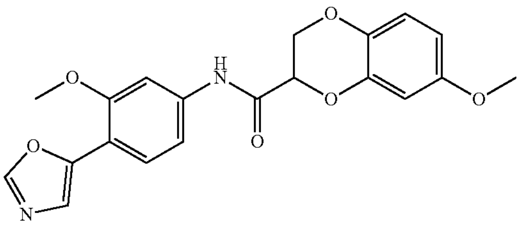 [SMILES: COc1ccc2c(c1)OC(C(=O)Nc1ccc(-c3cnco3)c(OC)c1)CO2] | 113 |
| 21 | 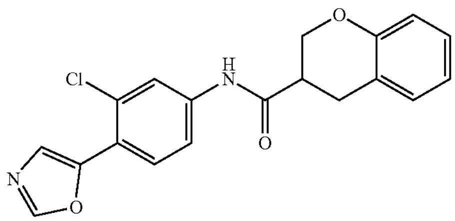 | 126 |
| 22 | 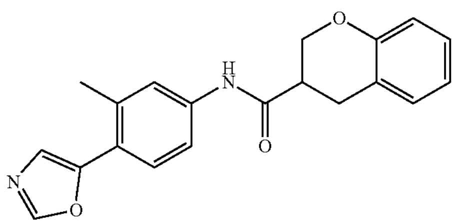 [SMILES: Cc1cc(NC(=O)C2COc3ccccc3C2)ccc1-c1cnco1] | 120 |
| 23 | 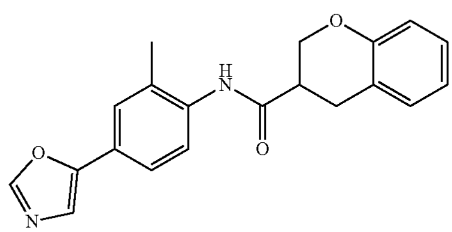 [SMILES: Cc1cc(-c2cnco2)ccc1NC(=O)C1COc2ccccc2C1] | 116 |
| 24 | 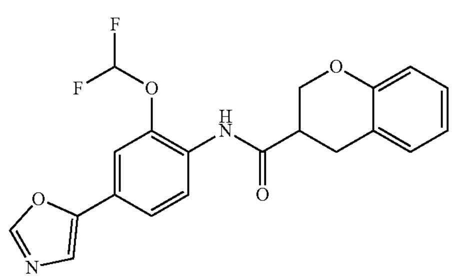 [SMILES: O=C(Nc1ccc(-c2cnco2)cc1OC(F)F)C1COc2ccccc2C1] | 126 |
| 25 | 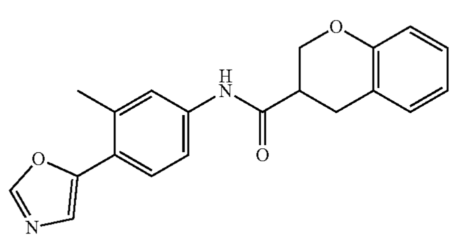 [SMILES: Cc1cc(NC(=O)C2COc3ccccc3C2)ccc1-c1cnco1] | 120 |

TABLE 10-continued

| Comp. No. | Chemical structure | Cell proliferation within one week [%] |
|---|---|---|
| 26 | 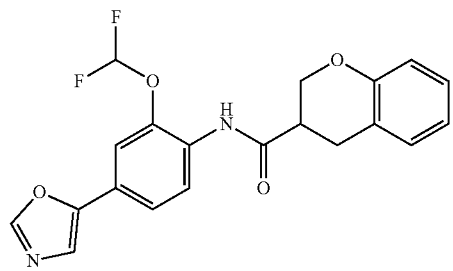 [SMILES: O=C(Nc1ccc(-c2cnco2)cc1OC(F)F)C1COc2ccccc2C1] | 138 |
| 27 | 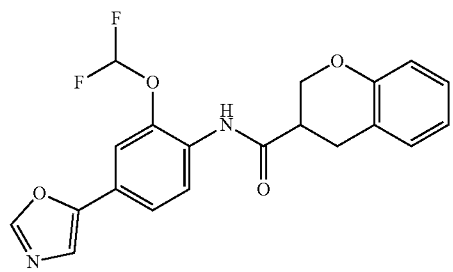 [SMILES: O=C(Nc1ccc(-c2cnco2)cc1OC(F)F)C1COc2ccccc2C1] | 106 |
| 28 | 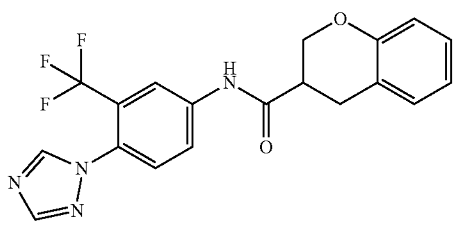 [SMILES: O=C(Nc1ccc(-n2cncn2)c(C(F)(F)F)c1)C1COc2ccccc2C1] | 118 |
| 29 | 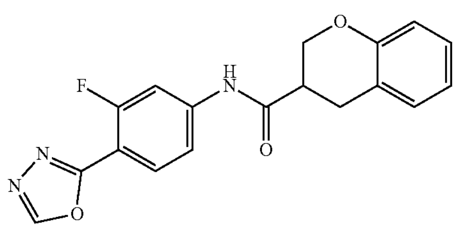 [SMILES: O=C(Nc1ccc(-c2nnco2)c(F)c1)C1COc2ccccc2C1] | 108 |
| 30 | 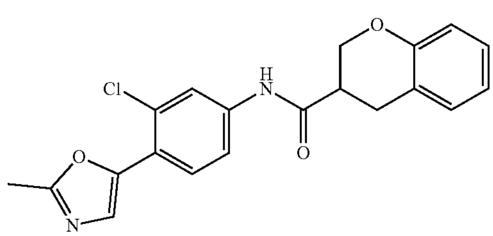 [SMILES: Cc1ncc(-c2ccc(NC(=O)C3COc4ccccc4C3)cc2Cl)o1] | 119 |
| 31 | 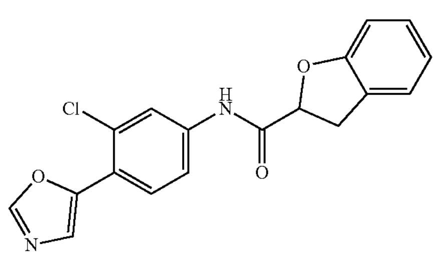 [SMILES: O=C(Nc1ccc(-c2cnco2)c(Cl)c1)C1Cc2ccccc2O1] | 137 |

TABLE 10-continued

| Comp. No. | Chemical structure | Cell proliferation within one week [%] |
|---|---|---|
| 32 | 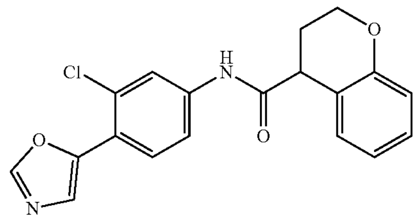 [SMILES: O=C(Nc1ccc(-c2cnco2)c(Cl)c1)C1CCOc2ccccc21] | 113 |
| 33 | 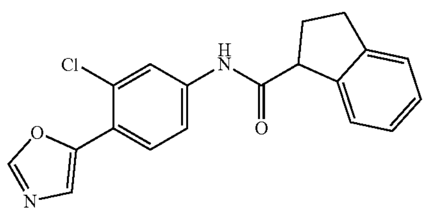 [SMILES: O=C(Nc1ccc(-c2cnco2)c(Cl)c1)C1CCc2ccccc21] | 116 |
| 34 | 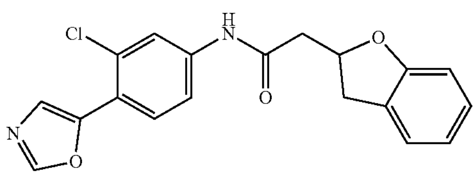 [SMILES: O=C(CC1Cc2ccccc2O1)Nc1ccc(-c2cnco2)c(Cl)c1] | 129 |
| 35 | 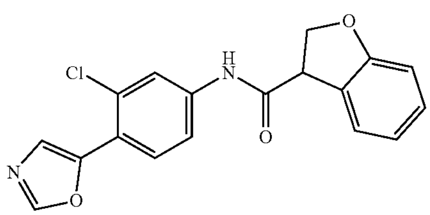 [SMILES: O=C(Nc1ccc(-c2cnco2)c(Cl)c1)C1COc2ccccc21] | 125 |
| 36 | 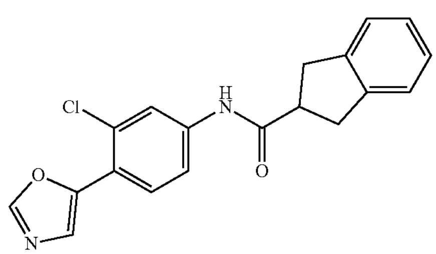 [SMILES: O=C(Nc1ccc(-c2cnco2)c(Cl)c1)C1Cc2ccccc2C1] | 124 |
| 37 | 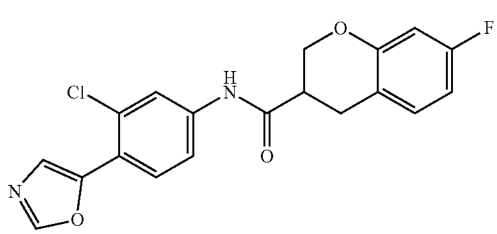 [SMILES: O=C(Nc1ccc(-c2cnco2)c(Cl)c1)C1COc2cc(F)ccc2C1] | 158 |
| 38 | 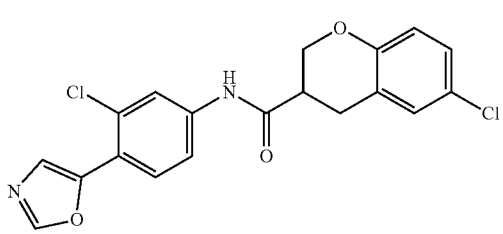 [SMILES: O=C(Nc1ccc(-c2cnco2)c(Cl)c1)C1COc2ccc(Cl)cc2C1] | 122 |

TABLE 10-continued

| Comp. No. | Chemical structure | Cell proliferation within one week [%] |
|---|---|---|
| 39 | 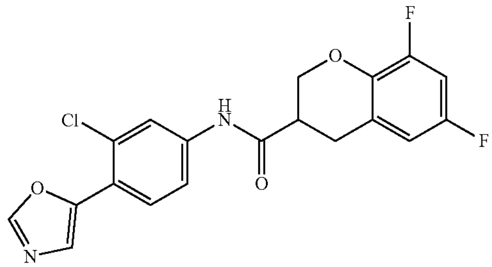 [SMILES: O=C(Nc1ccc(-c2cnco2)c(Cl)c1)C1COc2c(F)cc(F)cc2C1] | 132 |
| 40 | 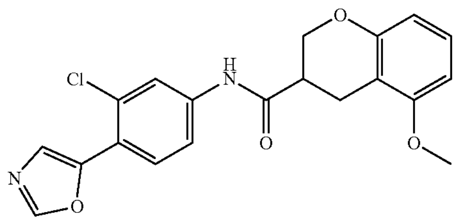 [SMILES: COc1cccc2c1CC(C(=O)Nc1ccc(-c3cnco3)c(Cl)c1)CO2] | 107 |
| 41 | 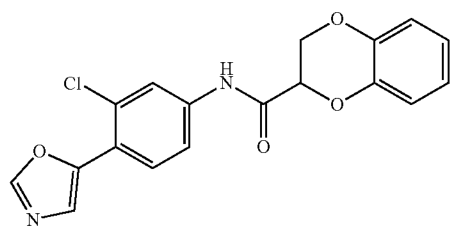 | 114 |
| 42 | 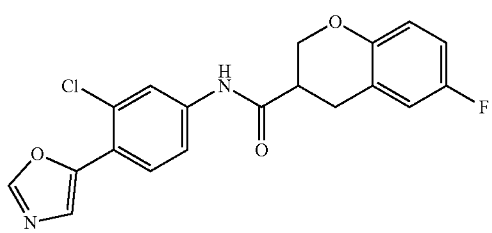 [SMILES: O=C(Nc1ccc(-c2cnco2)c(Cl)c1)C1COc2ccc(F)cc2C1] | 124 |
| C* | — | 100 |

The invention claimed is:

1. A compound of the formula (I)

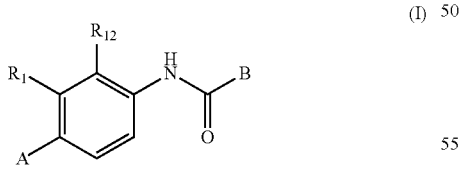

(I)

or a pharmaceutically acceptable salt, a racemic mixture, a corresponding enantiomer or, if applicable, a corresponding diastereomer thereof, wherein:

A is selected from the group consisting of a 5-oxazolyl, a pyridine-4-yl, a triazolyl, a oxadiazolyl, a imidazolyl and a 2-methyloxazol-5-yl residue, $R_1$, and $R_{12}$ are independently selected from the group consisting of hydrogen, fluoro, chloro, methoxy, trifluoromethyl, methyl and difluoromethoxy, B is selected from the group consisting of a residue of formula (II), (III), (V), (VI), (VII), (VIII) and (IX)

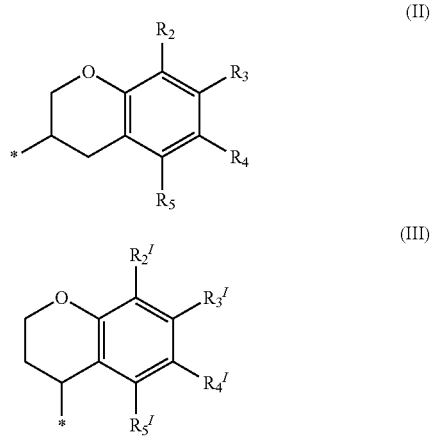

(II)

(III)

-continued

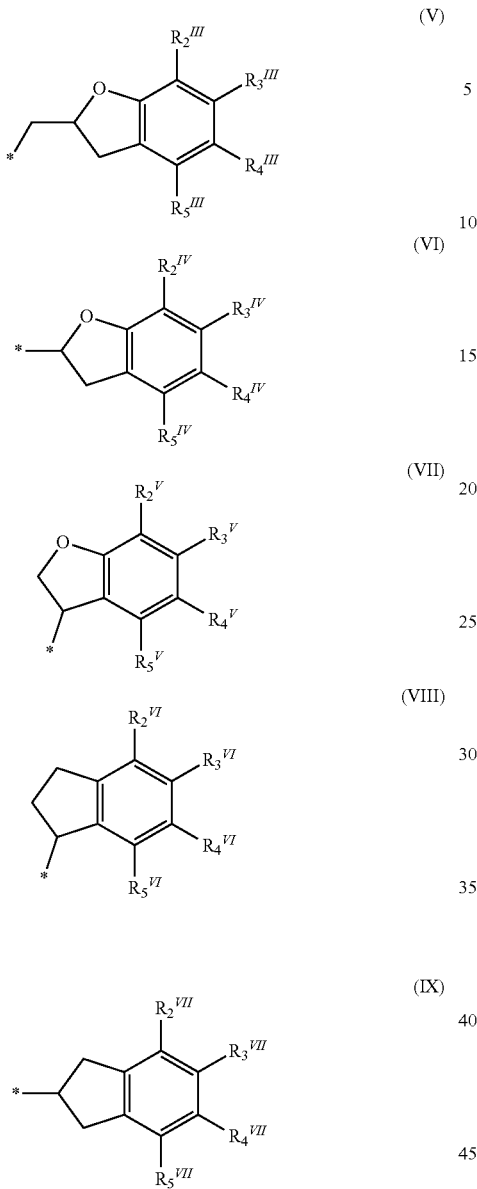

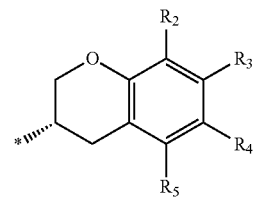

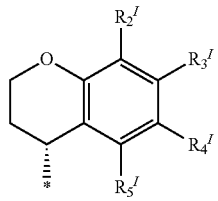

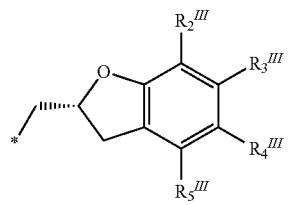

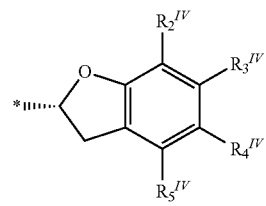

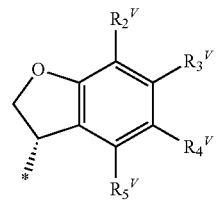

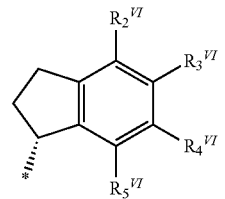

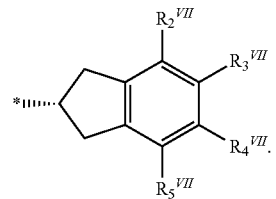

where:

"*" denotes the point of attachment to the remainder of the molecule, and $R_2$, $R_3$, $R_4$, $R_5$, $R_2^I$, $R_3^I$, $R_4^I$, $R_5^I$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$, $R_2^{VI}$, $R_3^{VI}$, $R_4^{VI}$, $R_5^{VI}$, $R_2^{VII}$, $R_3^{VII}$, $R_4^{VII}$, and $R_5^{VII}$ are independently selected from the group consisting of hydrogen, a linear or branched alkyl having 1 to 3 carbon atoms, fluoro, chloro, bromo, methoxy, ethoxy, propoxy, 2,2,2-trifluoromethyl and difluoromethoxy.

2. The compound according to claim 1 wherein B is selected from the group consisting of a residue of formula (II) or (III).

3. The compound according to claim 1, wherein the asymmetric center at ring position * of the residue of formula (II), (III), (V), (VI), (VII), (VIII) or (IX) has the following configuration 4. The compound according to claim 1, wherein the asymmetric center at ring position * of the residue of formula (II), (III), (V), (VI), (VII), (VIII) or (IX) is in the following configuration

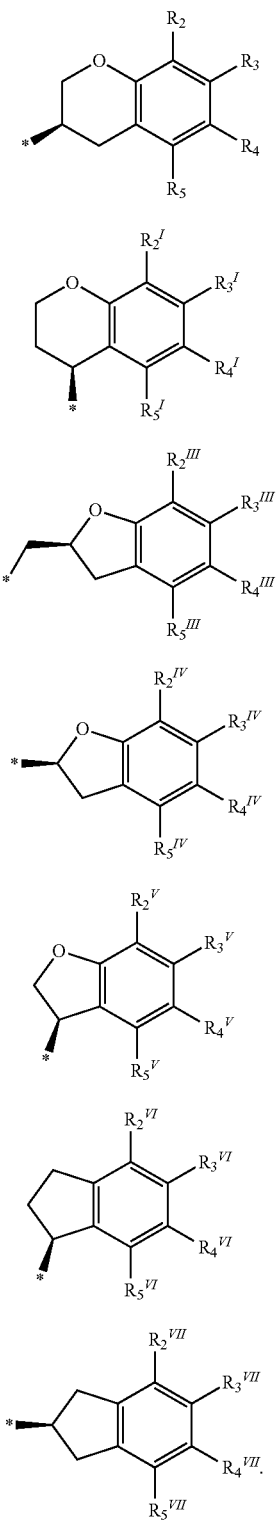

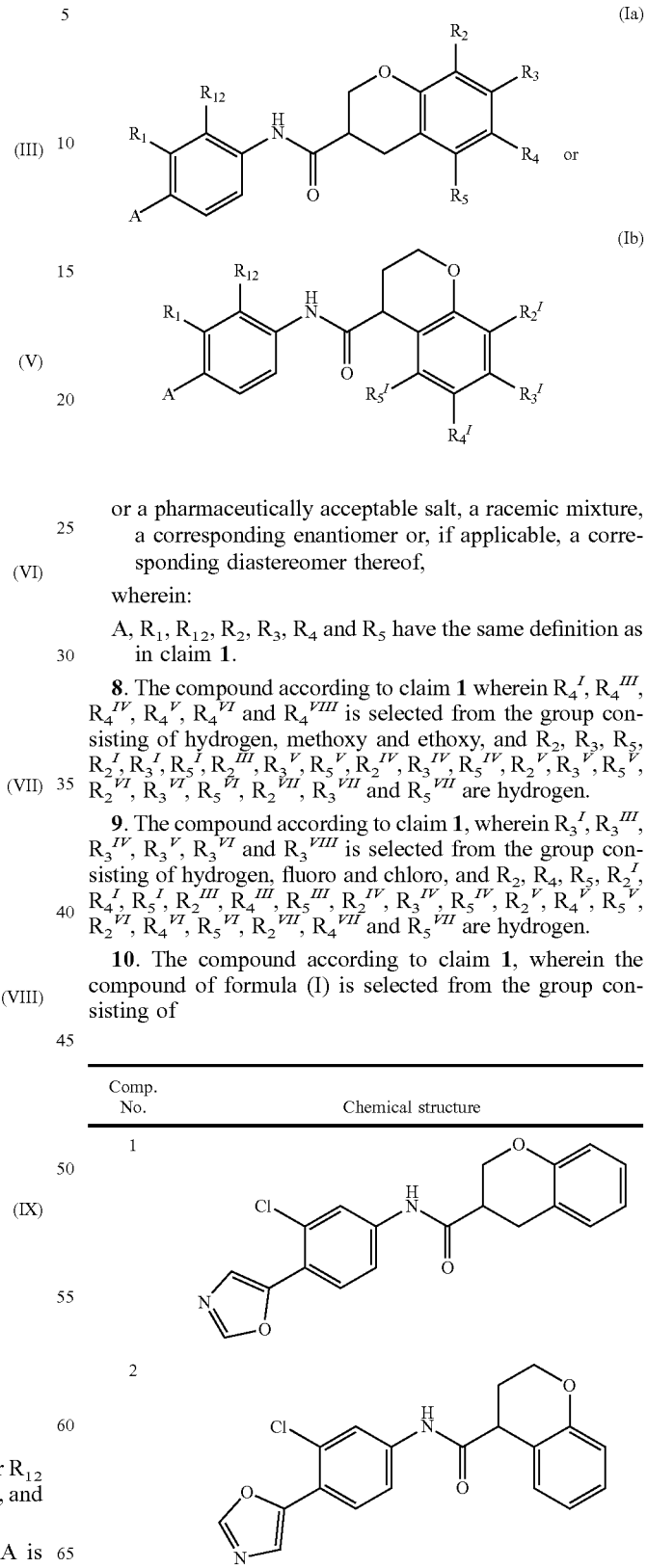

5. The compound according to claim 1, wherein $R_1$ or $R_{12}$ is selected from the group consisting of methoxy, chloro, and fluoro.

6. The compound according to claim 1, wherein A is selected from the group consisting a 5-oxazolyl residue, pyridine-4-yl residue and a triazolyl residue.

7. The compound according to claim 1 having the formula (Ia) or (Ib)

or a pharmaceutically acceptable salt, a racemic mixture, a corresponding enantiomer or, if applicable, a corresponding diastereomer thereof, wherein:

A, $R_1$, $R_{12}$, $R_2$, $R_3$, $R_4$ and $R_5$ have the same definition as in claim 1.

8. The compound according to claim 1 wherein $R_4{}^I$, $R_4{}^{III}$, $R_4{}^{IV}$, $R_4{}^V$, $R_4{}^{VI}$ and $R_4{}^{VIII}$ is selected from the group consisting of hydrogen, methoxy and ethoxy, and $R_2$, $R_3$, $R_5$, $R_2{}^I$, $R_3{}^I$, $R_5{}^I$, $R_2{}^{III}$, $R_3{}^V$, $R_5{}^V$, $R_2{}^{IV}$, $R_3{}^{IV}$, $R_5{}^{IV}$, $R_2{}^V$, $R_3{}^V$, $R_5{}^V$, $R_2{}^{VI}$, $R_3{}^{VI}$, $R_5{}^{VI}$, $R_2{}^{VII}$, $R_3{}^{VII}$ and $R_5{}^{VII}$ are hydrogen.

9. The compound according to claim 1, wherein $R_3{}^I$, $R_3{}^{III}$, $R_3{}^{IV}$, $R_3{}^V$, $R_3{}^{VI}$ and $R_3{}^{VIII}$ is selected from the group consisting of hydrogen, fluoro and chloro, and $R_2$, $R_4$, $R_5$, $R_2{}^I$, $R_4{}^I$, $R_5{}^I$, $R_2{}^{III}$, $R_4{}^{III}$, $R_5{}^{III}$, $R_2{}^{IV}$, $R_3{}^{IV}$, $R_5{}^{IV}$, $R_2{}^V$, $R_4{}^V$, $R_5{}^V$, $R_2{}^{VI}$, $R_4{}^{VI}$, $R_5{}^{VI}$, $R_2{}^{VII}$, $R_4{}^{VII}$ and $R_5{}^{VII}$ are hydrogen.

10. The compound according to claim 1, wherein the compound of formula (I) is selected from the group consisting of -continued
| Comp. No. | Chemical structure |
|---|---|
| 3 | 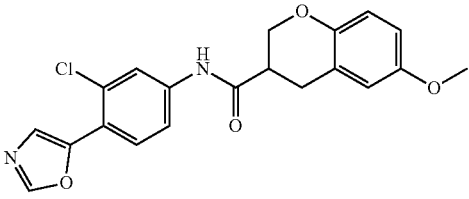 [SMILES: COc1ccc2c(c1)CC(C(=O)Nc1ccc(-c3cnco3)c(OC)c1)CO2] |
| 4 | 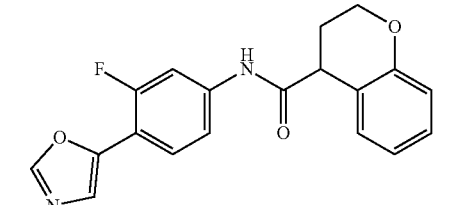 |
| 5 | 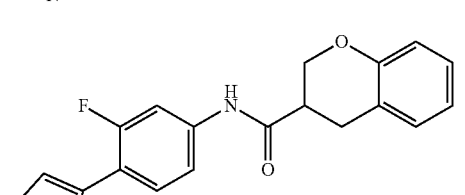 |
| 10 | 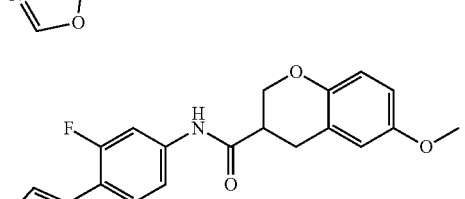 |
| 11 | 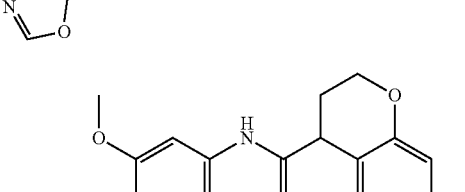 |
| 12 | 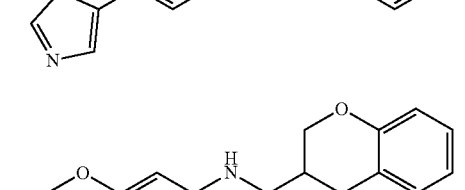 |
| 14 | 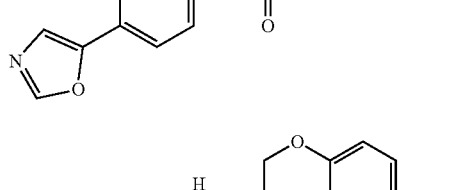 |
-continued
| Comp. No. | Chemical structure |
|---|---|
| 15 | 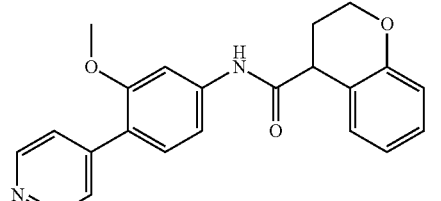 |
| 16 | 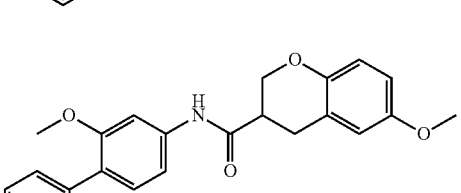 |
| 17 | 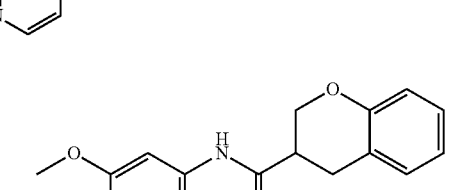 |
| 21 | 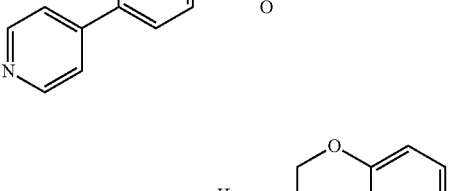 |
| 22 | 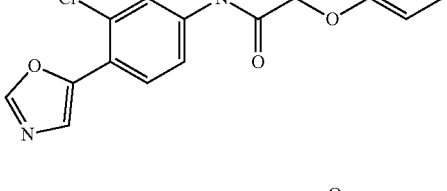 |
| 23 | 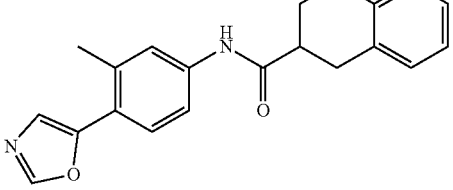 |

| Comp. No. | Chemical structure |
|---|---|
| 24 | 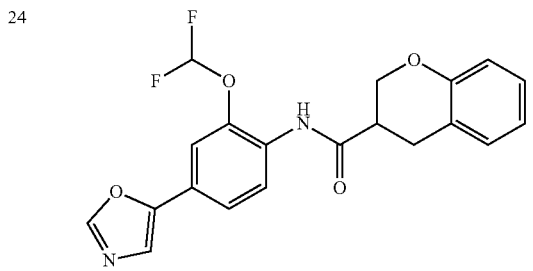 |
| 25 | 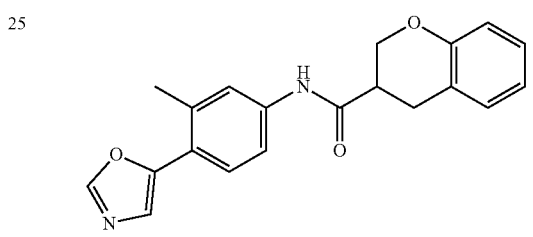 |
| 26 | 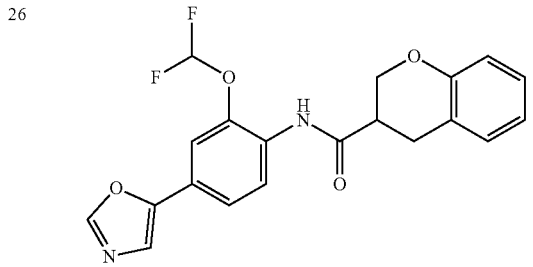 |
| 27 | 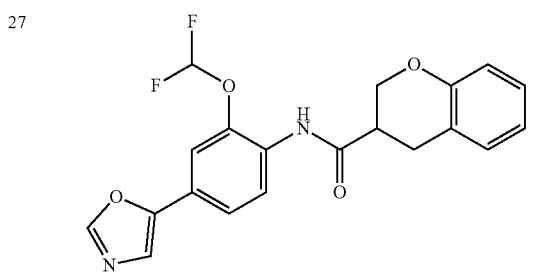 |
| 28 | 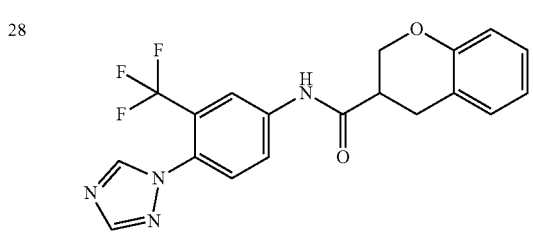 |
| 29 | 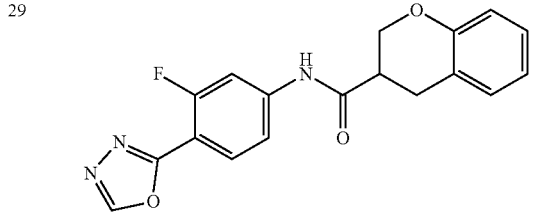 |
| Comp. No. | Chemical structure |
|---|---|
| 30 | 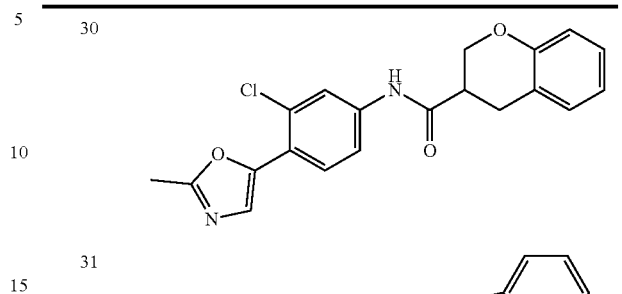 |
| 31 | 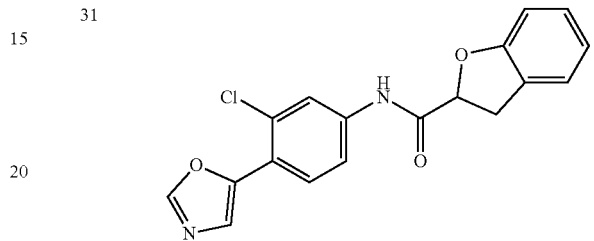 |
| 32 | 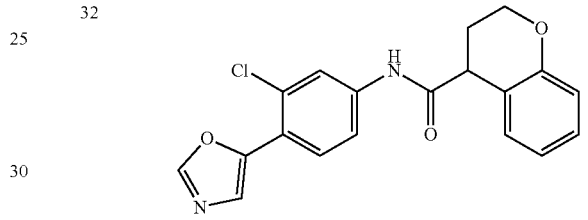 |
| 33 | 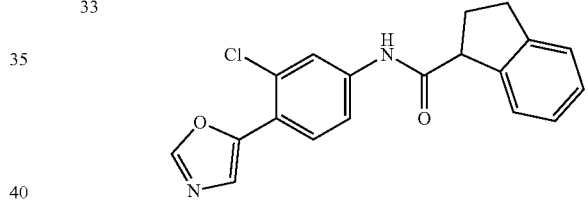 |
| 34 | 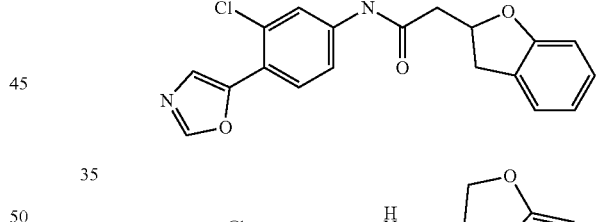 |
| 35 | 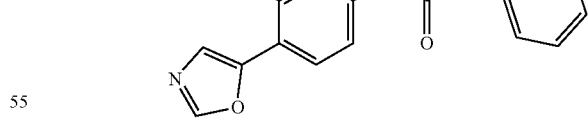 |
| 36 | 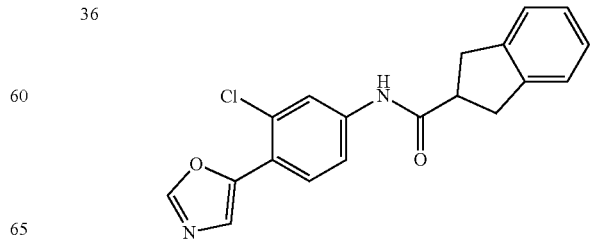 |

-continued

| Comp. No. | Chemical structure |
|---|---|
| 37 | 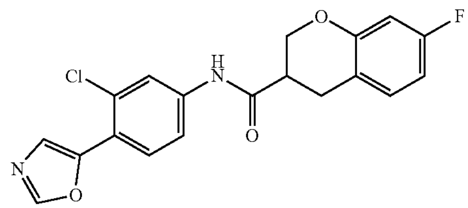 [SMILES: O=C(Nc1ccc(-c2cnco2)c(Cl)c1)C1COc2cc(F)ccc2C1] |
| 38 | 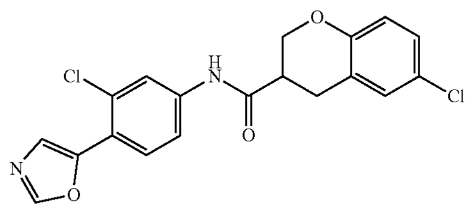 [SMILES: O=C(Nc1ccc(-c2cnco2)c(Cl)c1)C1COc2ccc(Cl)cc2C1] |
| 39 | 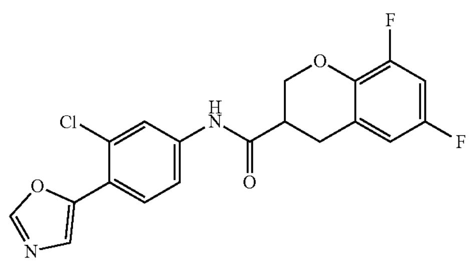 [SMILES: O=C(Nc1ccc(-c2cnco2)c(Cl)c1)C1COc2c(F)cc(F)cc2C1] |
| 40 | 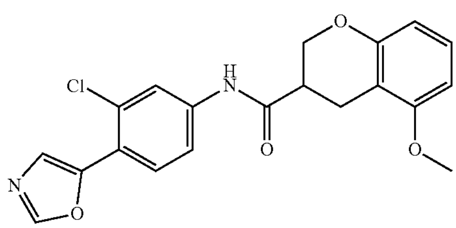 [SMILES: COc1cccc2c1CC(C(=O)Nc1ccc(-c3cnco3)c(Cl)c1)CO2] |
| 42 | 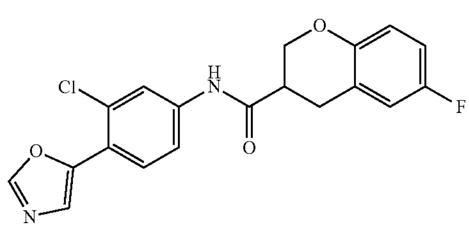 [SMILES: O=C(Nc1ccc(-c2cnco2)c(Cl)c1)C1COc2ccc(F)cc2C1] |

11. The compound according to claim 1 for use as a medicament.

12. The compound according to claim 1 for use in the treatment and/or prevention of a retinal disease that leads to photoreceptor loss or outer retina degradation.

13. The compound according to claim 12 for use in the treatment and/or prevention of a retinal disease selected from the group consisting of inherited retinal dystrophies, acquired degeneration, vascular related retinal degeneration, drug-induced maculopathies, infectious eye diseases, inflammatory eye diseases and white dot syndromes, wherein the compound, upon administration, treats the retinal disease by inducing proliferation of retinal precursor cells.

14. The compound according to claim 13 for use in the treatment and/or prevention of a retinal disease from the group consisting of retinitis pigmentosa (RP), rod-cone dystrophies, Usher's syndrome, Stargardt's disease, cone-rod dystrophies, cone dystrophies, achromatopsia, blue cone monochromacy, enhanced S-cone syndrome, rod dystrophies, choroideremia, Leber's congenital amaurosis, juvenile X-chromosome linked retinoschisis (JXLR), fundus albipunctatus, retinitis Punctata albescens, fleck retina of Kandori, bietti crystalline retinal dystrophy, fenestrated sheen macular dystrophy, adult-onset foveomacular vitelliform dystrophy, Batten's disease, congenital stationary night blindness, familial exudative vitreoretinopathy (FEVR), ocular albinism, oculocutaneous albinism, fovea hypoplasia, abetalipoproteinemia, Stickler syndrome, retinal dystrophy, crystalline maculopathy, solar retinopathy, talc retinopathy, diabetic retinopathy, sickle cell retinopathy, macular telangectasia, eales disease, peripheral retinoschisis, central/branch retinal artery occlusion (CRAO/BRAO), central/branch retinal vein occlusion (CRVO/BRVO), haemorrhagic occlusive retinal vasculitis (HORV), drug-induced maculopathies; cystoid macular edema (CME), progressive outer retinal necrosis (PORN), acute retinal necrosis (ARN), CMV-retinitis, Sarcoidosis, acute syphilitic posterior placoid chorioretinitis, tuberculosis chorioretinitis, toxoplasmic retinochoroiditis, posterior Uveitis and retinal vasculitis, intermediate uveitis, pars planitis+/−CME, anterior enophthalmitis, posterior enophthalmitis, posterior scleritis, masquerade syndromes, multifocal choroiditis and panuveitis (MCP), punctate inner choroidopathy (PIC), birdshot retinochoroidopathy, acute macular neuroretinopathy (AMN) and acute zonal occult outer retinopathy (AZOOR).

15. A pharmaceutical composition comprising a compound according to claim 1 as a therapeutically active substance and a pharmaceutically acceptable carrier and/or adjuvant.

16. The pharmaceutical composition according to claim 15, wherein the pharmaceutical composition is suitable for intraocular injection.

17. The compound according to claim 13 for use in the treatment and/or prevention of a retinal disease from the group consisting of:
  syndromic, non-syndromic, X-chromosome linked, recessive, dominant, and sporadic forms of retinitis pigmentosa (RP);
  Bothnia type retinal dystrophy;
  crystalline maculopathies induced by drugs selected from the group of tamoxifen, talc, canthaxanthine, methoxyflurane, and nitrofurantoin;
  hyperoxaluria;
  cystinosis;
  Sjogren-Larsson syndrome;
  west African crystalline maculopathy;
  maculopathies induced by drugs selected from the group of chloroquine, hydroxychloroquine, phenothiazine, quinine sulfate, thioridazine, clofazimine, cholopromazine, deferoxamine, chloroquine-derivatives, cisplatin, carmustine, chlofazimine and vigabatrin; and
  cystoid macular edema (CME) induced by one of epinephrine, latanoprost and nicotinic acid.

18. The compound according to claim 1, wherein the compound is one of the following compounds:
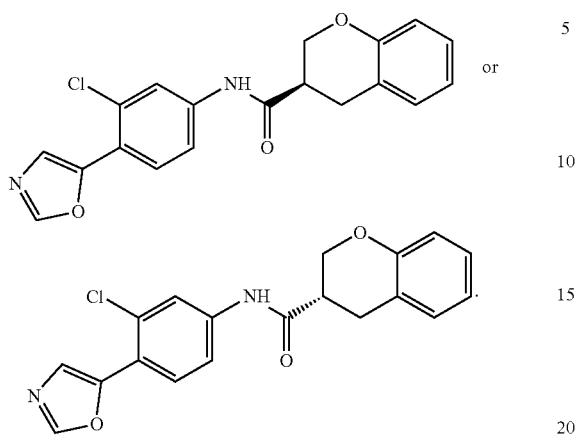
19. The compound according to claim 1, wherein the compound is an enantiomer with the shorter retention time from the chiral HPLC resolution.
* * * * *